(12) United States Patent
Yang et al.

(10) Patent No.: US 11,302,874 B2
(45) Date of Patent: Apr. 12, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Jeong-Eun Yang, Gyeonggi-do (KR); Hong-Se Oh, Gyeonggi-do (KR); Hee-Ryong Kang, Gyeonggi-do (KR); Young-Gil Kim, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 344 days.

(21) Appl. No.: 16/483,065

(22) PCT Filed: Feb. 26, 2018

(86) PCT No.: PCT/KR2018/002303
§ 371 (c)(1),
(2) Date: Aug. 2, 2019

(87) PCT Pub. No.: WO2018/159964
PCT Pub. Date: Sep. 7, 2018

(65) Prior Publication Data
US 2020/0013965 A1    Jan. 9, 2020

(30) Foreign Application Priority Data

Feb. 28, 2017 (KR) .................. 10-2017-0026014
Sep. 26, 2017 (KR) .................. 10-2017-0124285
(Continued)

(51) Int. Cl.
*H01L 51/00* (2006.01)
*C07D 403/14* (2006.01)
(Continued)

(52) U.S. Cl.
CPC ........ *H01L 51/0072* (2013.01); *H01L 51/006* (2013.01); *H01L 51/0067* (2013.01);
(Continued)

(58) Field of Classification Search
None
See application file for complete search history.

(56) References Cited

U.S. PATENT DOCUMENTS

2012/0235123 A1    9/2012  Lee et al.
2017/0117488 A1    4/2017  Ahn et al.

FOREIGN PATENT DOCUMENTS

KR    20150121337 A    10/2015
KR    20160060569 A    5/2016

OTHER PUBLICATIONS

Dopper et al. "Synthesis and Properties of Some Heterocirculenes" J. Org. Chem. 1975, 40, 1957-1966. (Year: 1975).*
(Continued)

*Primary Examiner* — Robert S Loewe
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, it is possible to provide an organic electroluminescent device having excellent thermal stability, low driving voltage, high luminous efficiency, and/or improved lifespan properties.

10 Claims, 1 Drawing Sheet

(30) Foreign Application Priority Data

Dec. 27, 2017 (KR) ........................ 10-2017-0180988
Feb. 23, 2018 (KR) ........................ 10-2018-0021961

(51) Int. Cl.

| | |
|---|---|
| C07D 407/14 | (2006.01) |
| C07D 409/14 | (2006.01) |
| C07D 471/16 | (2006.01) |
| C07D 495/04 | (2006.01) |
| C07D 513/04 | (2006.01) |
| H01L 51/50 | (2006.01) |

(52) U.S. Cl.
CPC ...... *H01L 51/0073* (2013.01); *H01L 51/0074* (2013.01); *C07D 403/14* (2013.01); *C07D 407/14* (2013.01); *C07D 409/14* (2013.01); *C07D 471/16* (2013.01); *C07D 495/04* (2013.01); *C07D 513/04* (2013.01); *H01L 51/0085* (2013.01); *H01L 51/5016* (2013.01); *H01L 51/5056* (2013.01); *H01L 51/5088* (2013.01); *H01L 51/5096* (2013.01)

(56) References Cited

OTHER PUBLICATIONS

M. B. Groen et al., Synthesis and Resolution of Some Heterohelicenes1, J. Org. Chem. vol. 36, No. 19, 1971, pp. 2797-2809.

Zander, M. et al., "Uber Carbazolo-carbazole", Chemische Berichte, 1969, vol. 102, No. 8, pp. 2728-2738 see compound 21 p. 2733.

Upadhya Y, G. M. et al., "Synthesis and Photophysical Properties of Aza[n]helicenes", Journal of Organic Chemistry, 2016, vol. 81, No. 17, pp. 7751-7759.

Dopper, J. H. et al., "Dehydrogenation of Heterohelicenes by a Scholl Type Reaction. The Dehydrohelicenes", J. Org. Chem., 1975 (Nov. 1, 1975), 40(23), p. 3399.

\* cited by examiner

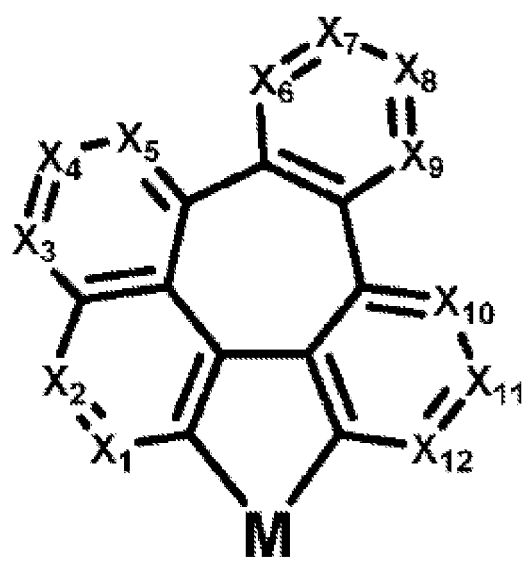

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

An organic EL device (OLED) changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc., if necessary. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions. In the OLED, holes from an anode and electrons from a cathode are injected into a light-emitting layer by the application of electric voltage, and an exciton having high energy is produced by the recombination of the holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and uniformality and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an organic EL device having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

In addition, a material having an excellent thermal stability and capable of improving the performance of an organic electroluminescent device, such as driving voltage, luminescent efficiency, and lifespan properties, in a hole transport layer, a buffer layer, an electron transport layer, and the like, is required to be developed.

DISCLOSURE OF THE INVENTION

Problems to be Solved

The objective of the present disclosure is to provide an organic electroluminescent compound effective for producing an organic electroluminescent device having excellent thermal stability, low driving voltage, high luminous efficiency, and/or improved lifespan properties.

Solution to Problems

A compound having a low Tg may reduce the charge mobility in a thin film and degrade the performance of the OLED device. As a result of intensive studies, the present inventors have developed a novel organic electroluminescent compound having a planar main core, which can assist pi-pi stacking in a vacuum deposition layer to lead to rapid charge mobility, and having a high glass transition temperature (Tg) in spite of its relatively low molecular weight, which can provide excellent morphological stability. Specifically, the present inventors found that the above objective can be achieved by an organic electroluminescent compound represented by the following formula 1:

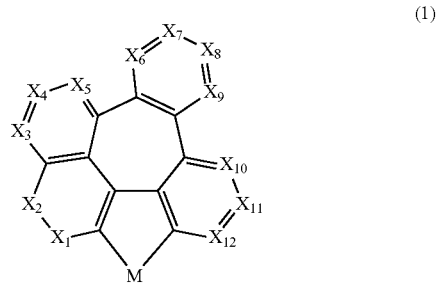

(1)

wherein
M represents

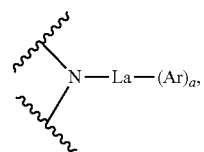

O or S;
$X_1$ to $X_{12}$, each independently, represent N or $CR_1$;
La represents a single bond, a substituted or unsubstituted (C1-C30)alkylene, a substituted or unsubstituted (C6-C30) arylene, a substituted or unsubstituted (3- to 30-membered) heteroarylene, or a substituted or unsubstituted (C3-C30) cycloalkylene;

Ar and $R_1$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;

the heteroaryl(ene) contains at least one heteroatom selected from B, N, O, S, Si, and P; and a represents an integer of 1 or 2, where if a is 2, each of Ar may be the same or different.

Effects of the Invention

The organic electroluminescent compound according to the present disclosure can provide an organic electroluminescent device having, low driving voltage, high luminous efficiency, and/or improved lifespan properties. In addition or alternatively, the organic electroluminescent compound according to the present disclosure has excellent thermal stability compared to other organic electroluminescent compounds having similar molecular weights.

BRIEF DESCRIPTION OF THE FIGURE

The FIGURE is a representative formula of the organic electroluminescent compound according to the present disclosure.

EMBODIMENTS OF THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. Although not limited thereto, the compound of formula 1 may be included in the light-emitting layer. In this case, the compound of formula 1 may be included as a host. Also, the compound of formula 1 may be included in the electron transport zone, and not limited thereto, the compound of formula 1 may be included in the electron buffer layer.

The term "composite material for an organic electroluminescent device" in the present disclosure means that two or more materials usable in the organic electroluminescent device are present together or are prepared to be present together, wherein "present together" means not only a state in which two or more materials are mixed, but also a state in which they are separated from each other. In addition, the composite material for an organic electroluminescent device is a concept encompassing not only a material before being included in an organic electroluminescent device (e.g., before deposition), but also a material included in an organic electroluminescent device (e.g., after deposition). For example, the composite material for an organic electroluminescent device may comprise at least two of a hole injection material, a hole transport material, a hole auxiliary material, a light-emitting auxiliary material, an electron blocking material, a light-emitting material (a host material and a dopant material), an electron buffer material, a hole blocking material, an electron transport material and an electron injection material, or may comprise at least two hole injection materials, at least two hole transport materials, at least two hole auxiliary materials, at least two light-emitting auxiliary materials, at least two electron blocking materials, at least two light-emitting materials (host materials and dopant materials), at least two electron buffer materials, at least two hole blocking materials, at least two electron transport materials, or at least two electron injection materials. The composite material for an organic electroluminescent device of the present disclosure may be comprised in any layer constituting an organic electroluminescent device. The two or more materials included in the composite material may be comprised together in one layer, or may be comprised in different layers, respectively. In case that two or more materials are comprised in one layer, they may be mixed-deposited to form a layer, or they may be co-deposited separately to form a layer.

Hereinafter, the organic electroluminescent compound represented by formula 1 will be described in more detail.

In formula 1, M represents

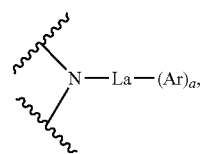

O or S.

In formula 1, $X_1$ to $X_{12}$, each independently, represent N or $CR_1$. According to one embodiment of the present disclosure, all of $X_1$ to $X_{12}$ may represent $CR_1$. According to another embodiment of the present disclosure, any one of $X_1$ to $X_{12}$ may represent N. According to further embodiment of the present disclosure, two of $X_1$ to $X_{12}$ may represent N.

In formula 1, La represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene; preferably, a single bond, a substituted or unsubstituted (C6-C25)arylene, or a substituted or unsubstituted (5- to 25-membered)heteroarylene; more preferably, a single bond, an unsubstituted (C6-C18) arylene, or an unsubstituted (5- to 18-membered)heteroarylene. The heteroarylene may comprise at least one of N, O, and S, and preferably at least one of N and S. According to one embodiment of the present disclosure, La may represent a single bond, phenylene, naphthylene, biphenylene, pyridylene, pyrimidinylene, triazinylene, isoquinolinylene, quinazolinylene, naphthyridinylene, quinoxalinylene, benzoquinoxalinylene, indoloquinoxalinylene, benzothienopyrimidinylene, or benzoquinazolinylene.

In formula 1, Ar and $R_1$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur.

The above Ar may represent, preferably, a substituted or unsubstituted (C6-C25)aryl, a substituted or unsubstituted (5- to 25-membered)heteroaryl, or a substituted or unsubstituted di(C6-C25)arylamino, and more preferably, an unsubstituted (C6-C18)aryl, a (5- to 25-membered)heteroaryl unsubstituted or substituted with (C1-C10)alkyl and/or (C6-C12)aryl, or a di(C6-C25)arylamino unsubstituted or substituted with (C1-C6)alkyl. According to one embodiment of the present disclosure, Ar may represent a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted fluoranthenyl, a substituted or unsubstituted triazinyl, a substituted or unsubstituted pyridyl, a substituted or unsubstituted pyrimidinyl, a substituted or unsubstituted benzothienopyrimidinyl, a substituted or unsubstituted acenaphthopyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted dibenzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted benzothienoquinolyl, a substituted or unsubstituted benzofuroquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothiazolinyl, a substituted or unsubstituted phenanthroimidazolyl, a substituted or unsubstituted diphenylamino, a substituted or unsubstituted phenylbiphenylamino, a substituted or unsubstituted fluorenylphenylamino, a substituted or unsubstituted dibenzothiophenylphenylamino, or a substituted or unsubstituted dibenzofuranylphenylamino. According to another embodiment of the present disclosure, Ar may represent a phenyl unsubstituted or substituted with at least one of deuterium and naphthyl, an unsubstituted naphthyl, an unsubstituted biphenyl, a fluorenyl unsubstituted or substituted with at least one methyl, an unsubstituted fluoranthenyl, a triazinyl unsubstituted or substituted with at least one of phenyl and naphthyl, a pyridyl unsubstituted or substituted with at least one phenyl, a pyrimidinyl unsubstituted or substituted with at least one phenyl, a quinazolinyl unsubstituted or substituted with at least one phenyl, a isoquinolyl unsubstituted or substituted with at least one phenyl, a carbazolyl unsubstituted or substituted with at least one phenyl, an unsubstituted dibenzothiophenyl, an unsubstituted dibenzofuranyl, a naphthyridinyl unsubstituted or substituted with at least one phenyl, an unsubstituted diphenylamino, an unsubstituted phenylbiphenylamino, a dimethylfluorenylphenylamino, a benzothienopyrimidinyl substituted with at least one phenyl, an unsubstituted benzothienoquinolyl, an unsubstituted benzofuroquinolyl, a benzoquinazolinyl substituted with at least one phenyl, a benzothiazolinyl substituted with at least one phenyl, a benzoquinoxalinyl substituted with at least one phenyl, an unsubstituted dibenzoquinoxalinyl, a phenanthroimidazolyl substituted with at least one phenyl, an unsubstituted dibenzothiophenylphenylamino, an unsubstituted dibenzofuranylphenylamino, a nitrogen-containing 17-membered heteroaryl substituted with at least one methyl, a 25-membered heteroaryl containing nitrogen and oxygen, or an acenaphthopyrimidinyl substituted with at least one phenyl.

The above $R_1$ may represent, preferably, a substituted or unsubstituted (C6-C25)aryl, or a substituted or unsubstituted (3- to 25-membered)heteroaryl; or may be linked to an adjacent substituent to form a substituted or unsubstituted, mono- or polycyclic, (C3-C25) alicyclic or aromatic ring, or the combination thereof, whose carbon atom(s) may be replaced with at least one heteroatom selected from nitrogen, oxygen, and sulfur; more preferably, a substituted or unsubstituted (C6-C18)aryl, or a substituted or unsubstituted (5- to 18-membered)heteroaryl; or may be linked to an adjacent substituent to form a substituted or unsubstituted, mono- or polycyclic, (C3-C18) alicyclic or aromatic ring, or the combination thereof, whose carbon atom(s) may be replaced with at least one heteroatom selected from nitrogen, oxygen, and sulfur; and most preferably, a (C6-C12)aryl unsubstituted or substituted with a (5- to 18-membered)heteroaryl, or a (5- to 13-membered)heteroaryl unsubstituted or substituted with a (C6-C18)aryl; or may be linked to an adjacent substituent to form a substituted or unsubstituted, mono- or polycyclic, (C3-C10) aromatic ring, whose carbon atom(s) may be replaced with at least one heteroatom selected from nitrogen, oxygen, and sulfur. According to one embodiment of the present disclosure, $R_1$ may represent a phenyl unsubstituted or substituted with diphenyltriazinyl, a diphenyltriazinyl, a quinazolinyl substituted with a phenyl(s), or an unsubstituted pyridyl; or may be linked to an adjacent substituent to form an unsubstituted benzene ring, an indene ring substituted with at least one of methyl and phenyl, an unsubstituted pyridine ring, an unsubstituted benzothiophene ring, an unsubstituted benzofuran ring, or an indole ring substituted with a phenyl(s) or a phenylquinoxalinyl(s).

According to one embodiment of the present disclosure, two adjacent $X_1$ to $X_{12}$ in formula 1 are $CR_1$, two adjacent $R_1$ may be fused to any one of the following formulas 2 to 6 to form a ring, and one or more of the rings may be formed in one compound represented by formula 1. For example, the ring may be a dibenzothiophene ring, a dibenzofuran ring, a naphthalene ring, a phenanthrene ring, or a substituted or unsubstituted carbazole ring.

(2)
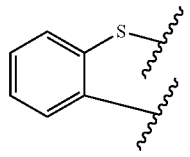

(3)
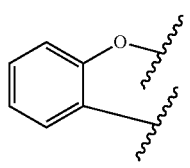

(4)
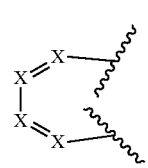

(5)
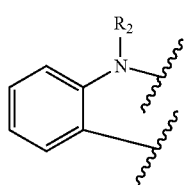

(6)
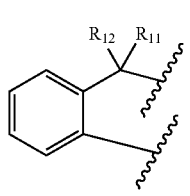

In formulas 2 to 6, ✦ represents a connecting site between C and $R_1$ in $CR_1$.

In formula 4, X represents N or CH. According to one embodiment of the present disclosure, all of X may represent CH. According to another embodiment of the present disclosure, any one of X may represent N.

In formula 5, $R_2$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably, a substituted or unsubstituted (C6-C25)aryl, or a substituted or unsubstituted (5- to 25-membered)heteroaryl; more preferably, an unsubstituted (C6-C18)aryl, or a (5- to 18-membered)heteroaryl unsubstituted or substituted with (C6-C18)aryl. According to one embodiment of the present disclosure, $R_2$ may represent an unsubstituted phenyl, or a quinoxalinyl substituted with a phenyl(s).

In formula 6, $R_{11}$ and $R_{12}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; or may be linked to each other to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur; preferably, hydrogen, a substituted or unsubstituted (C1-C6)alkyl, or a substituted or unsubstituted (C6-C12)aryl; or may be linked to each other to form a substituted or unsubstituted, mono- or polycyclic, (C5-C10) alicyclic or aromatic ring, or the combination thereof; and more preferably, hydrogen, an unsubstituted (C1-C6)alkyl, or an unsubstituted (C6-C12) aryl; or may be linked to each other to form a spiro ring.

In formula 1, a represents an integer of 1 or 2, where if a is 2, each of Ar may be the same or different.

The heteroaryl(ene) contains at least one heteroatom selected from B, N, O, S, Si, and P, and preferably, at least one N.

The compound represented by formula 1 may be represented by any one of the following formulas 7 to 10:

(7)
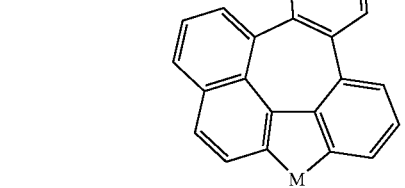

(8)
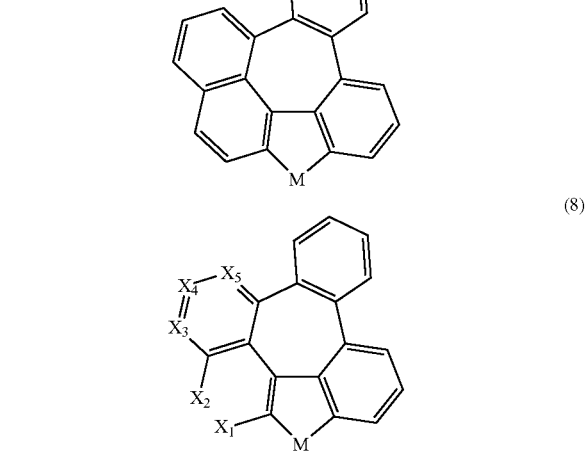

(9)
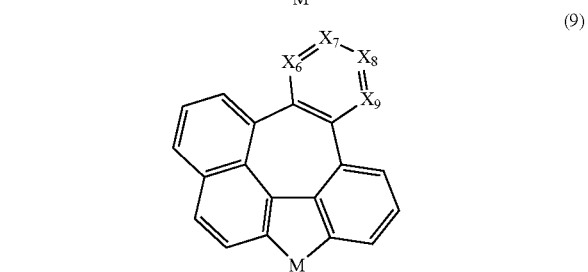

(10)
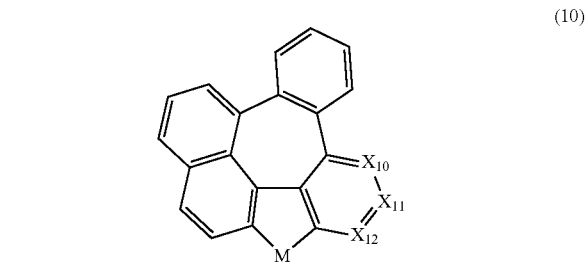

wherein, $X_1$ to $X_{12}$, and M are as defined in formula 1.

Herein, the term "(C1-C30)alkyl(ene)" is meant to be a linear or branched alkyl(ene) having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl(ene)" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered) heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered)heteroaryl(ene)" is an aryl having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted (C1-C30)alkyl(ene), the substituted (C6-C30) aryl(ene), the substituted (3- to 30-membered)heteroaryl (ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30) alkylamino, the substituted mono- or di-(C6-C30)arylamino, the substituted (C1-C30)alkyl(C6-C30)arylamino, and the substituted mono- or polycyclic, (C3-C30) alicyclic or aromatic ring, or the combination thereof in La, Ar, and $R_1$ of formulas 1 to 7, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthiol, a (5- to 30-membered)heteroaryl unsubstituted or substituted with a (C6-C30)aryl, a (C6-C30)aryl unsubstituted or substituted with a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino unsubstituted or substituted with a (C1-C30) alkyl, a (C1-C30)alkyl(C6-C30)arylamino, a (C1-C30)alkylcarbonyl, a (C1-C30)alkoxycarbonyl, a (C6-C30) arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl; preferably, at least one selected from the group consisting of a (C1-C20)alkyl, an unsubstituted (C6-C25)aryl, and a (5- to 25-membered)heteroaryl unsubstituted or substituted with a (C6-C25)aryl; more preferably, at least one selected from the group consisting of a (C1-C10)alkyl, an unsubstituted (C6-C18)aryl, and a (5- to 18-membered)heteroaryl substituted with a (C6-C18)aryl; and for example, at least one selected from the group consisting of a methyl, a phenyl, a diphenyltriazinyl, and a phenylquinoxalinyl.

The compound represented by formula 1 includes the following compounds, but is not limited thereto.

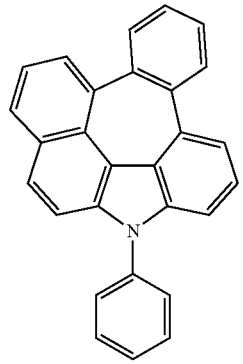

C-1

C-2
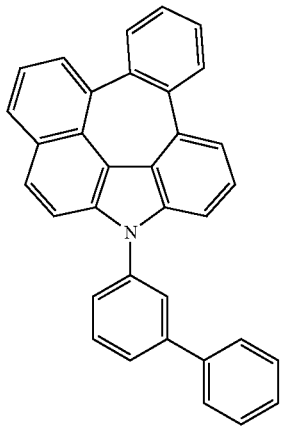
C-3
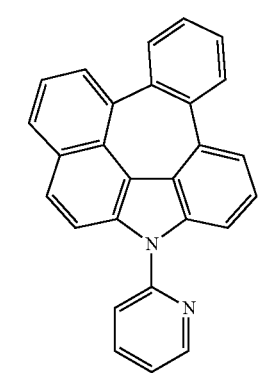
C-4
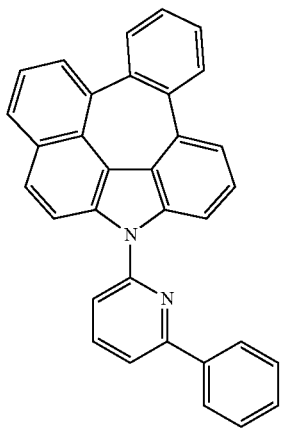
C-5
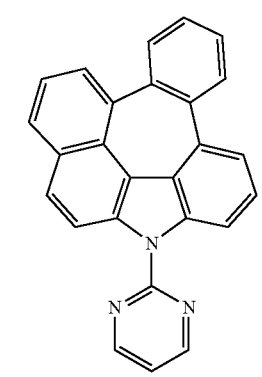
C-6
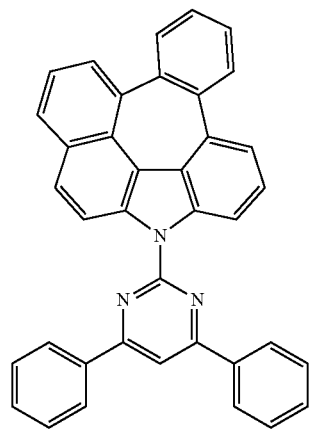
C-7
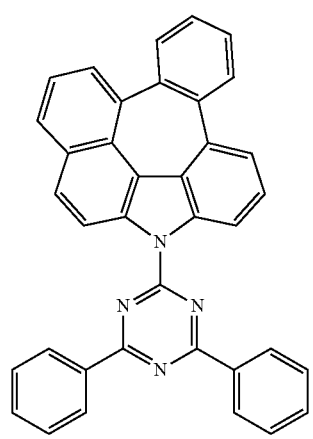
C-8
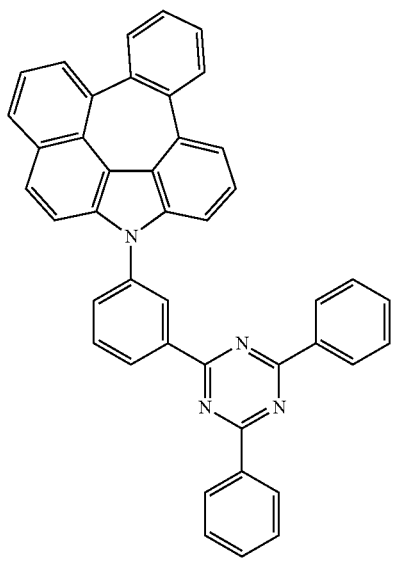

C-9
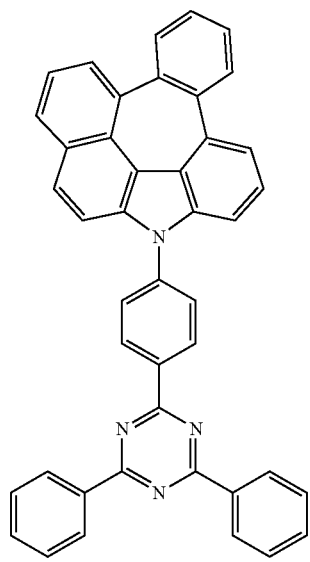
C-10
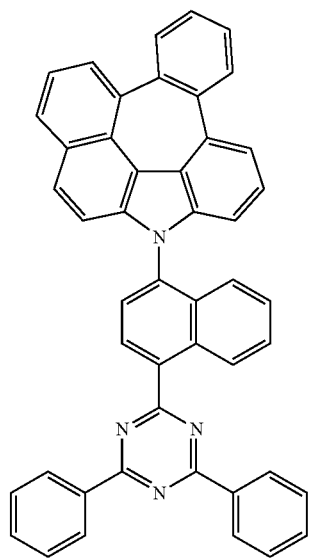
C-11
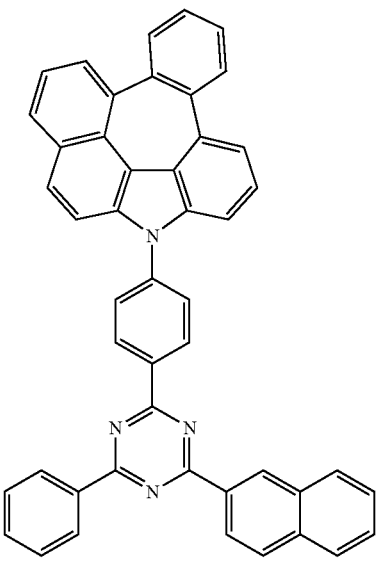
C-12
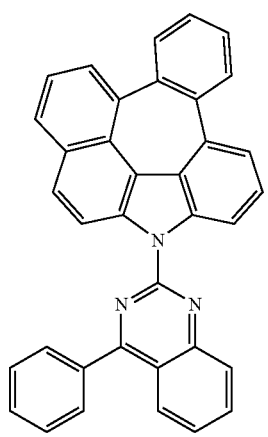
C-13
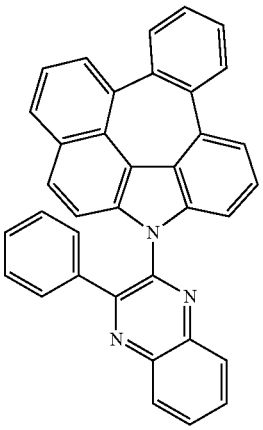

C-14
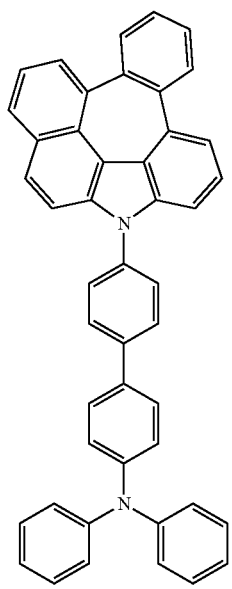
C-15
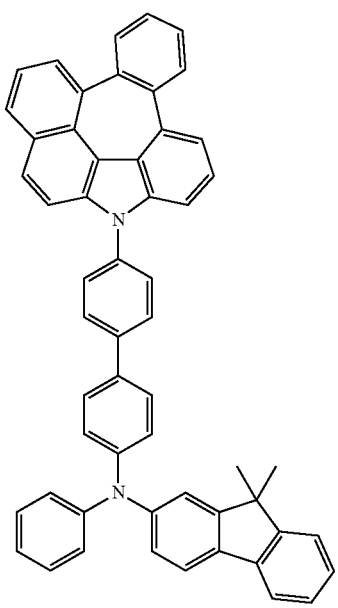
C-16
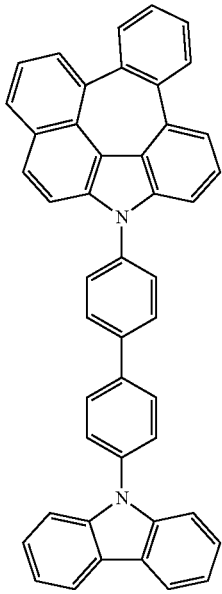
C-17
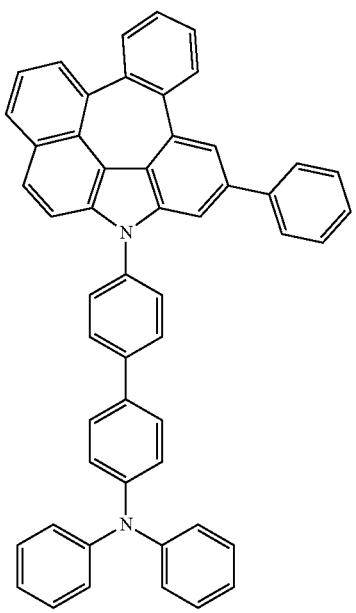

C-18
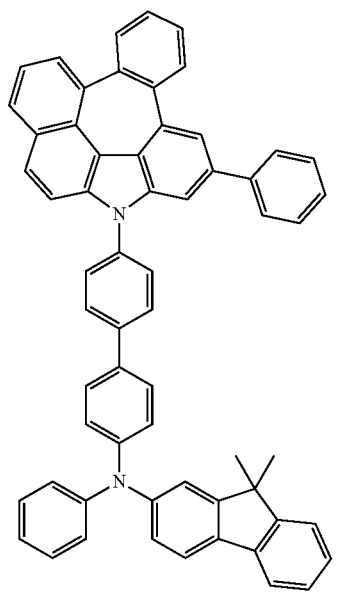
C-19
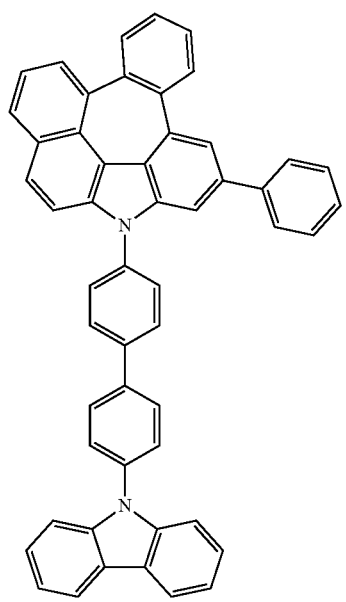
C-20
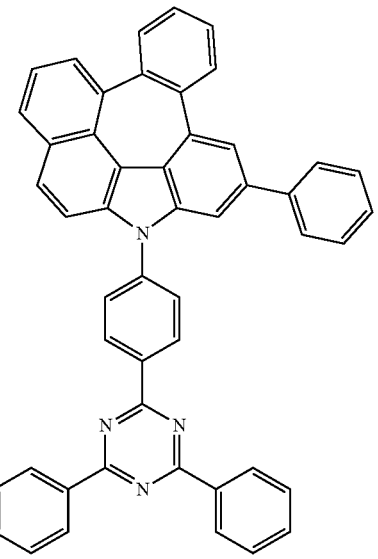
C-21
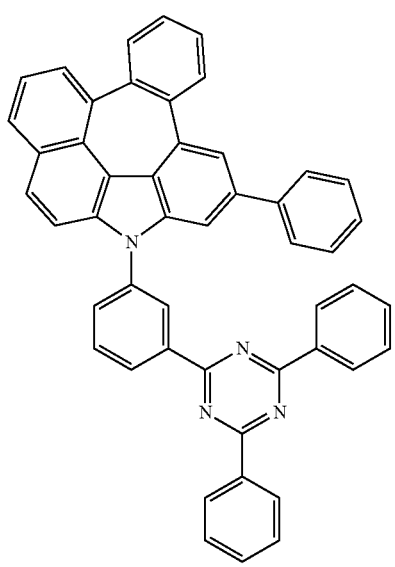
C-22
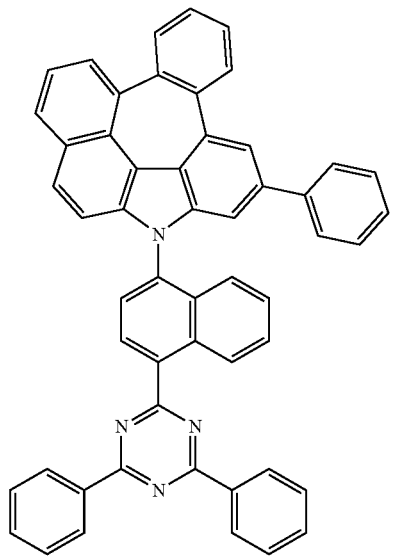

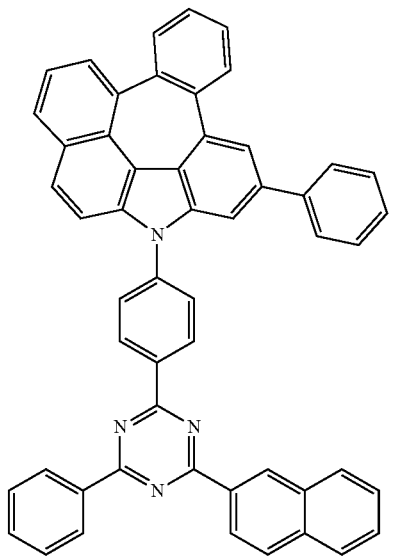
C-23
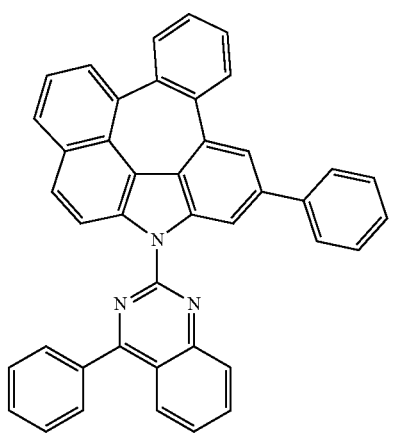
C-24
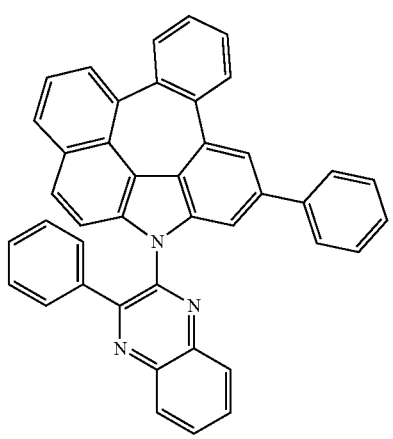
C-25
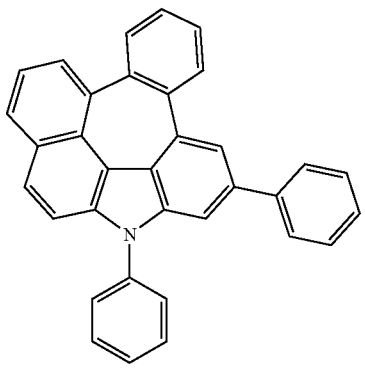
C-26
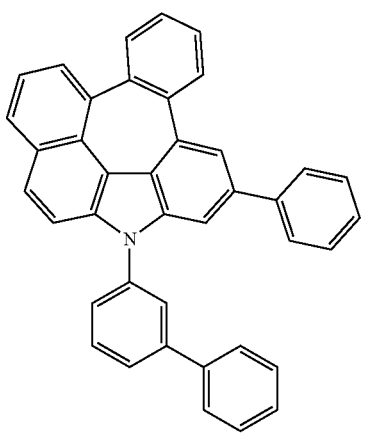
C-27
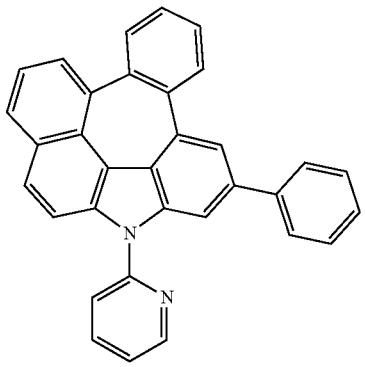
C-28
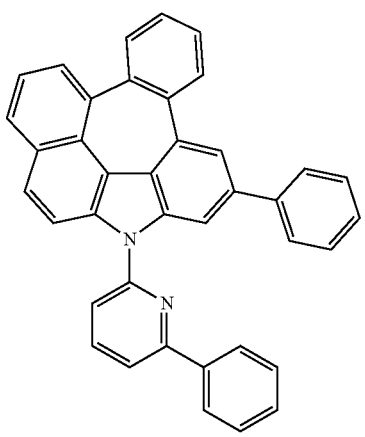
C-29

C-30 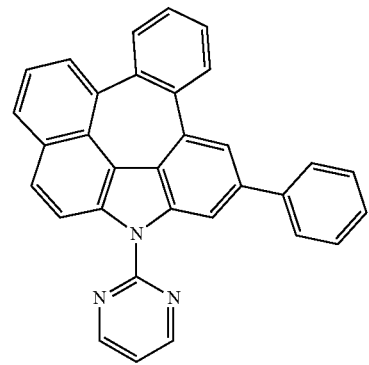
C-31 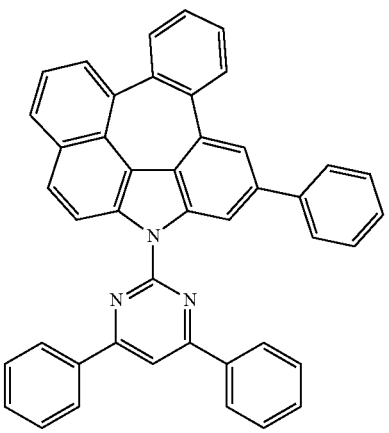
C-32 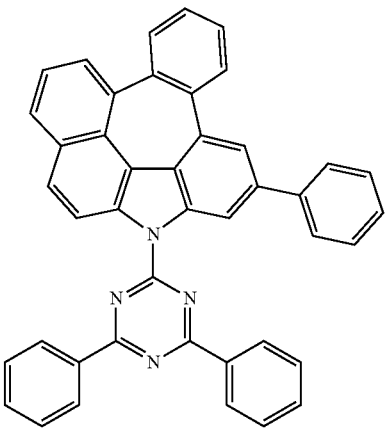
C-33 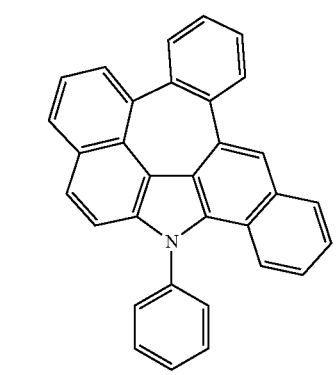
C-34 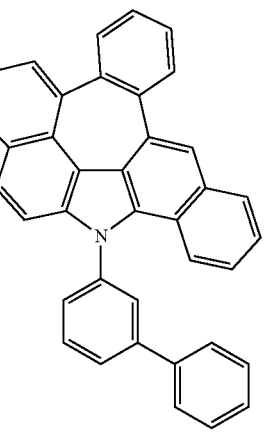
C-35 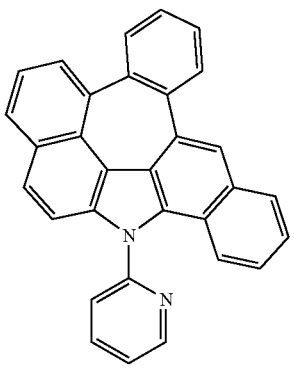
C-36 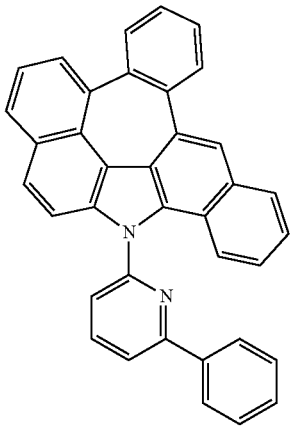
C-37 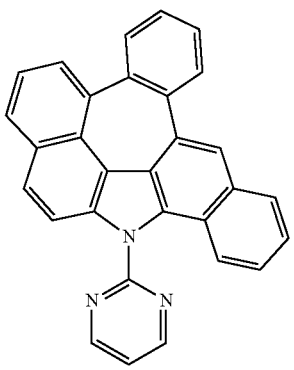

C-38
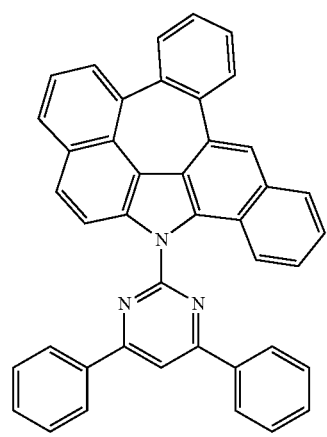
C-41
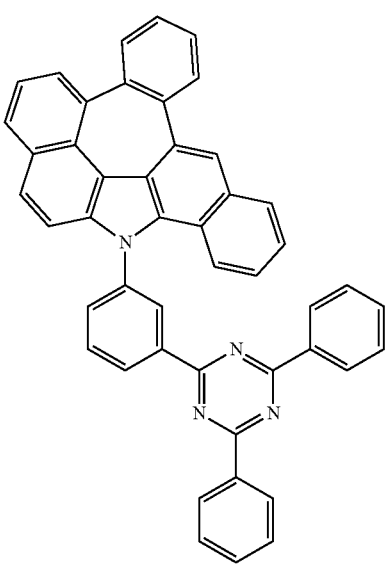
C-39
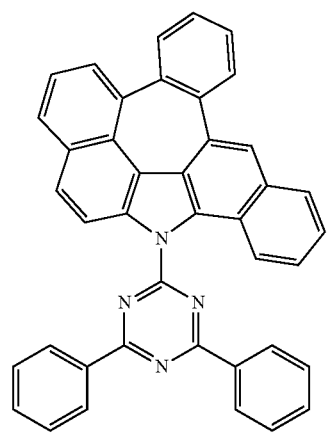
C-40
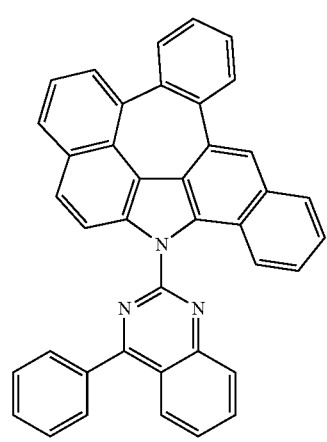
C-42
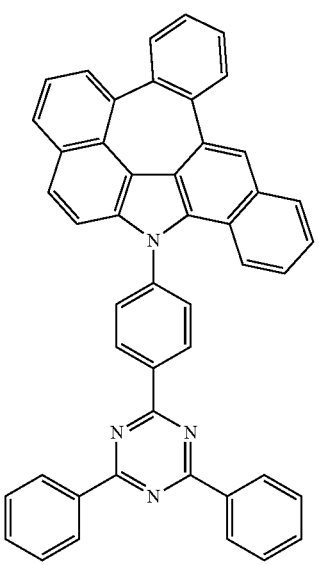

C-43
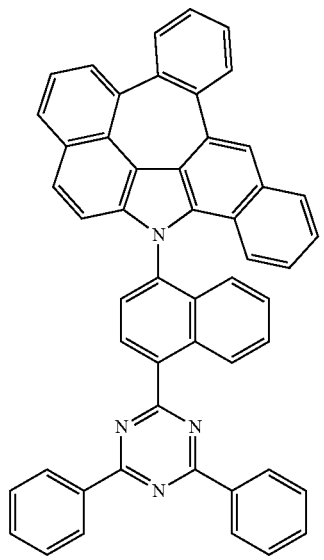
C-44
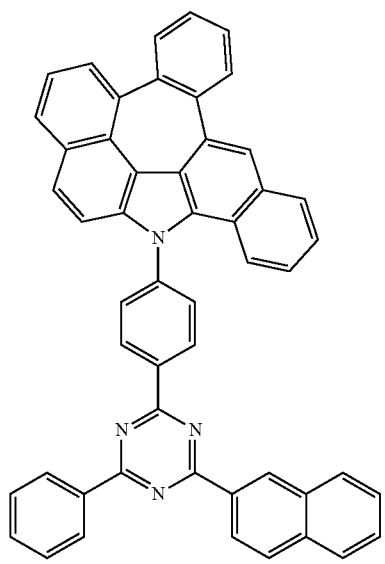
C-45
C-46
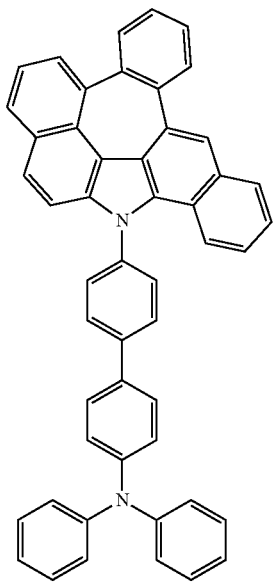
C-47
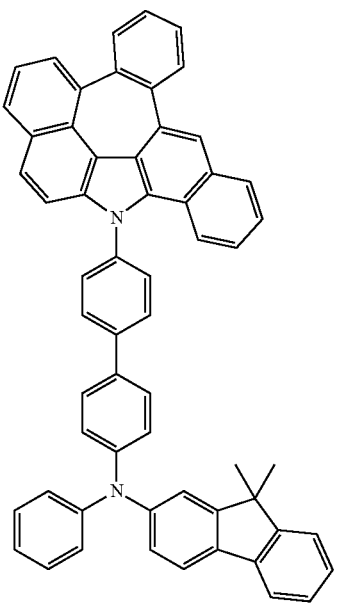

C-48
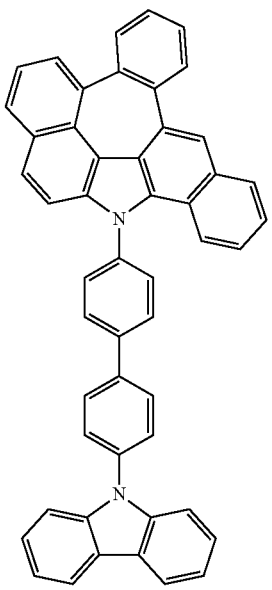
C-49
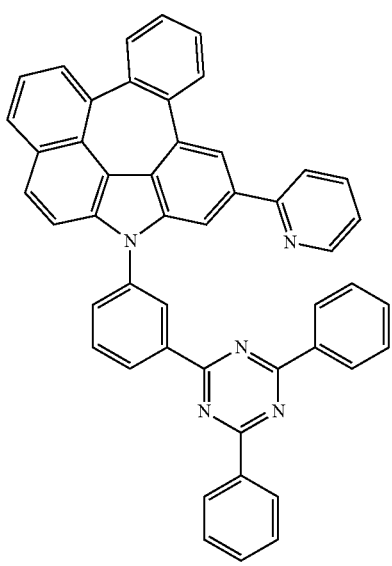
C-50
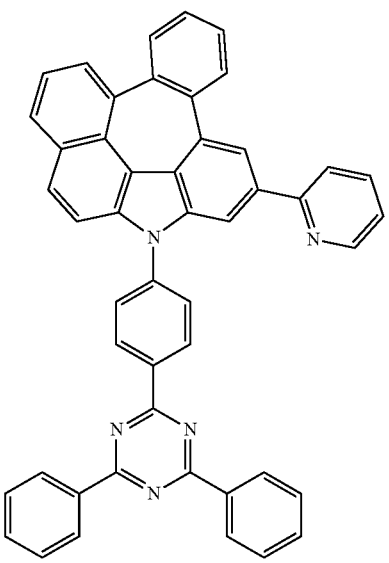
C-51
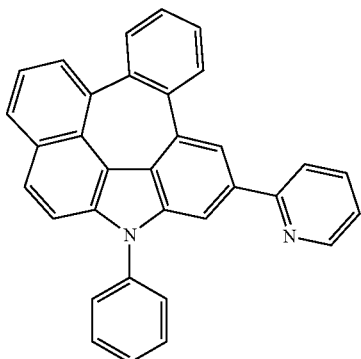
C-52
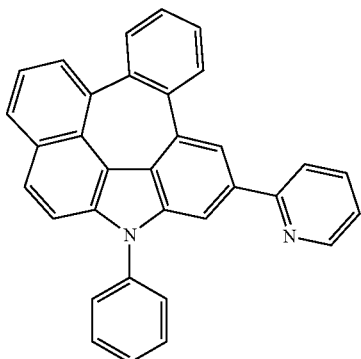

C-53
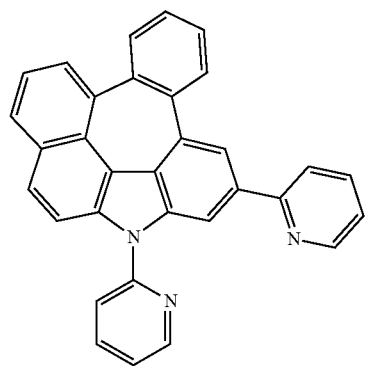
C-54
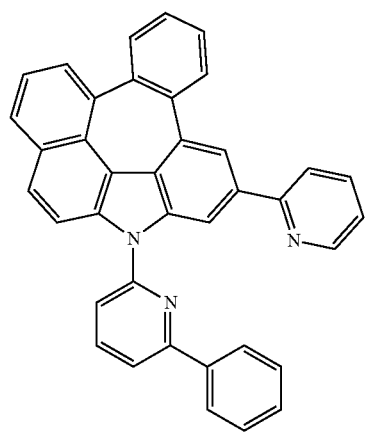
C-55
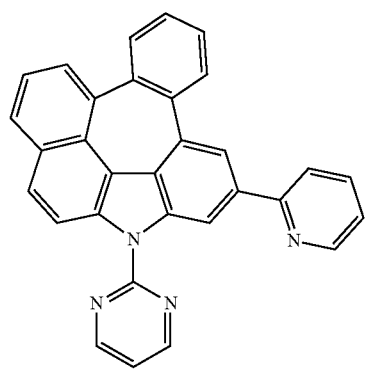
C-56
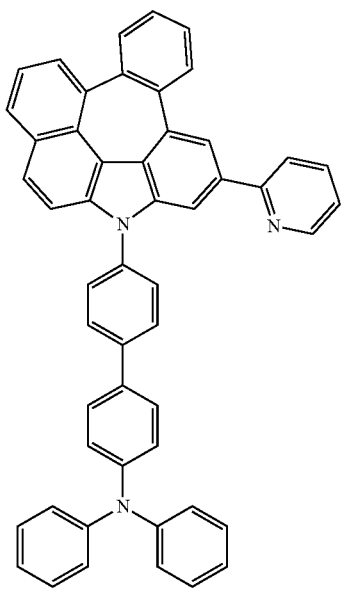
C-57
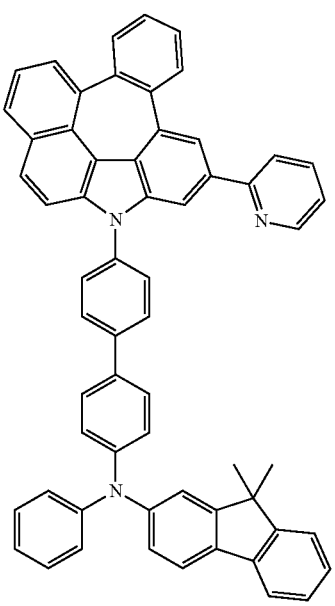

C-58
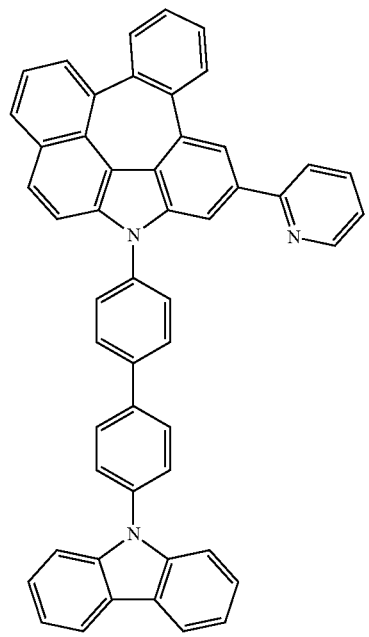
C-59
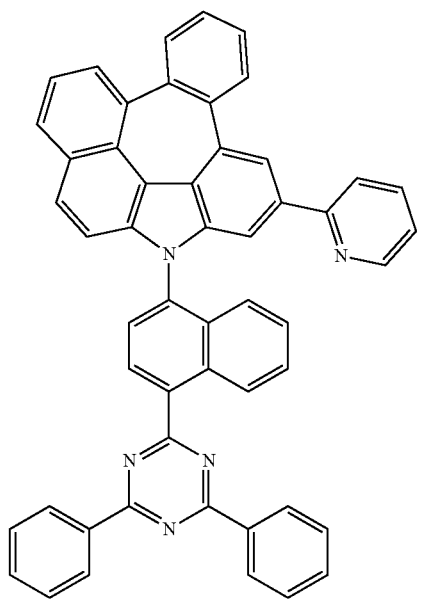
C-60
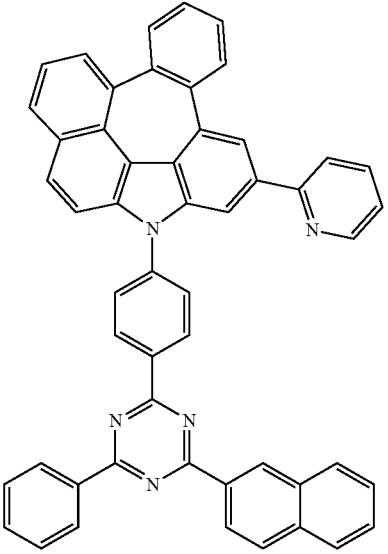
C-61
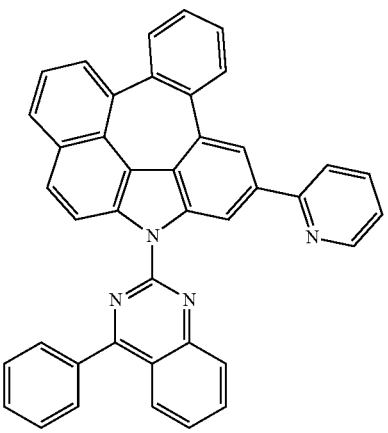
C-62
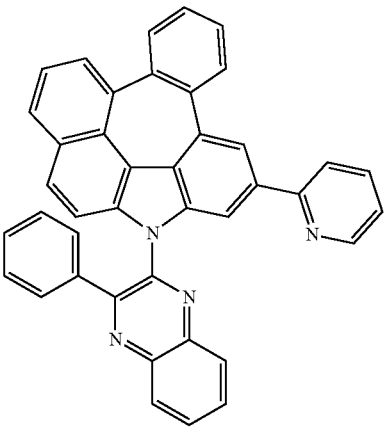

C-63
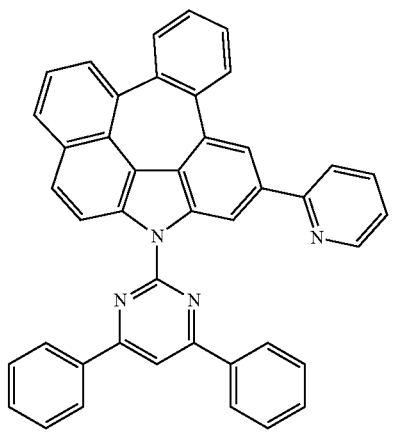
C-64
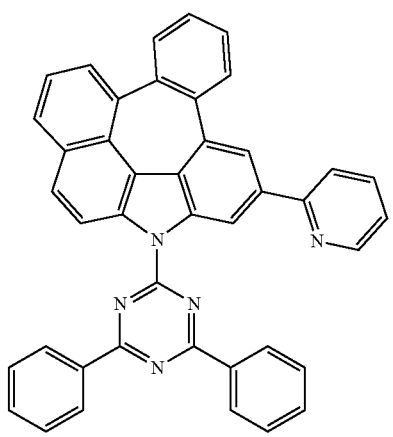
C-65
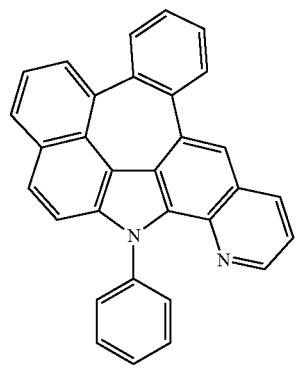
C-66
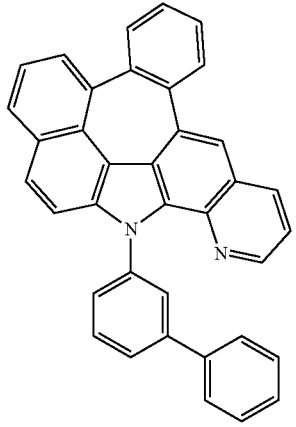
C-67
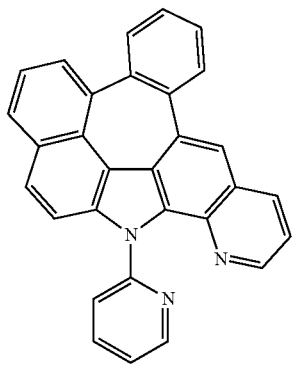
C-68
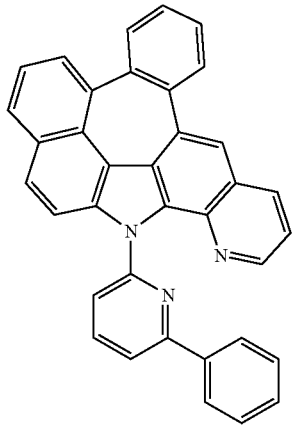
C-69
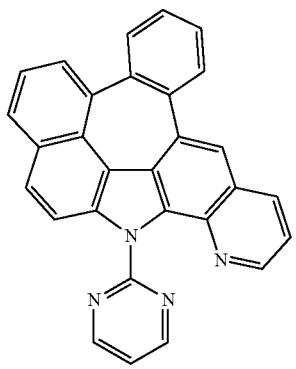

C-70
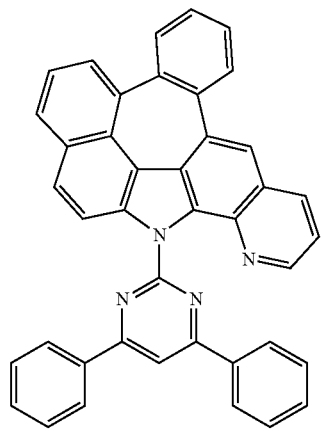
C-71
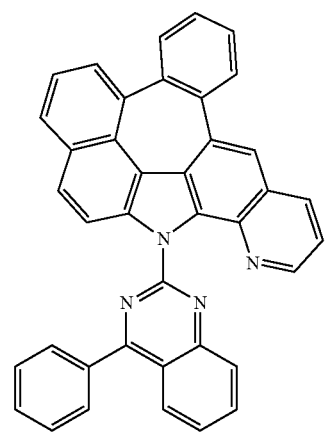
C-72
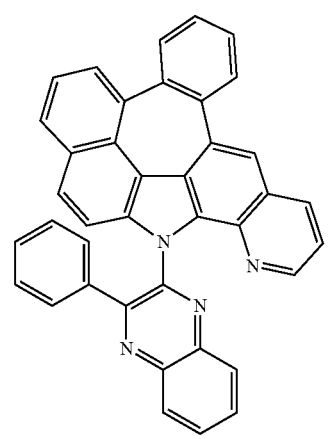
C-73
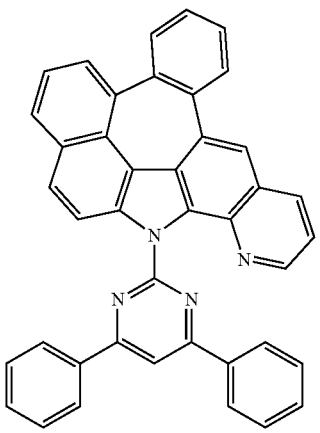
C-74
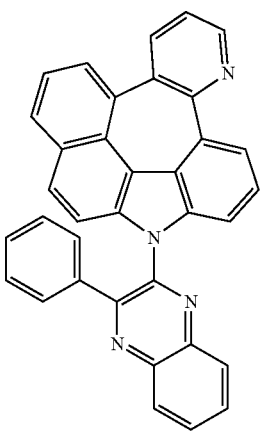
C-75
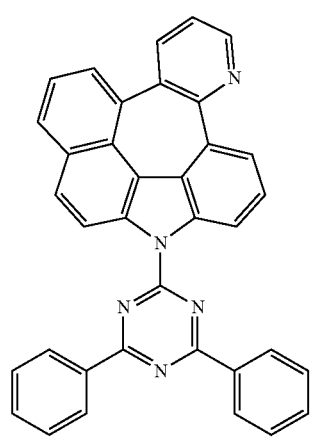

C-76
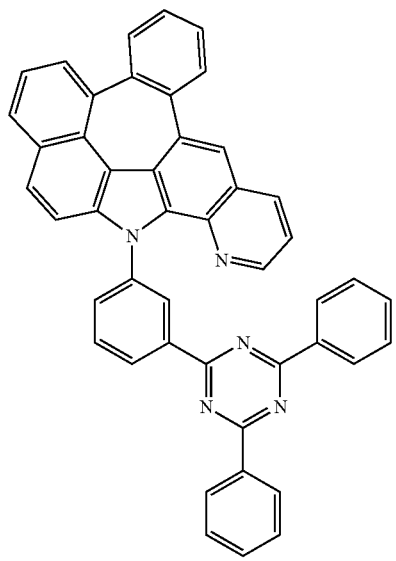
C-78
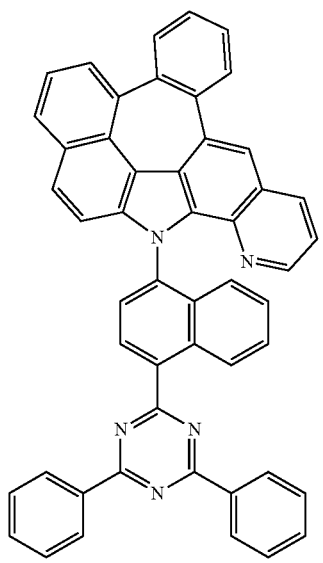
C-77
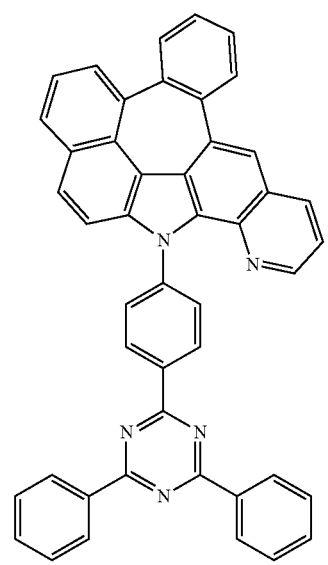
C-79
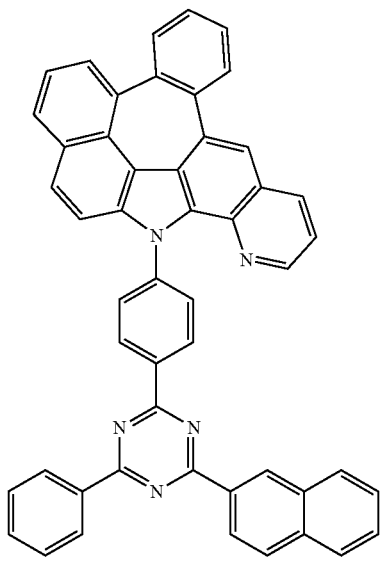

C-80
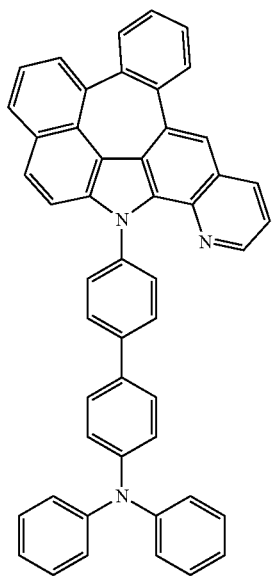
C-82
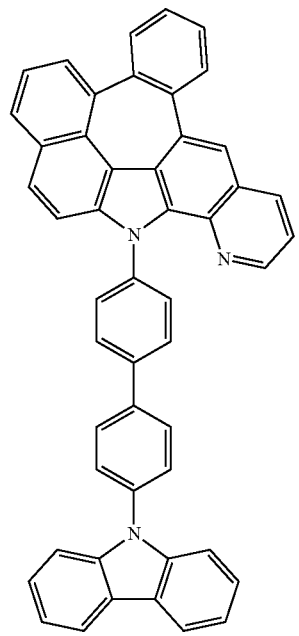
C-81
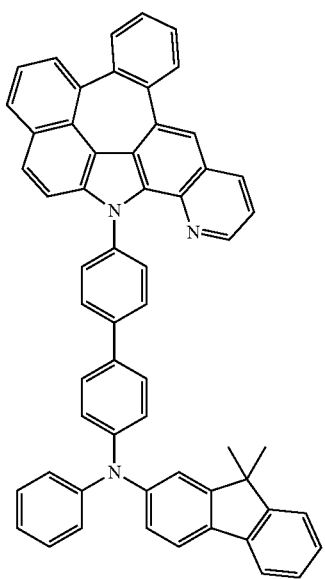
C-83
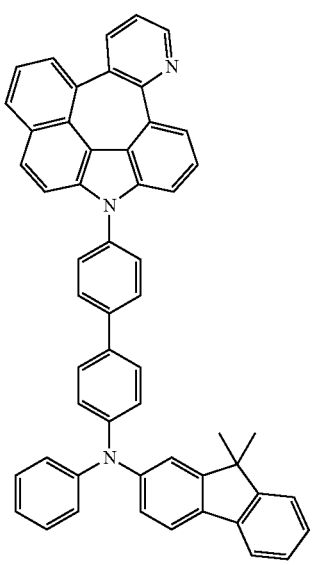

C-84
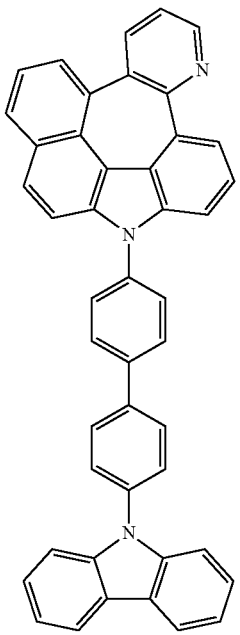
C-85
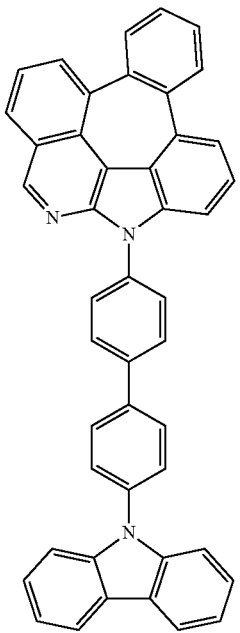
C-86
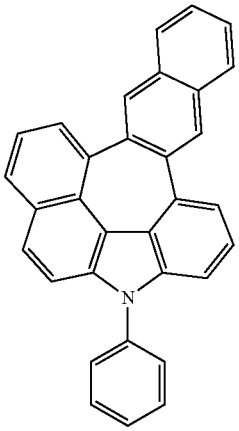
C-87
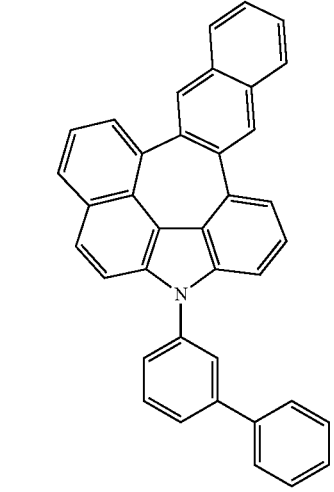
C-88
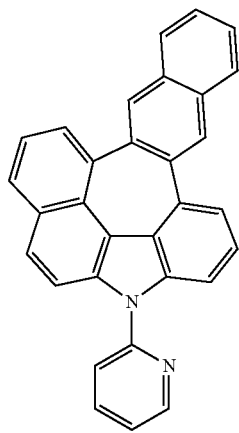

-continued
C-89
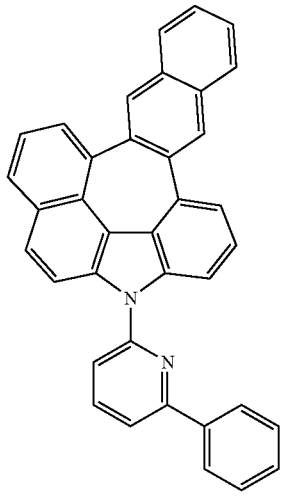
C-90
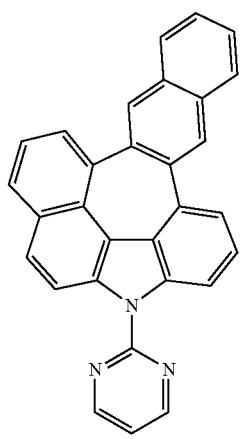
C-91
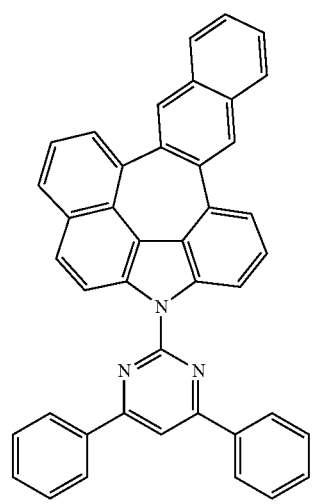
-continued
C-92
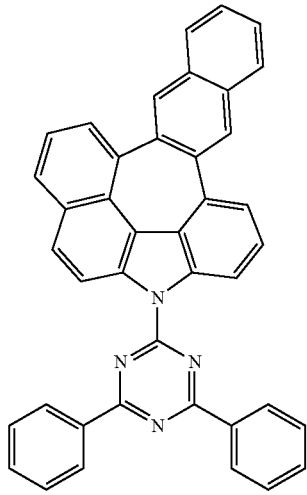
C-93
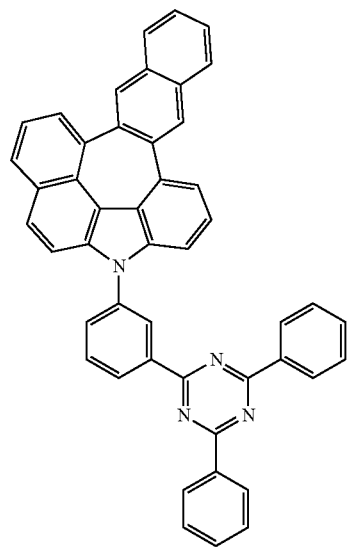
C-94
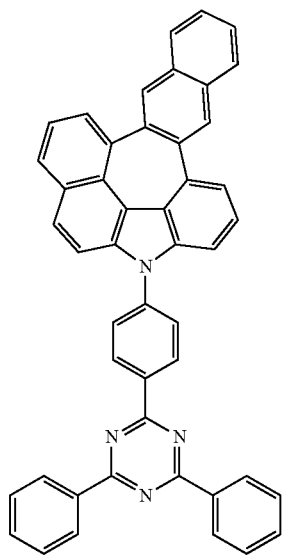

C-95
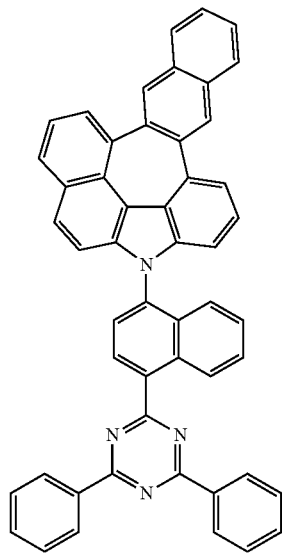
C-96
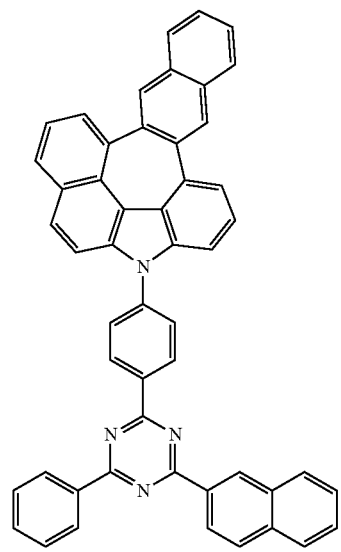
C-97
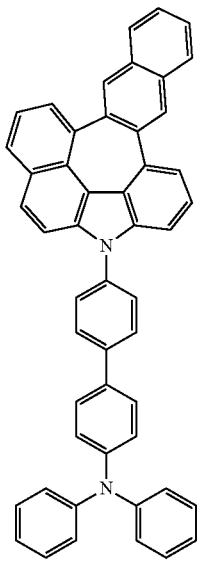
C-98
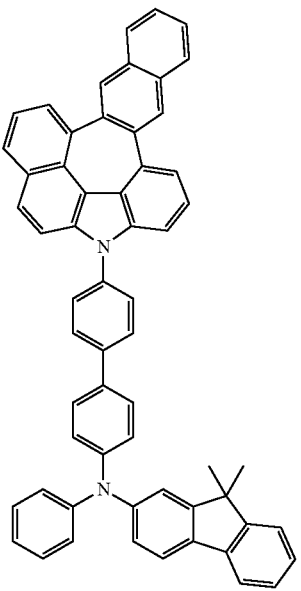

-continued
C-99
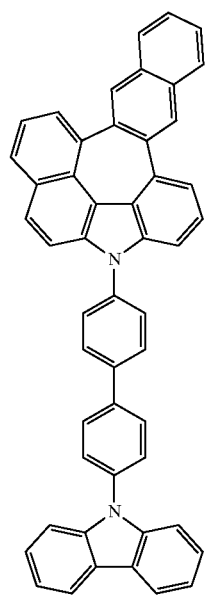
C-100
C-101
-continued
C-102
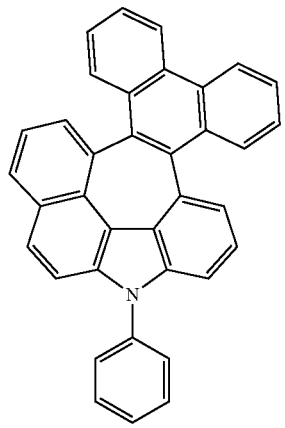
C-103
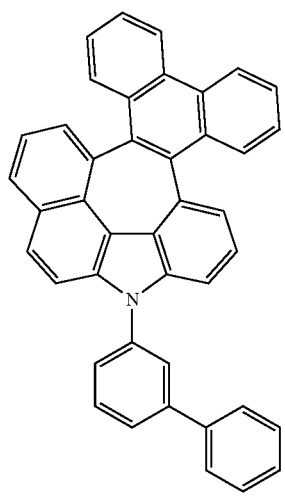
C-104
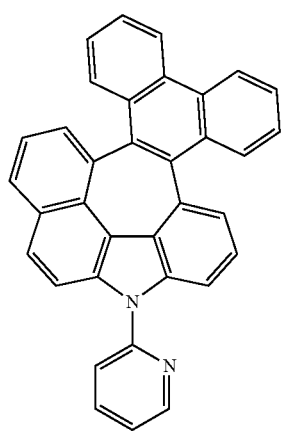

C-105
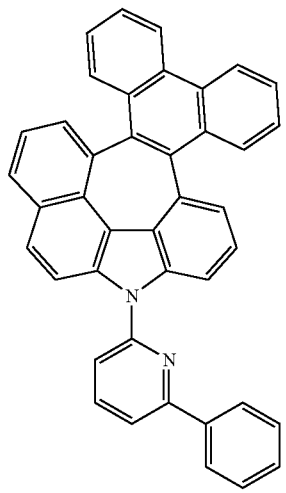
C-106
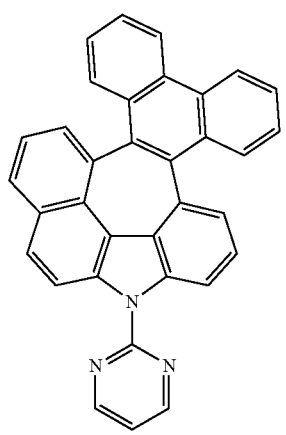
C-107
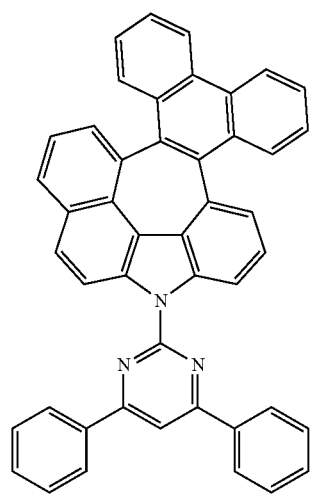
C-108
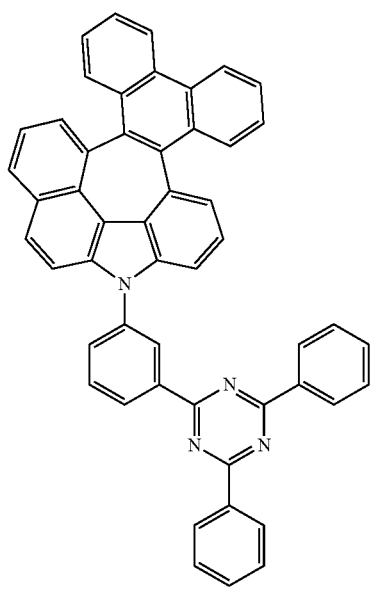
C-109
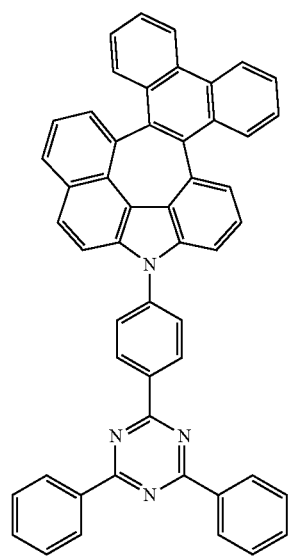

C-110
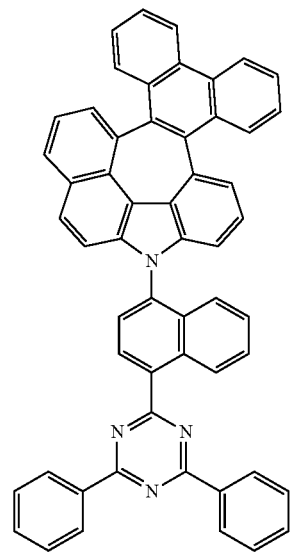
C-111
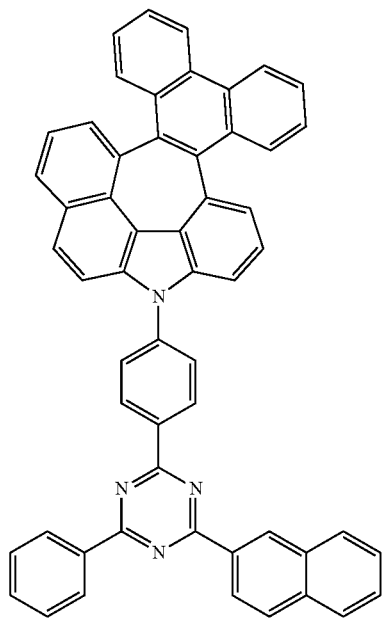
C-112
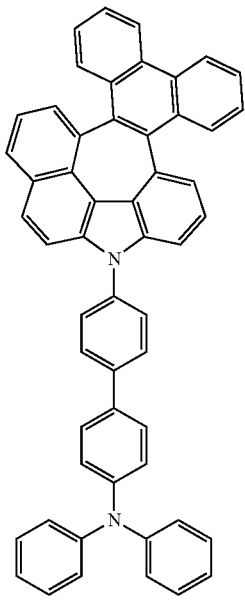
C-113
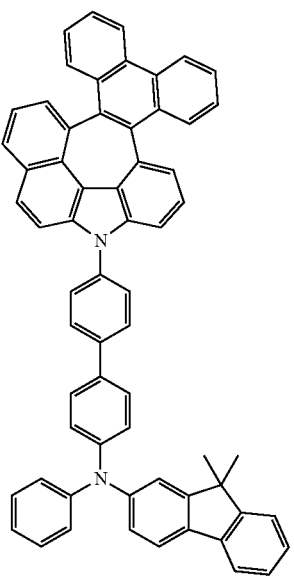

C-114
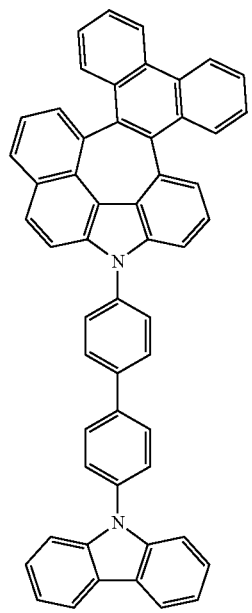
C-115
C-116
C-117
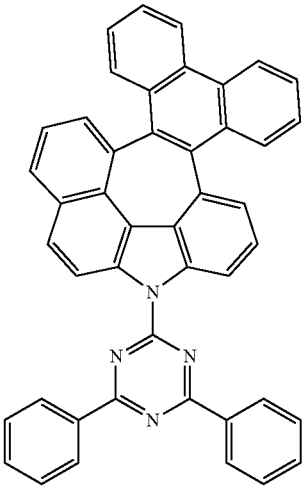
C-118
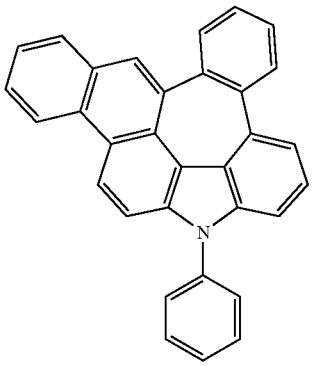
C-119
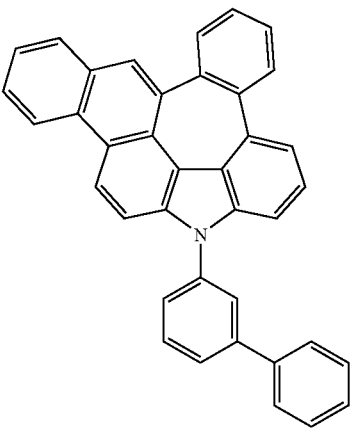
C-120
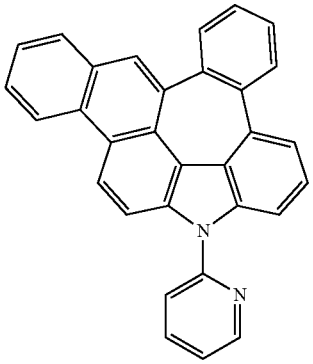

C-121
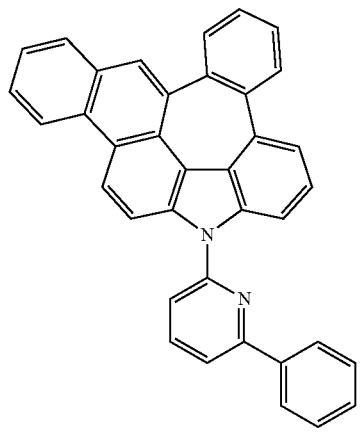
C-122
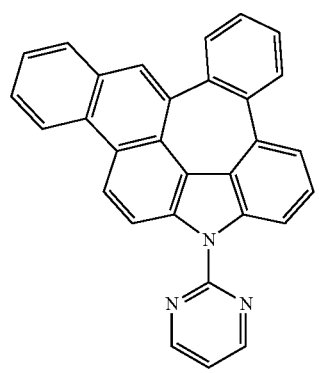
C-123
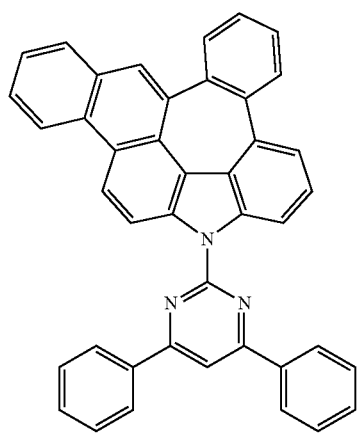
C-124
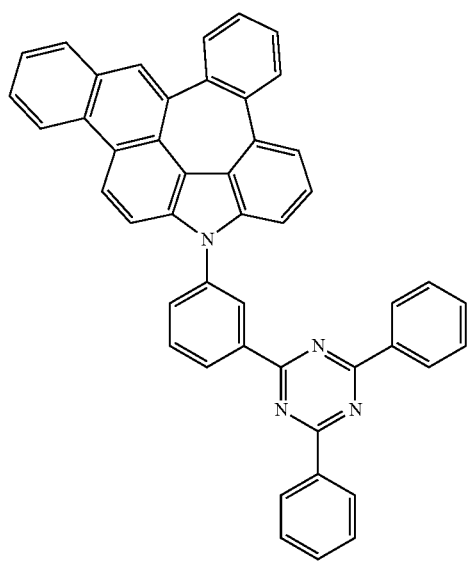
C-125
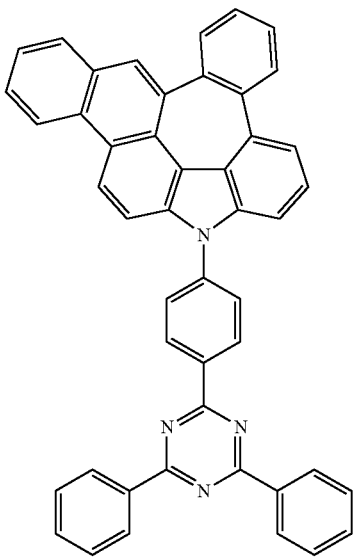

C-126
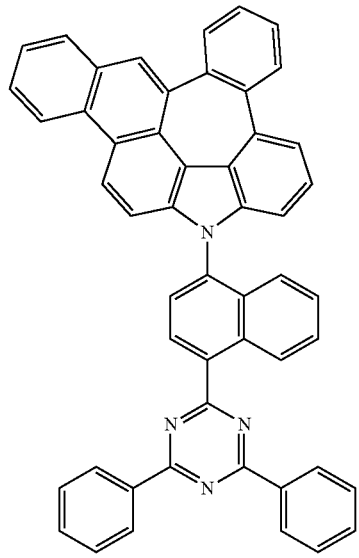
C-127
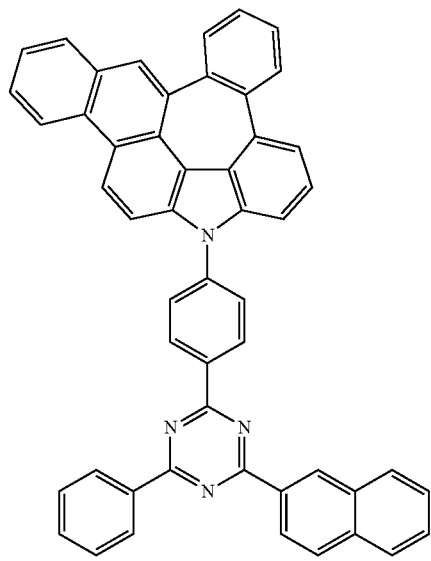
C-128
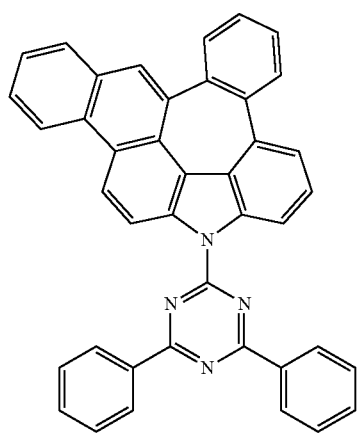
C-129
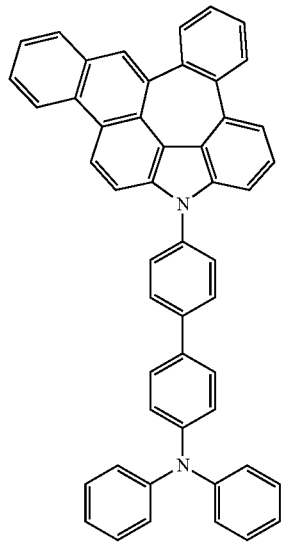
C-130
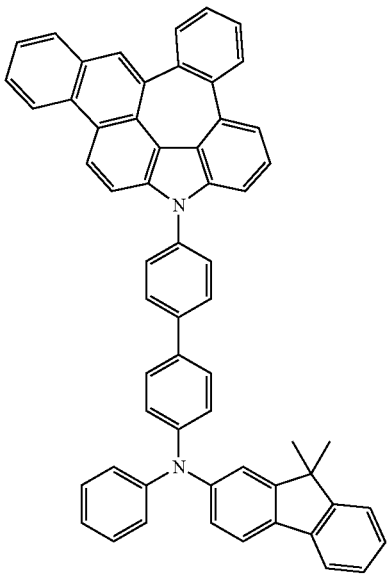

C-131
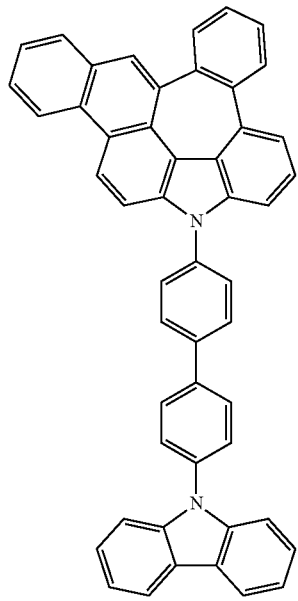
C-132
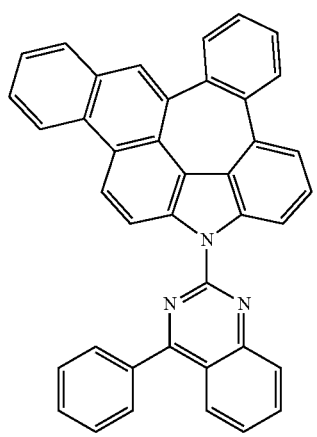
C-133
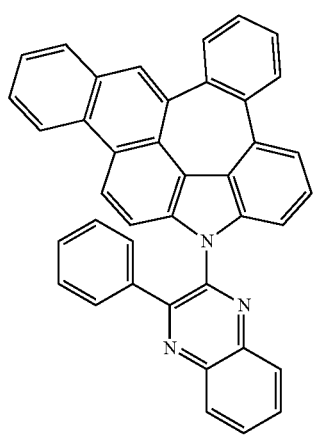
C-134
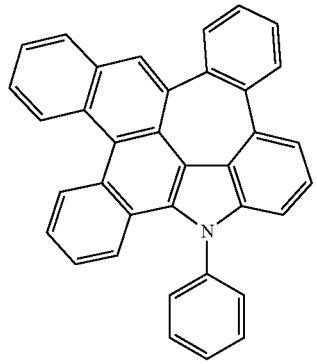
C-135
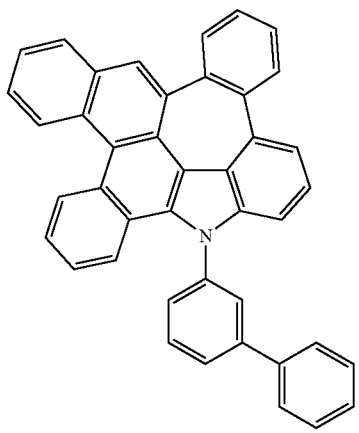
C-136
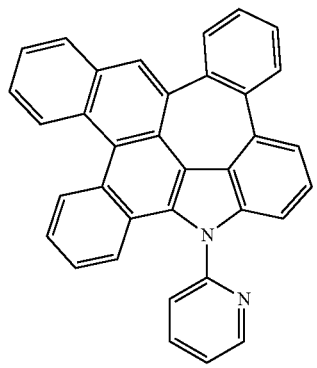
C-137
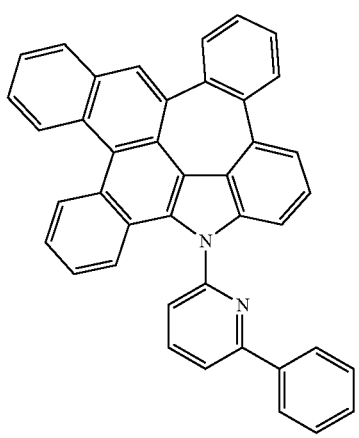

-continued
C-138
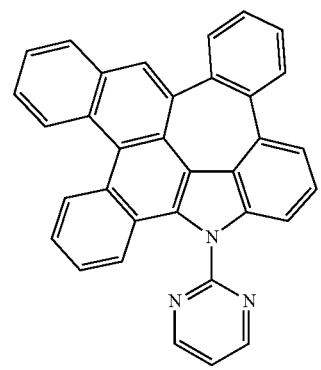
C-139
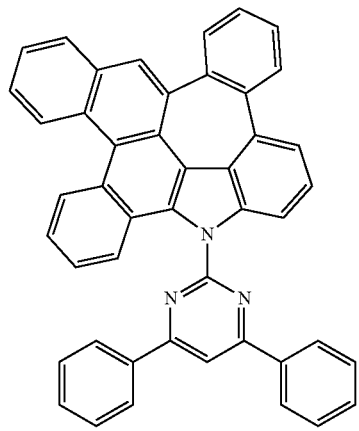
C-140
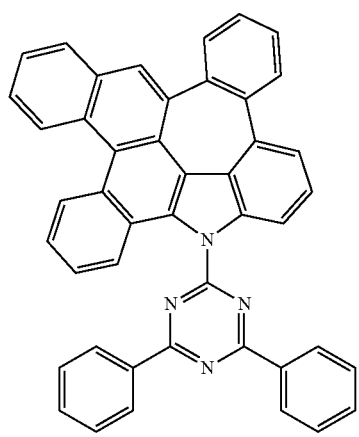
-continued
C-141
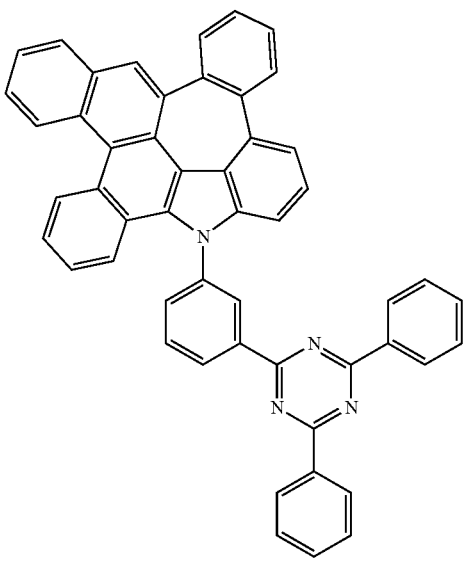
C-142
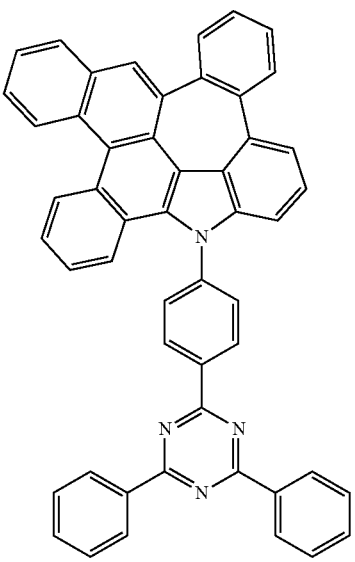
C-143
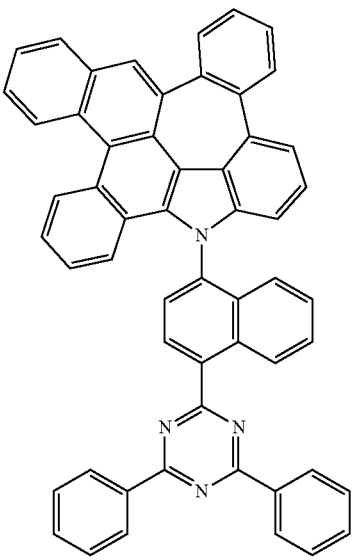

C-144
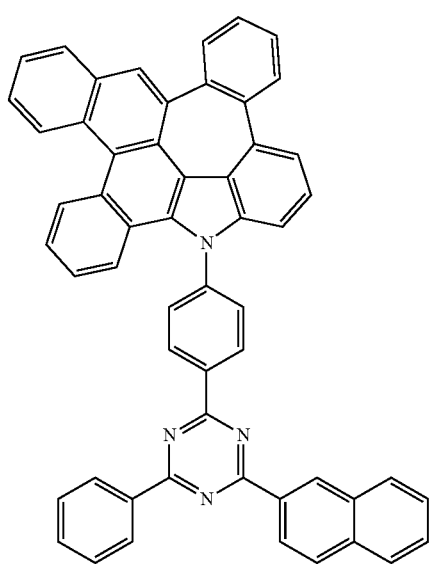
C-145
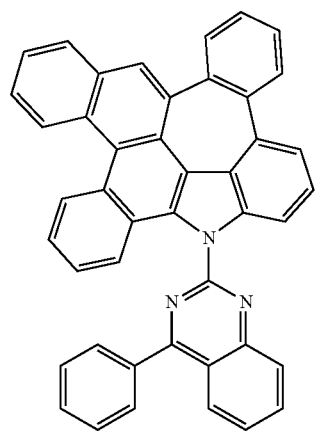
C-146
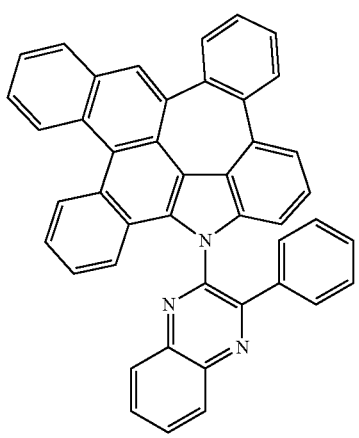
C-147
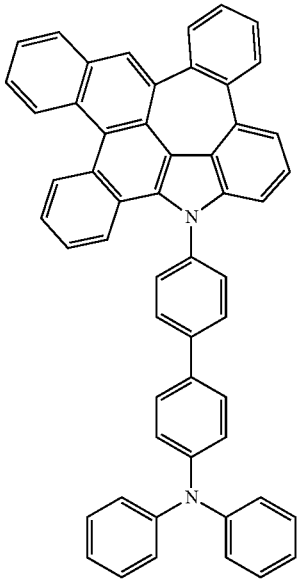
C-148
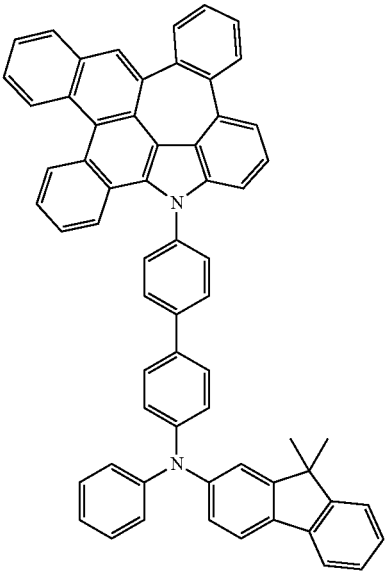

C-149
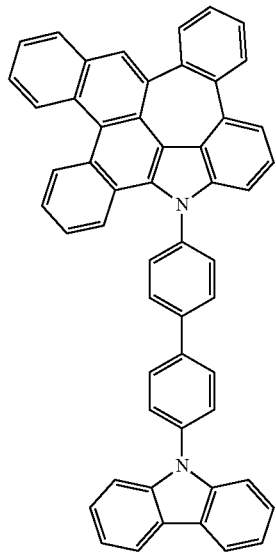
C-150
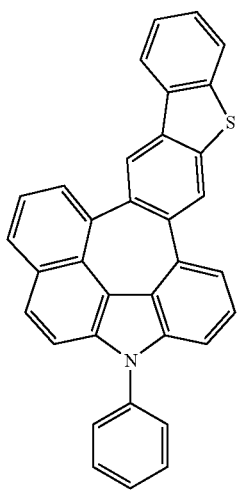
C-151
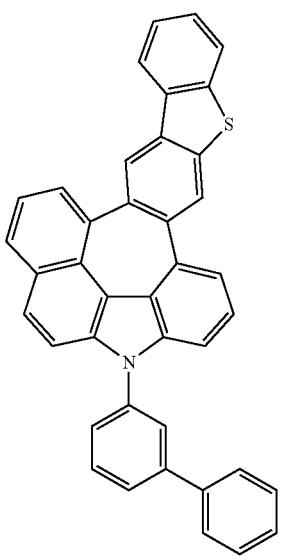
C-152
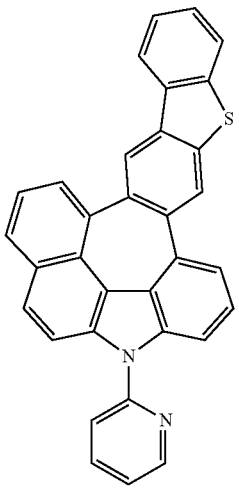
C-153
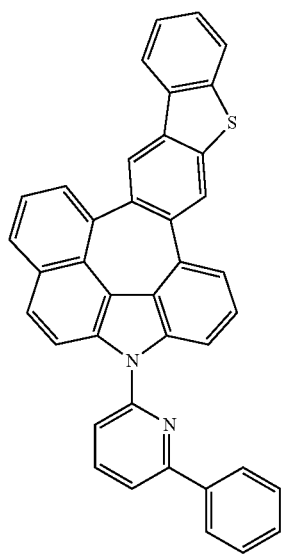
C-154
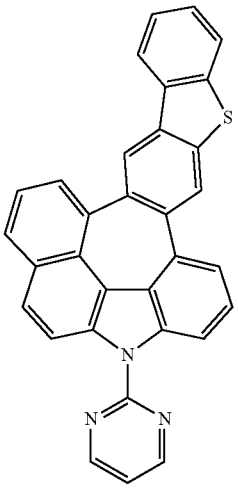

-continued
C-155
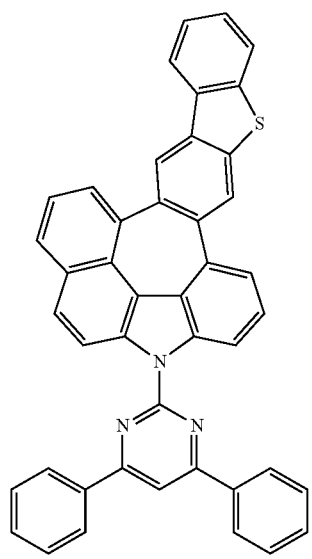
C-157
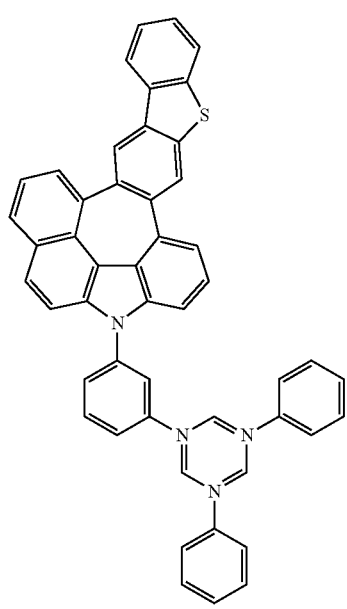
C-156
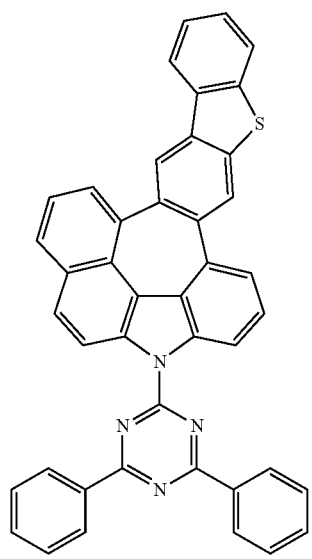
C-158
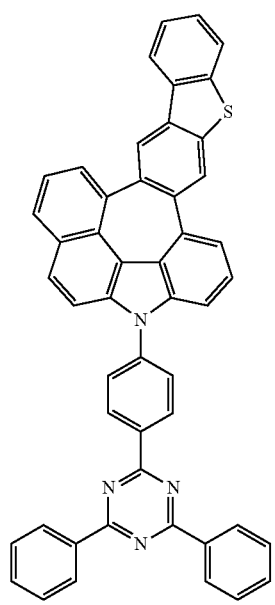

C-159
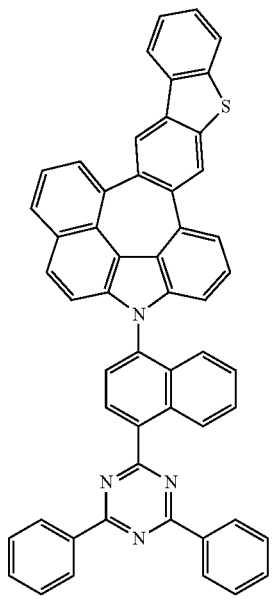
C-160
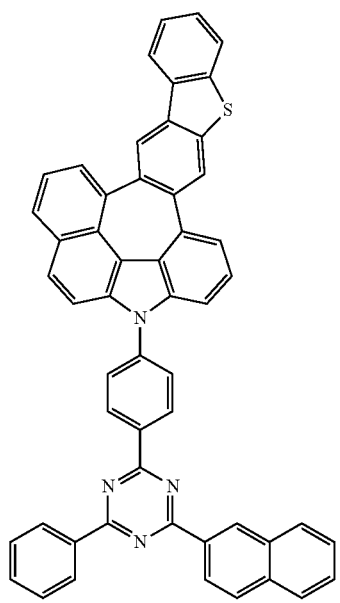
C-161
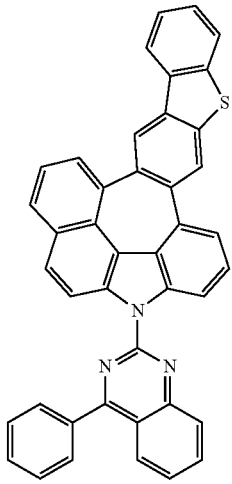
C-162
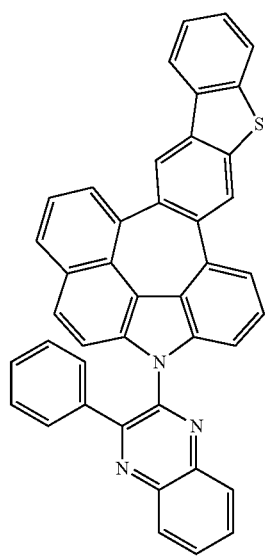
C-163
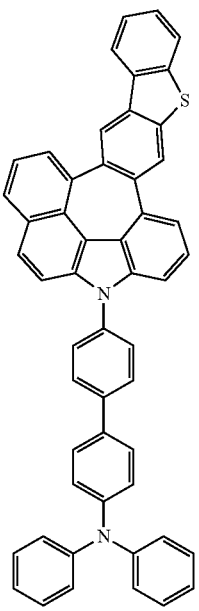

US 11,302,874 B2
71
-continued
C-164
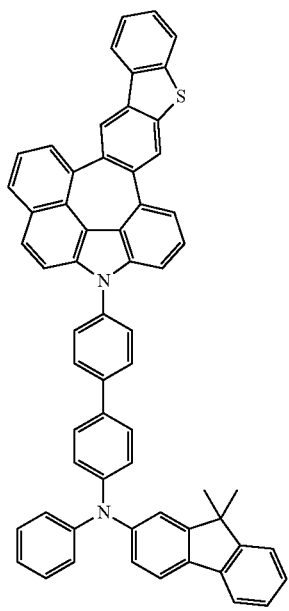
C-165
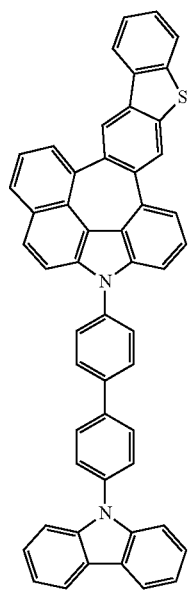
72
-continued
C-166
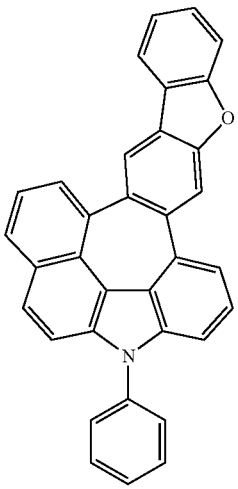
C-167
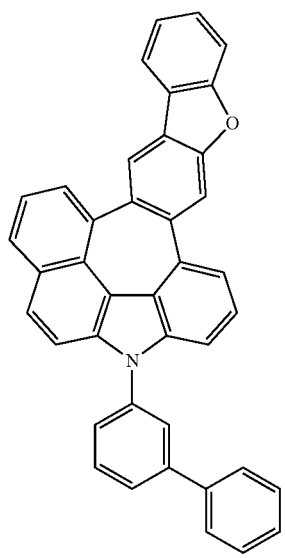
C-168

C-169
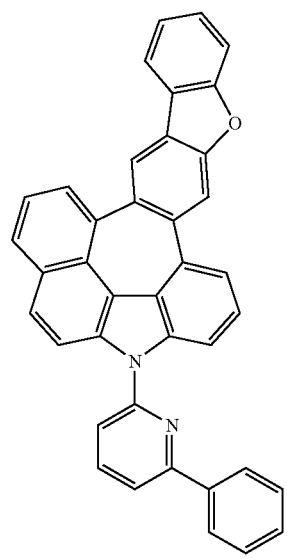
C-170
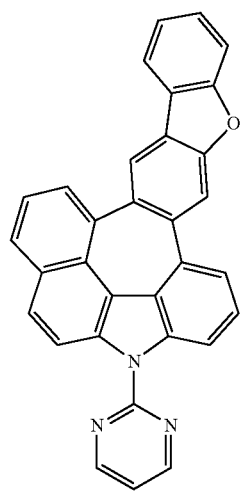
C-171
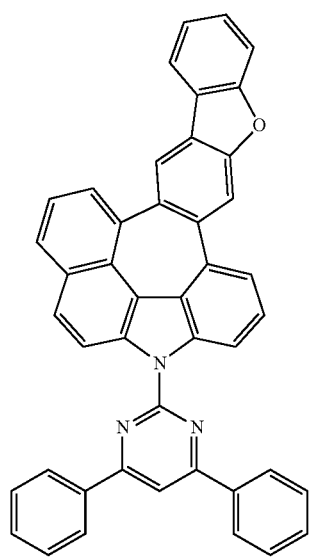
C-172
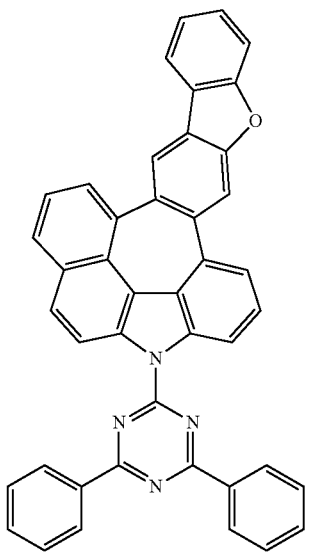
C-173
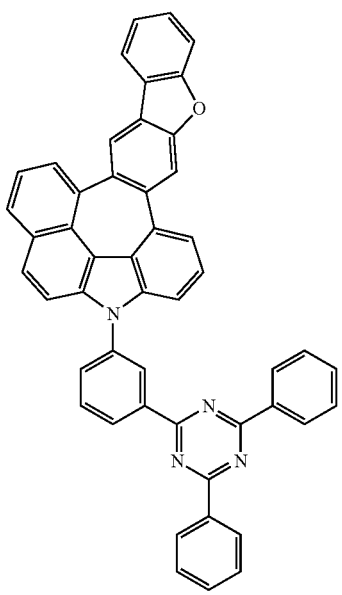

-continued
C-174
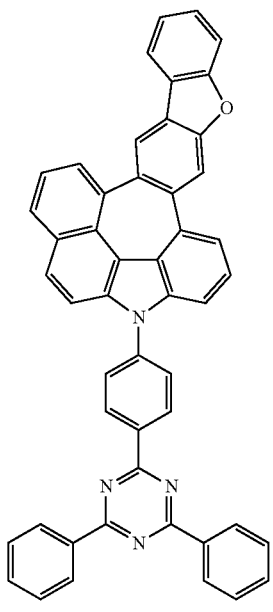
C-175
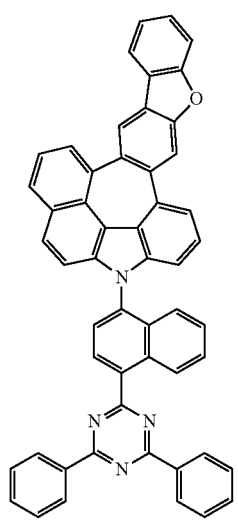
C-176
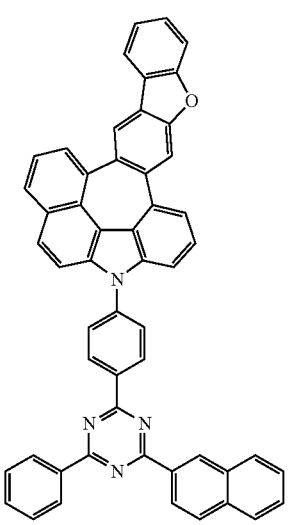
-continued
C-177
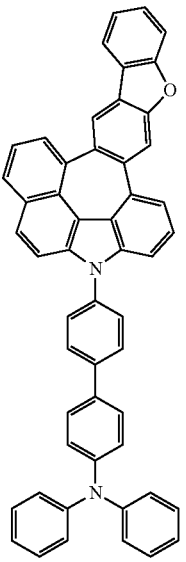
C-178
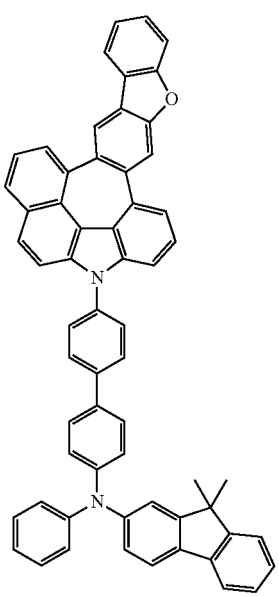

C-179
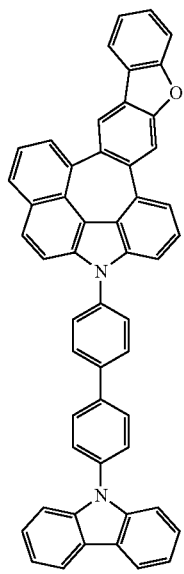
C-180
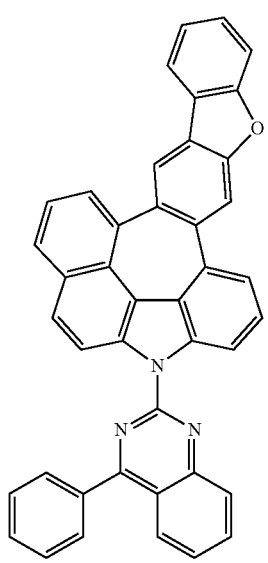
C-181
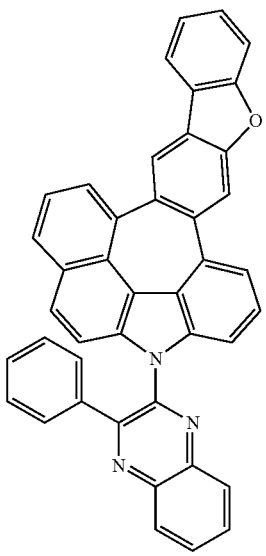
C-182
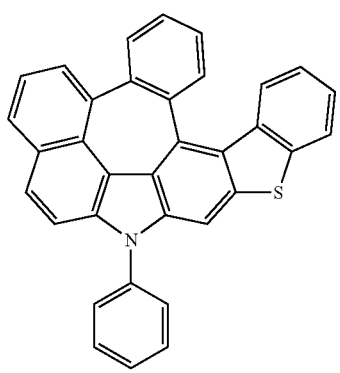
C-183
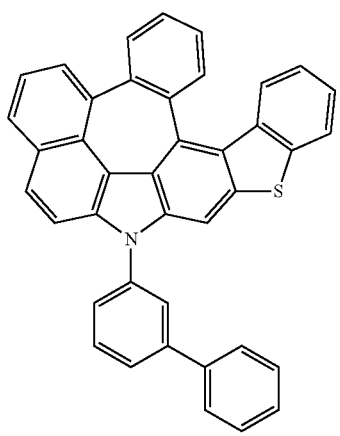

C-184
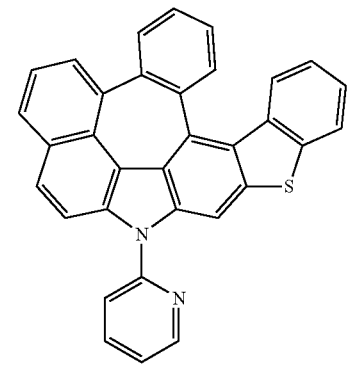
C-185
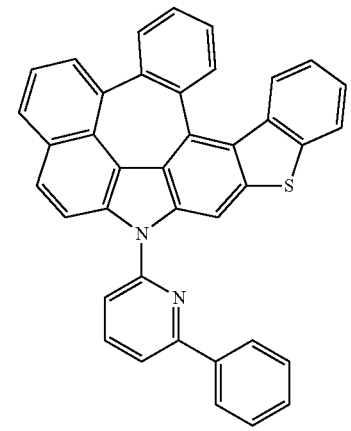
C-186
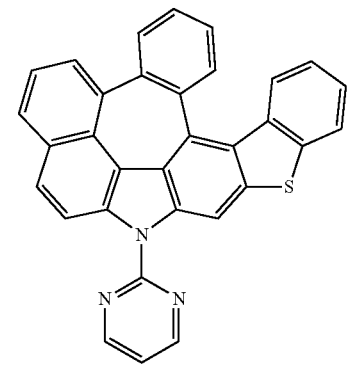
C-187
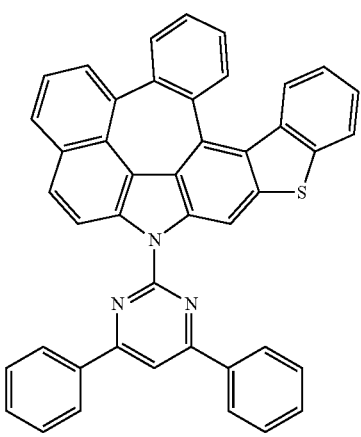
C-188
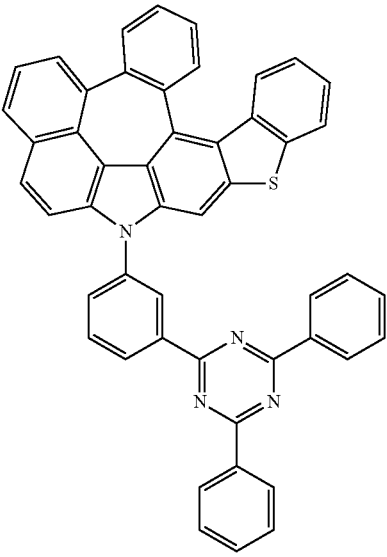
C-189
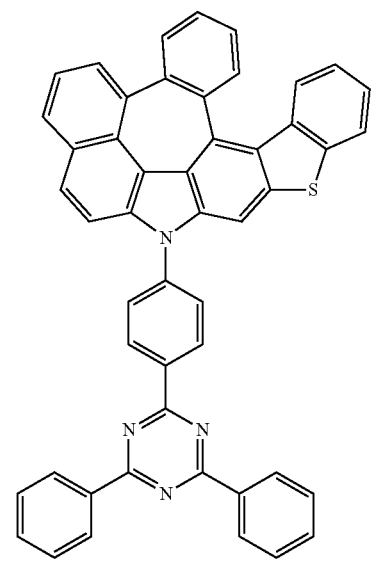

-continued
C-190
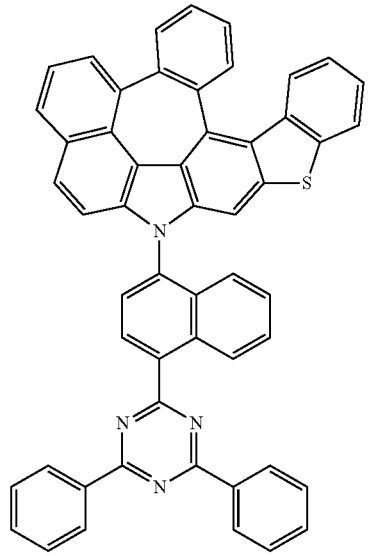
C-191
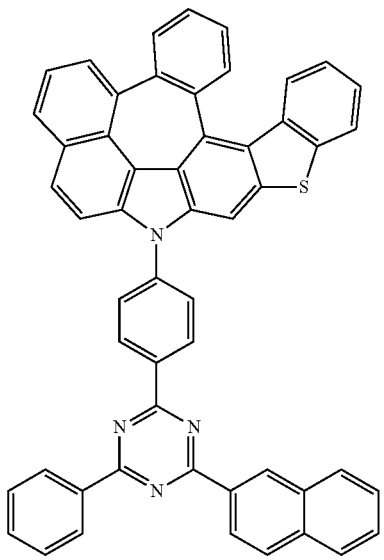
C-192
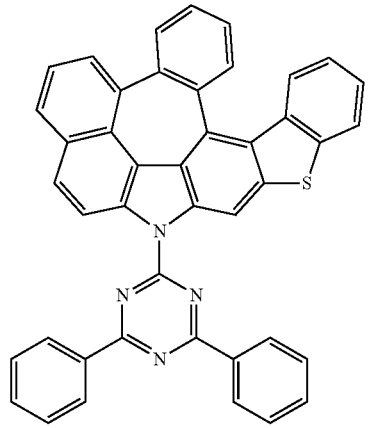
-continued
C-193
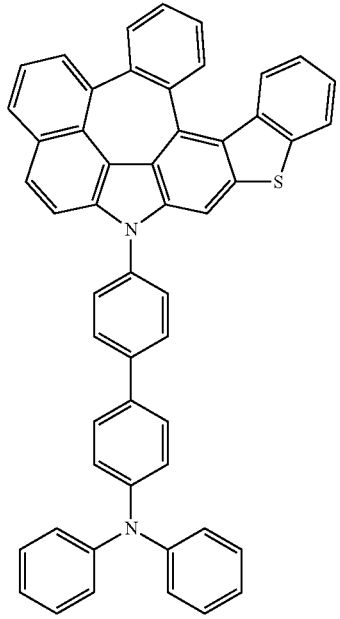
C-194
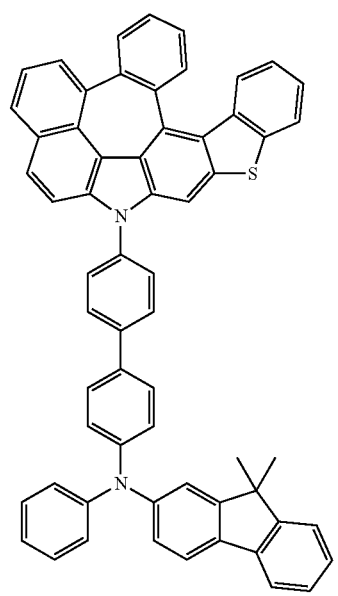

C-195
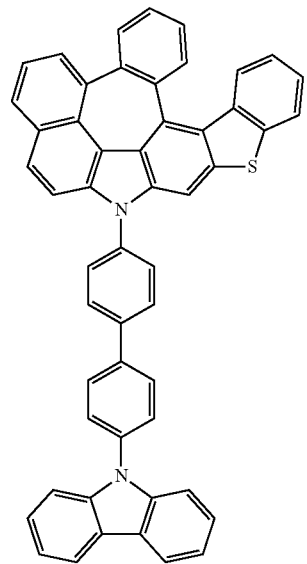
C-196
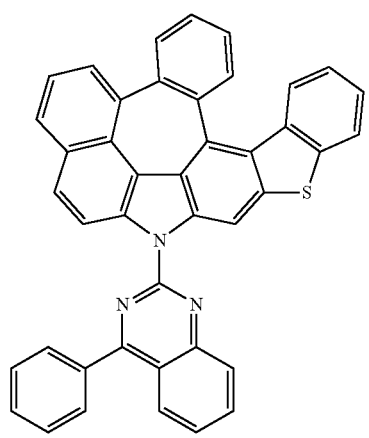
C-197
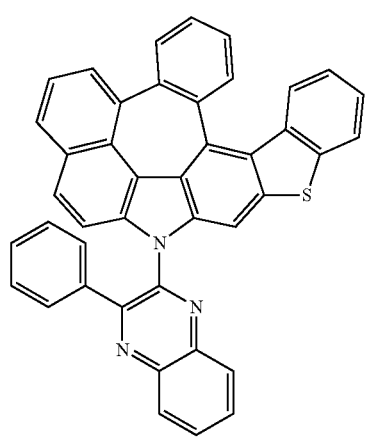
C-198
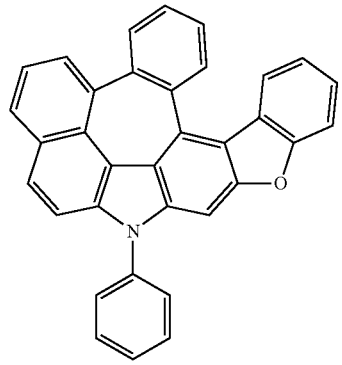
C-199
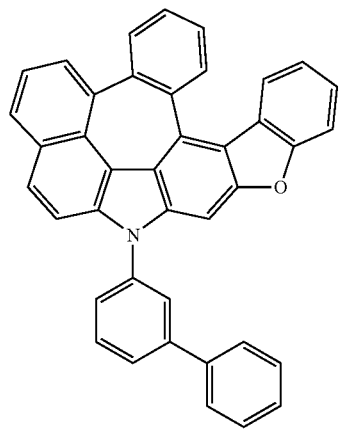
C-200
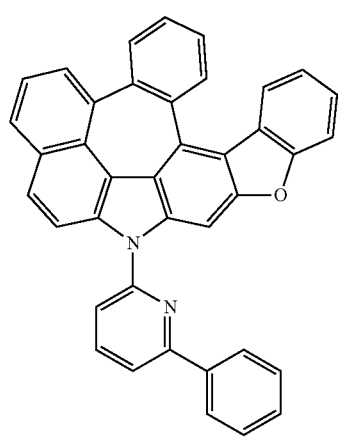
C-201

C-202
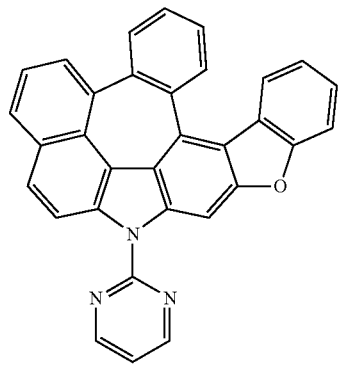
C-203
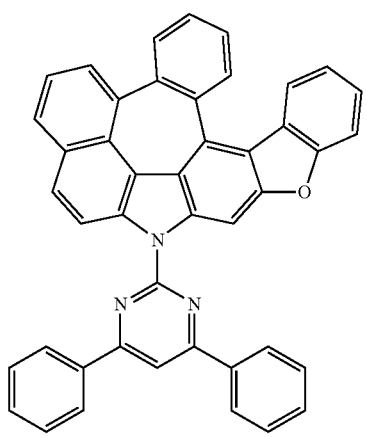
C-204
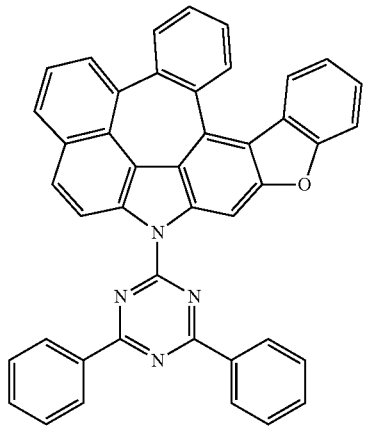
C-205
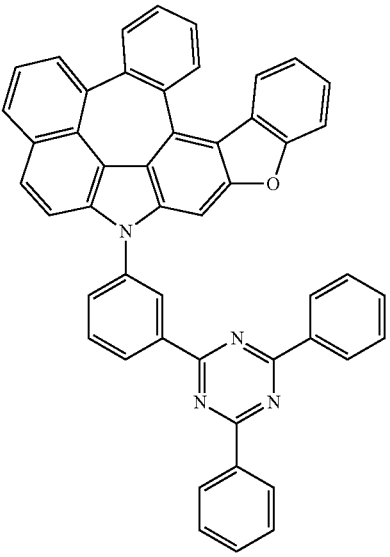
C-206
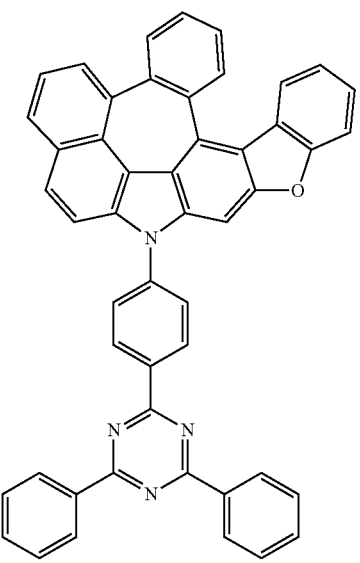
C-207
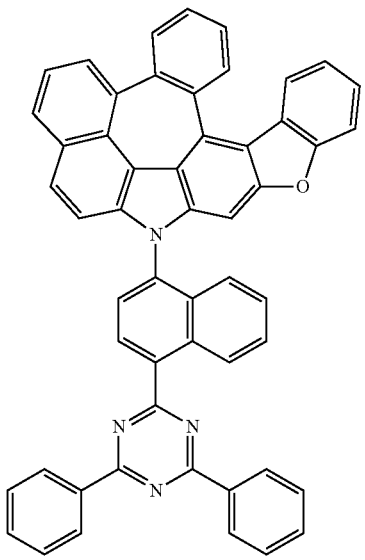

-continued
C-208
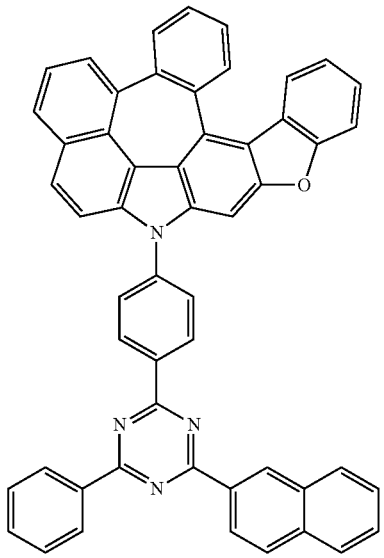
C-209
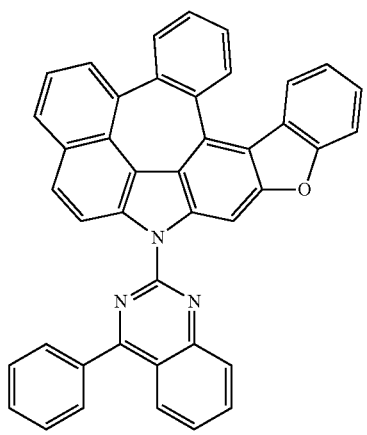
C-210
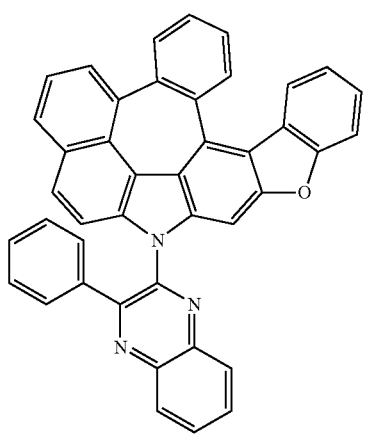
-continued
C-211
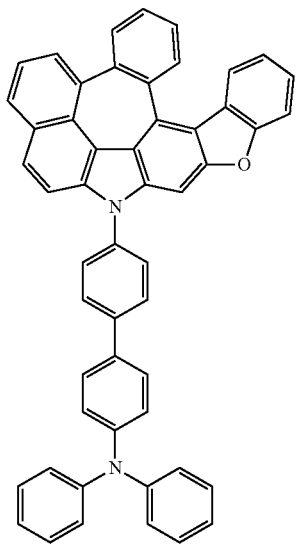
C-212
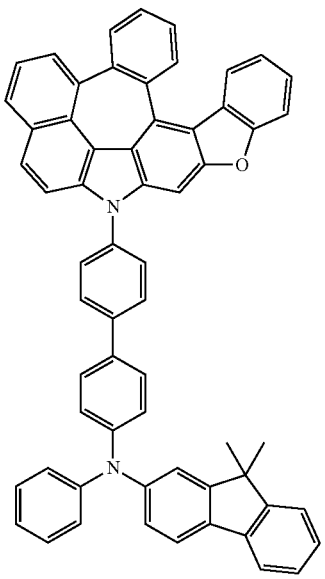

C-213
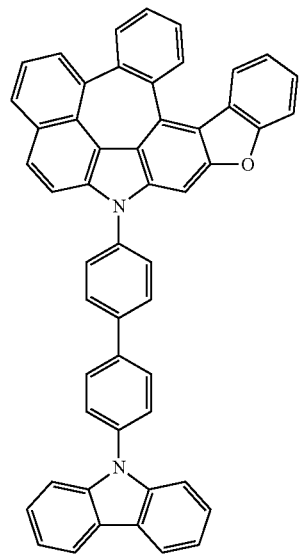
C-214
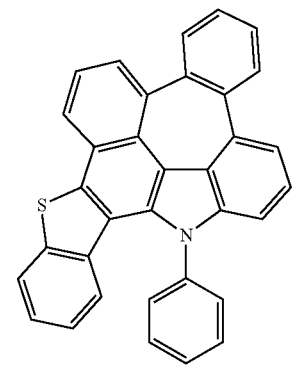
C-215
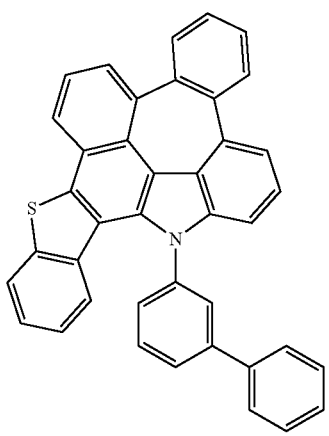
C-216
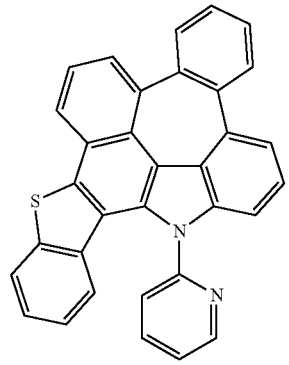
C-217
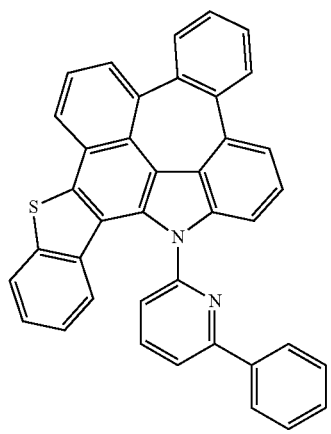
C-218
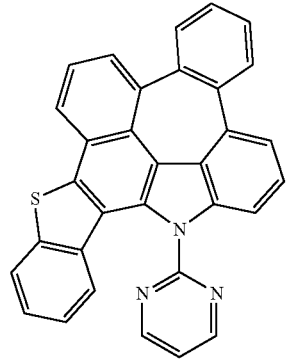
C-219
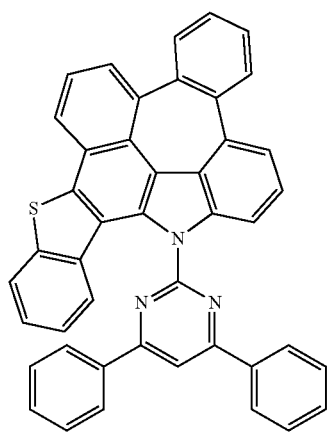

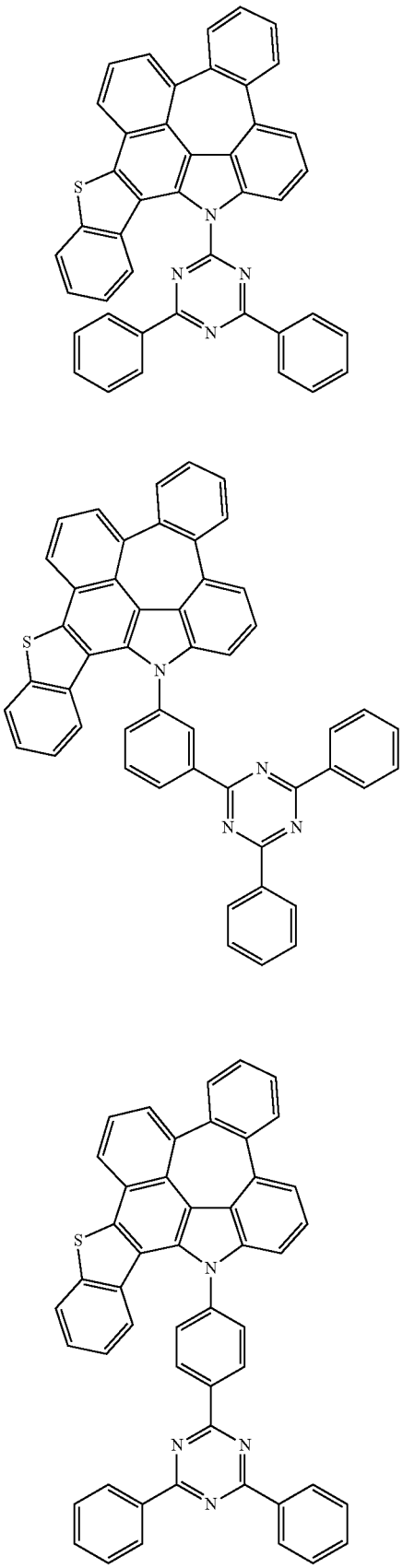
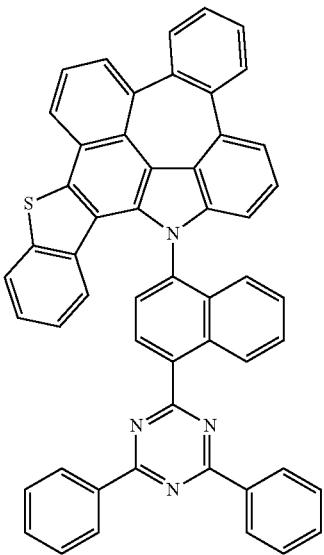
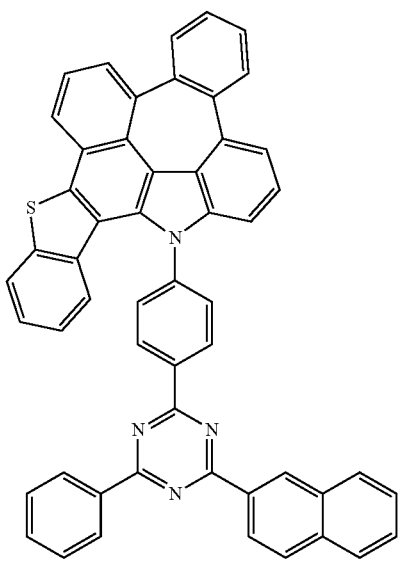
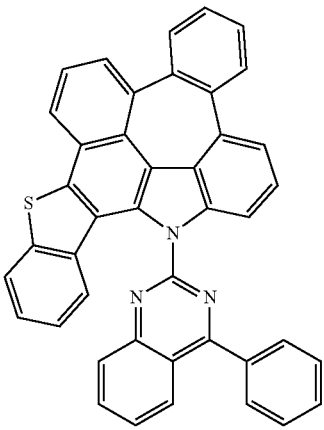

-continued
C-226
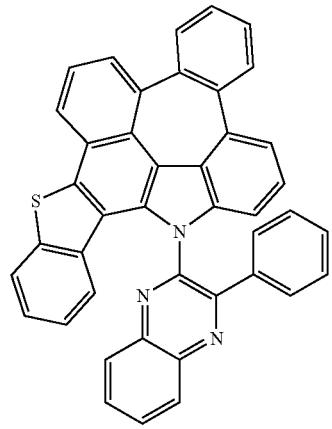
C-227
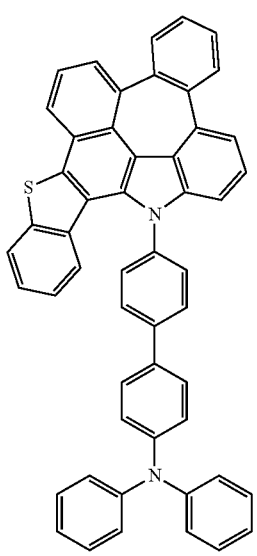
C-228
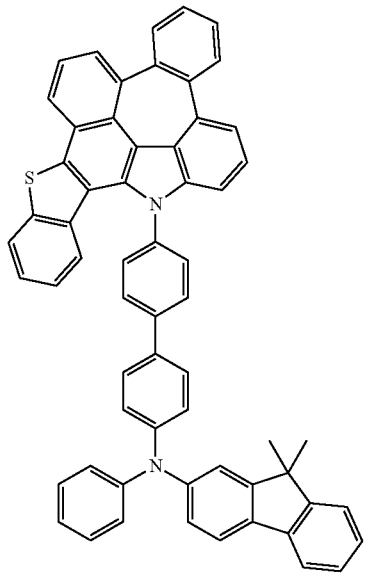
-continued
C-229
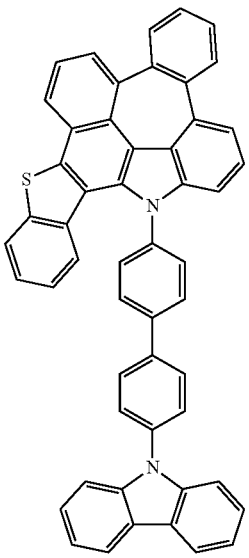
C-230
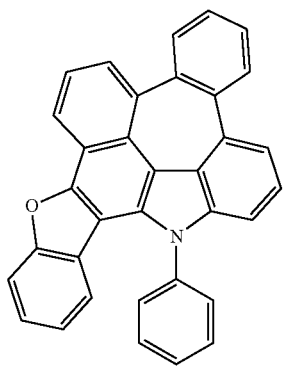
C-231
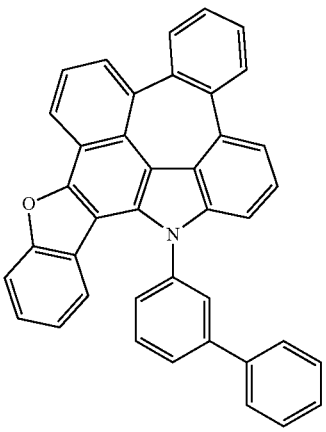

C-232 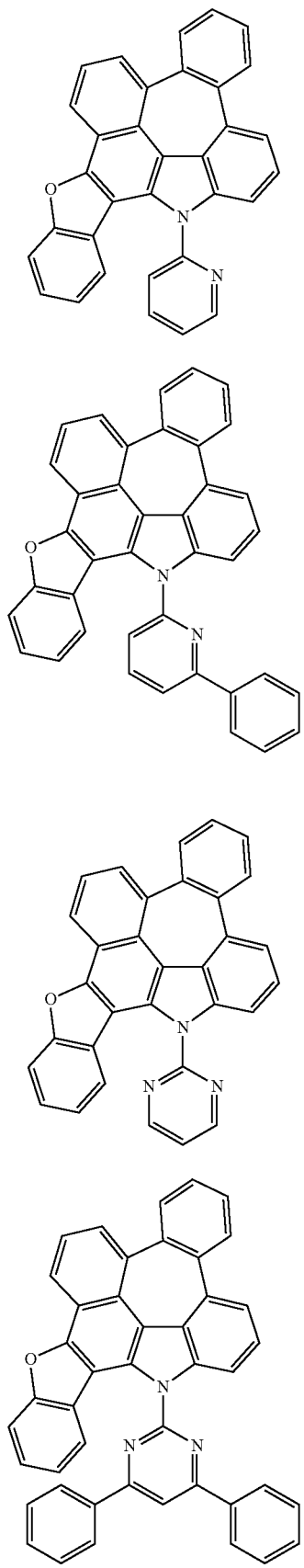 C-236 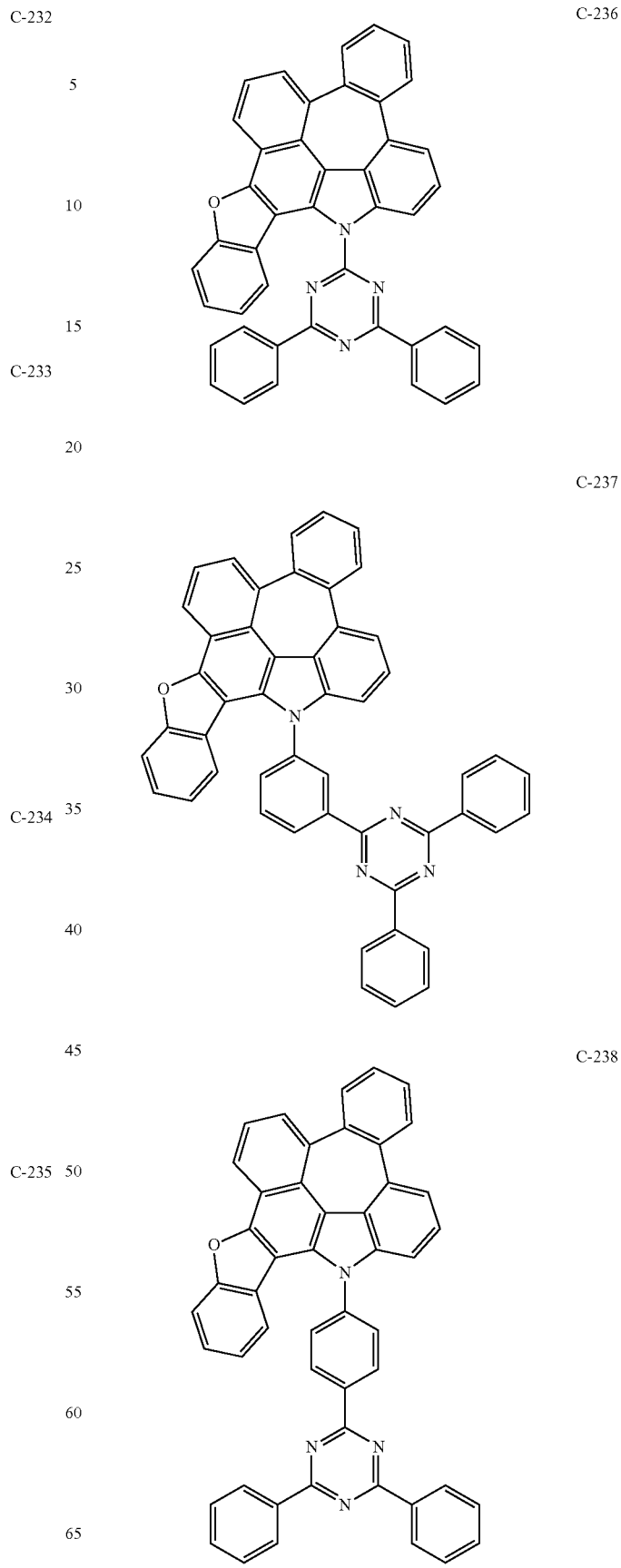
C-233
C-234
C-235

C-239
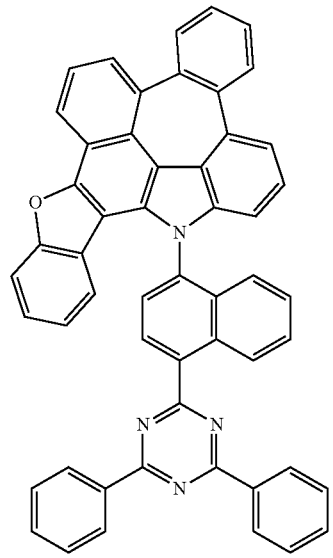
C-240
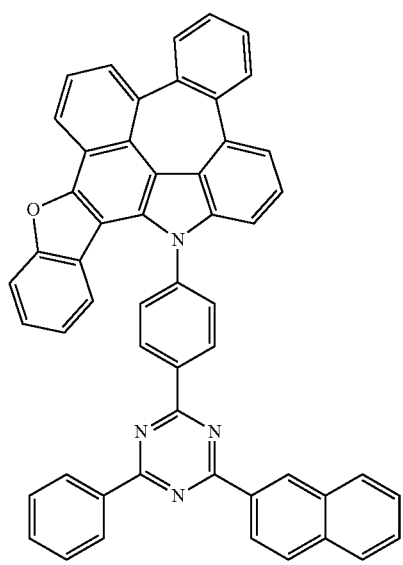
C-241
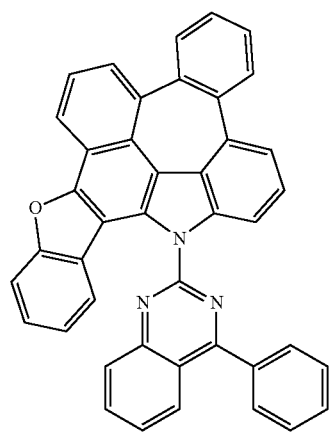
C-242
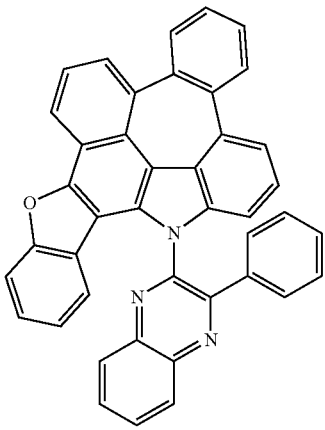
C-243
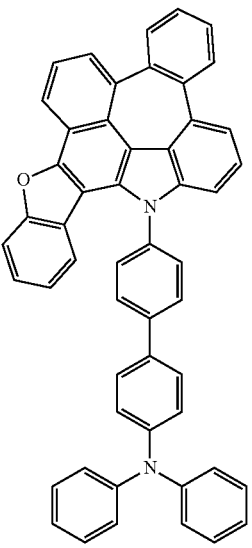
C-244
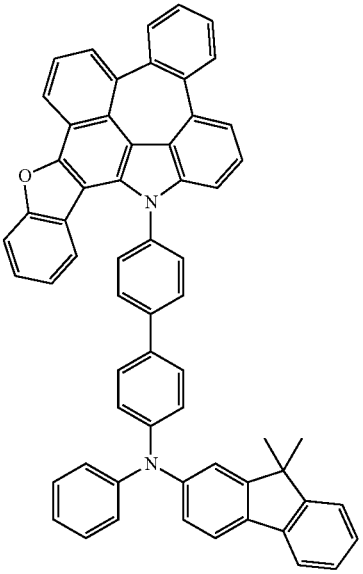

C-245
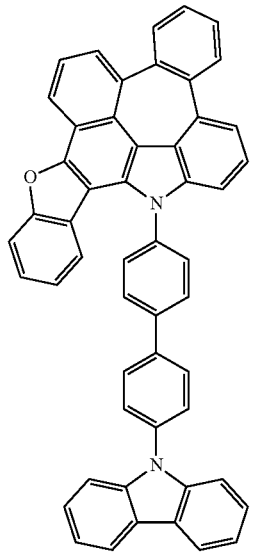
C-246
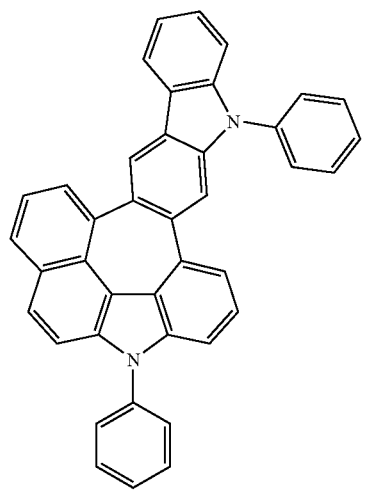
C-247
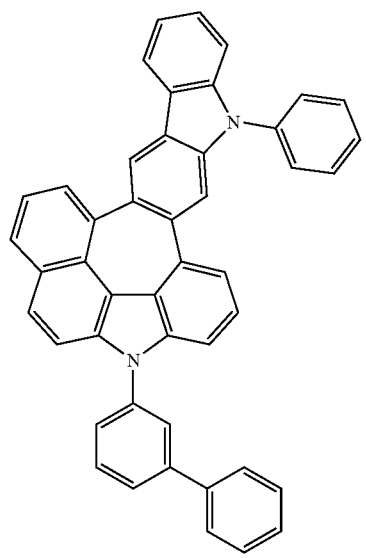
C-248
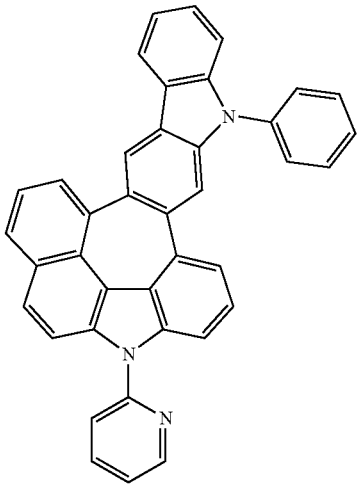
C-249
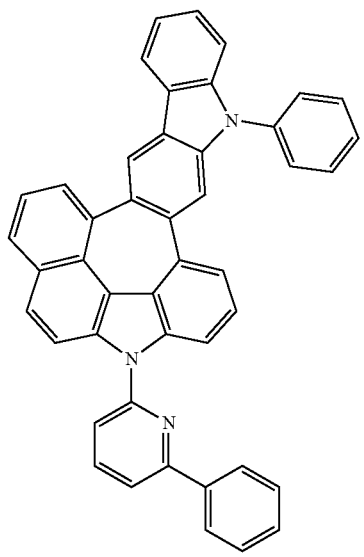
C-250
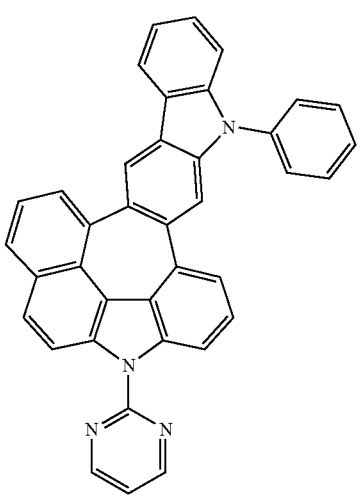

C-251
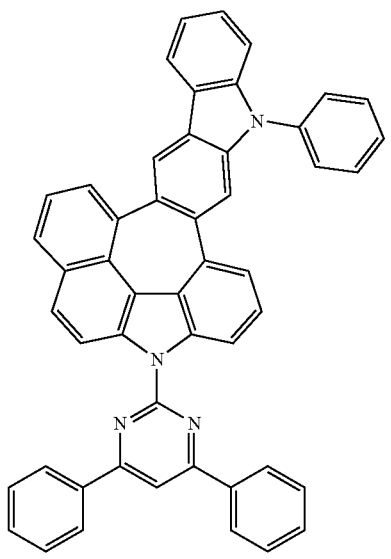
C-253
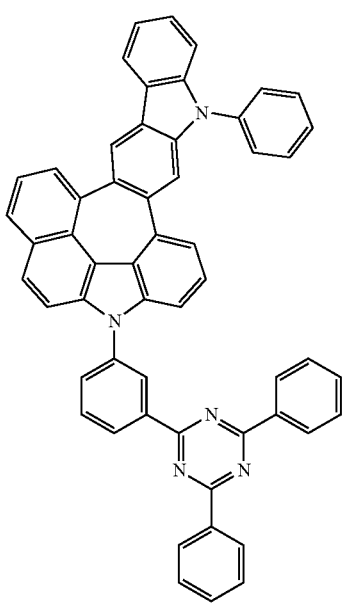
C-252
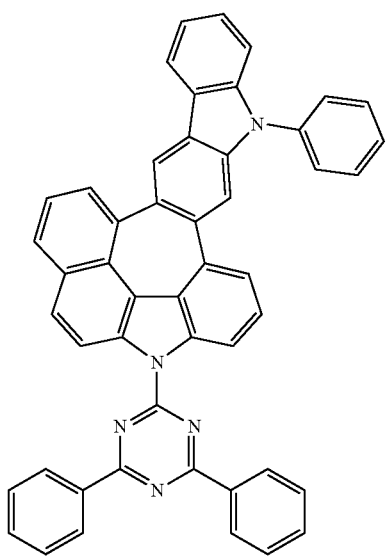
C-254
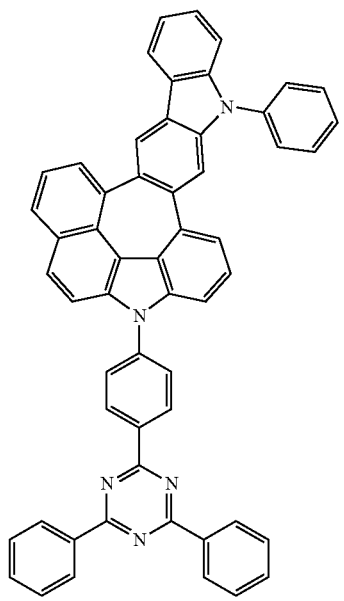

C-255
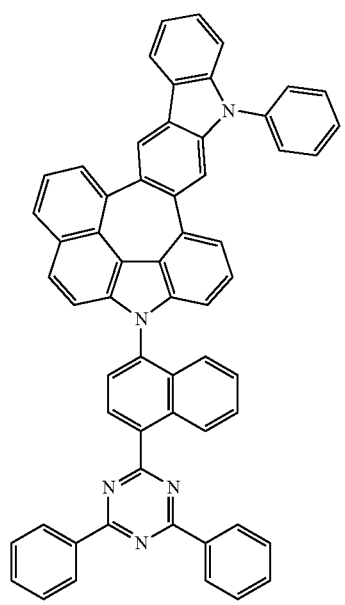
C-256
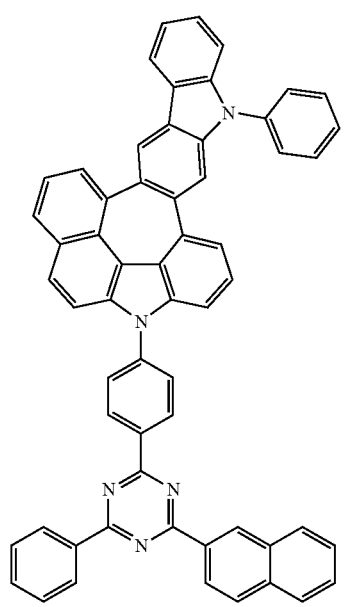
C-257
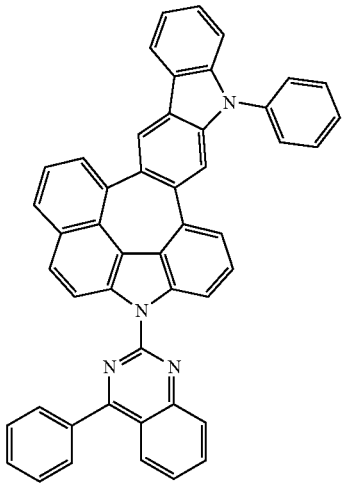
C-258
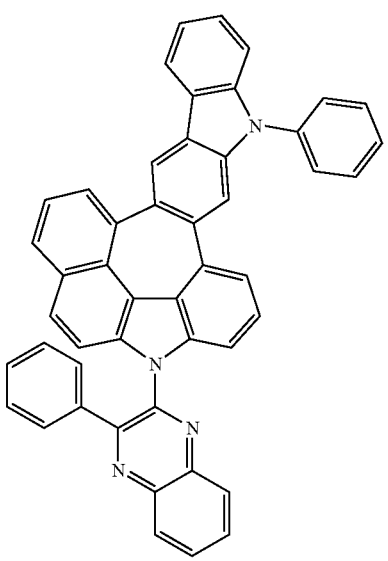
C-259
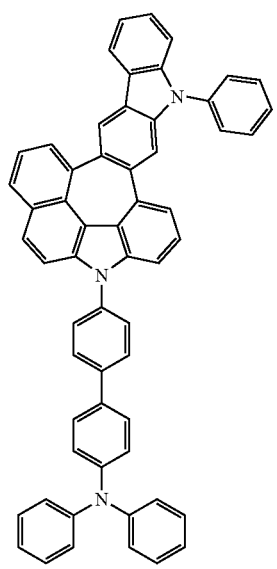

C-260
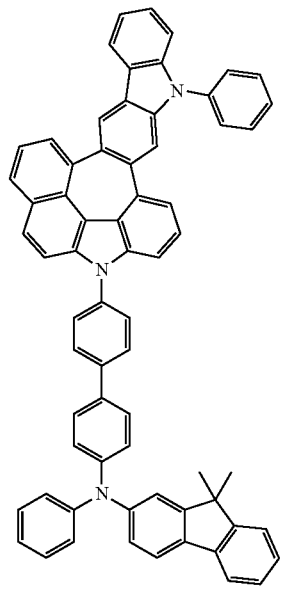
C-261
C-262
C-263
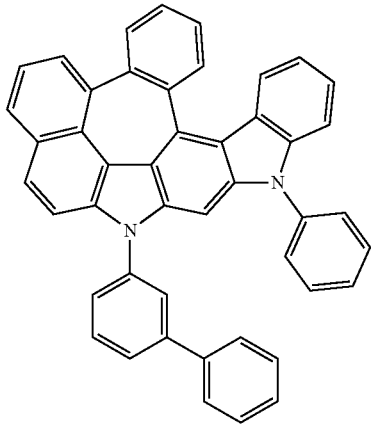
C-264
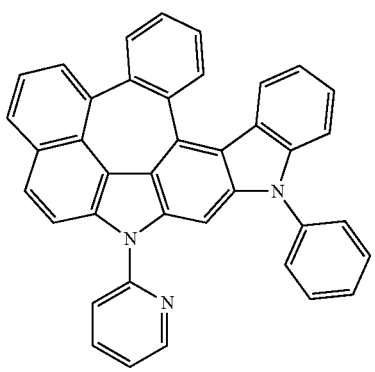
C-265
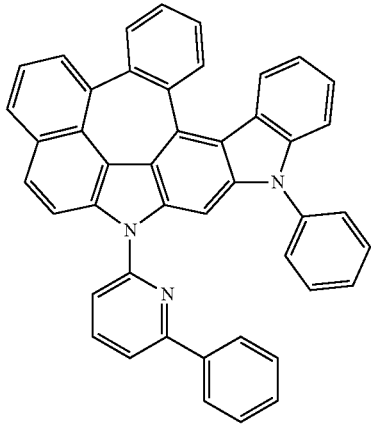
C-266
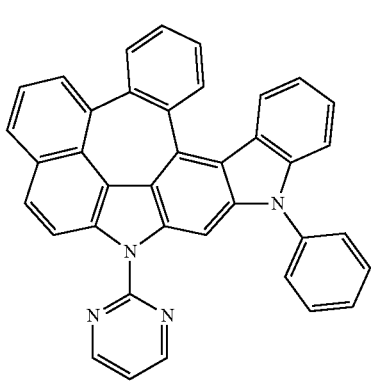

C-267
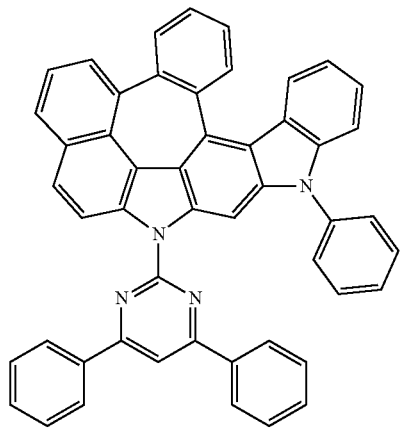
C-270
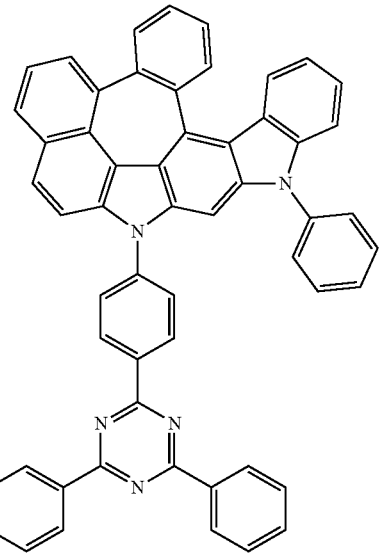
C-268
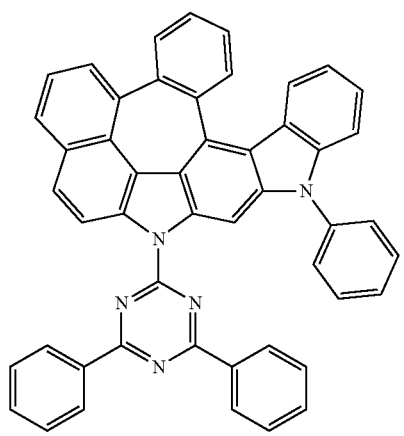
C-271
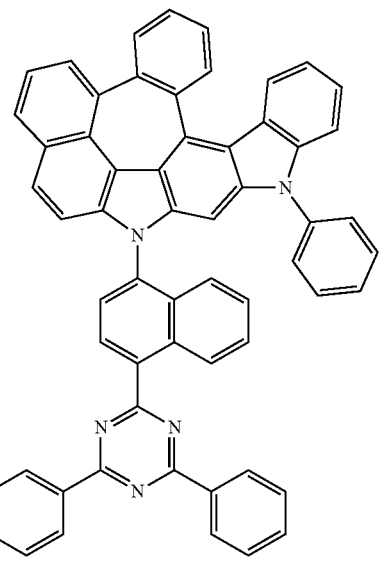
C-269
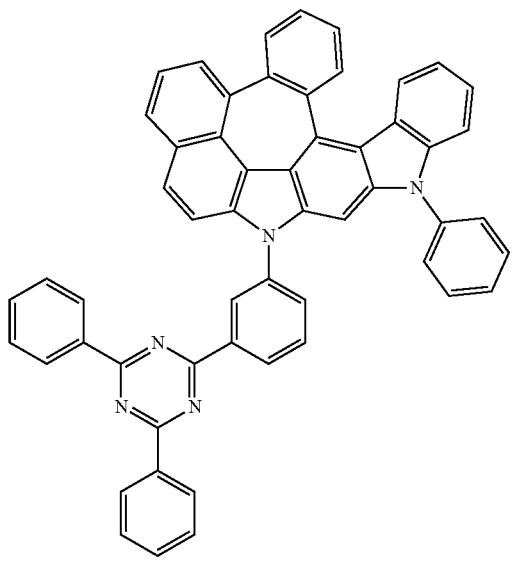
C-272
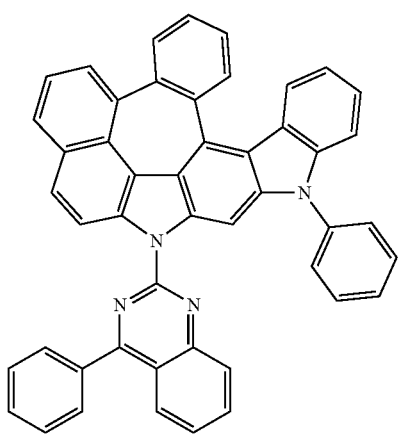

-continued
C-273
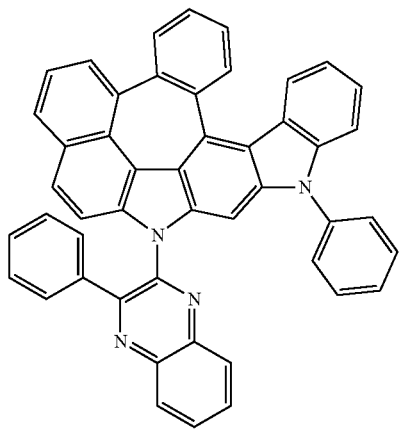
C-274
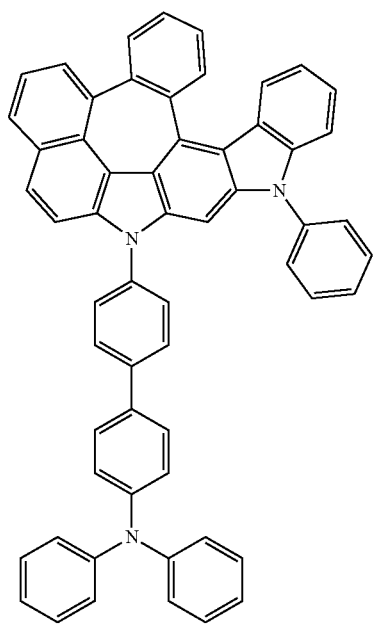
C-275
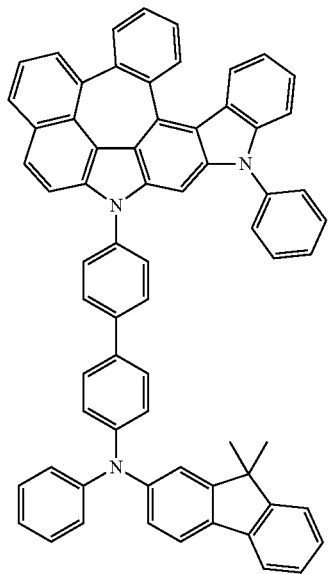
-continued
C-276
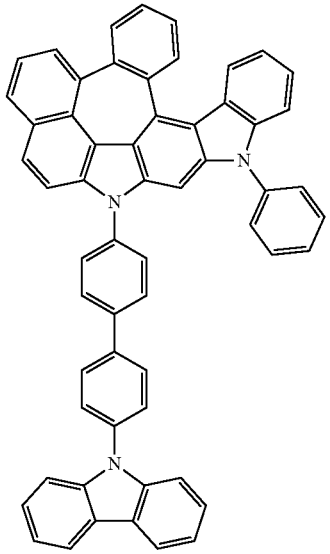
C-277
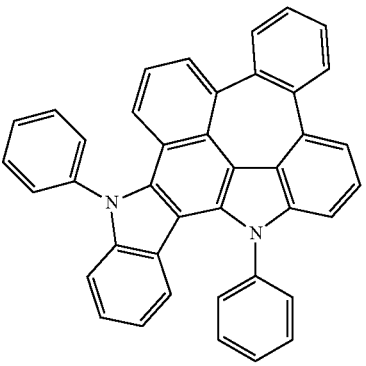
C-278
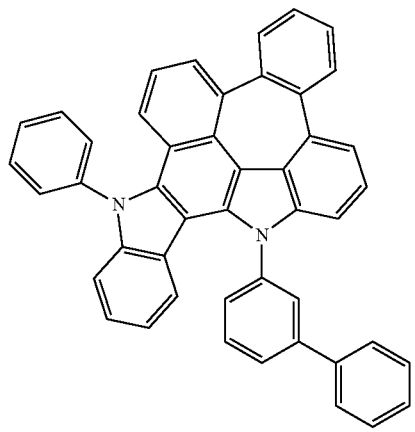

-continued
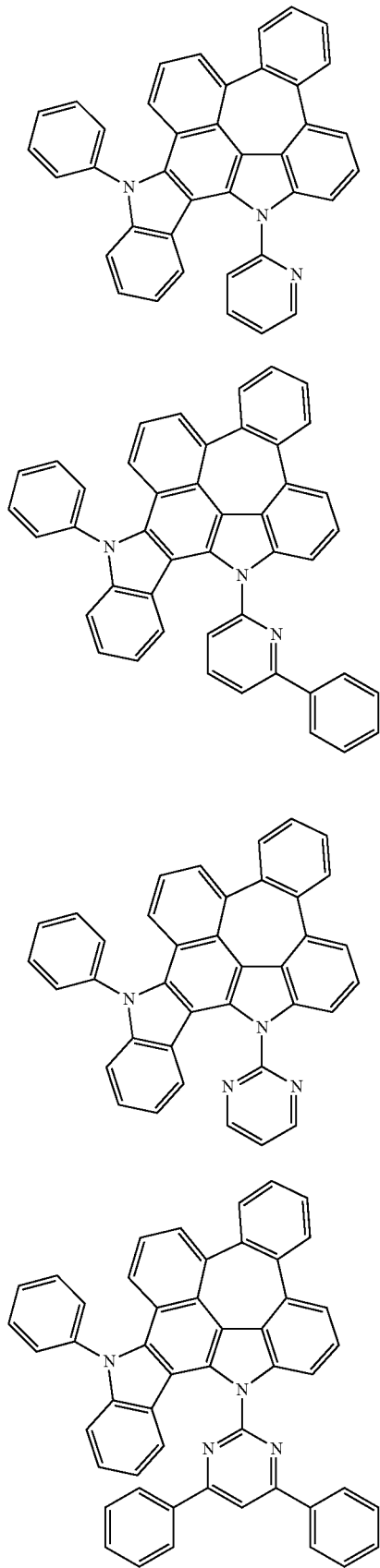
C-279
C-280
C-281
C-282
-continued
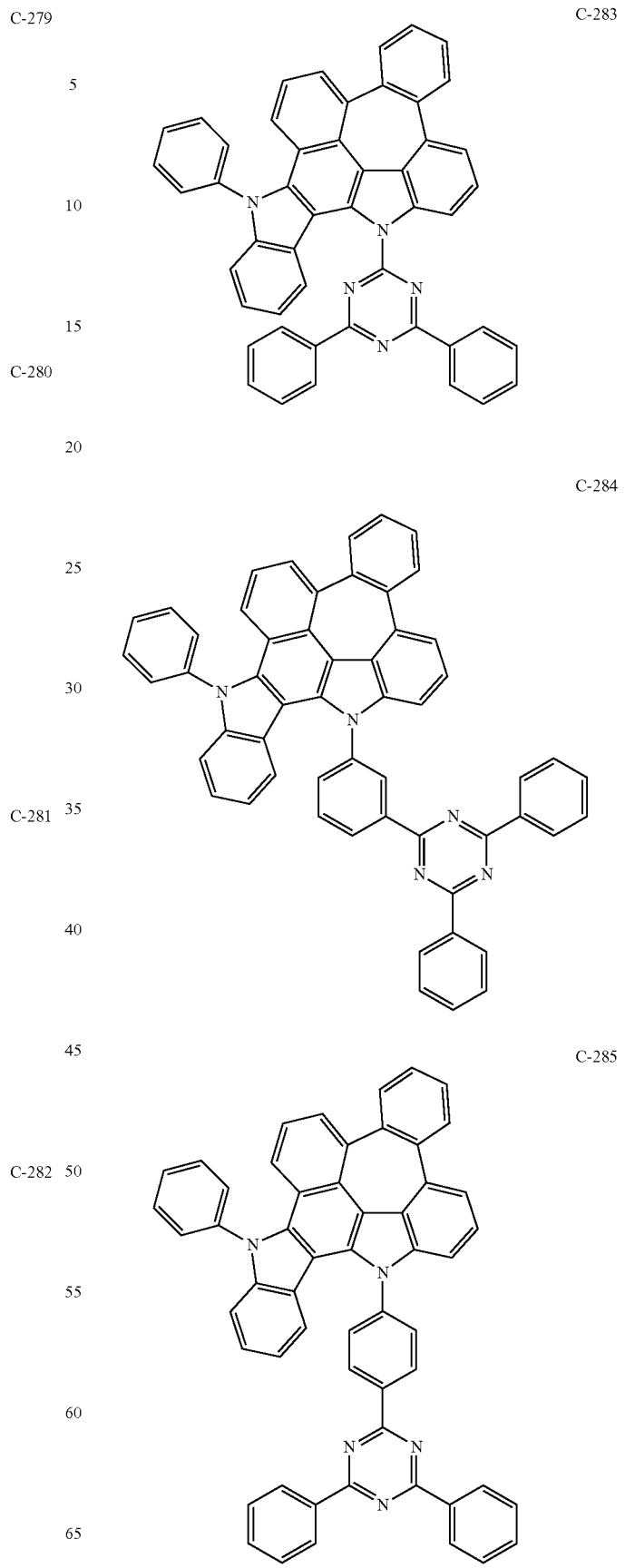
C-283
C-284
C-285

C-286
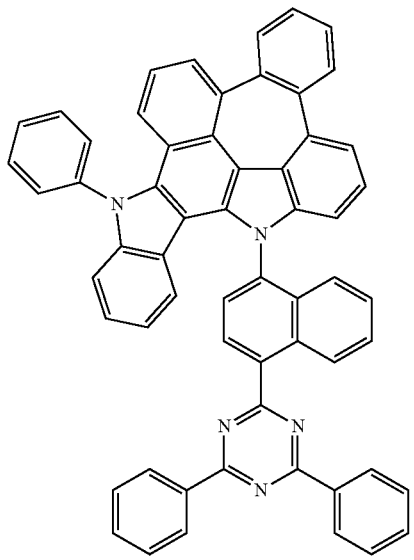
C-287
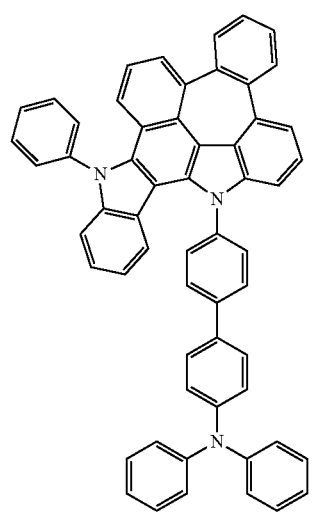
C-288
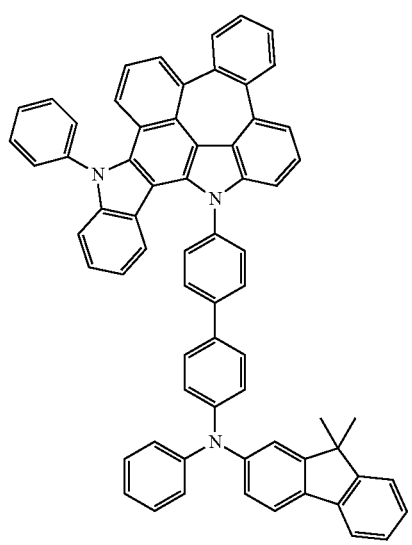
C-289
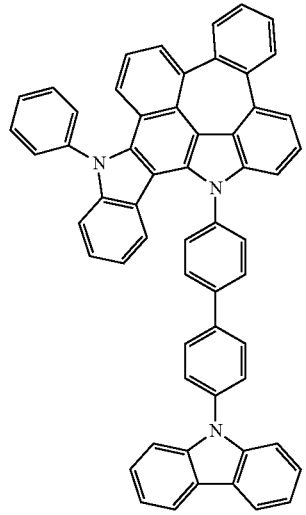
C-290
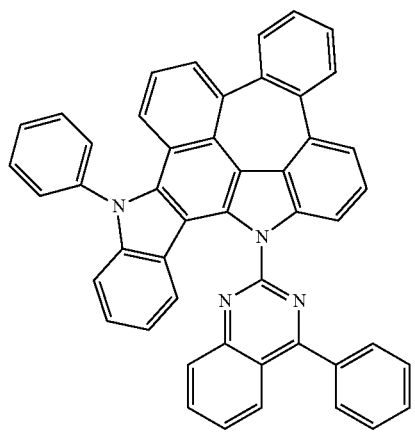
C-291
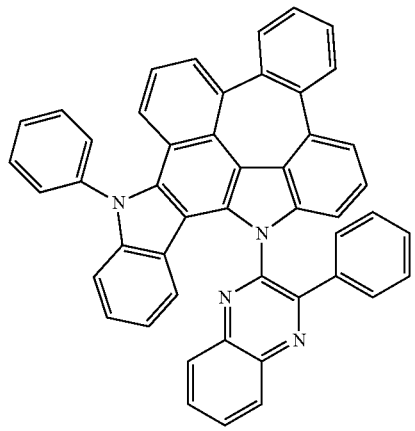

C-292
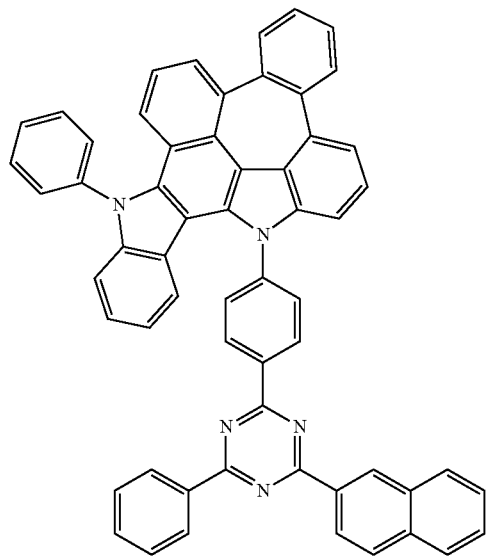
C-293
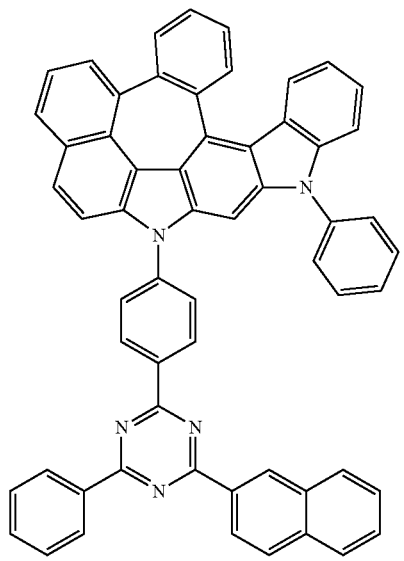
C-294
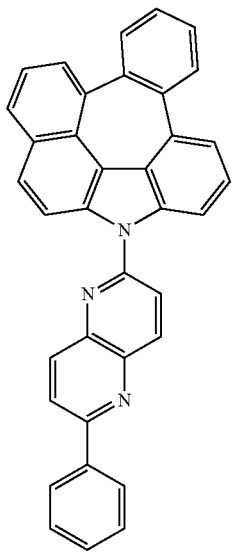
C-295
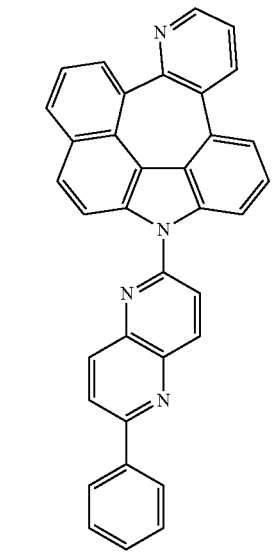
C-296
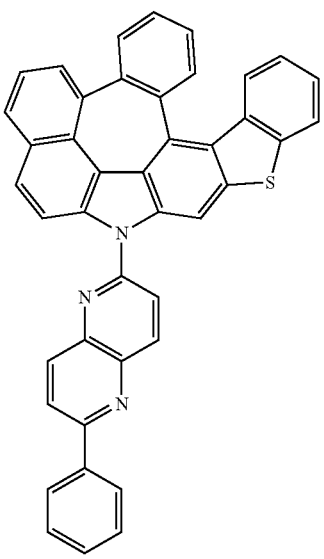

C-297 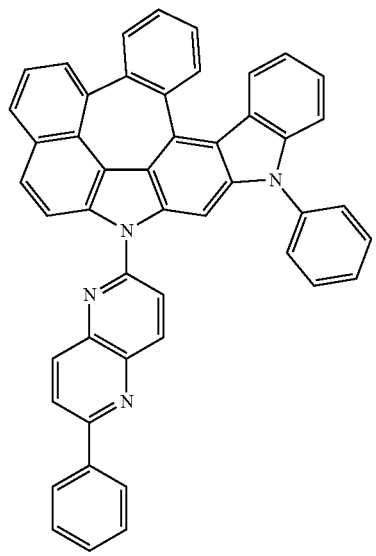
C-298 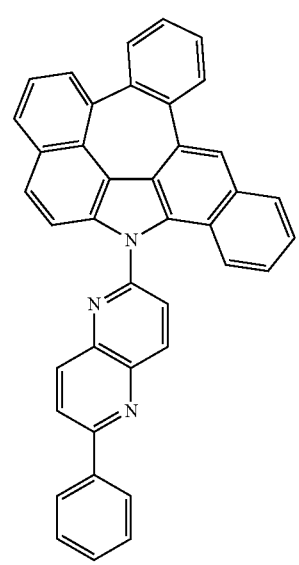
C-299 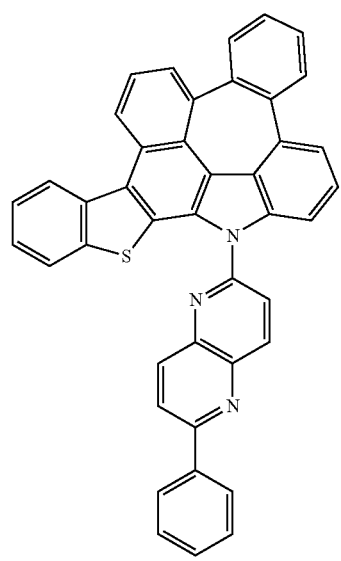
C-300 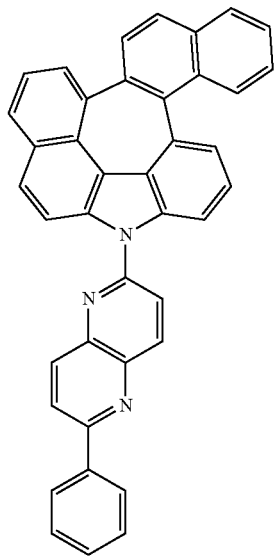
C-301 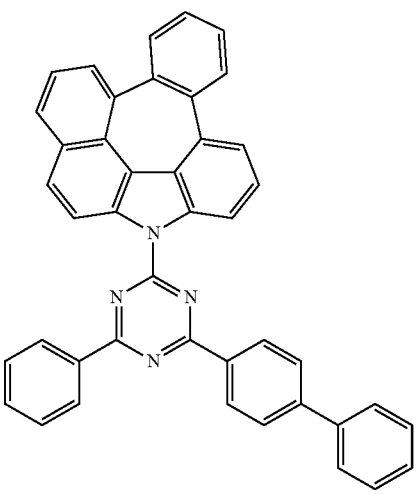
C-302 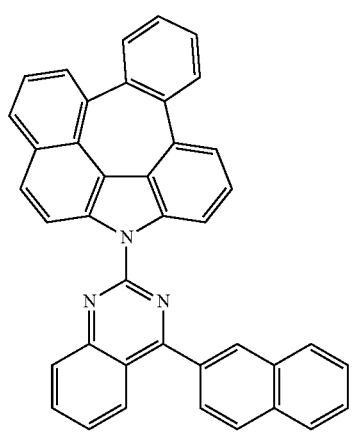

C-303
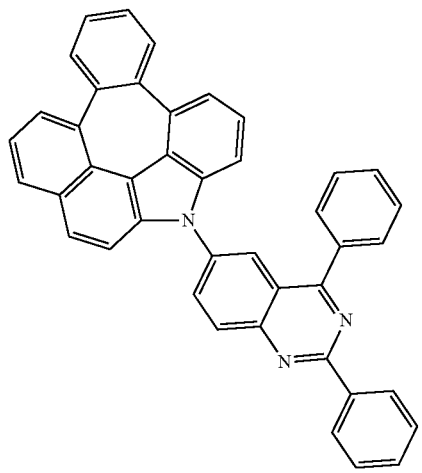
C-304
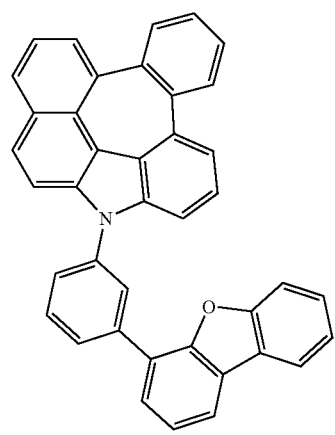
C-305
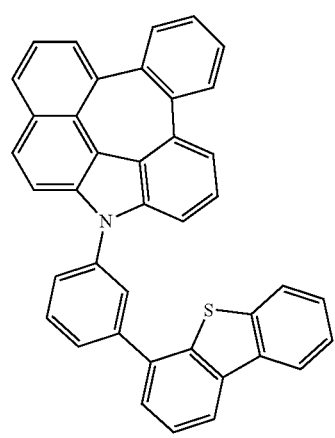
C-306
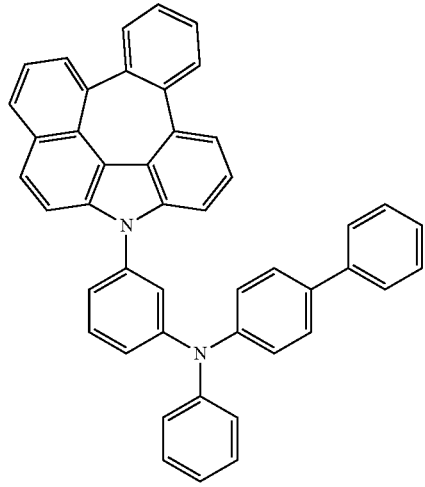
C-307
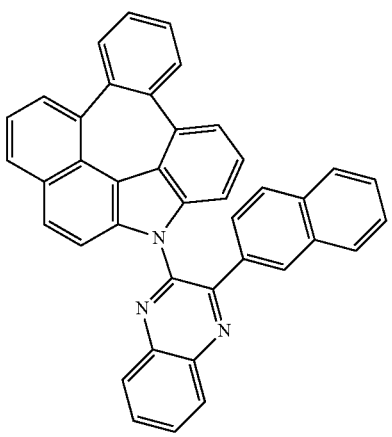
C-308
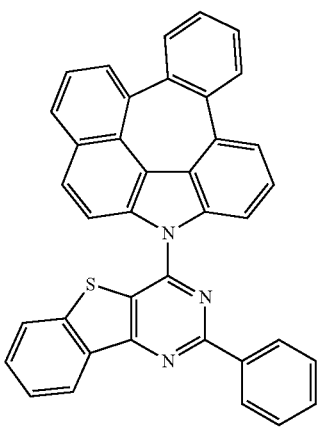

C-309
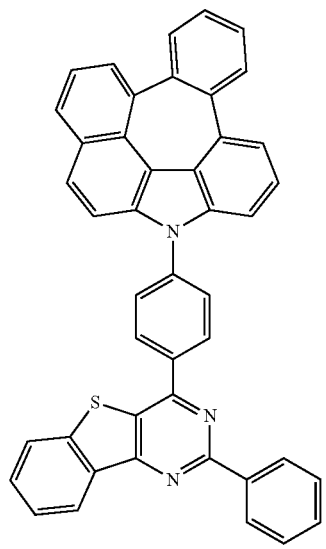
C-310
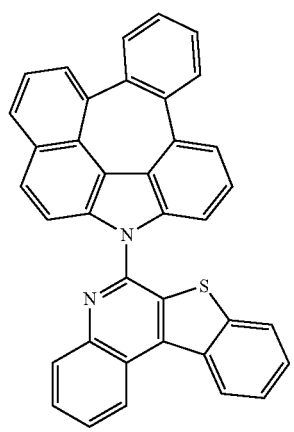
C-311
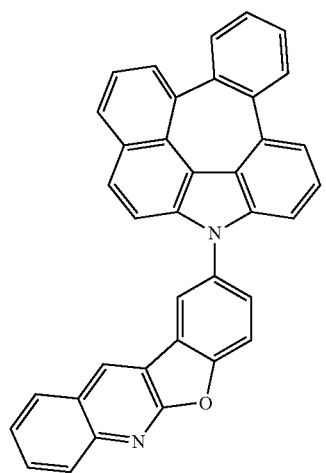
C-312
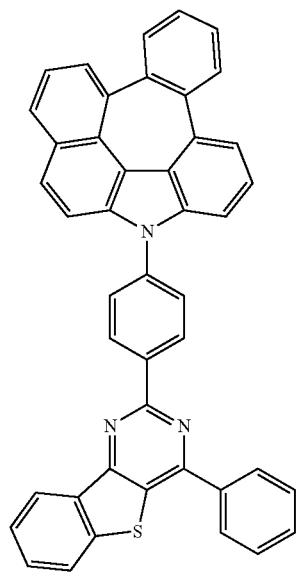
C-313
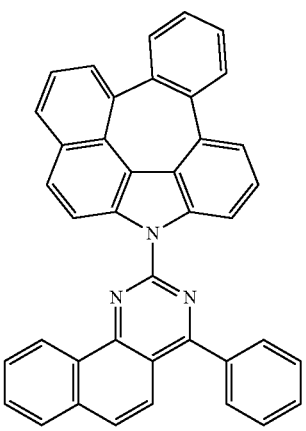
C-314
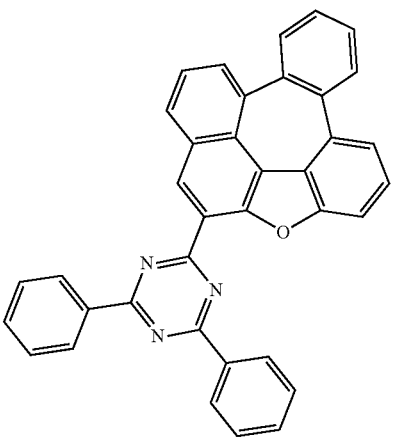

C-315
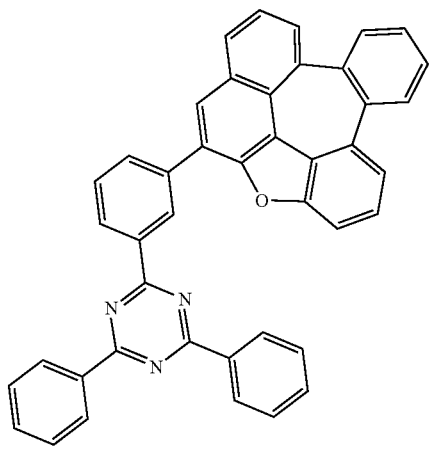
C-316
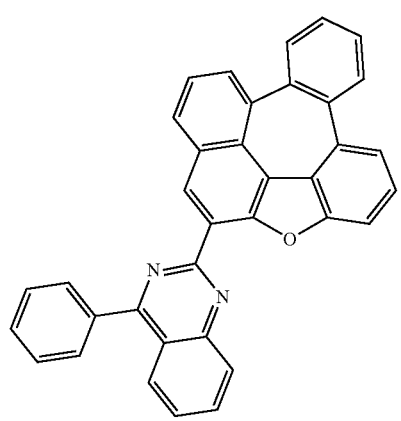
C-317
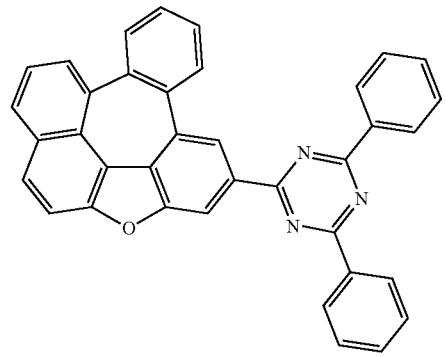
C-318
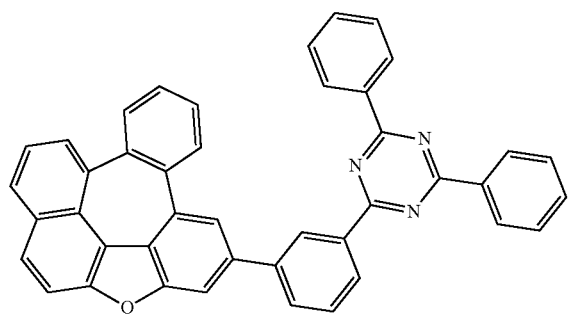
C-319
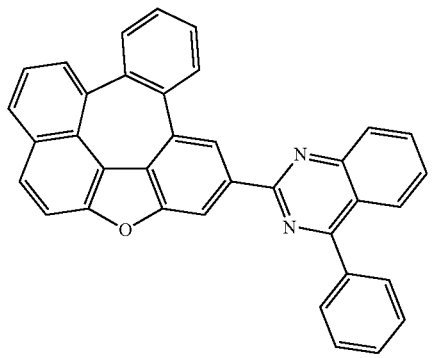
C-320
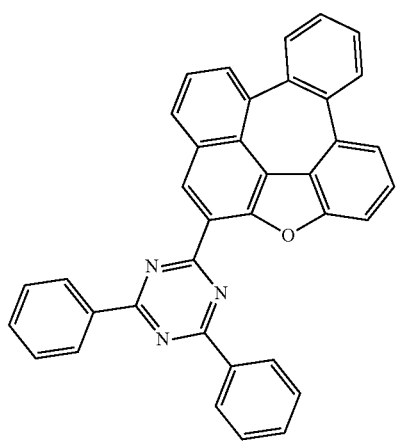
C-321
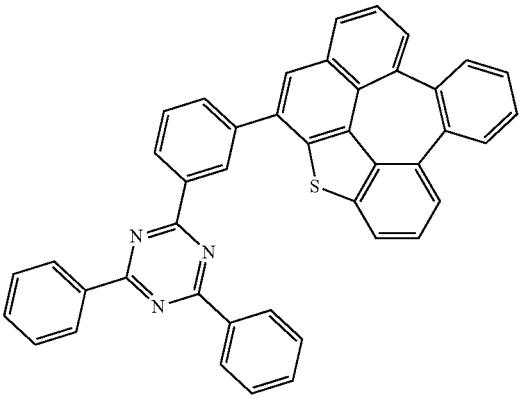
C-322
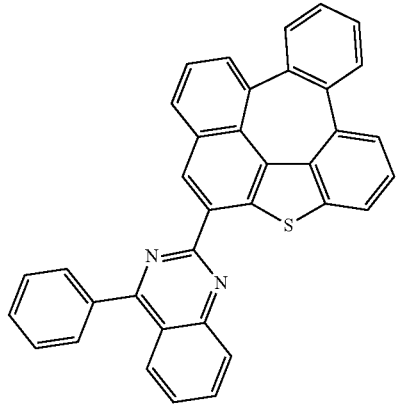

C-323
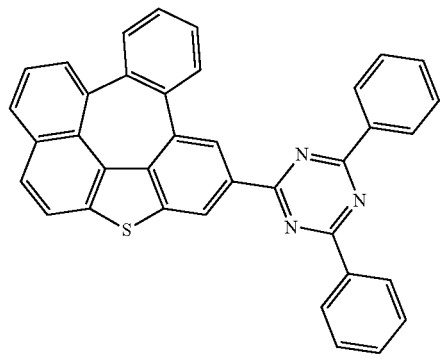
C-326
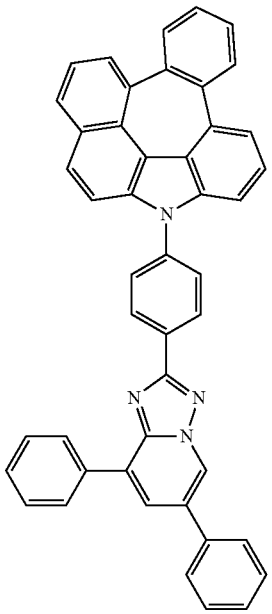
C-324
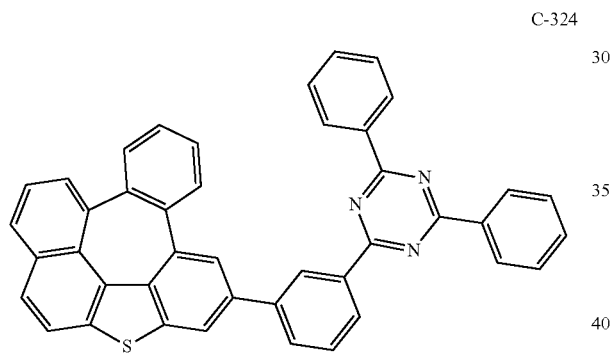
C-325
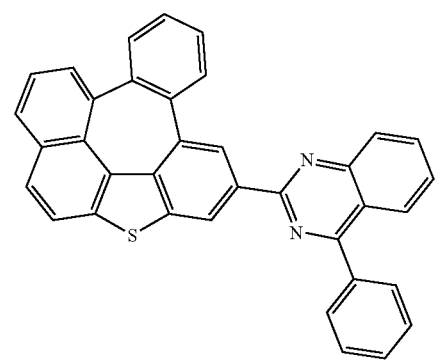
C-327
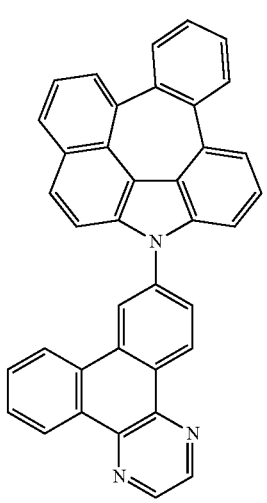

-continued
C-328
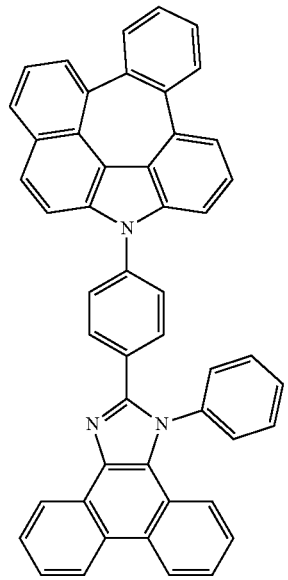
C-329
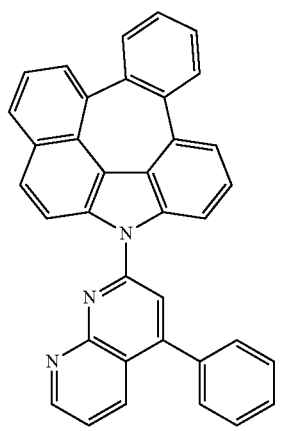
C-330
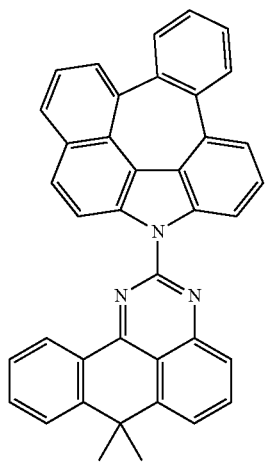
C-331
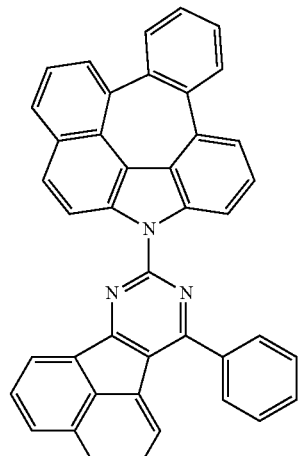
C-332
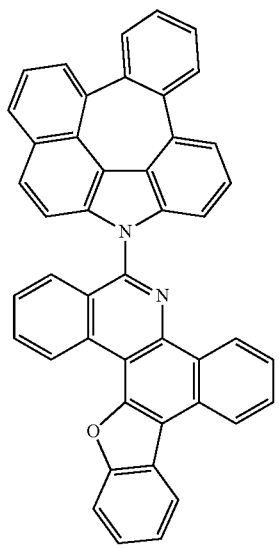
C-333
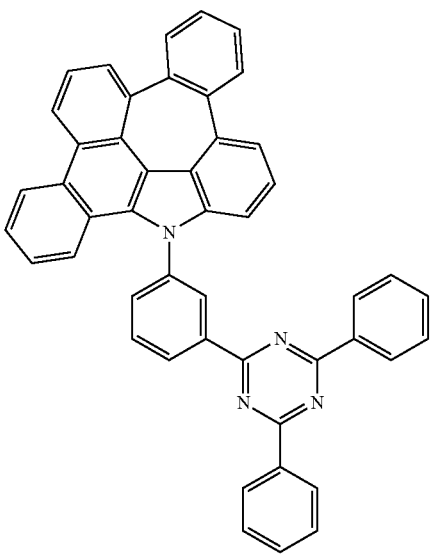

C-334
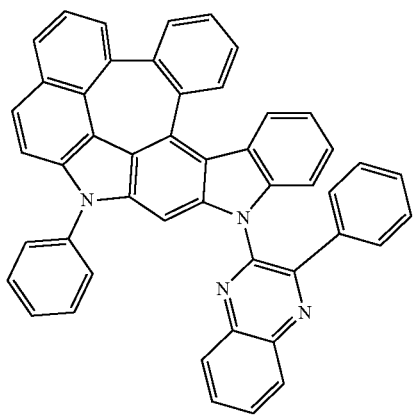
C-335
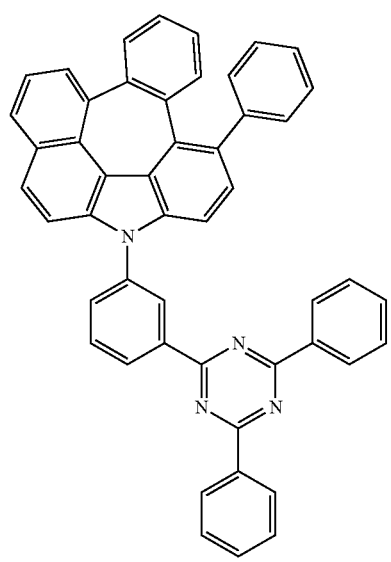
C-336
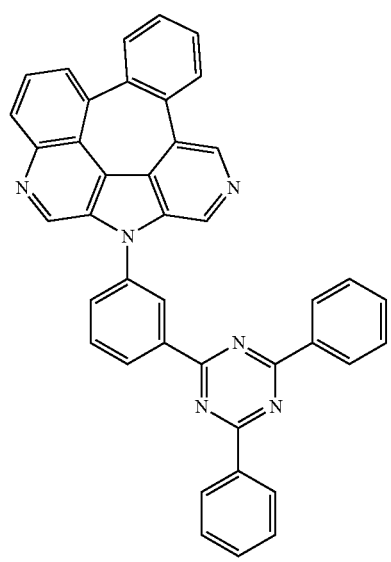
C-337
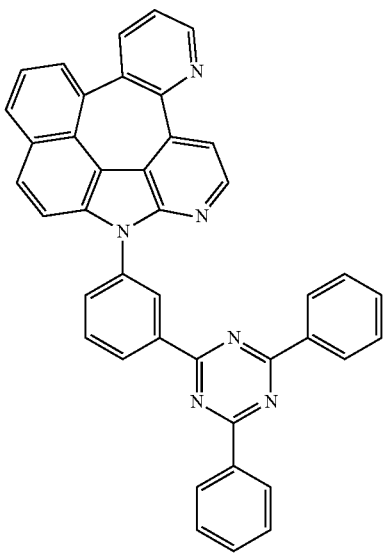
C-338
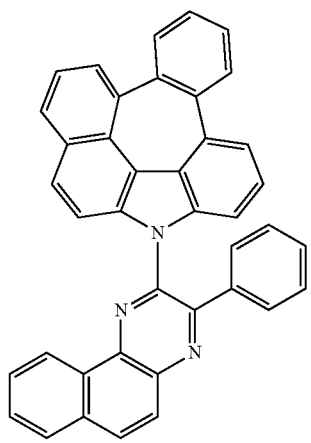
C-339
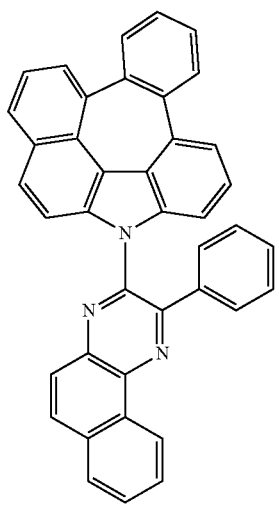

C-340
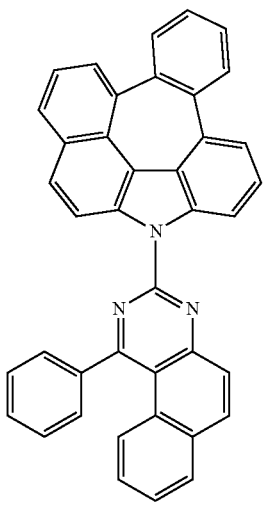
C-341
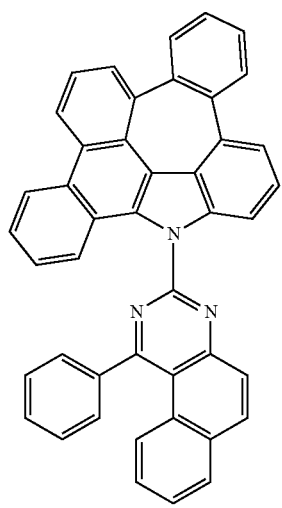
C-342
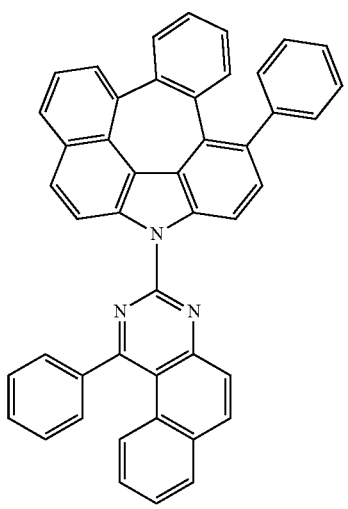
C-343
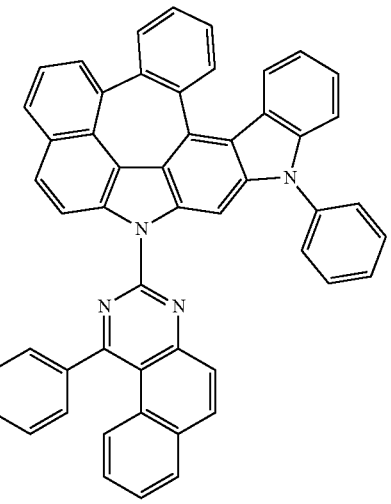
C-344
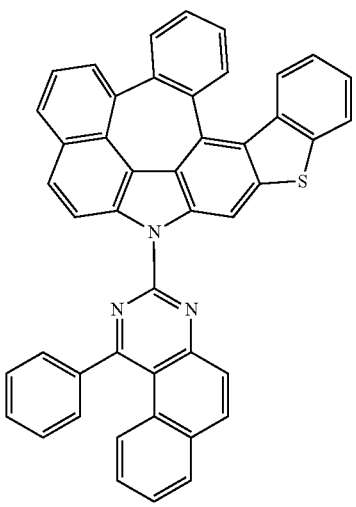
C-345
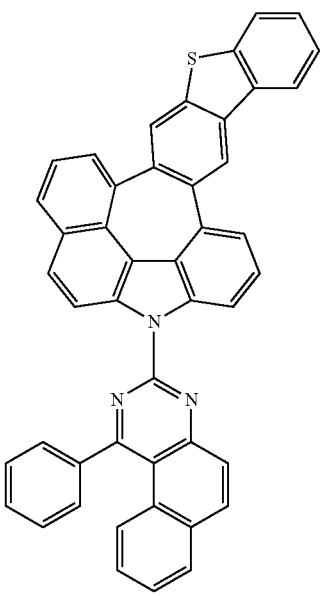

C-346
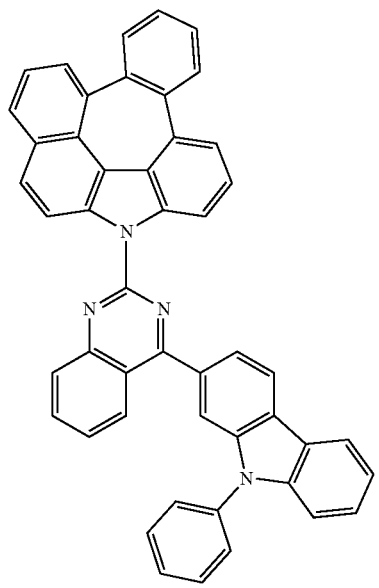
C-347
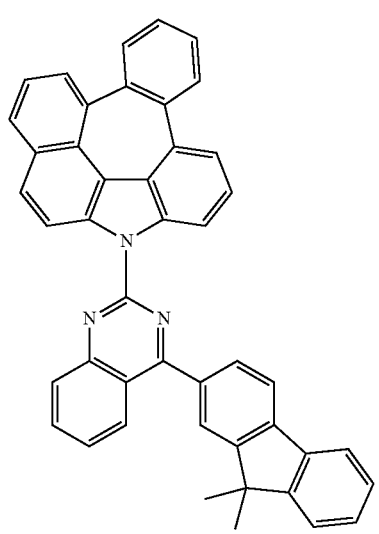
C-348
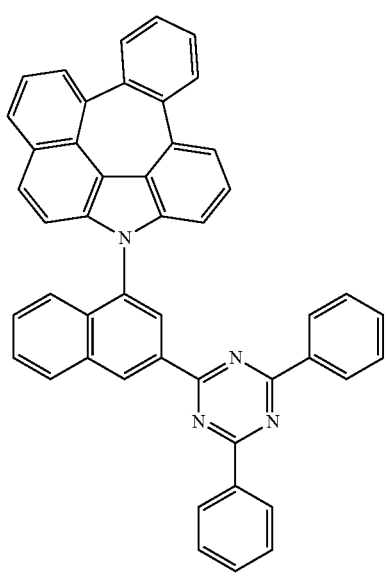
C-349
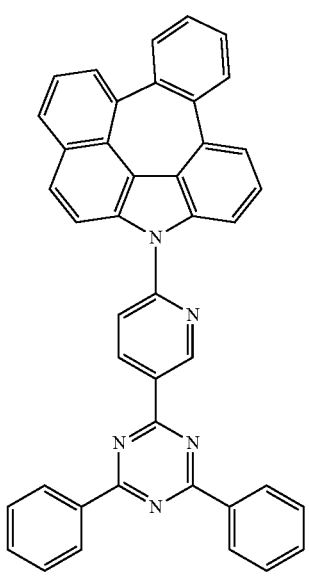
C-350
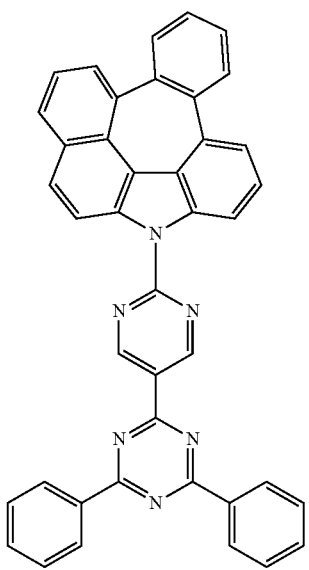

C-351
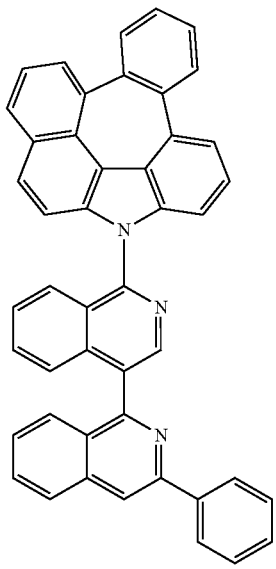
C-353
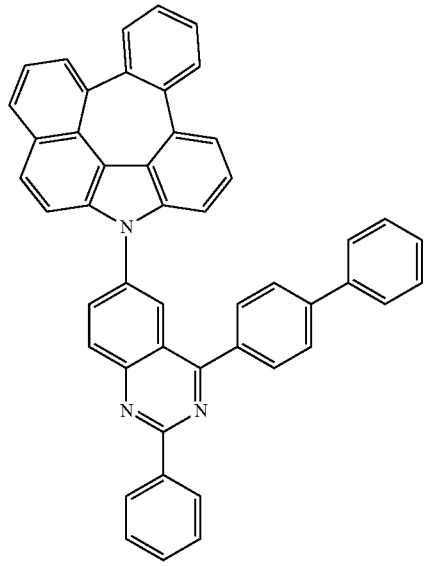
C-352
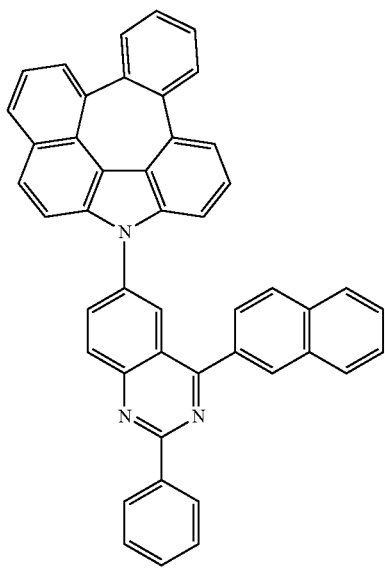
C-354
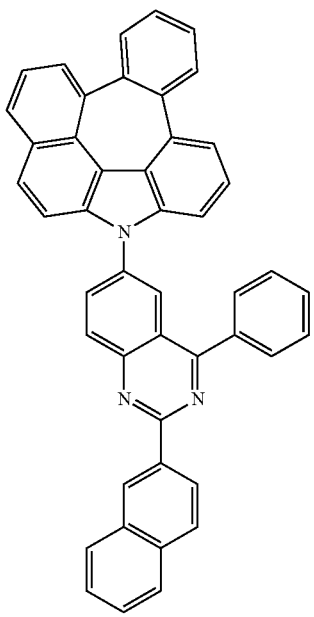

-continued
C-355
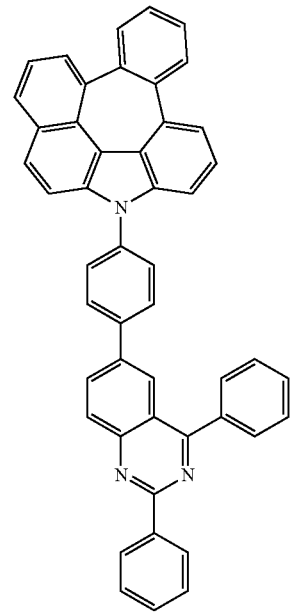
C-356
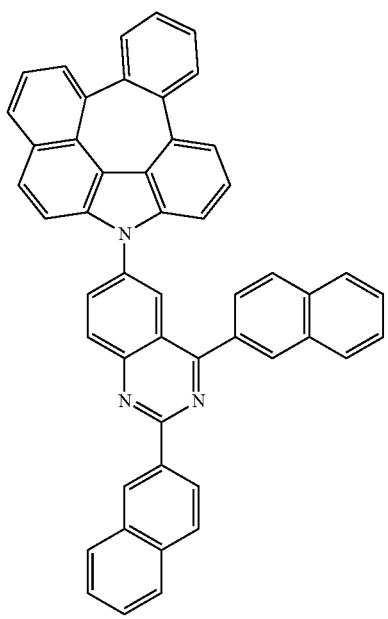
C-357
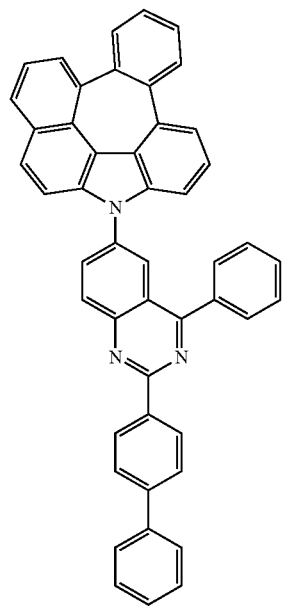
C-358
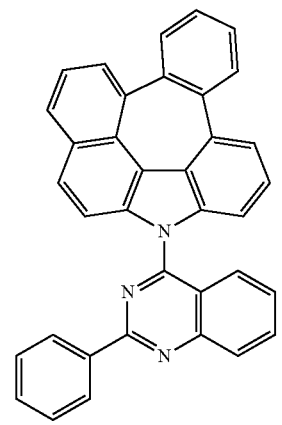
C-359
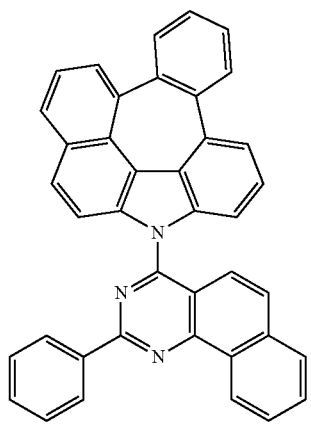

C-360
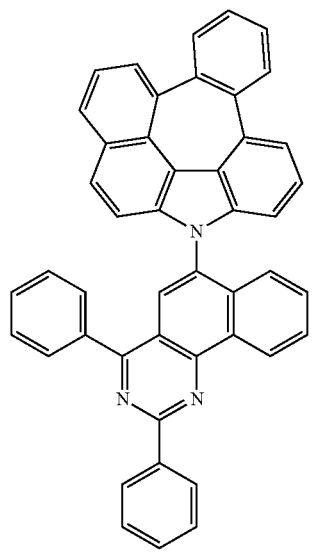
C-361
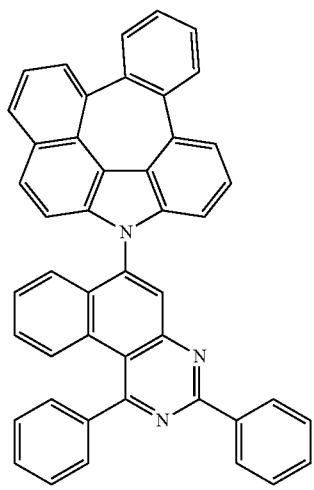
C-362
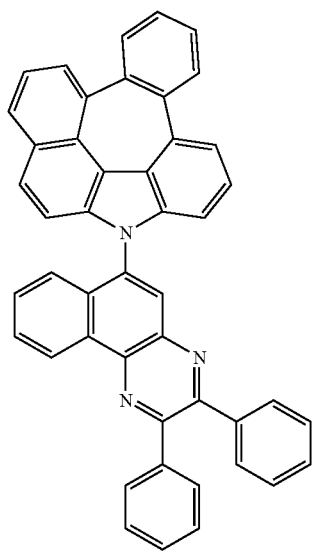
C-363
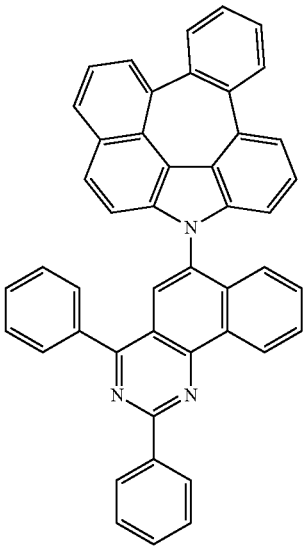
C-364
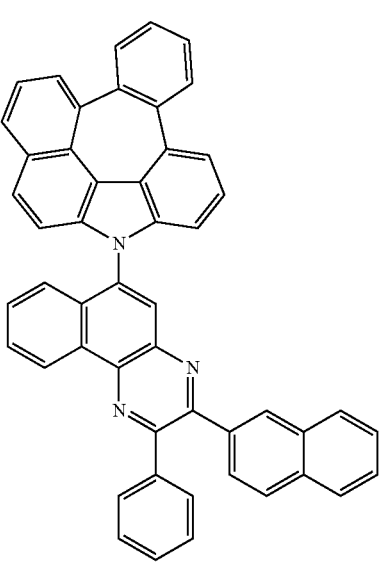
C-365
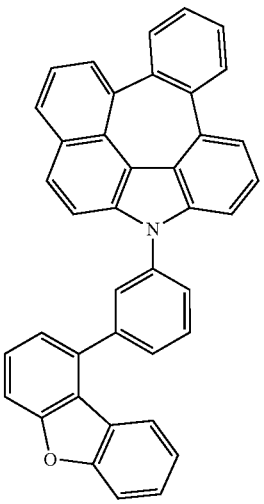

C-366 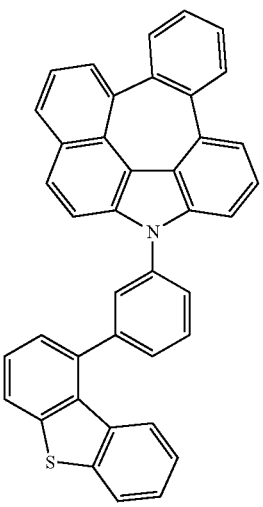
C-367 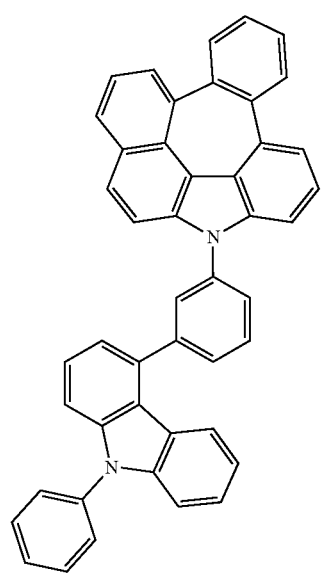
C-368 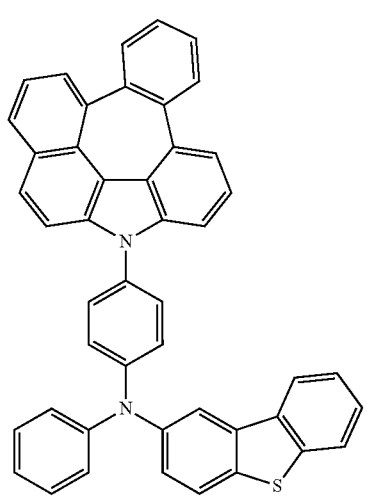
C-369 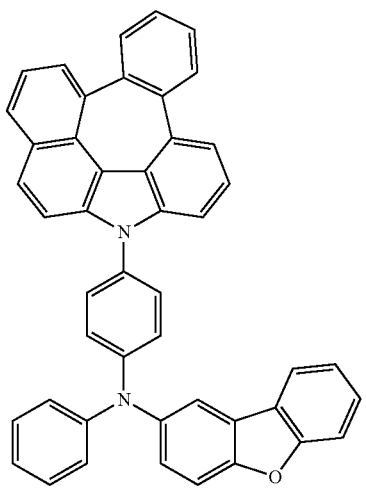
C-370 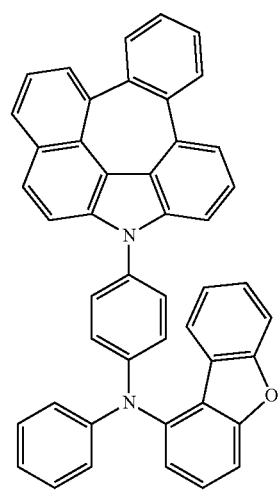
C-371 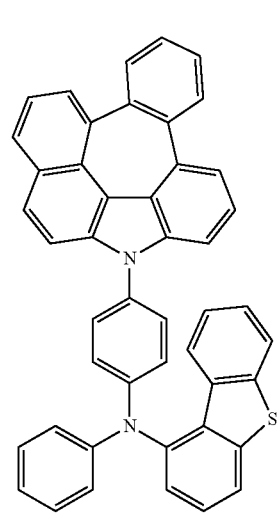

C-372
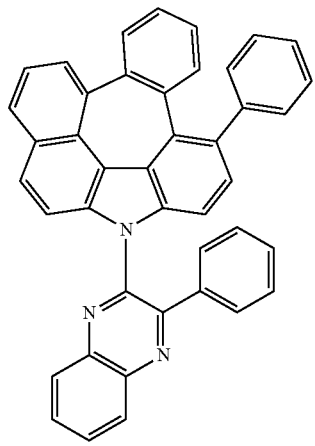
C-375
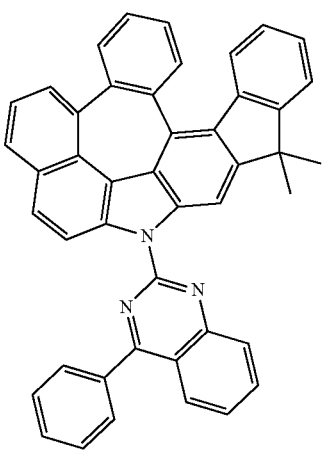
C-373
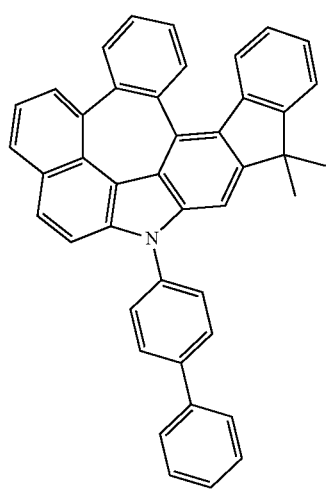
C-376
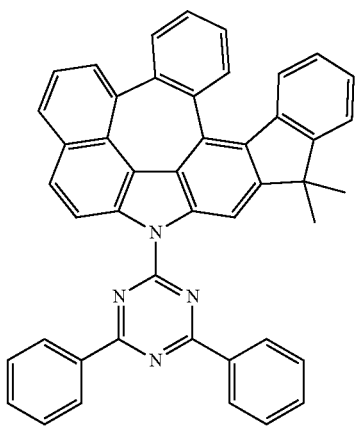
C-374
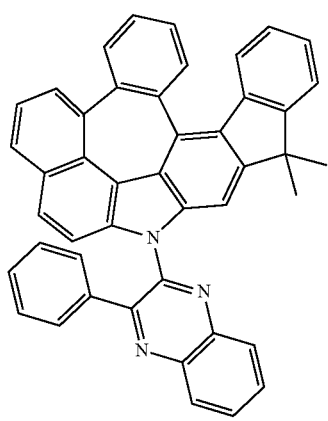
C-377
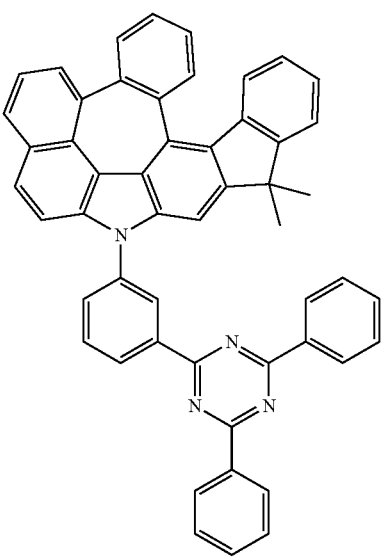

C-378
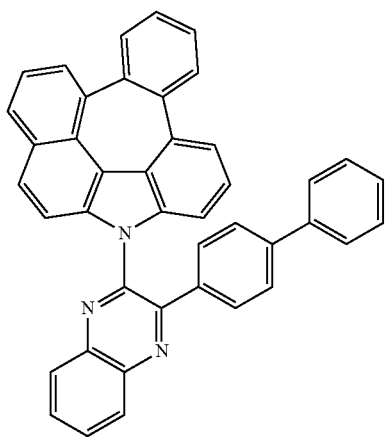
C-379
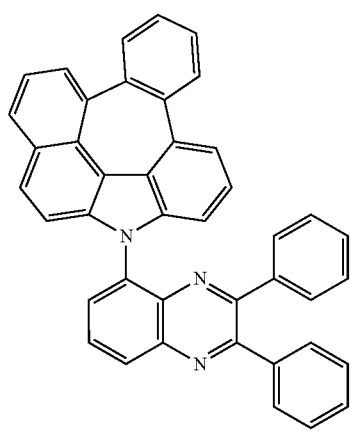
C-380
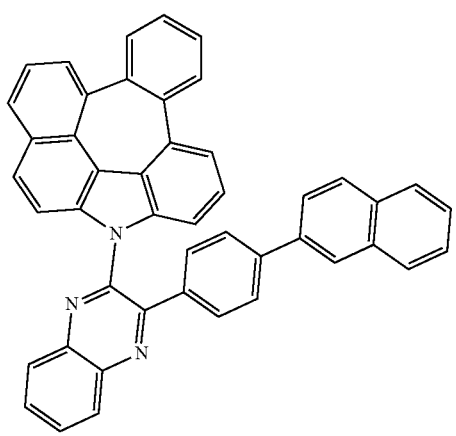
C-381
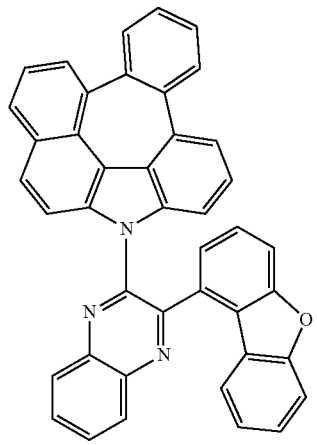
C-382
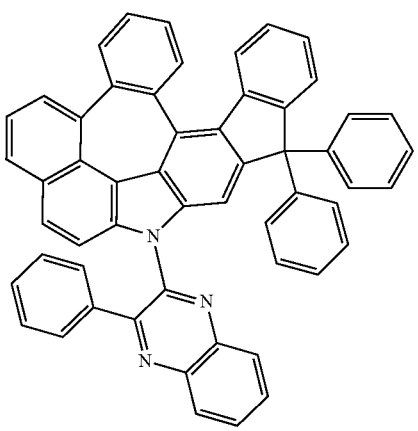
C-383
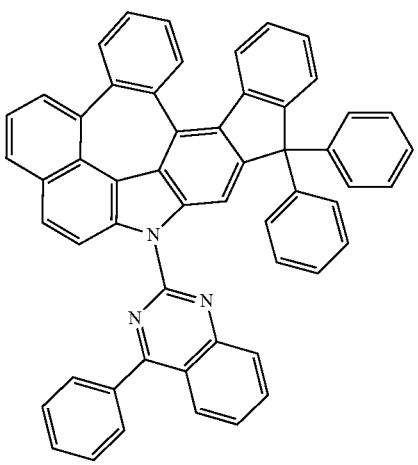

C-384
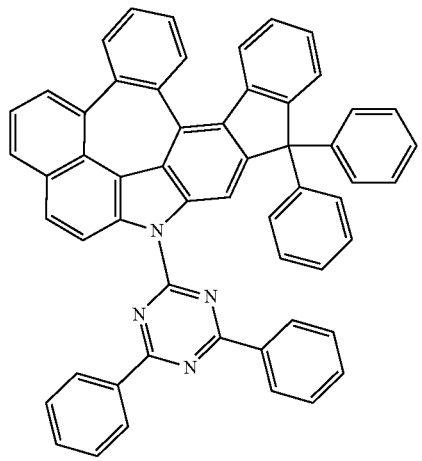
C-385
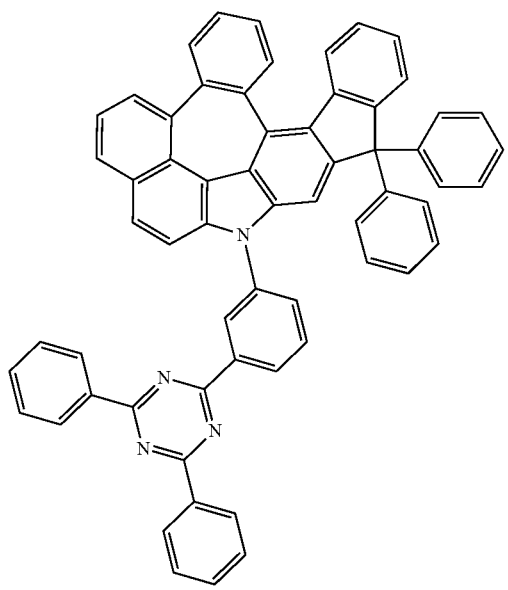
C-386
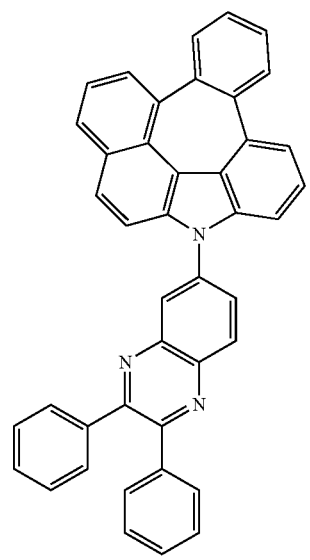
C-387
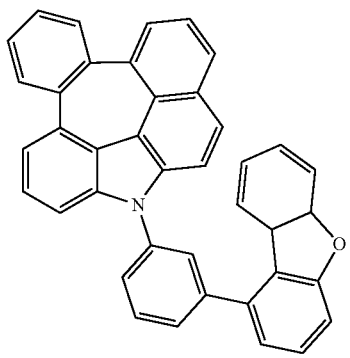
C-388
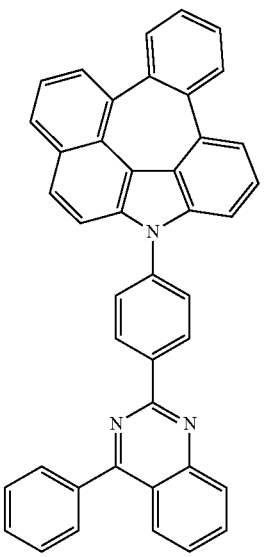
C-389
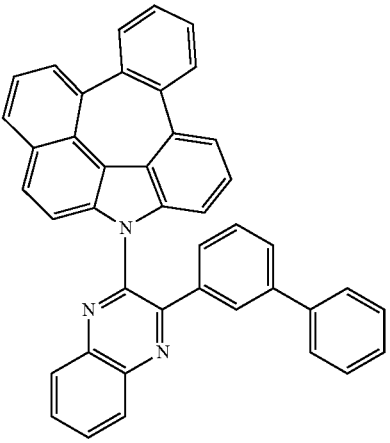

-continued
C-390
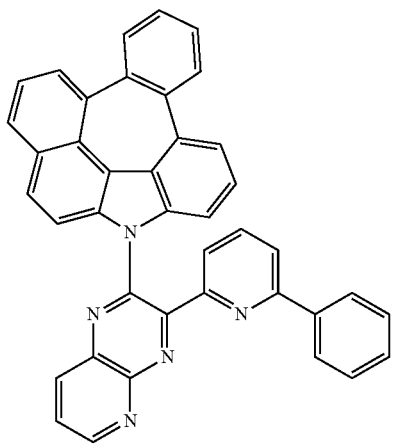
C-391
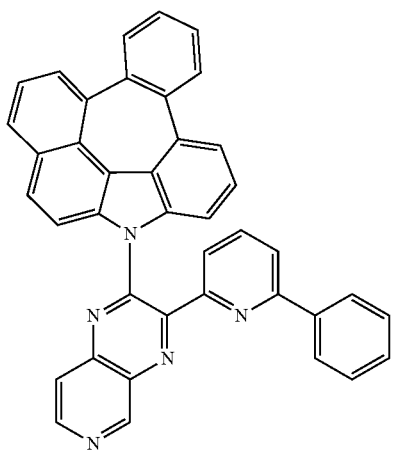
C-392
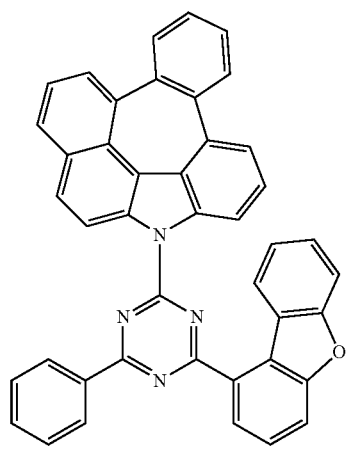
-continued
C-393
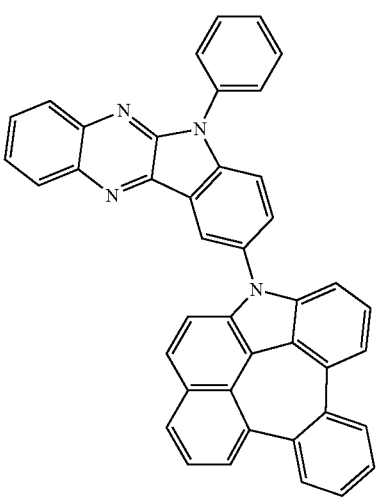
C-394
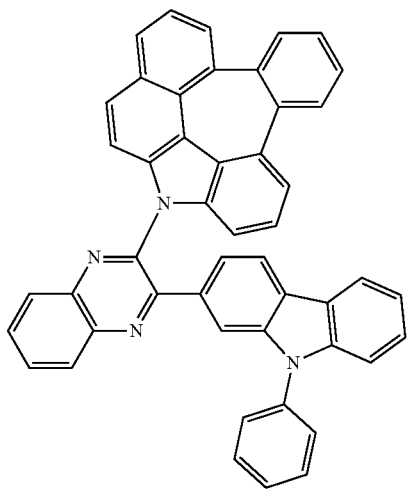
C-395
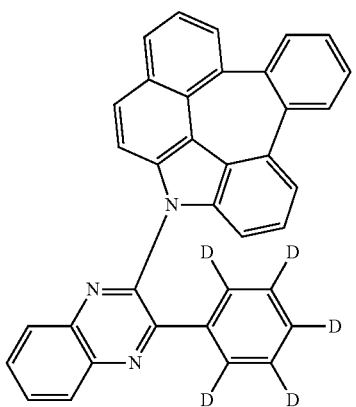

-continued
C-396
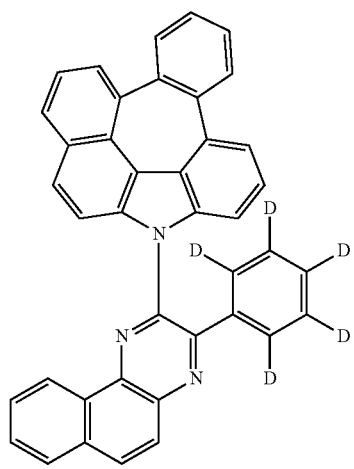
C-397
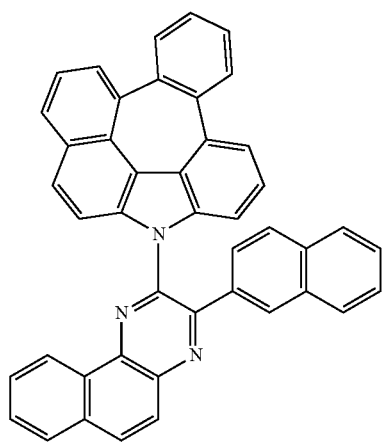
C-398
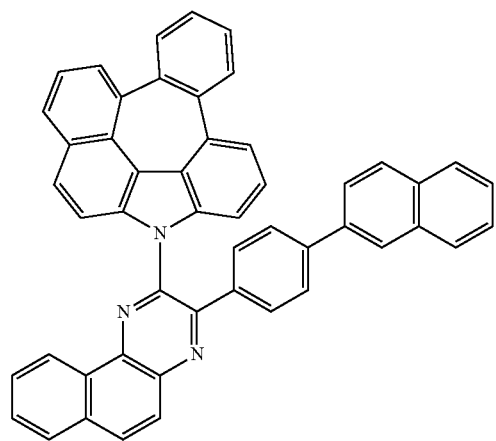
-continued
C-399
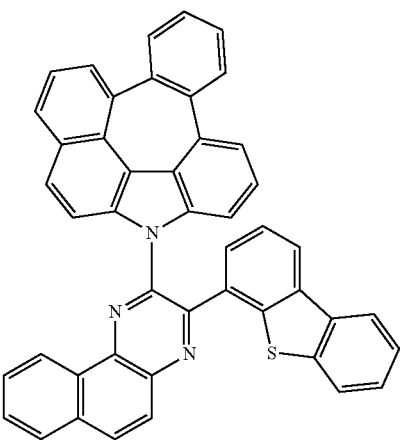
C-400
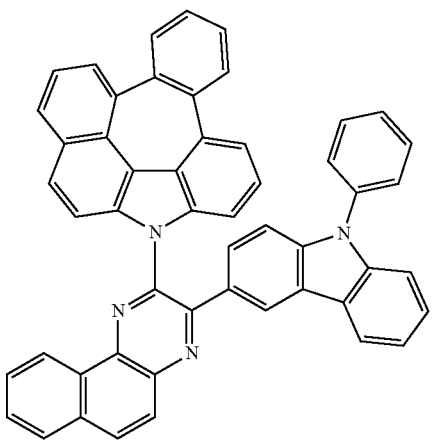
C-401
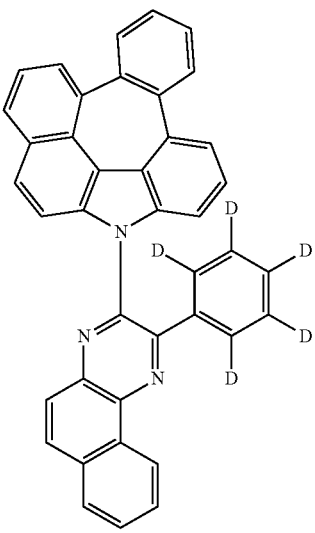

C-402
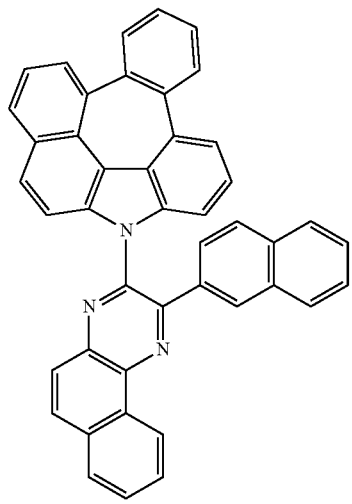
C-405
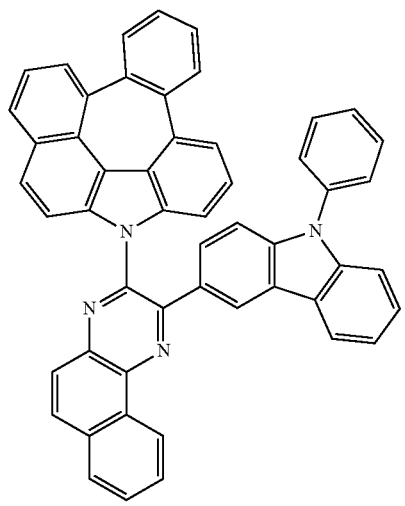
C-403
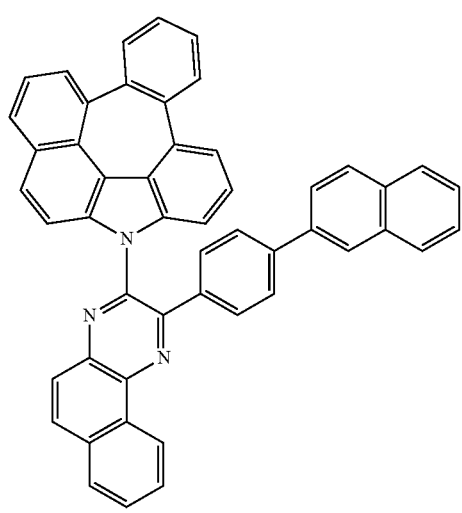
C-406
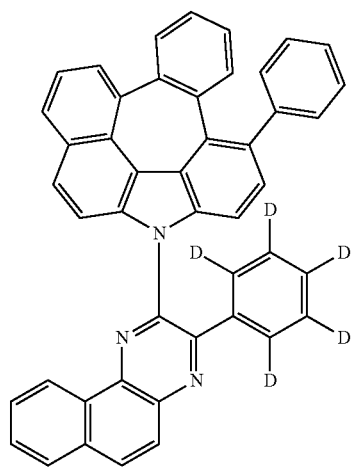
C-404
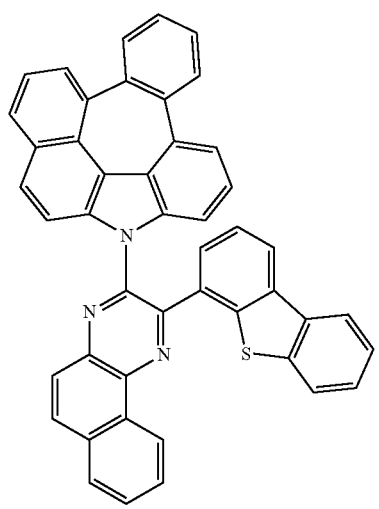
C-407
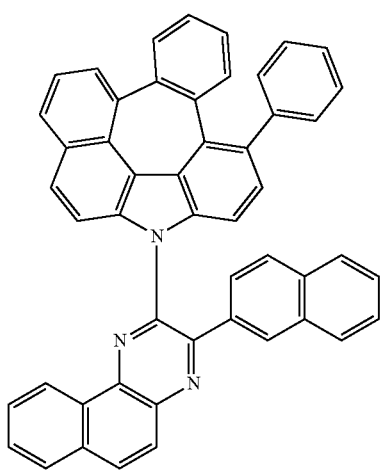

C-408
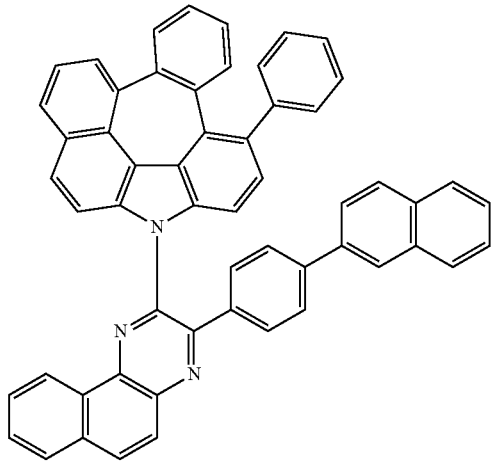
C-409
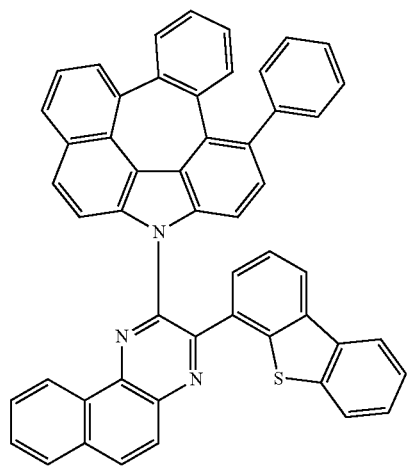
C-410
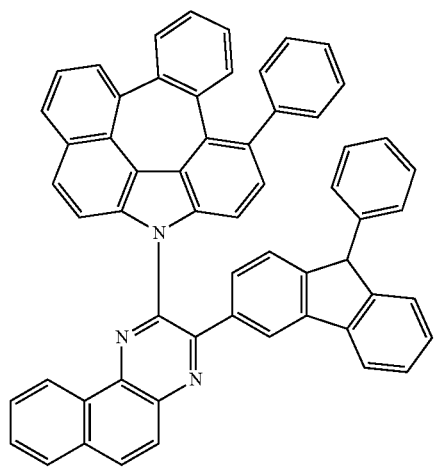
C-411
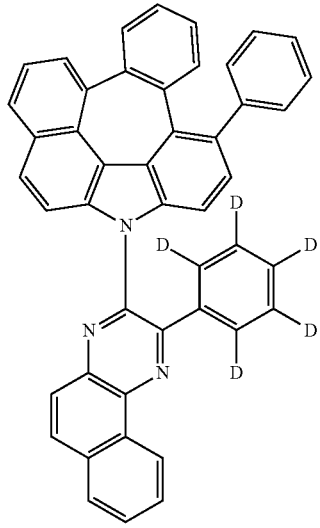
C-412
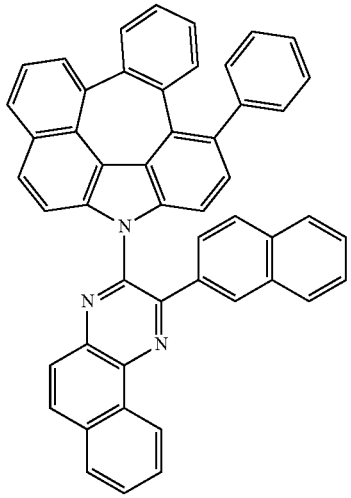
C-413
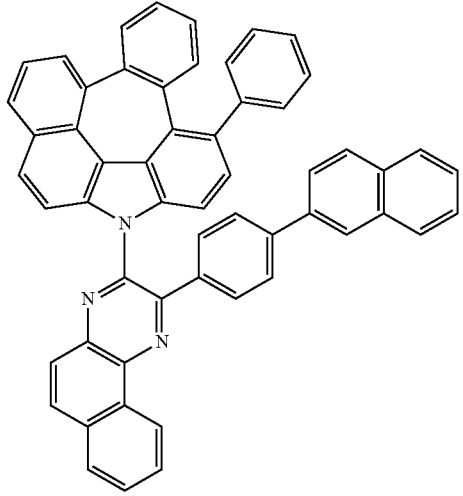

C-414
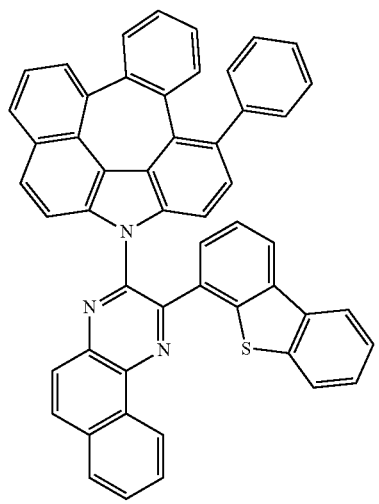
C-415
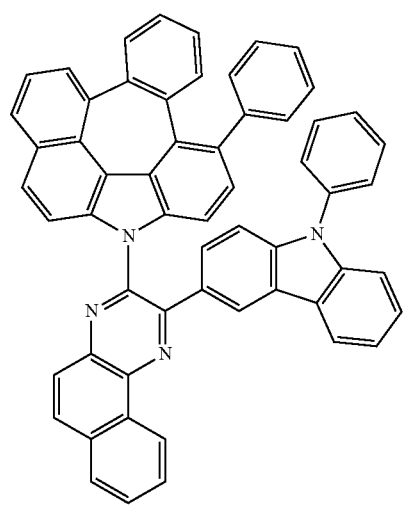
C-416
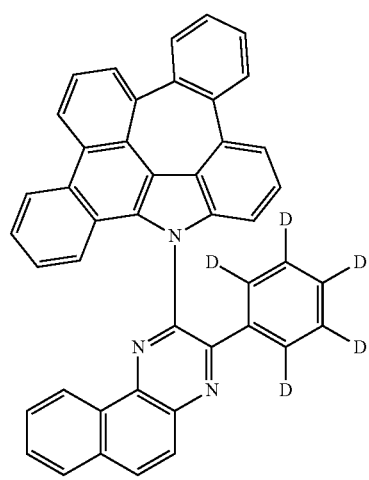
C-417
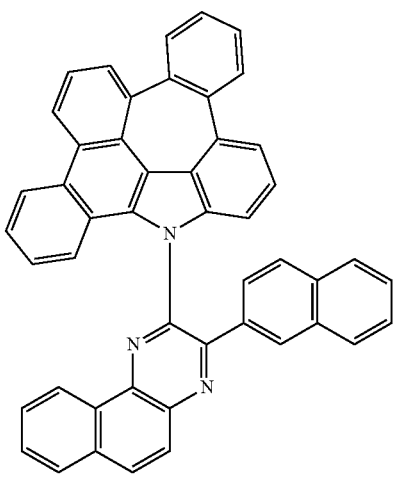
C-418
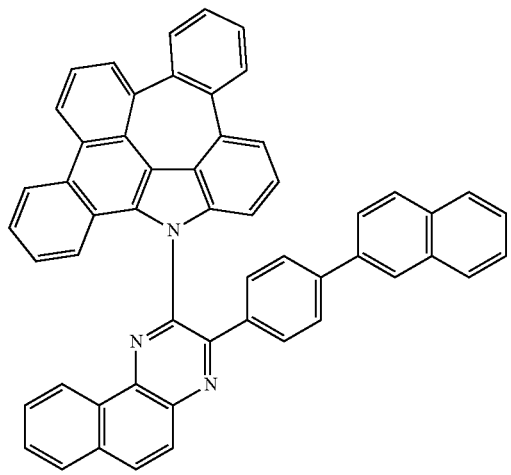
C-419
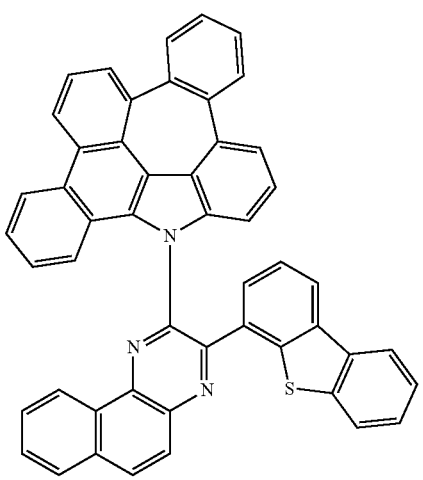

C-420
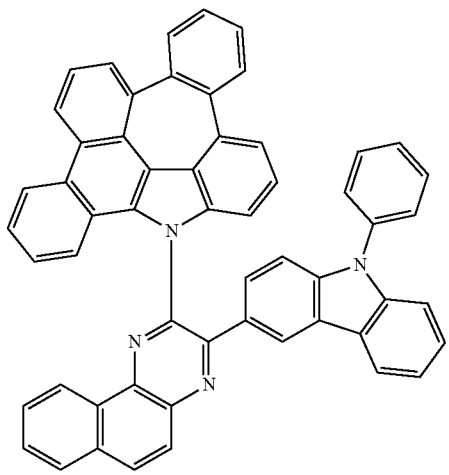
C-421
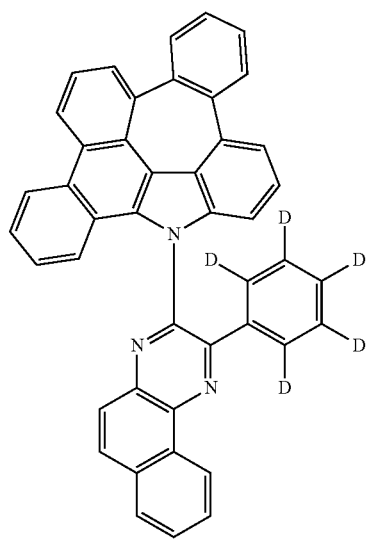
C-422
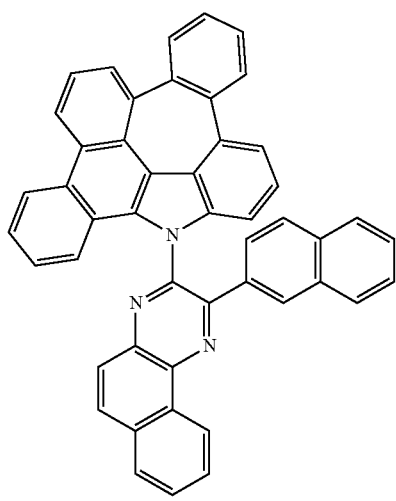
C-423
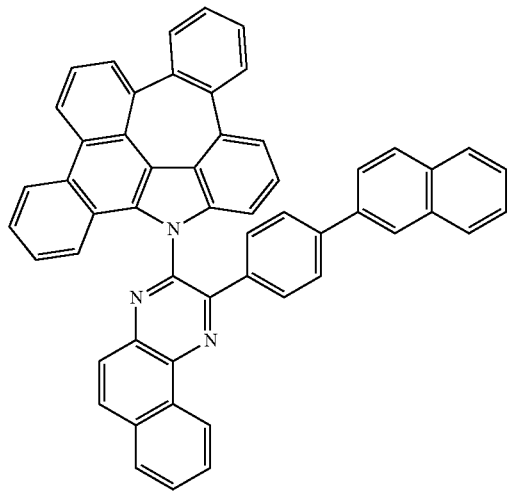
C-424
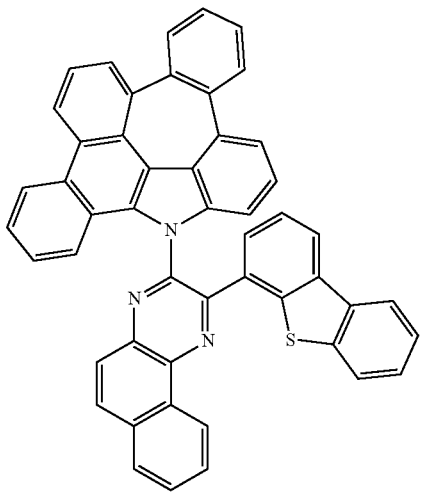
C-425
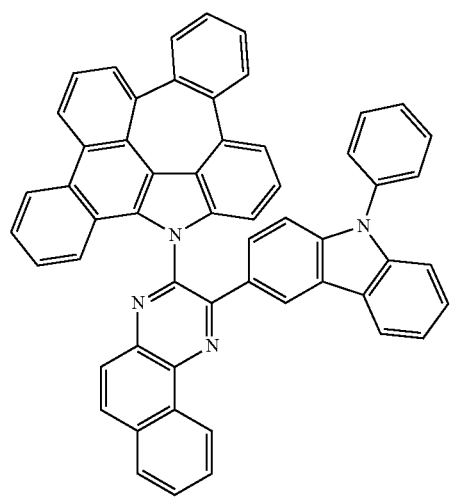

C-426
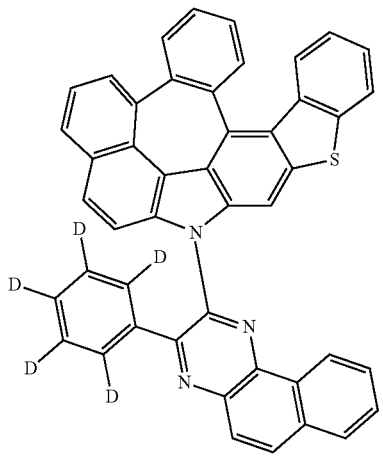
C-429
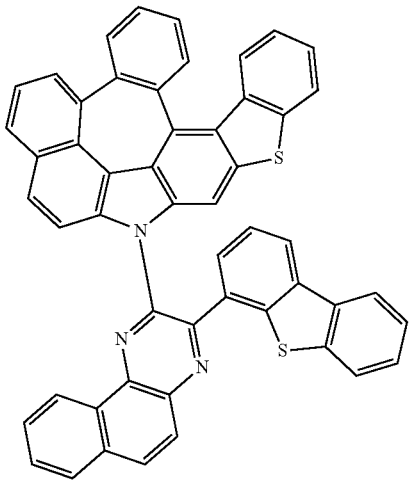
C-427
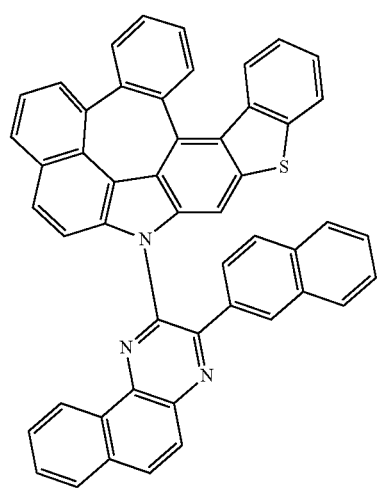
C-430
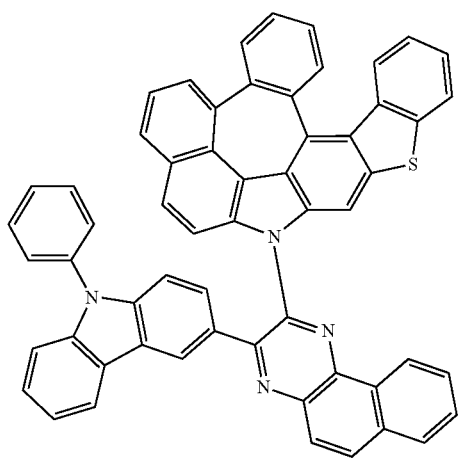
C-428
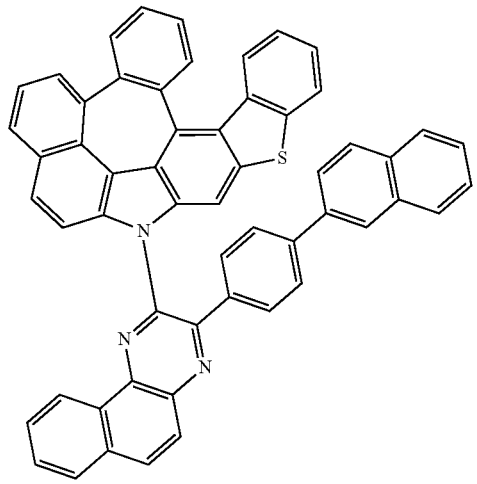
C-431
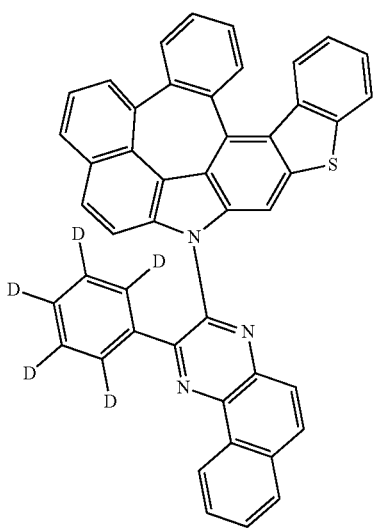

C-432
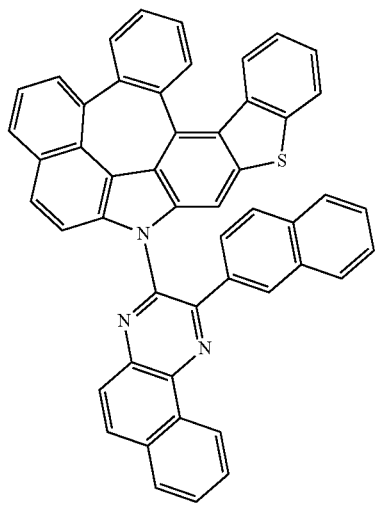
C-433
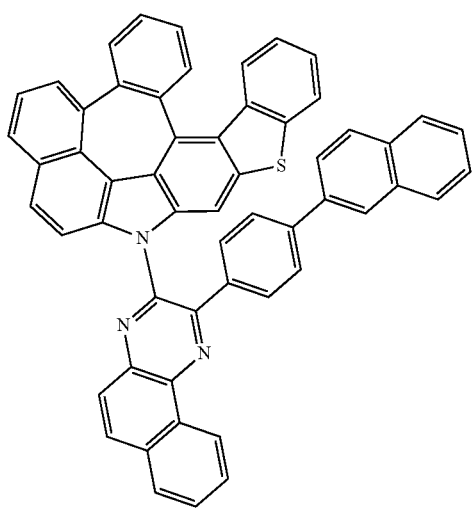
C-434
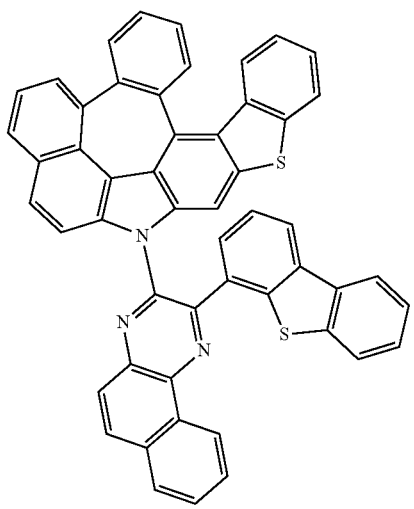
C-435
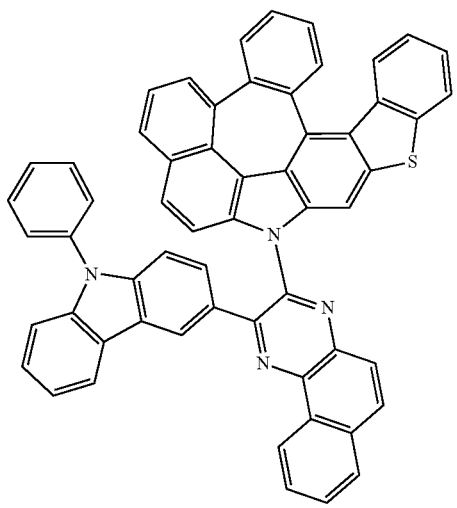
C-436
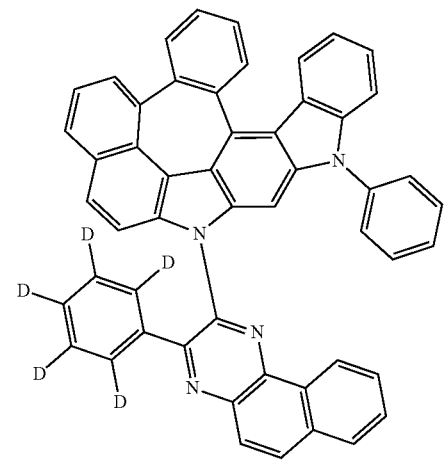
C-437
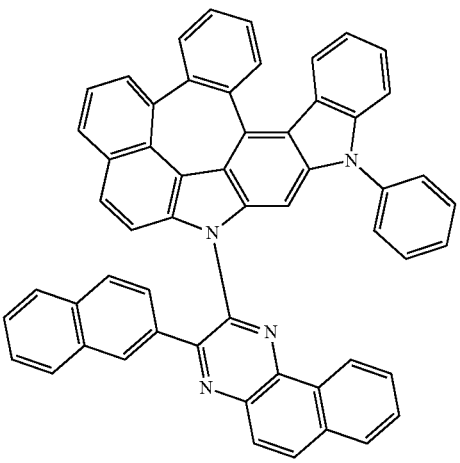

C-438
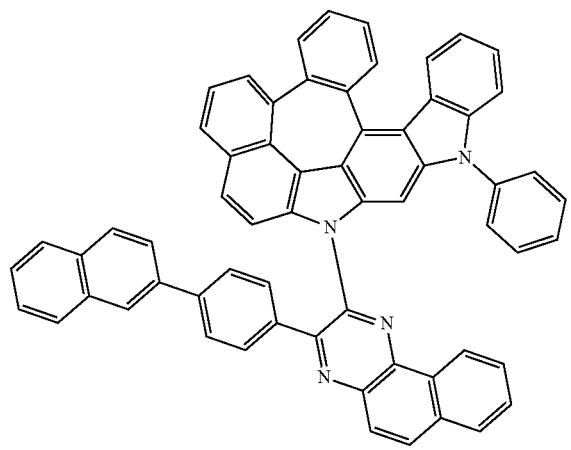
C-441
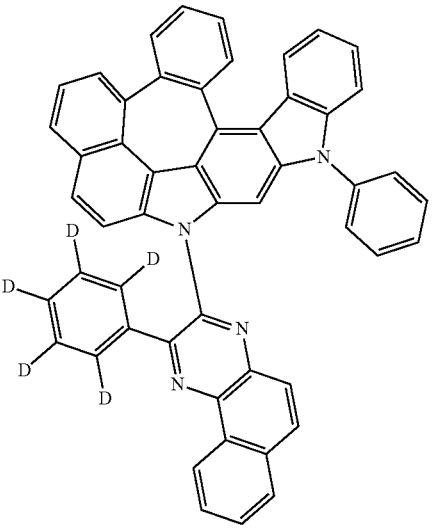
C-439
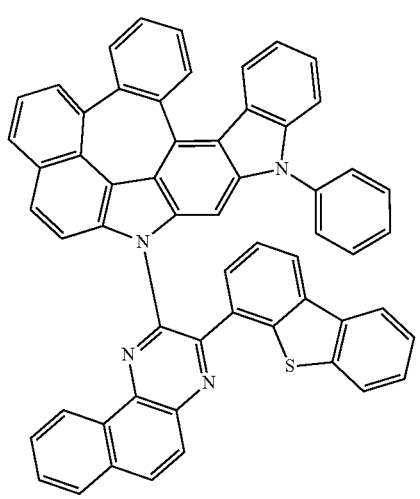
C-442
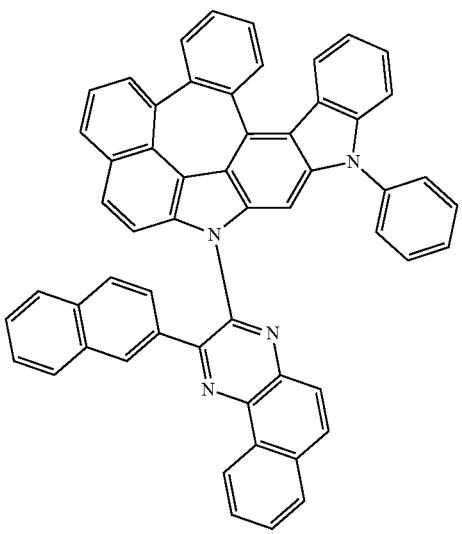
C-440
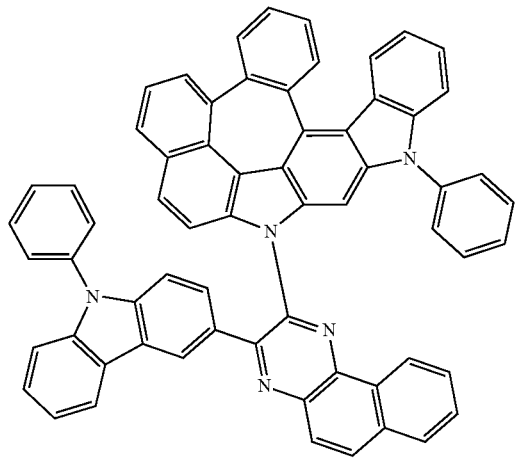
C-443
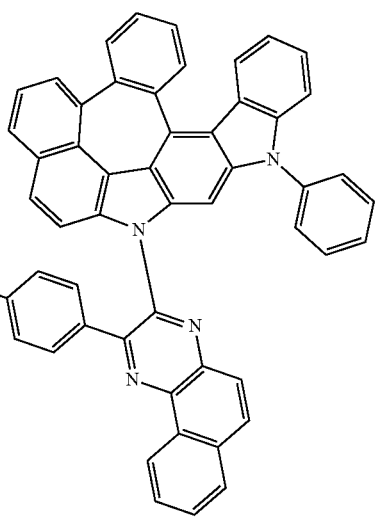

C-444
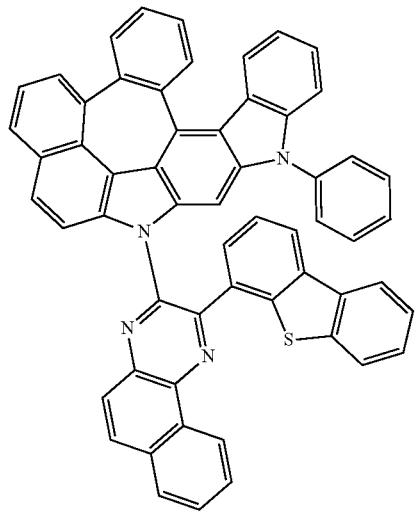
C-445
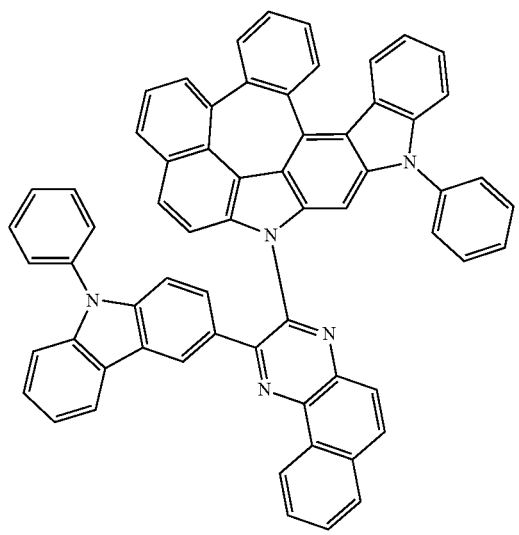
C-446
-continued
C-447
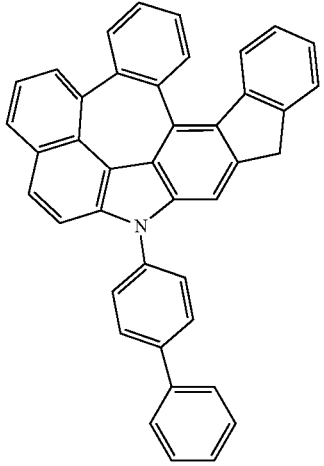
The compound of formula 1 according to the present disclosure may be produced by a synthetic method known to one skilled in the art, and for example, as shown in the following reaction schemes 1 to 7, but is not limited thereto.
[Reaction Scheme 1]
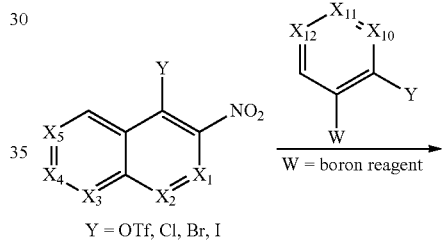
Y = OTf, Cl, Br, I
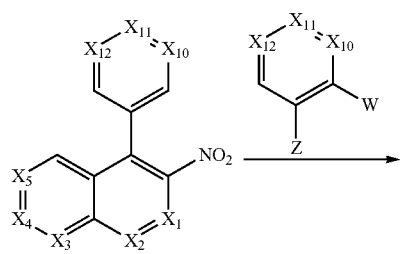
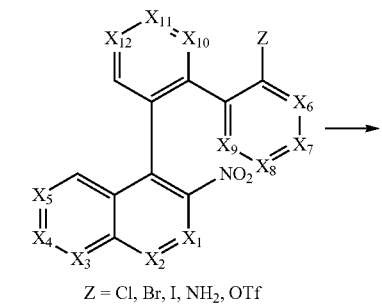
Z = Cl, Br, I, $NH_2$, OTf

169
-continued
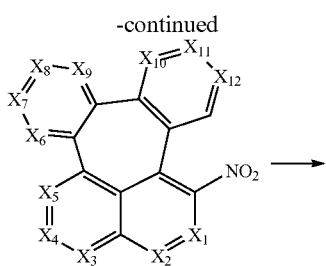
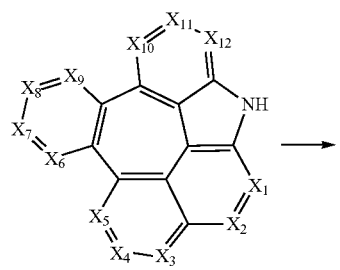
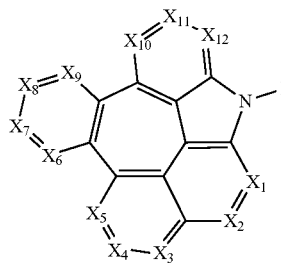
[Reaction Scheme 2]
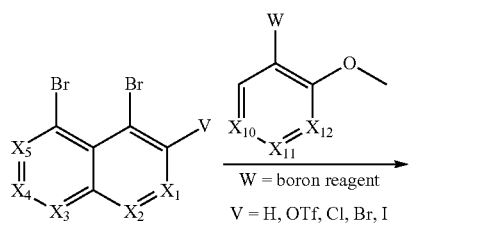
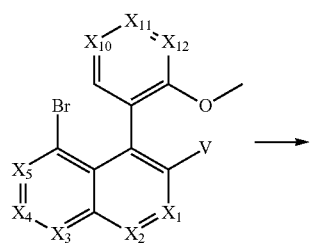
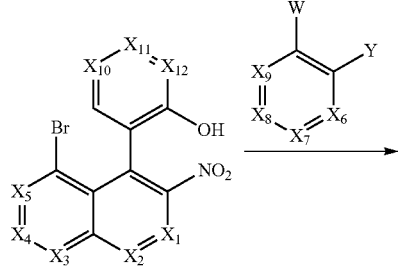
170
-continued
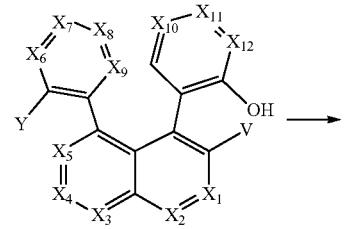
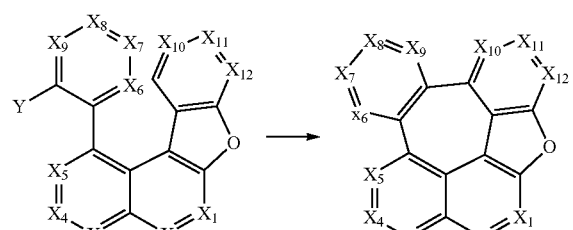
[Reaction Scheme 3]
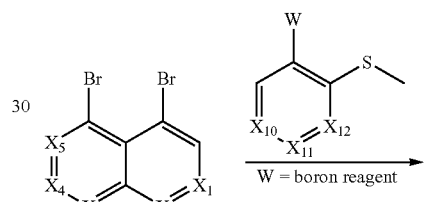
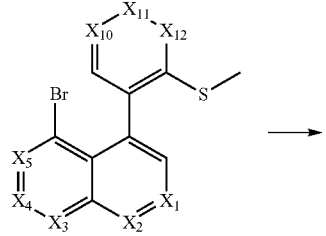
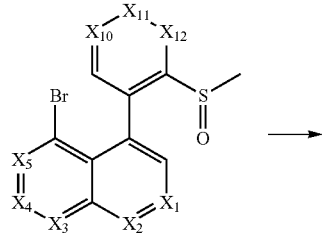
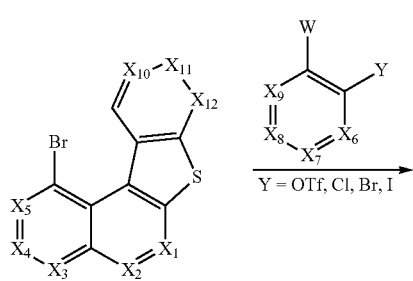

171
-continued
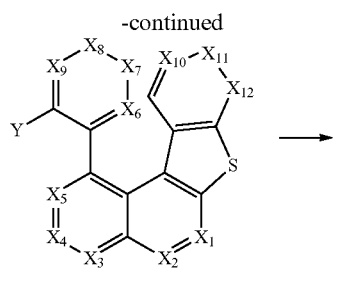
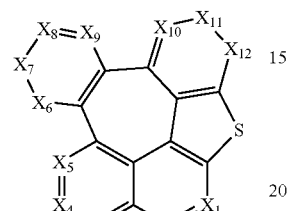
[Reaction Scheme 4]
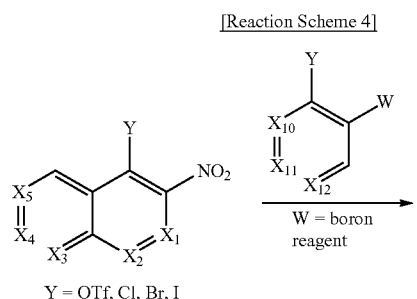
Y = OTf, Cl, Br, I     W = boron reagent
172
-continued
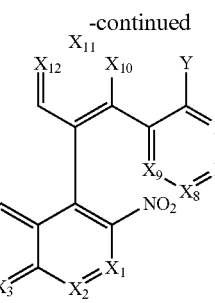
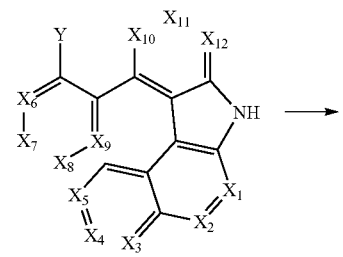
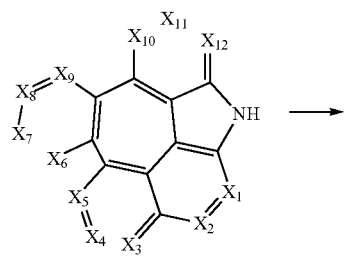
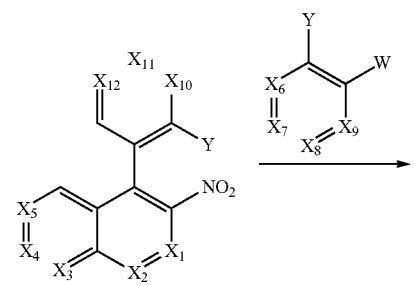
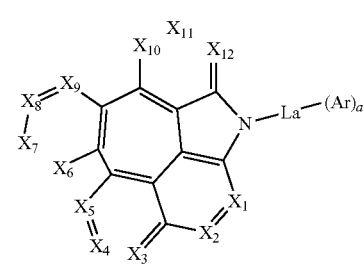
[Reaction Scheme 5]
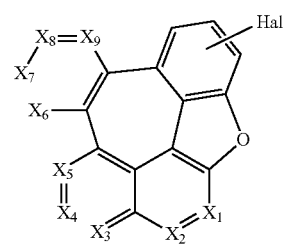
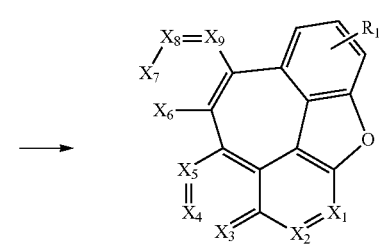

173
174
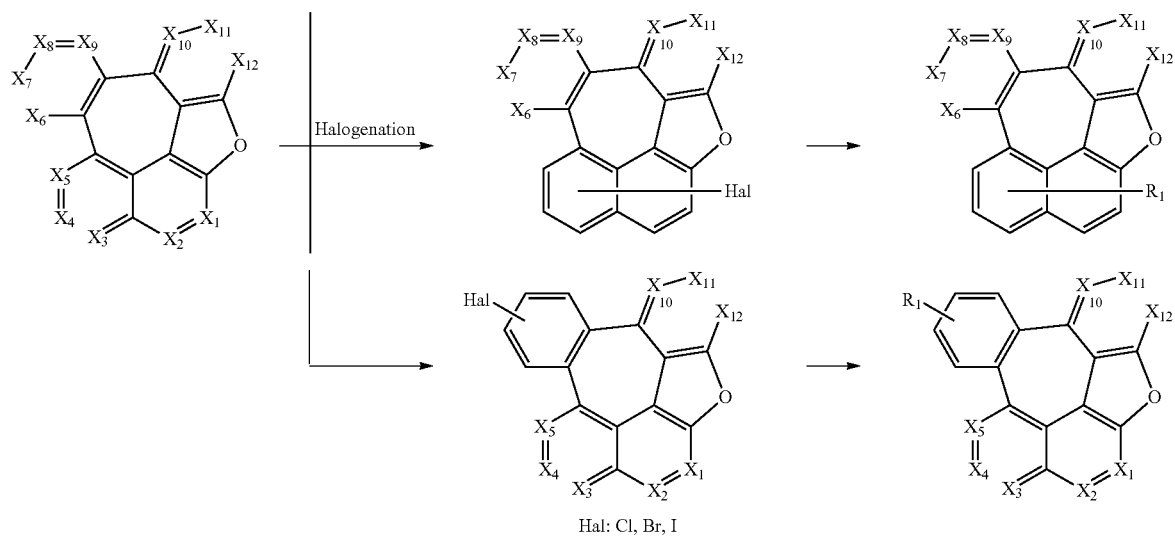
-continued
Hal: Cl, Br, I
[Reaction Scheme 6]
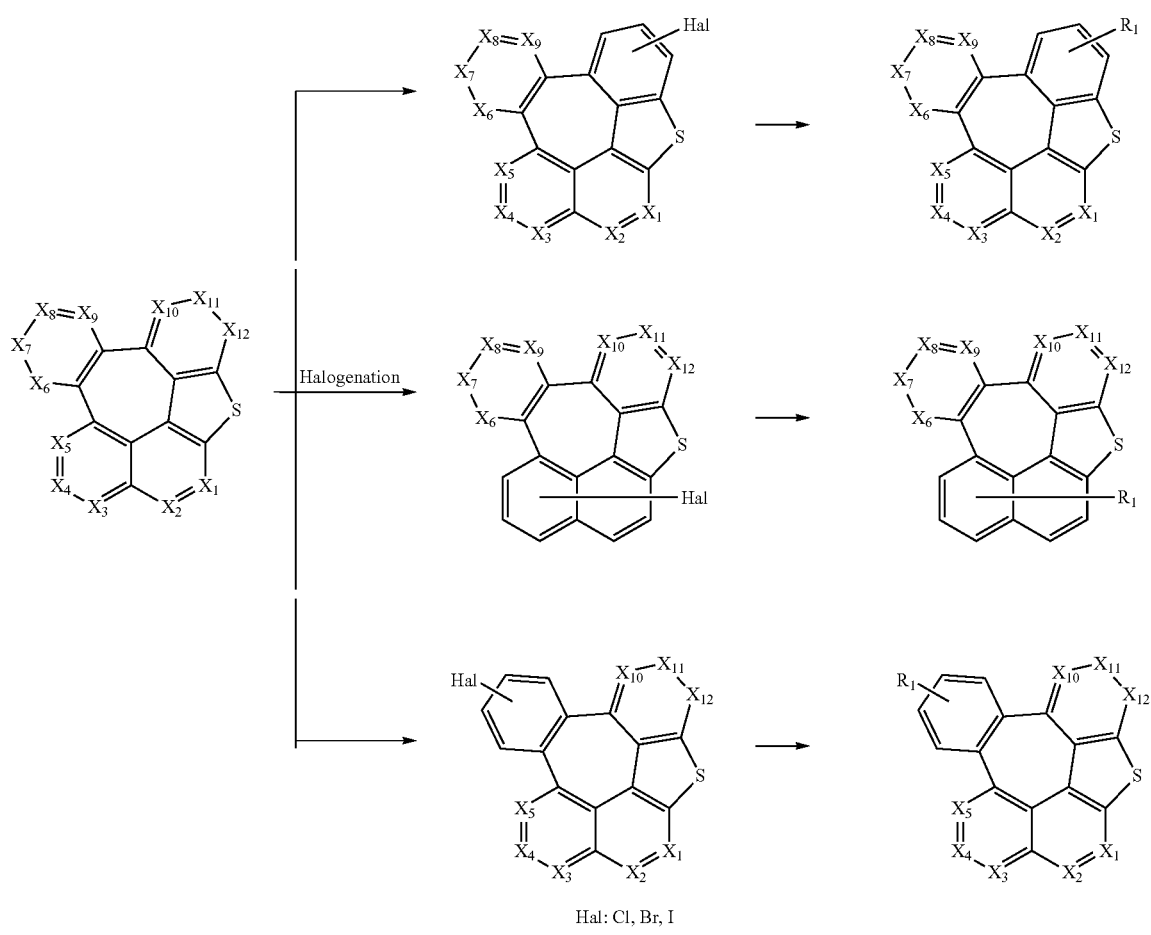
Hal: Cl, Br, I

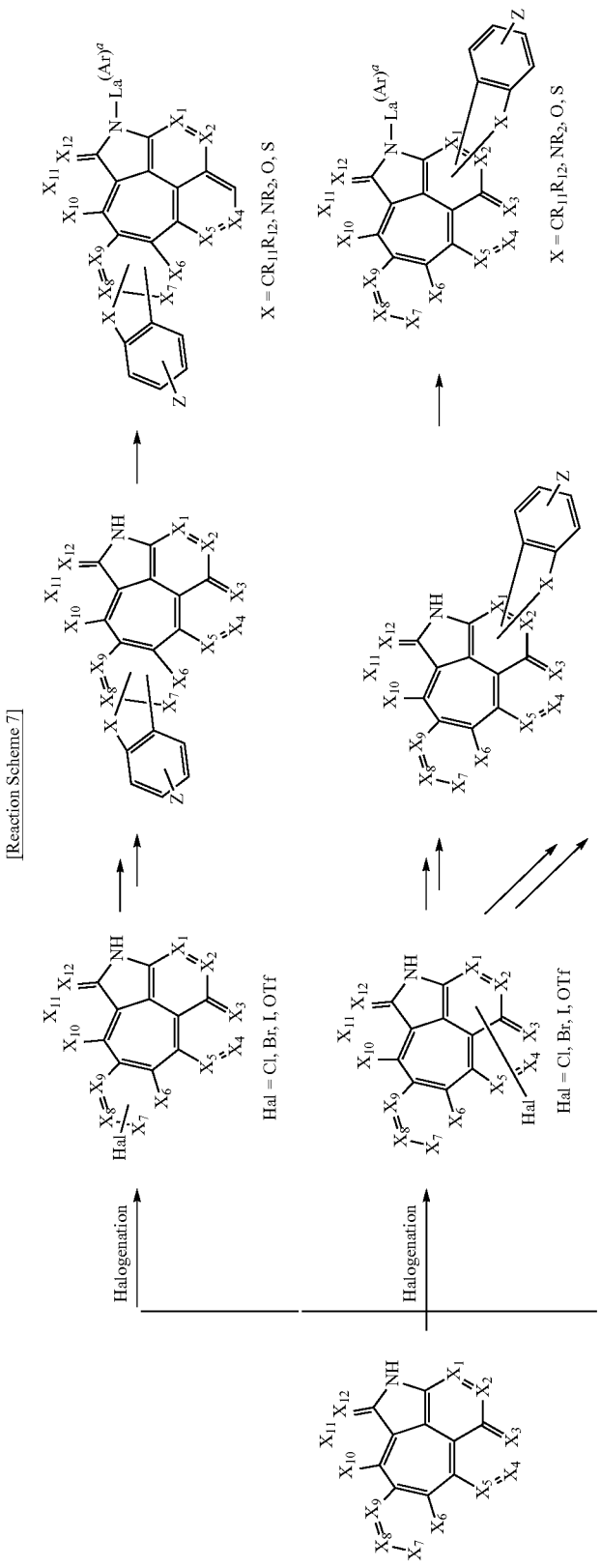
[Reaction Scheme 7]

-continued
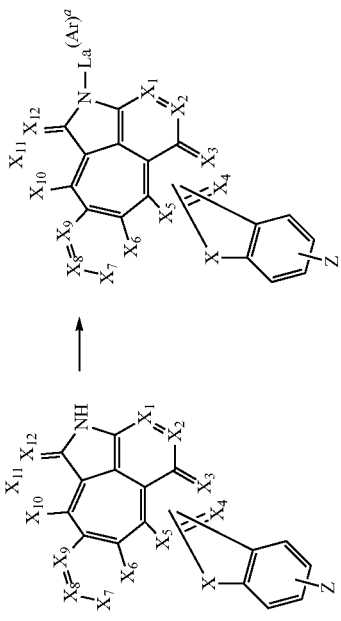
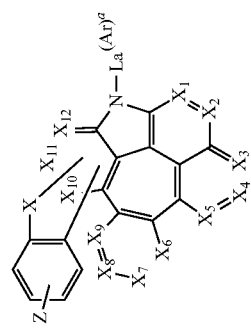
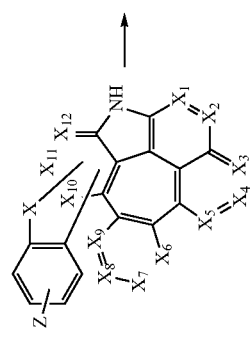
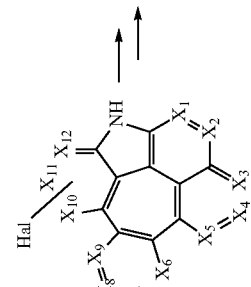

In reaction schemes 1 to 7, $X_1$ to $X_{12}$, $R_1$, La, Ar, and a are as defined in formula 1; $R_2$, $R_{11}$, and $R_{12}$ are as defined in formulas 5 and 6; Z is the same as defined for $R_1$; and OTf represents a trifluoromethanesulfonate.

The present disclosure may provide a composite material for an organic electroluminescent device, comprising the organic electroluminescent compound represented by formula 1, and further comprising at least one other organic electroluminescent compound. For example, the composite material for an organic electroluminescent device of the present disclosure may comprise at least one compound represented by formula 1, and at least one compound represented by the following formula 11:

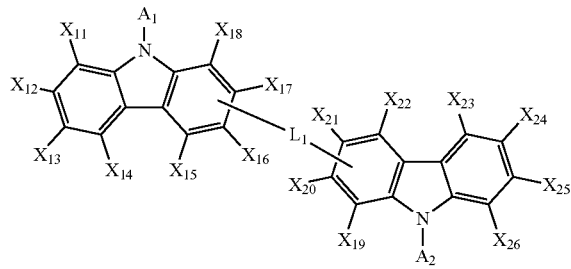
(11)

wherein $A_1$ and $A_2$, each independently, represent a substituted or unsubstituted (C6-C30)aryl;

$L_1$ represents a single bond, or a substituted or unsubstituted (C6-C30)arylene;

$X_{11}$ to $X_{26}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or are linked to an adjacent substituent to form a substituted or unsubstituted, mono- or polycyclic, (C3-C30) alicyclic or aromatic ring, or the combination thereof, wherein the carbon atom(s) of the alicyclic or aromatic ring, or the combination thereof may be replaced with at least one heteroatom selected from nitrogen, oxygen, and sulfur.

The compound represented by formula 11 may be represented by any one of the following formulas 12 to 15:

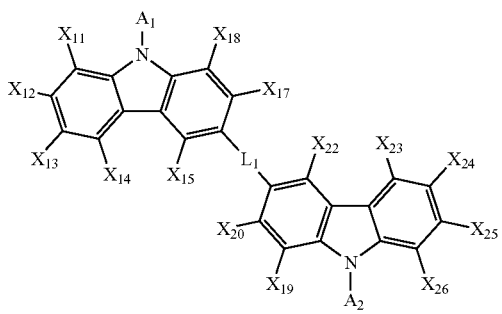
(12)

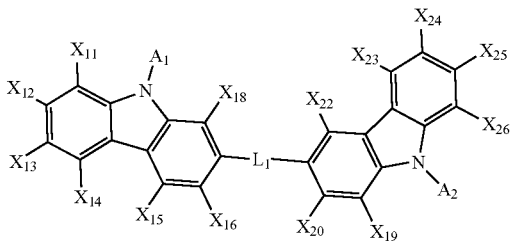
(13)

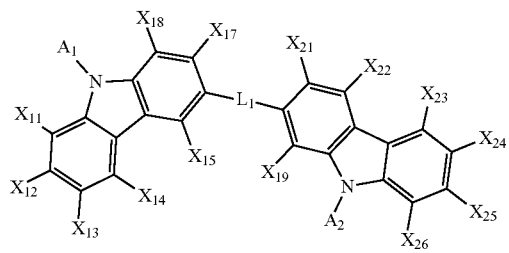
(14)

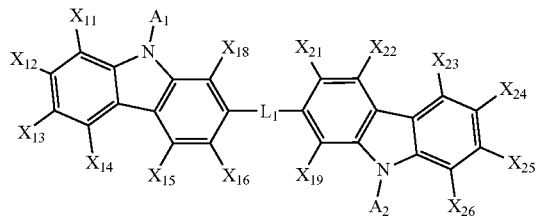
(15)

wherein, $A_1$, $A_2$, $L_1$, and $X_{11}$ to $X_{26}$ are as defined in formula 11.

In formulas 11 to 15, $A_1$ and $A_2$, each independently, represent, preferably, a substituted or unsubstituted (C6-C18)aryl; more preferably, a (C6-C18)aryl unsubstituted or substituted with a (C1-C6)alkyl, a (C6-C18)aryl, a (5- to 20-membered)heteroaryl, or tri(C6-C12)arylsilyl. Specifically, $A_1$ and $A_2$, each independently, may be selected from the group consisting of a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, and a substituted or unsubstituted fluoranthenyl.

In formulas 11 to 15, $L_1$ represents, preferably, a single bond, or a substituted or unsubstituted (C6-C18)arylene; more preferably, a single bond, or an unsubstituted (C6-C18)arylene. Specifically, $L_1$ may represent a single bond, a substituted or unsubstituted phenylene, a substituted or unsubstituted naphthylene, or a substituted or unsubstituted biphenylene.

In formulas 11 to 15, $X_{11}$ to $X_{26}$, each independently, represent, preferably, hydrogen, or a substituted or unsubstituted (5- to 20-membered)heteroaryl; or are linked to an adjacent substituent to form a substituted or unsubstituted, mono- or polycyclic, (C6-C12) alicyclic or aromatic ring; more preferably, hydrogen, or an unsubstituted (5- to 20-membered)heteroaryl; or are linked to an adjacent substituent to form an unsubstituted mono- or polycyclic (C6-C12) aromatic ring.

The compound represented by formula 11 includes the following compounds, but is not limited thereto.

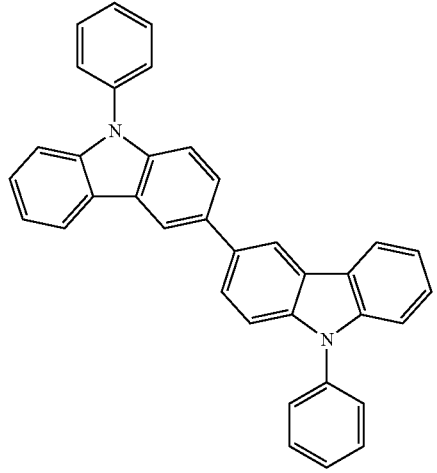

H2-1

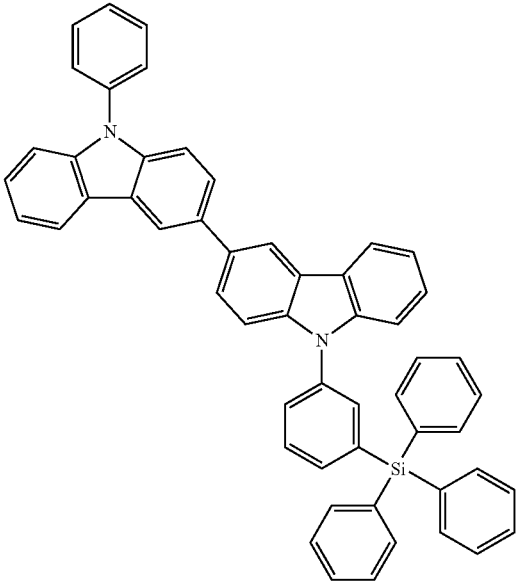

H2-3

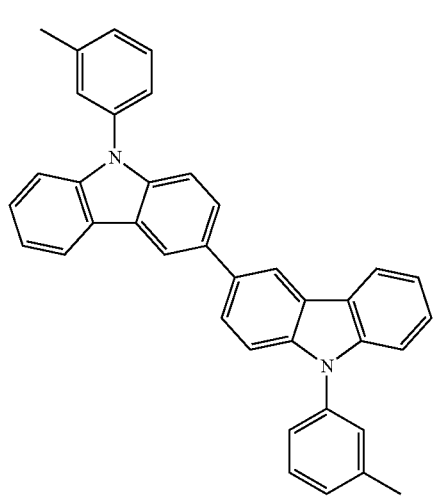

H2-2

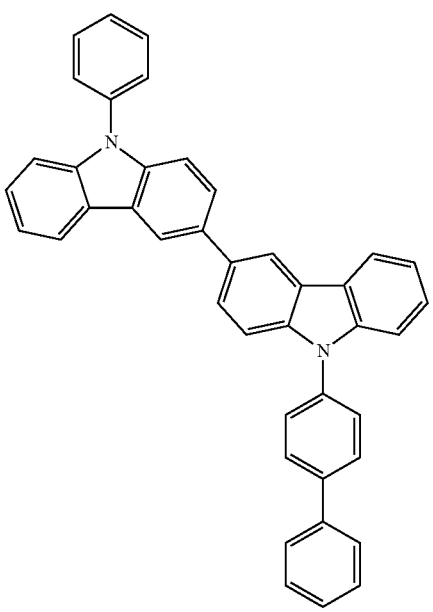

H2-4

H2-5
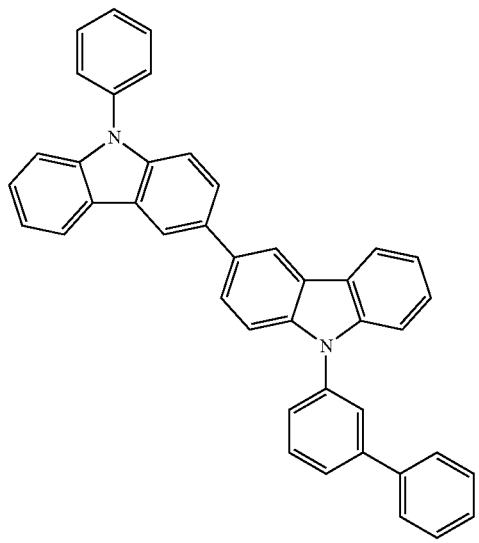
H2-6
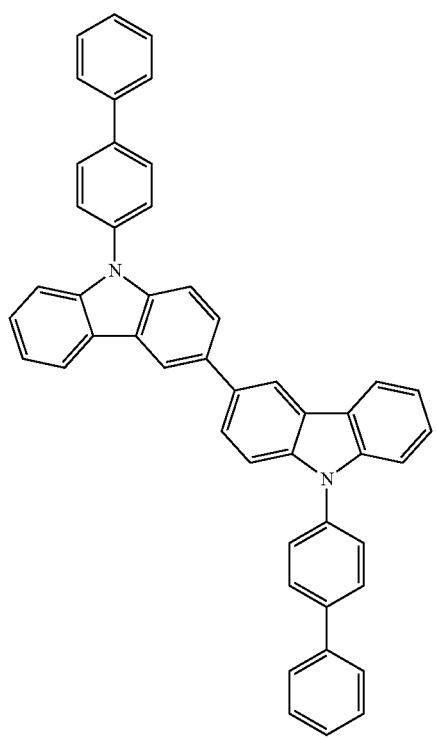
H2-7
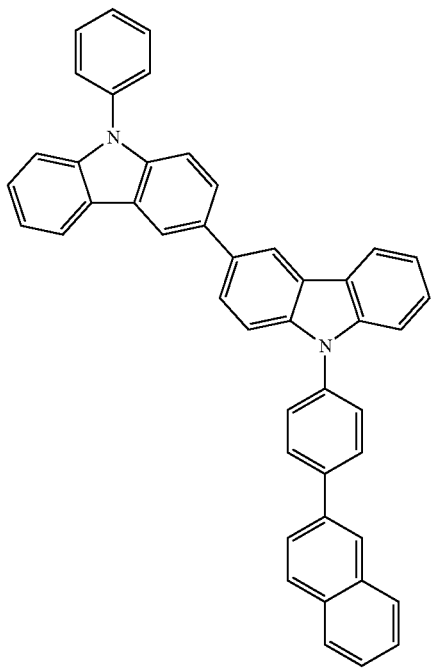
H2-8
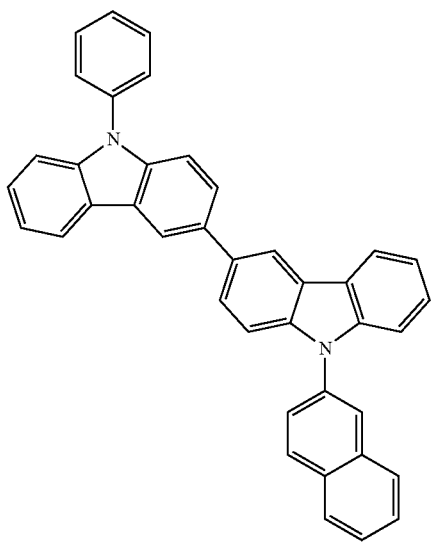

H2-9
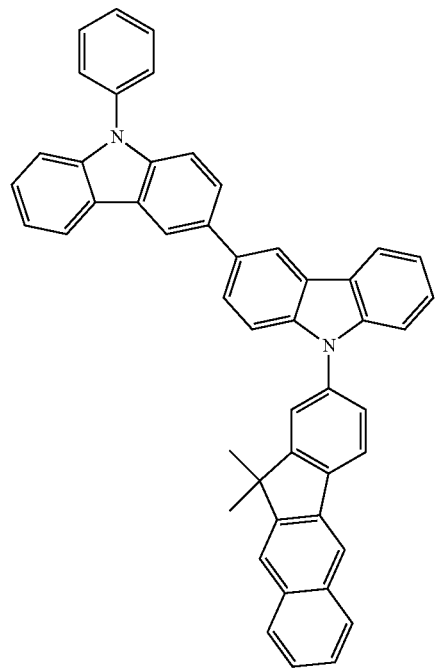
H2-10
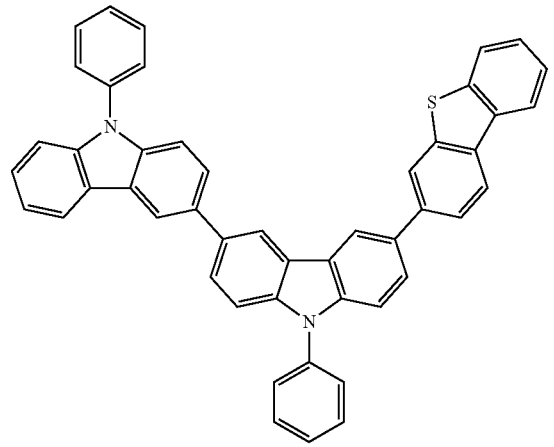
H2-11
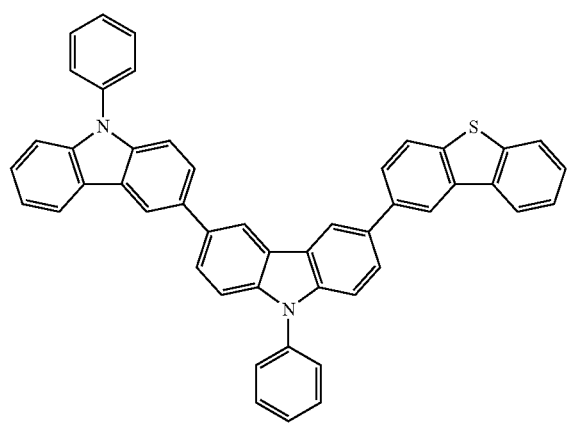
H2-12
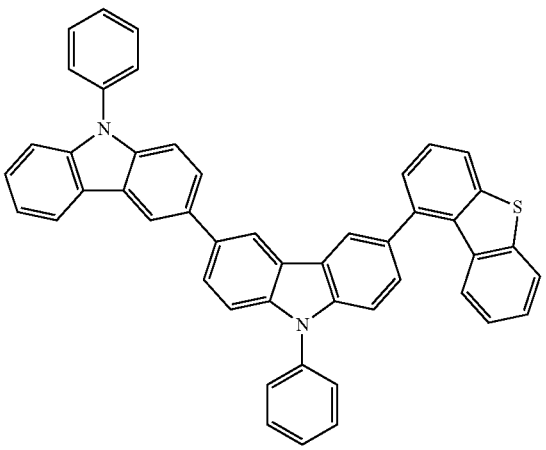
H2-13
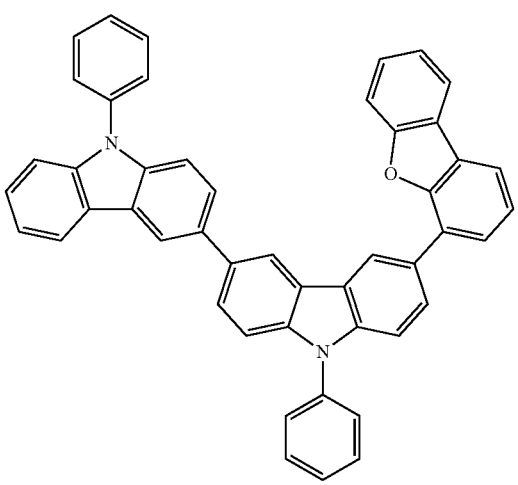
H2-14
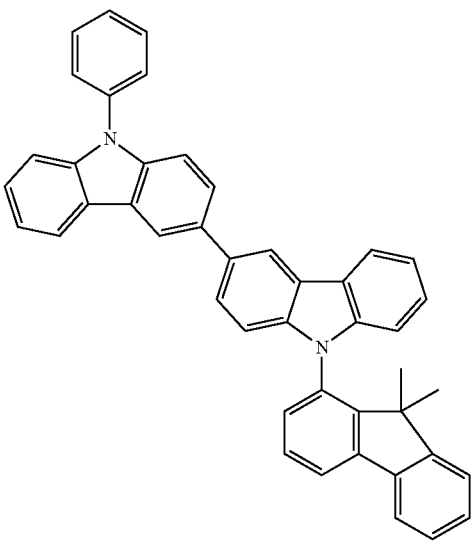

-continued
H2-15
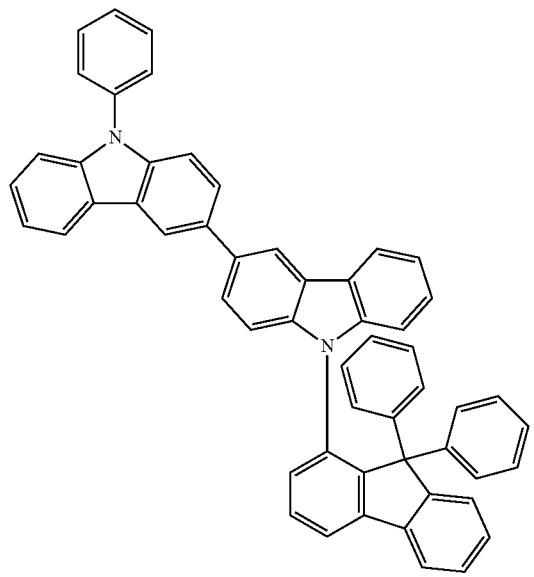
H2-16
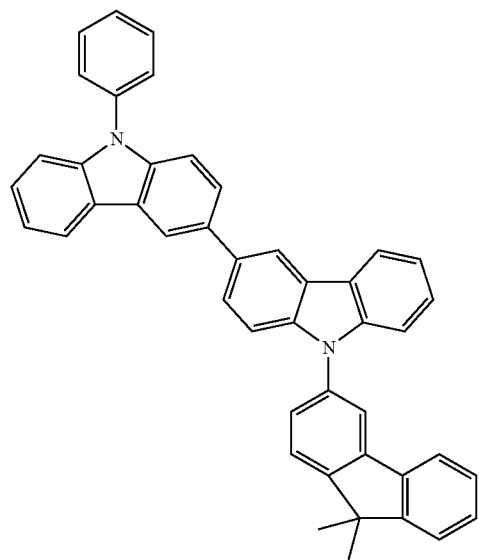
H2-17
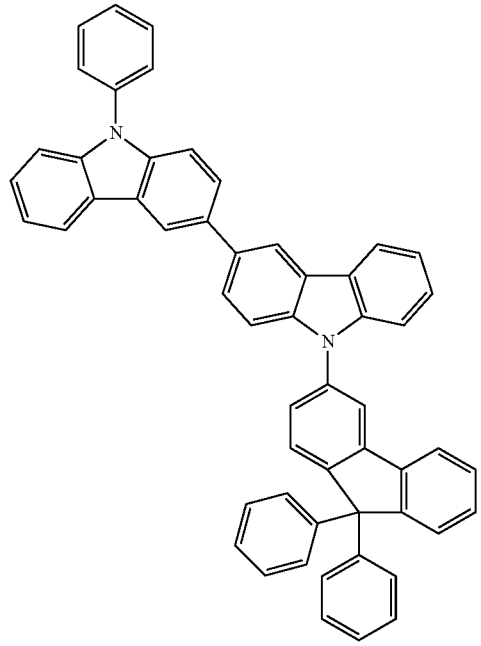
H2-18
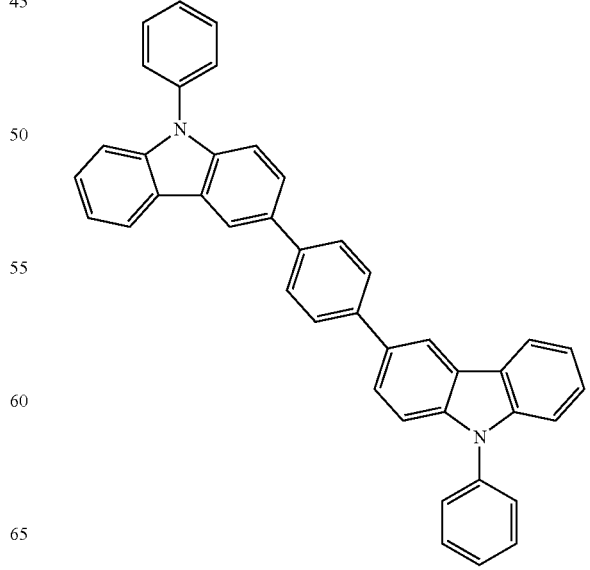

H2-19
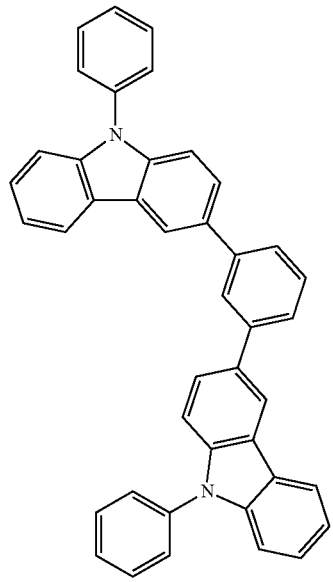
H2-20
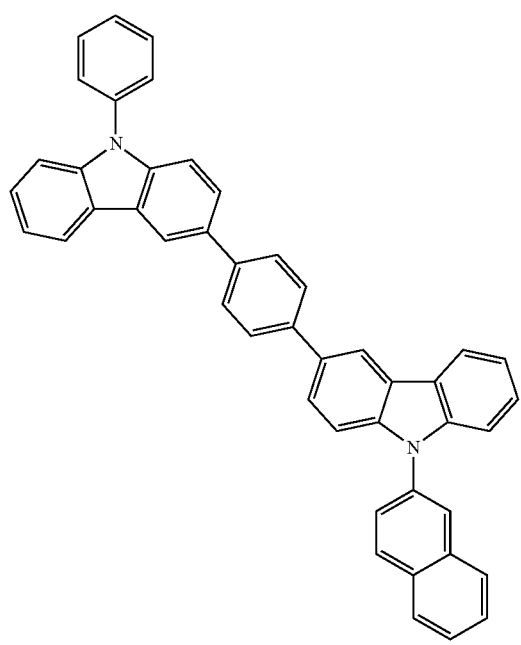
H2-21
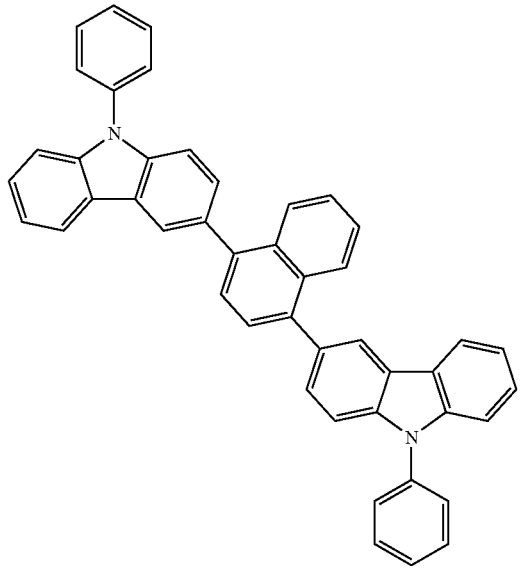
H2-22
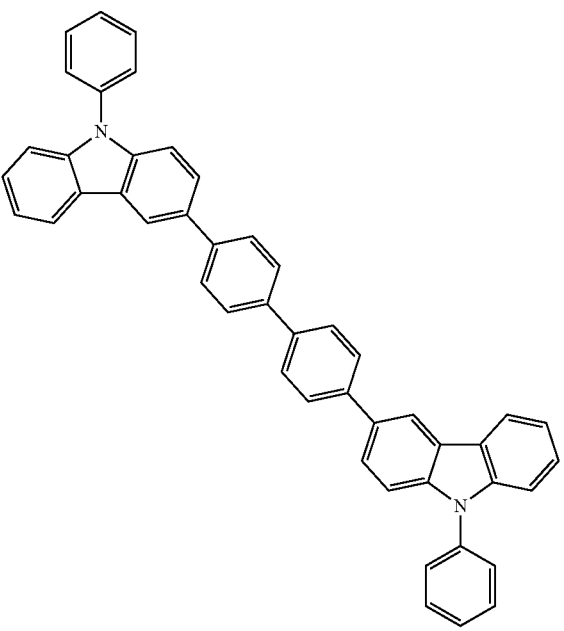

H2-23
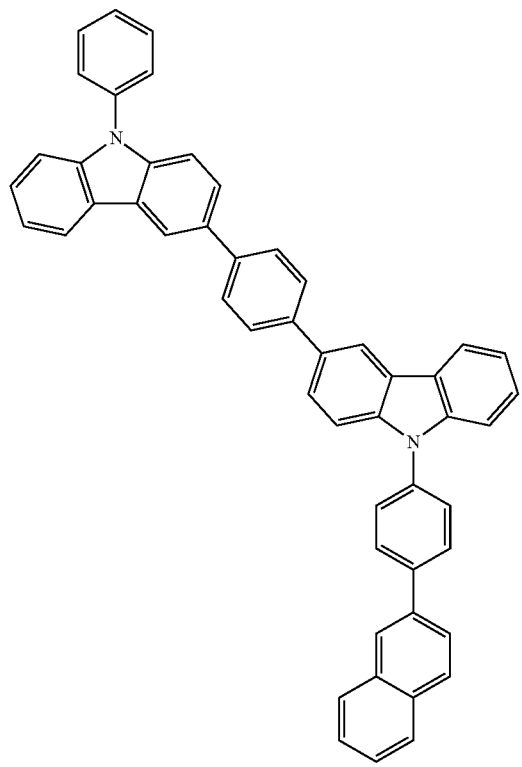
H2-24
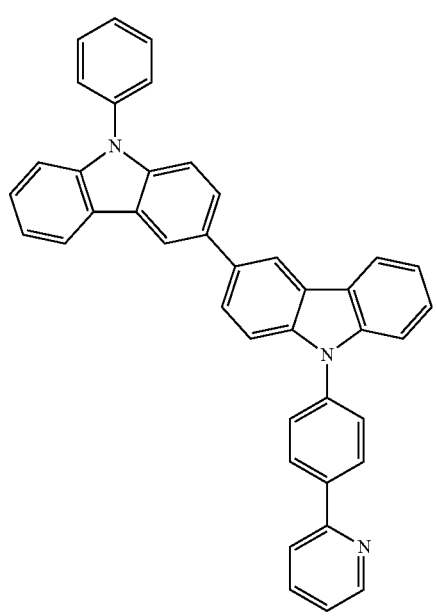
H2-25
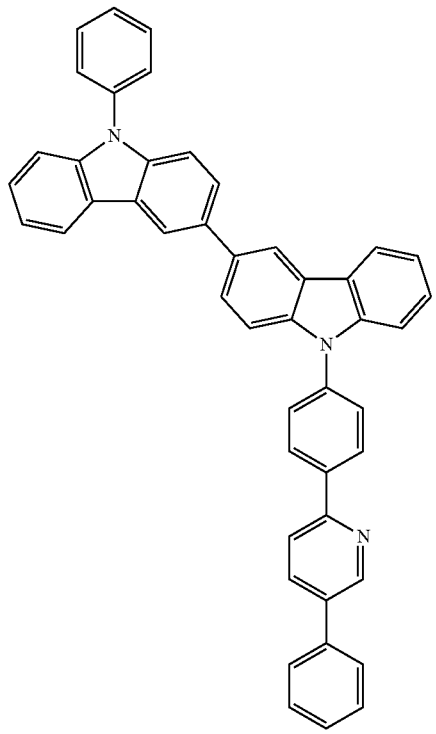
H2-26
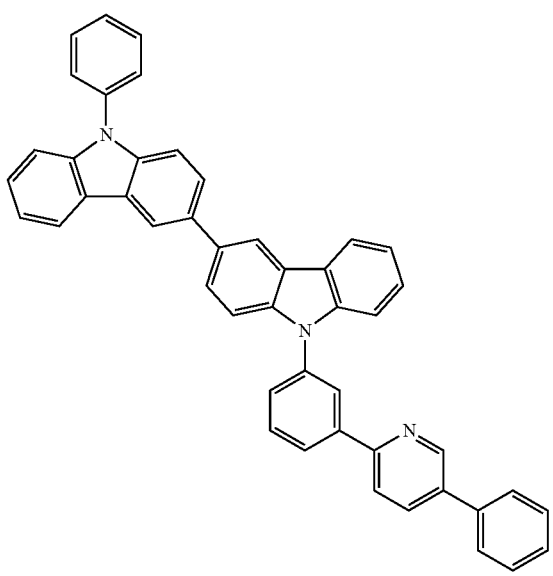

H2-27
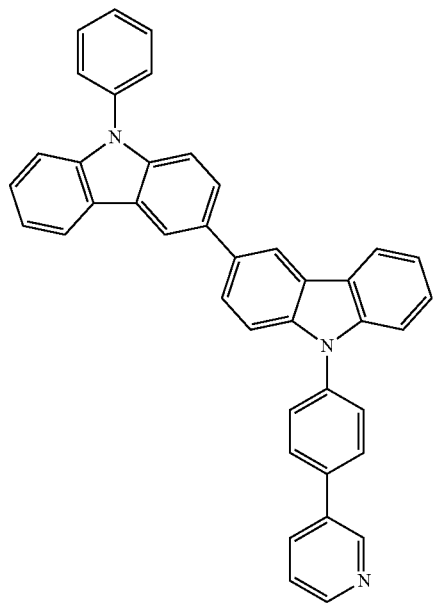
H2-28
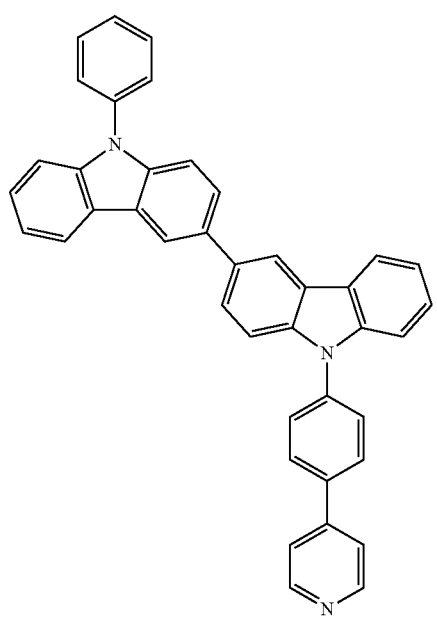
H2-29
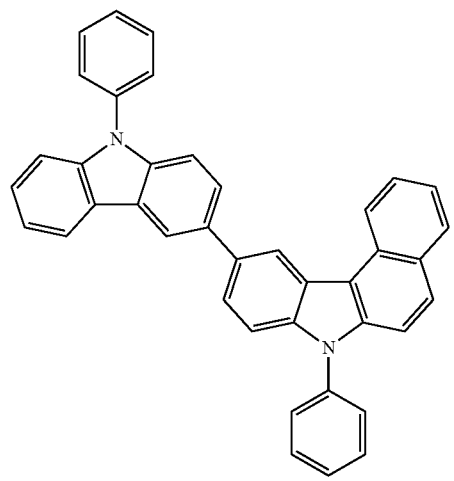
H2-30
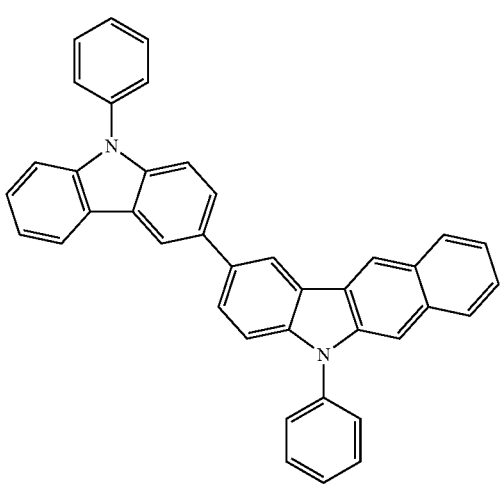
H2-31
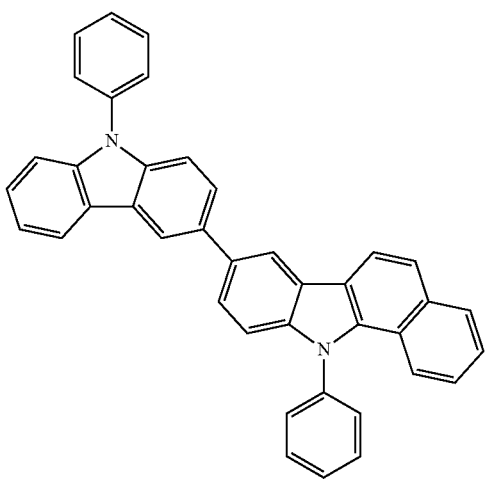

H2-32

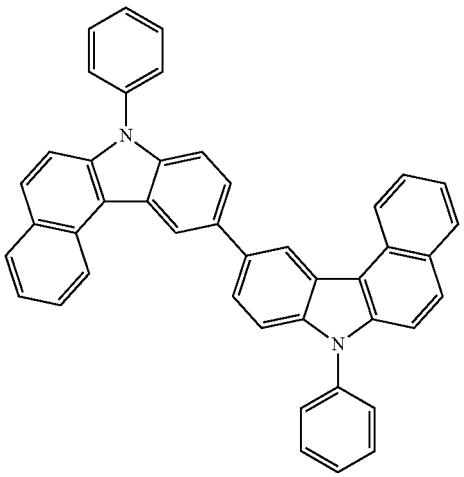

H2-33

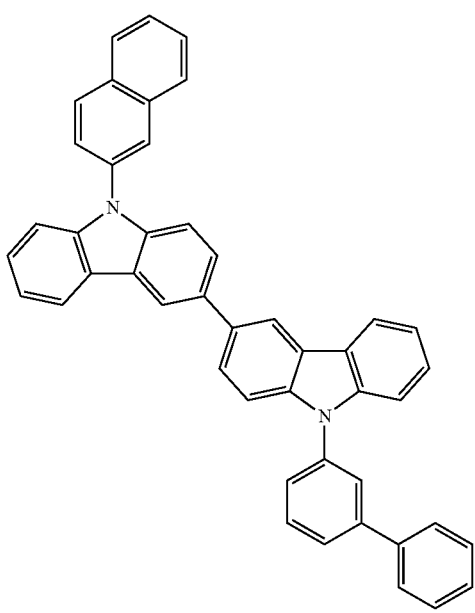

H2-34

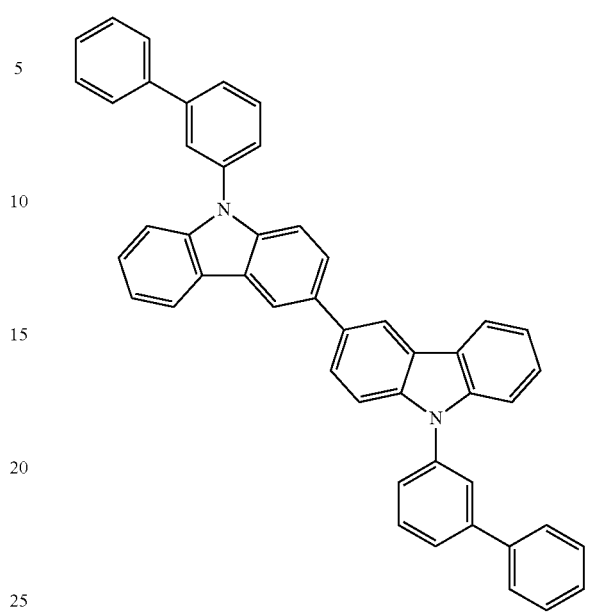

According to one embodiment of the present disclosure, in the materials included in the composite material for an organic electroluminescent device, the compound represented by formula 1 may be a first host material, and the compound represented by formula 11 may be a second host material. Herein, the first and second host materials may be comprised in one light-emitting layer, or may be comprised in different ones of the plurality of light-emitting layers, separately. The composite material for an organic electroluminescent device of the present disclosure may comprise the compound represented by formula 1 to the compound represented by formula 11 in a ratio of 1:99 to 99:1, preferably 10:90 to 90:10, more preferably 30:70 to 70:30. Also, the compound represented by the formula 1 and the compound represented by formula 11 may be mixed in an amount of a desired ratio by mixing them in a shaker, by placing them in a glass tube and dissolving them with heat and thereafter collecting them, or by dissolving them in a solvent.

The present disclosure may provide an organic electroluminescent device comprising the compound represented by formula 1, or the composite material for an organic electroluminescent device according to one embodiment of the present disclosure. Specifically, the organic electroluminescent device may comprise a compound represented by formula 1, and may further comprise at least one other organic electroluminescent compound. For example, the organic electroluminescent device may comprise at least one compound represented by formula 1, and at least one compound represented by formula 11.

In addition, the present disclosure may provide an organic electroluminescent material comprising the organic electroluminescent compound of formula 1, and an organic electroluminescent device comprising the material. The organic electroluminescent material may consist of the organic electroluminescent compound of the present disclosure as a sole compound, or may further comprise conventional materials generally used in organic electroluminescent materials.

Meanwhile, the organic electroluminescent device of the present disclosure may comprise a first electrode, a second electrode, and at least one organic layer between the first and second electrodes. The organic layer may comprise at least one organic electroluminescent compound of formula 1. The organic layer may further comprise at least one compound selected from the group consisting of arylamine-based compounds and styrylarylamine-based compounds. Also, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

The present disclosure may comprise a hole transport zone between an anode and a light-emitting layer, and the hole transport zone may comprise at least one of a hole injection layer, a hole transport layer, a hole auxiliary layer, a light-emitting auxiliary layer and an electron blocking layer. The hole injection layer, the hole transport layer, the hole auxiliary layer, the light-emitting auxiliary layer and the electron blocking layer, respectively, may be a single layer or a plurality of layers in which two or more layers are stacked. The hole injection layer may be multi-layers in order to lower the hole injection barrier (or hole injection voltage) from the anode to the hole transport layer or the electron blocking layer, wherein each of the multi-layers may use two compounds simultaneously. The electron blocking layer may be placed between the hole transport layer (or the hole injection layer) and the light-emitting layer, and can confine the excitons within the light-emitting layer by blocking the overflow of electrons from the light-emitting layer to prevent a light-emitting leakage.

In addition, the hole transport zone may comprise a p-doped hole injection layer, a hole transporting layer, and a light-emitting auxiliary layer. Herein, the p-doped hole injection layer means a hole injection layer doped with a p-dopant. The p-dopant is a material capable of imparting p-type semiconductor properties. The p-type semiconductor properties mean the properties of injecting or transporting holes at the HOMO energy level, i.e., the properties of a material having a high hole conductivity.

The present disclosure may comprise an electron transport zone between the light-emitting layer and the cathode. The electron transport zone may comprise at least one of a hole blocking layer, an electron transport layer, an electron buffer layer and an electron injection layer. The hole blocking layer, the electron transport layer, the electron buffer layer, and the electron injection layer, respectively, may be a single layer or a plurality of layers in which two or more layers are stacked. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifespan of the organic electroluminescent device.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The operation stability for the organic electroluminescent device may be obtained by the surface layer. Preferably, the chalcogenide includes $SiO_X(1 \leq X \leq 2)$, $AlO_X(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent compound represented by formula 1 may be comprised in the light-emitting layer. When used in the light-emitting layer, the organic electroluminescent compound of formula 1 may be comprised as a host material. Preferably, the light-emitting layer may further comprise at least one dopant. If necessary, another compound besides the organic electroluminescent compound of formula 1 may be further comprised as a second host material. Herein, the weight ratio of the first host material to the second host material is in the range of 1:99 to 99:1.

The second host material can use any of the known phosphorescent hosts. In terms of luminous efficiency, the second host material may use preferably the compound represented by the formula 11, but is not limited thereto.

The dopant comprised in the organic electroluminescent device of the present disclosure may be at least one phosphorescent or fluorescent dopont, and is preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise the compound represented by the following formula 101, but is not limited thereto.

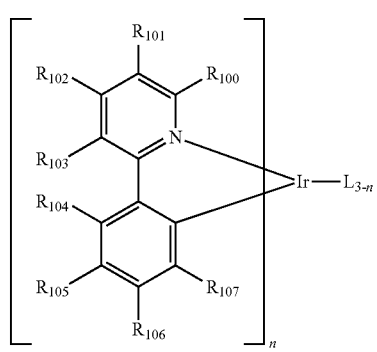

In formula 101, L is selected from the following structures 1 and 2:

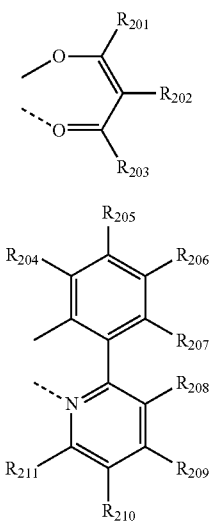

$R_{100}$ to $R_{103}$, and $R_{104}$ to $R_{107}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or $R_{100}$ to $R_{103}$ may be linked to adjacent $R_{100}$ to $R_{103}$, to form a substituted or unsubstituted fused ring, e.g., to form a substituted or unsubstituted, quinoline, benzofuropyridine, benzothienopyridine, indenopyridine, benzofuroquinoline, benzothienoquinoline or indenoquinoline ring; and $R_{104}$ to $R_{107}$ may be linked to adjacent $R_{104}$ to $R_{107}$ to form a substituted or unsubstituted fused ring, e.g., a substituted or unsubstituted, naphthyl, fluorene, dibenzothiophene, dibenzofuran, indenopyridine, benzofuropyridine or benzothienopyridine ring;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a substituted or unsubstituted (C6-C30)aryl; or may be linked to adjacent $R_{201}$ to $R_{211}$ to form a substituted or unsubstituted fused ring; and n represents an integer of 1 to 3.

The specific examples of the dopant compound are as follows, but are not limited thereto.

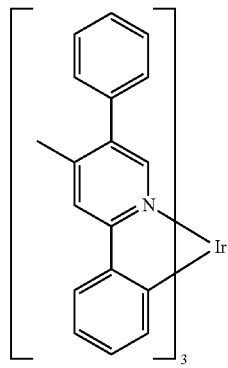

D-1

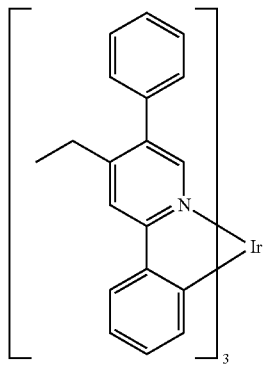

D-2

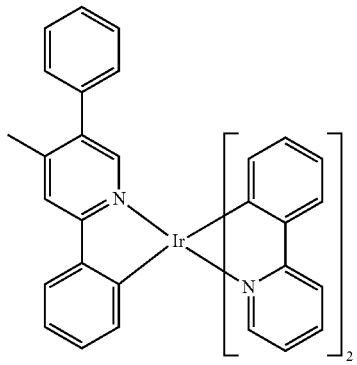

D-3

-continued
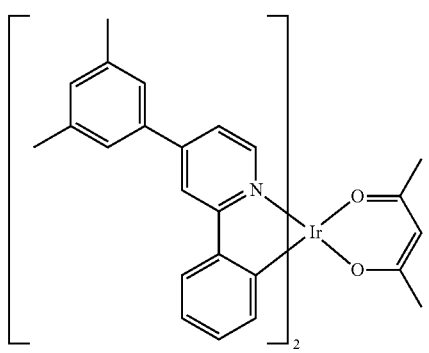
D-4
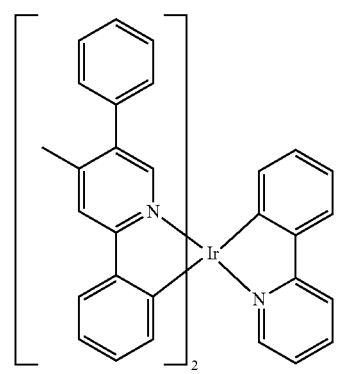
D-5
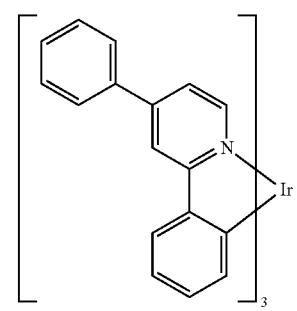
D-6
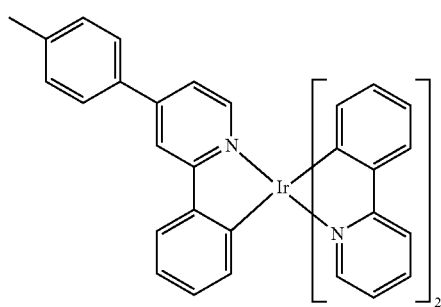
D-7
-continued
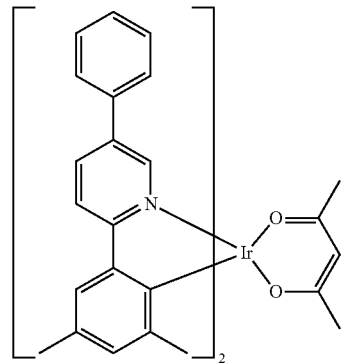
D-8
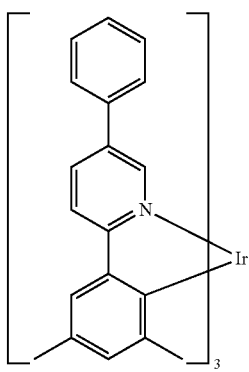
D-9
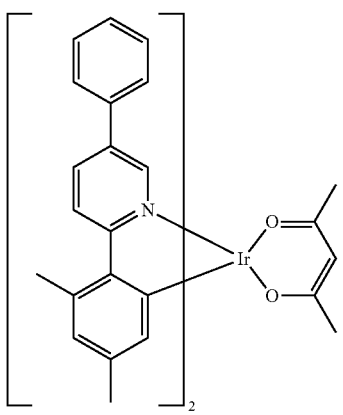
D-10
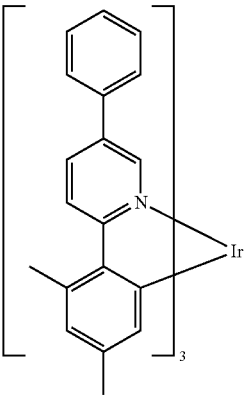
D-11

-continued
D-12
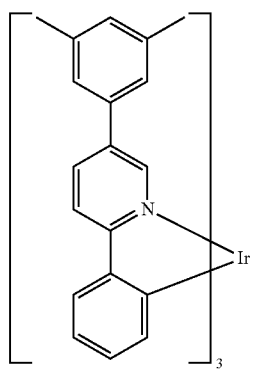
D-13
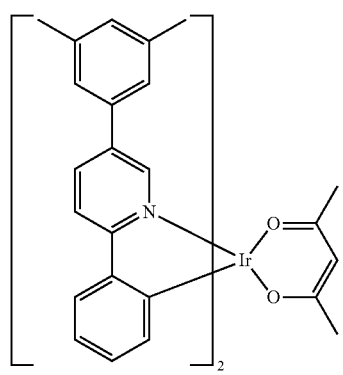
D-14
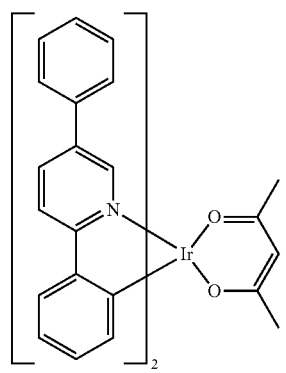
D-15
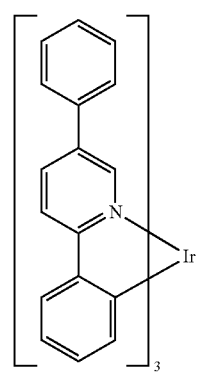
-continued
D-16
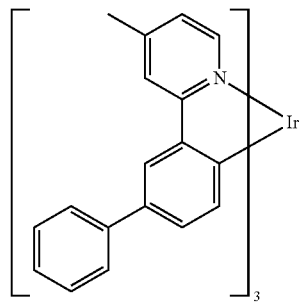
D-17
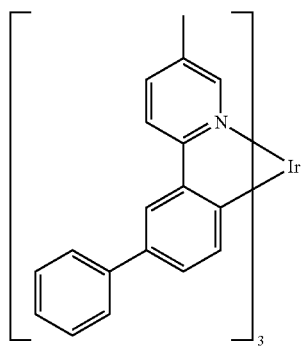
D-18
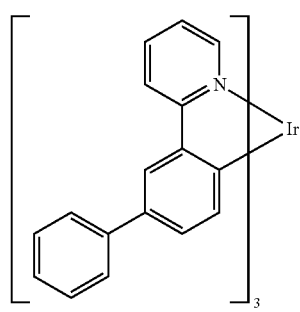
D-19
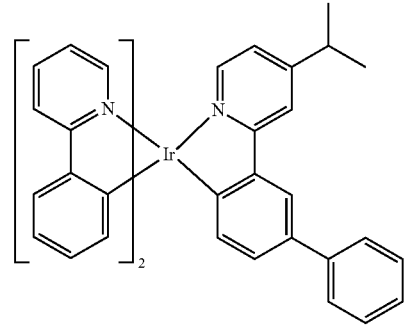
D-20
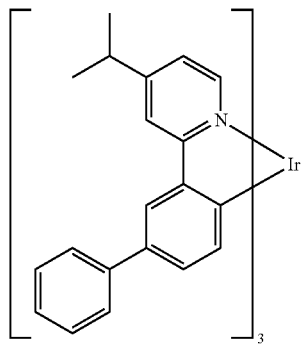

D-21 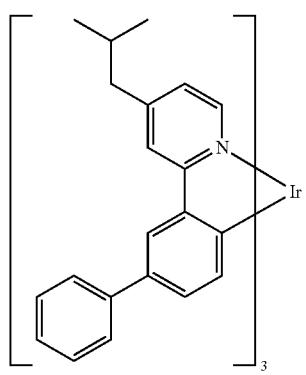
D-25 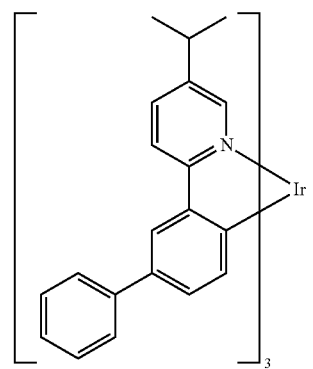
D-22
D-26 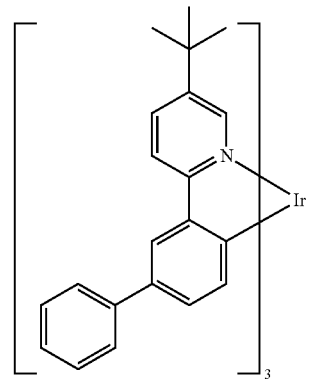
D-23
D-27 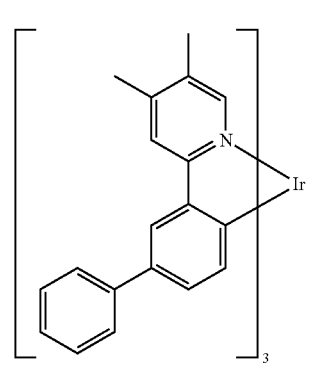
D-24
D-28 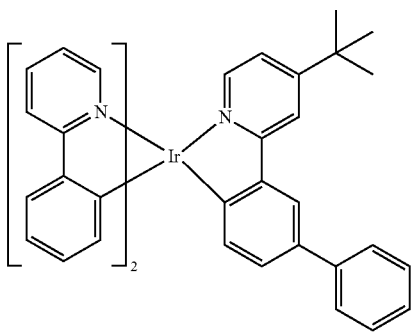

D-29 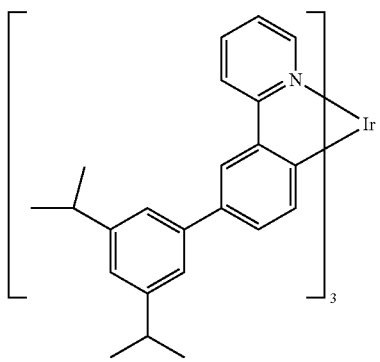
D-30 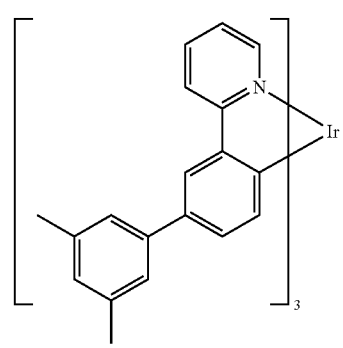
D-31 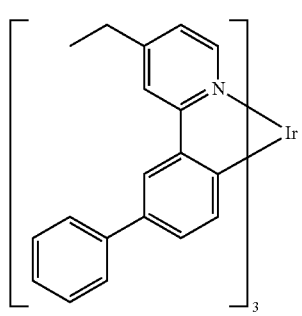
D-32 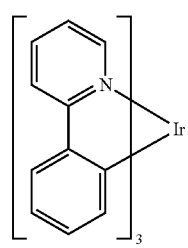
D-33 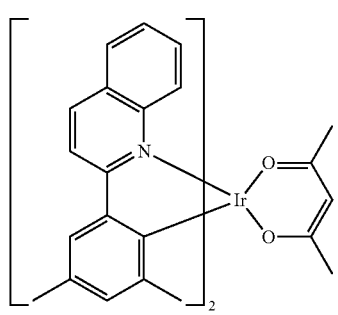
D-34 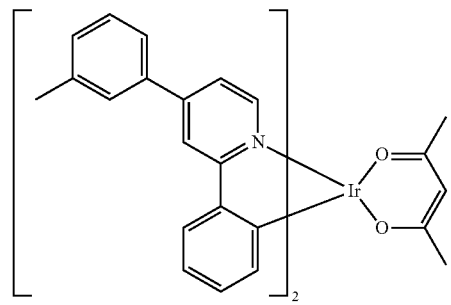
D-35 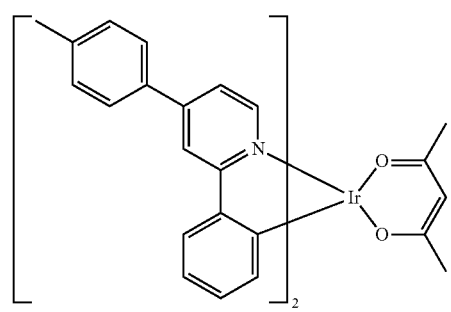
D-36 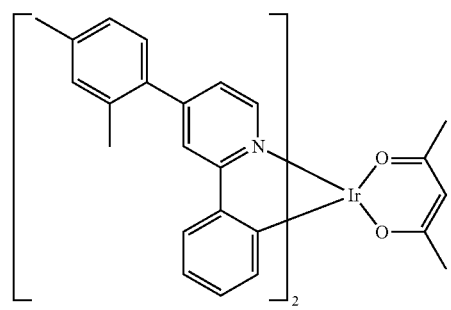
D-37 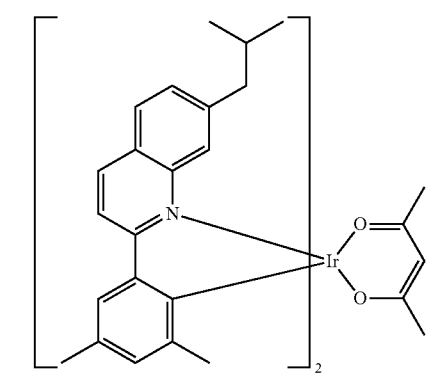
D-38 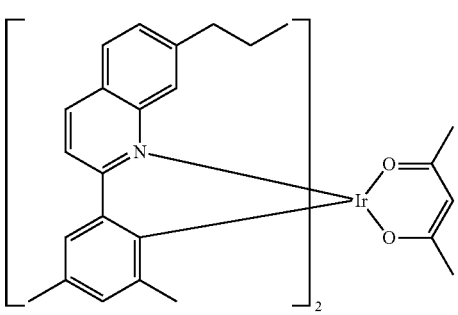

D-39
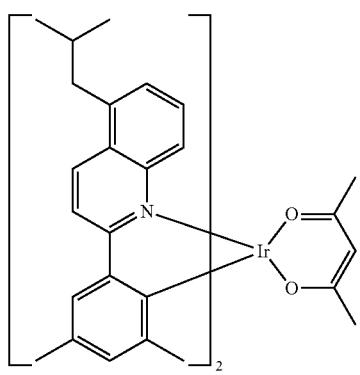
D-40
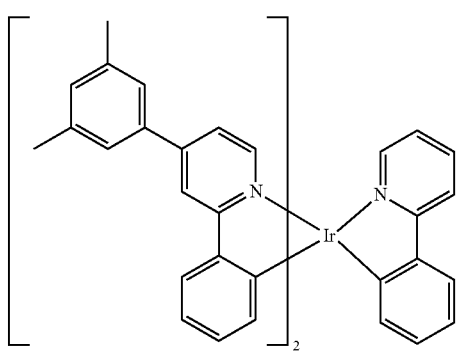
D-41
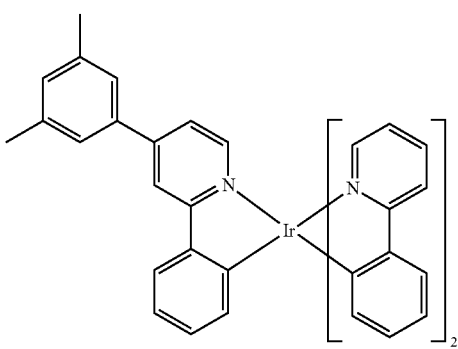
D-42
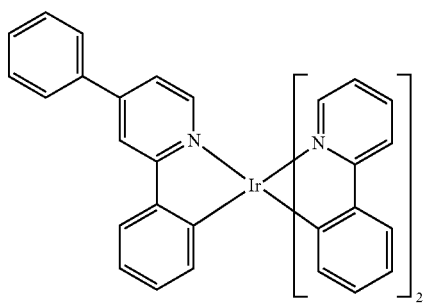
D-43
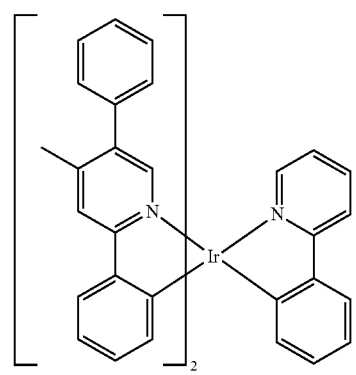
D-44
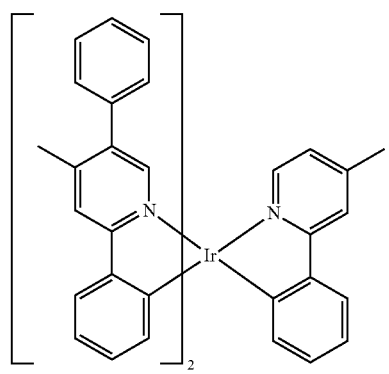
D-45
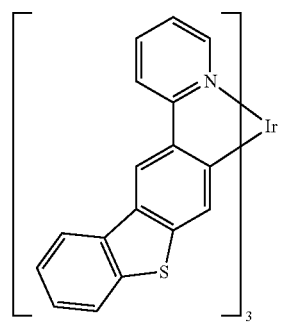
D-46
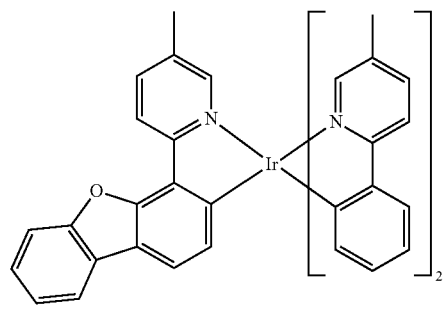

-continued
D-47
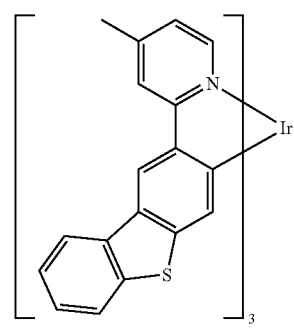
D-48
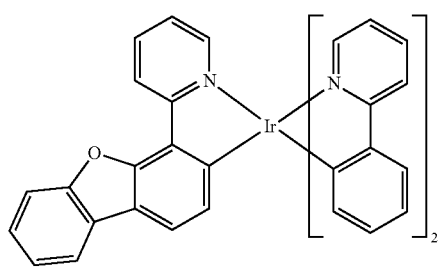
D-49
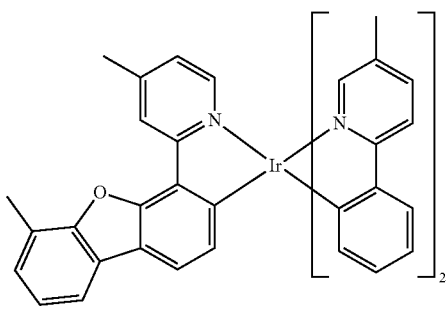
D-50
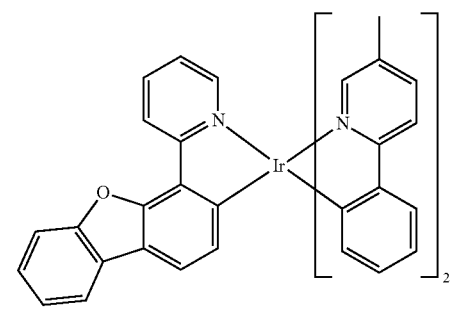
D-51
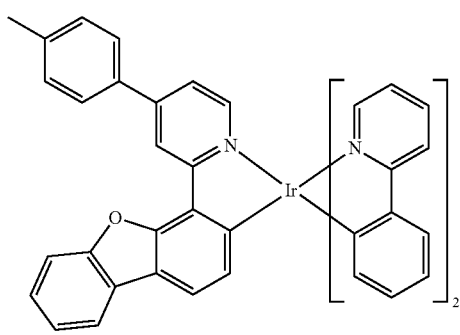
-continued
D-52
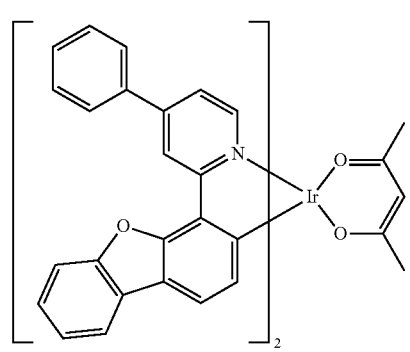
D-53
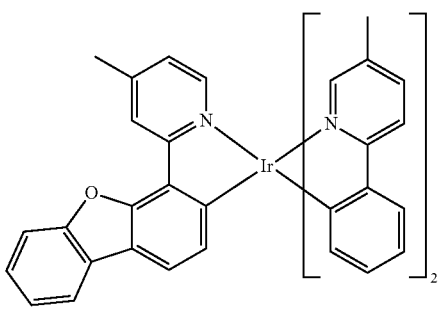
D-54
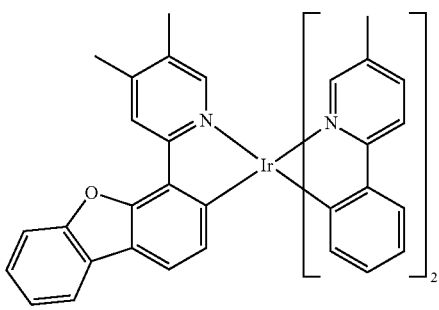
D-55
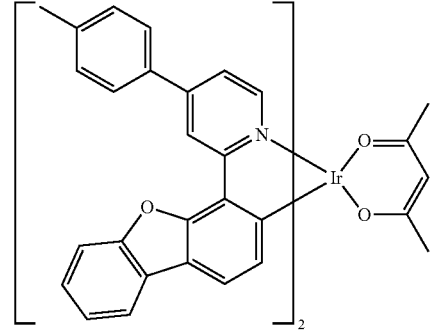
D-56
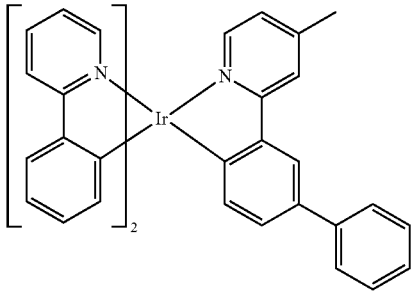

D-57
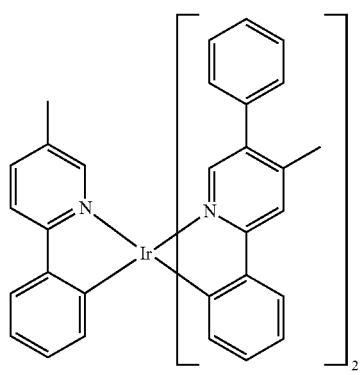
D-58
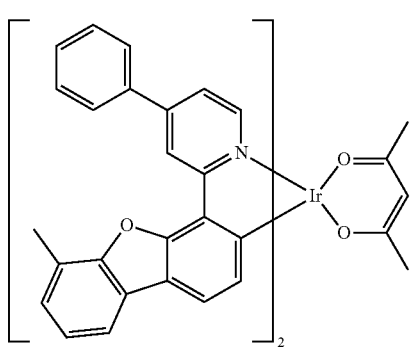
D-59
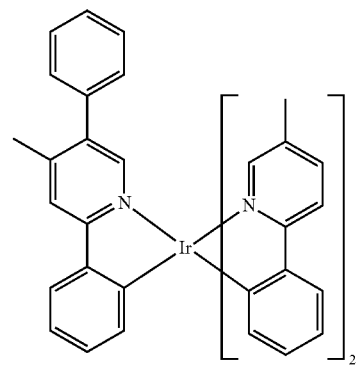
D-60
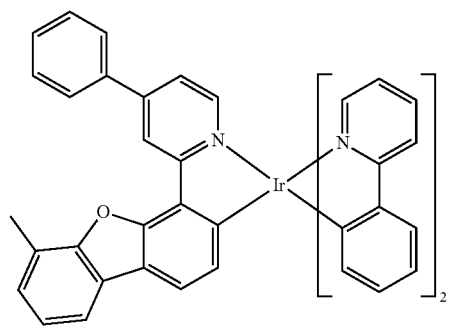
D-61
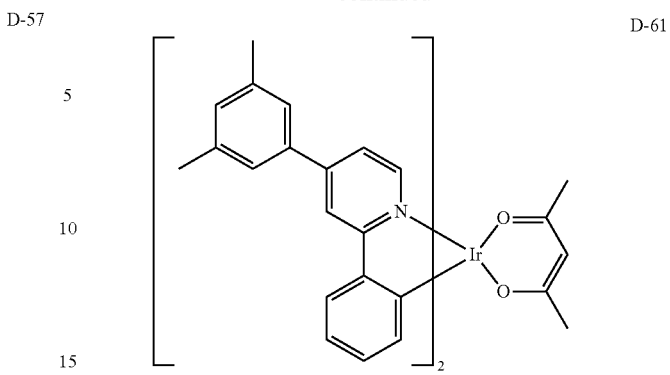
D-62
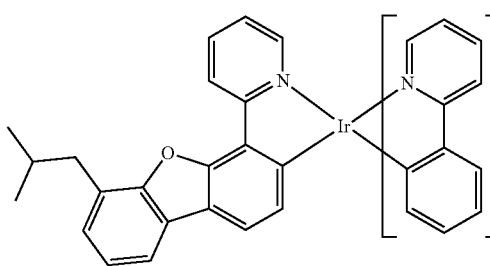
D-63
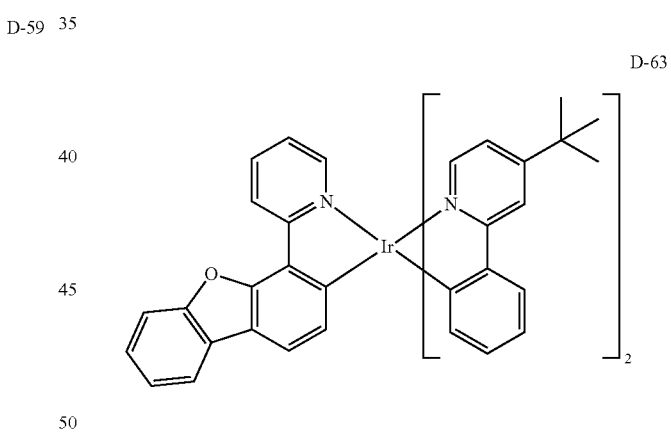
D-64
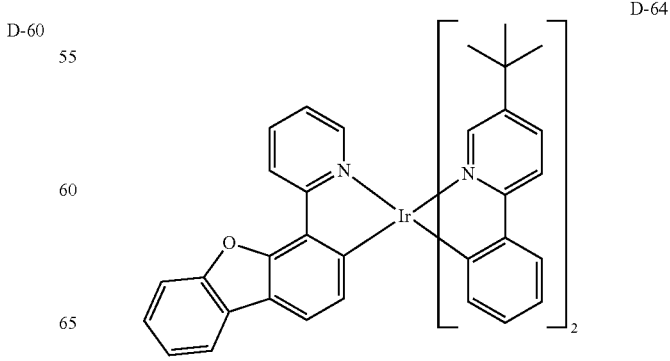

D-65
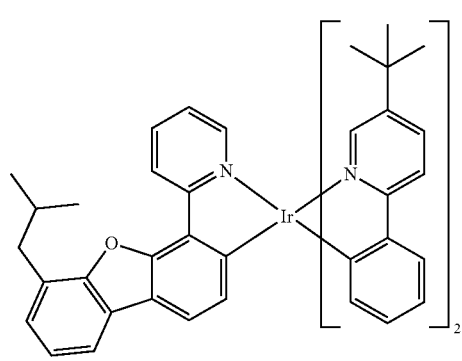
D-66
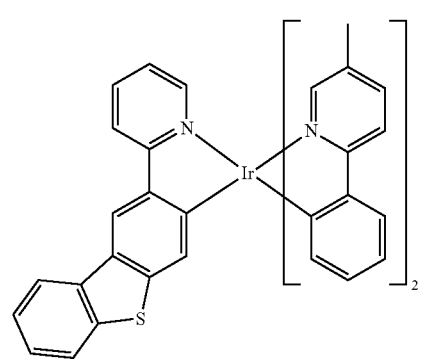
D-67
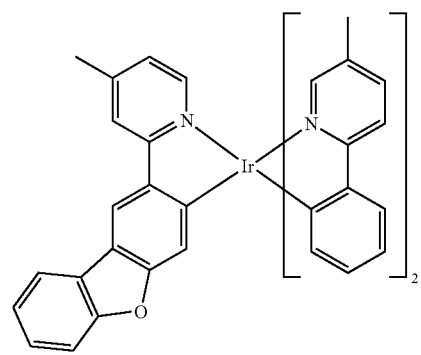
D-68
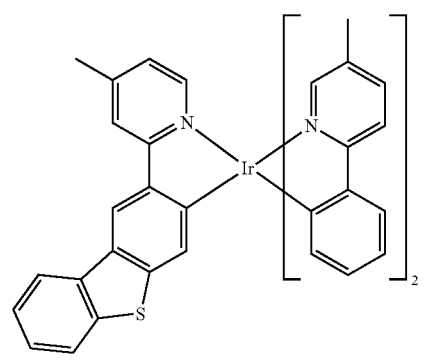
D-69
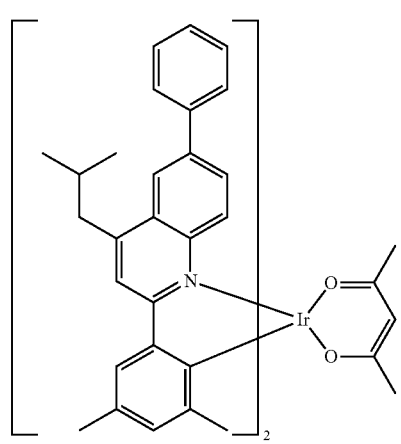
D-70
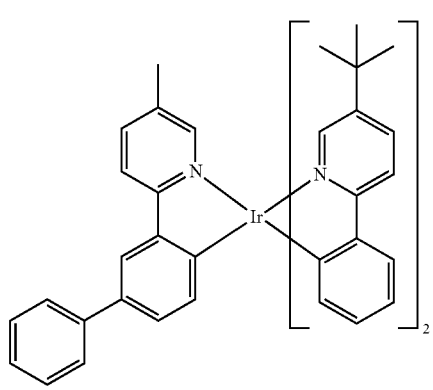
D-71
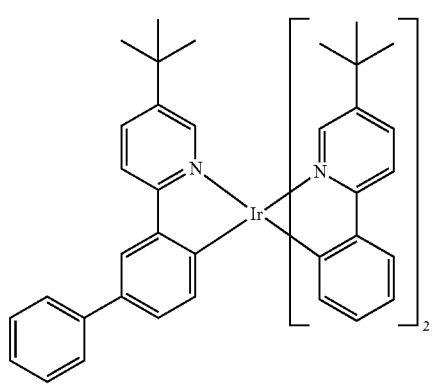
D-72
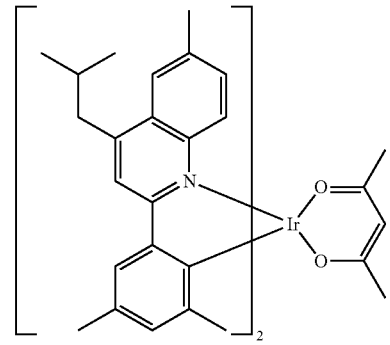

D-73 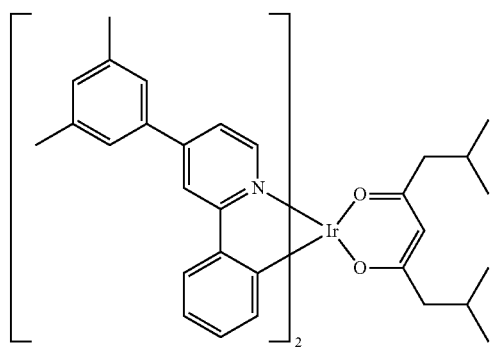
D-74 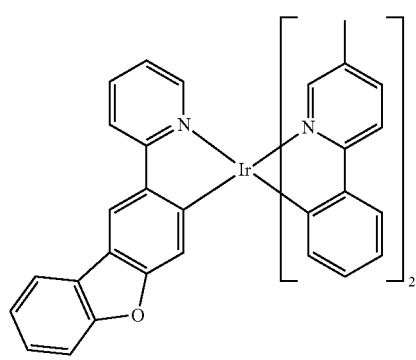
D-75 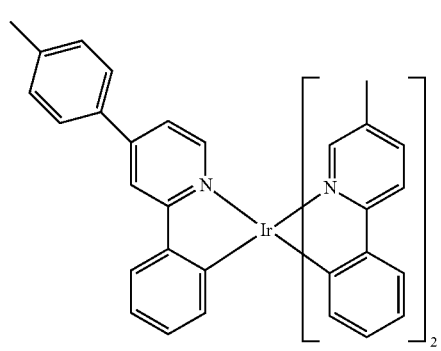
D-76 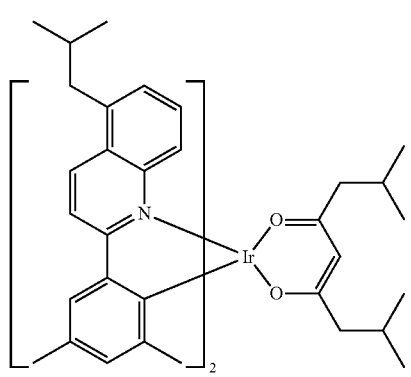
D-77 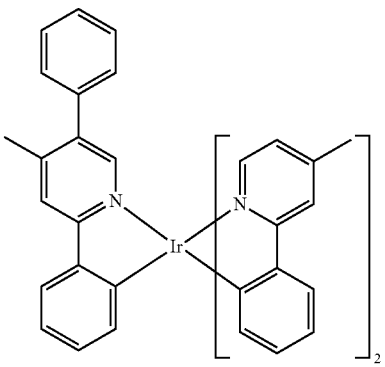
D-78 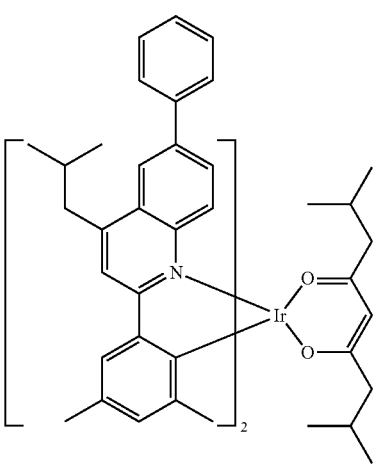
D-79 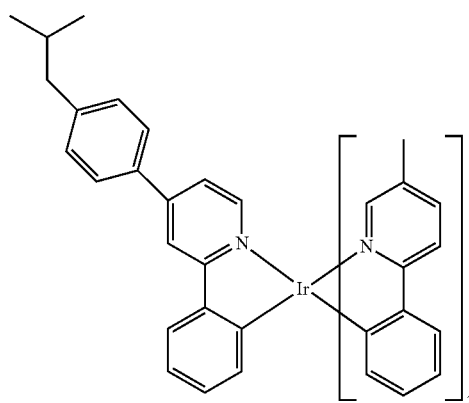
D-80 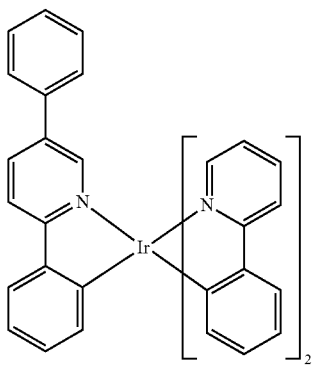

-continued
D-81
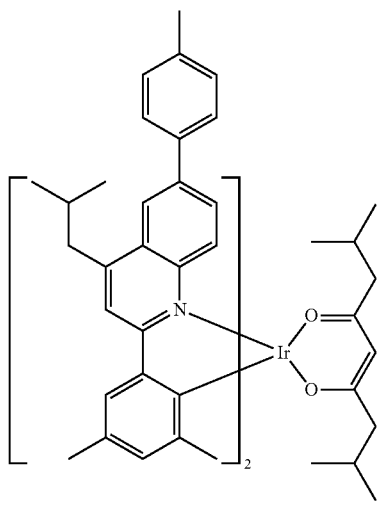
D-82
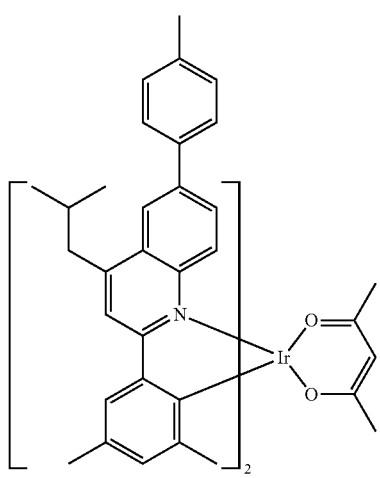
D-83
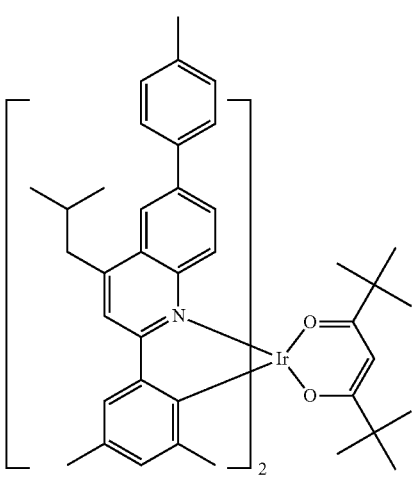
-continued
D-84
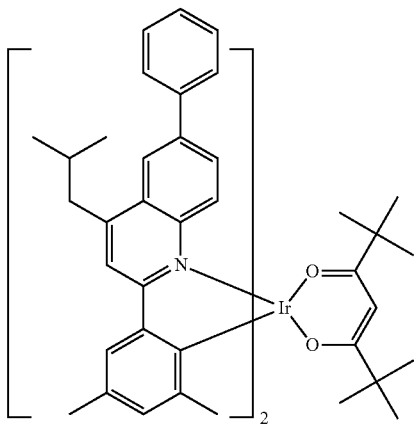
D-85
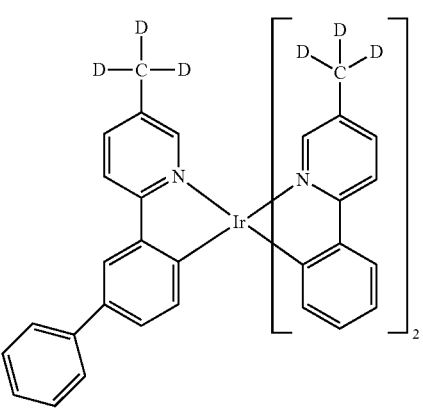
D-86
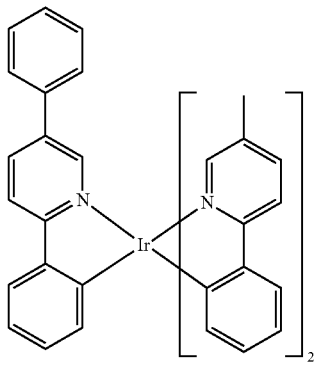
D-87
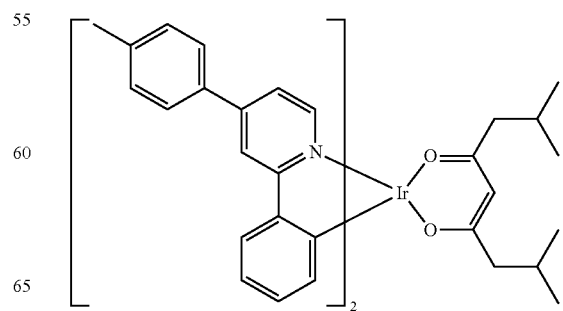

D-88
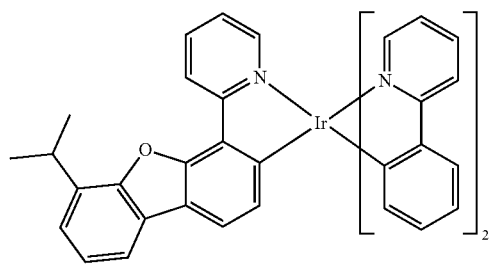
D-89
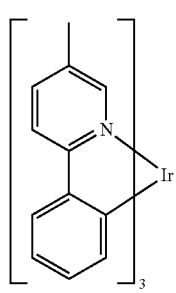
D-90
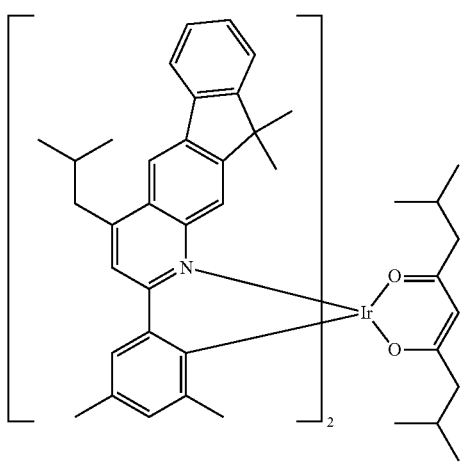
D-91
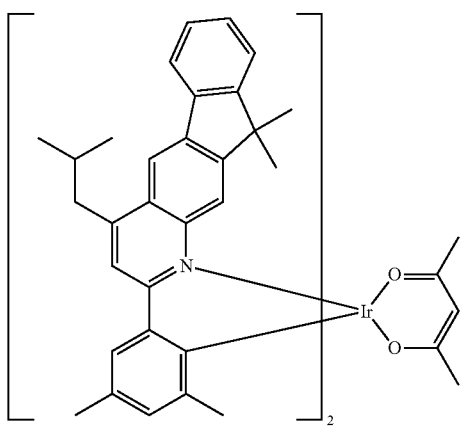
D-92
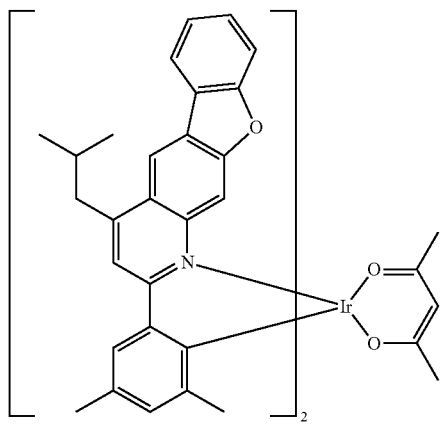
D-93
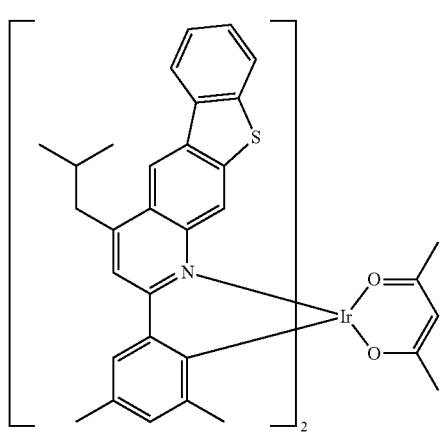
D-94
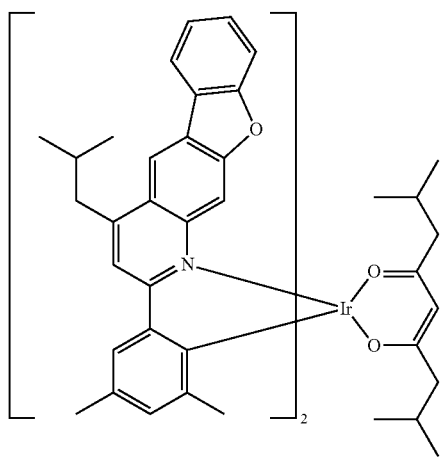

D-95
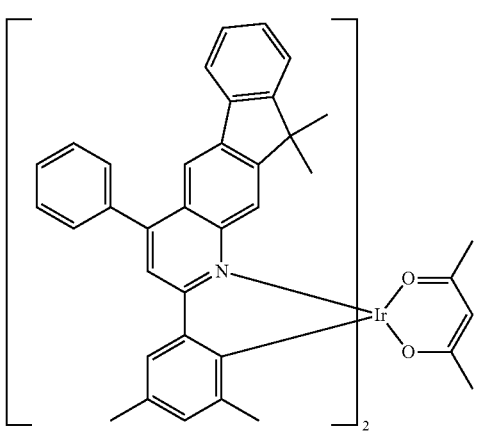
D-99
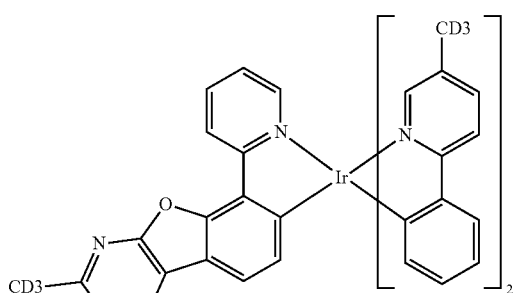
D-96
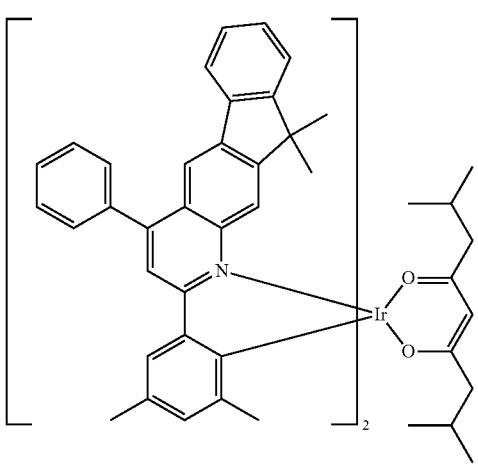
D-100
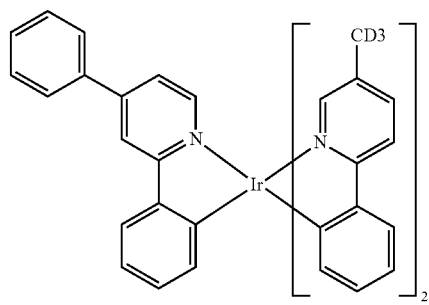
D-97
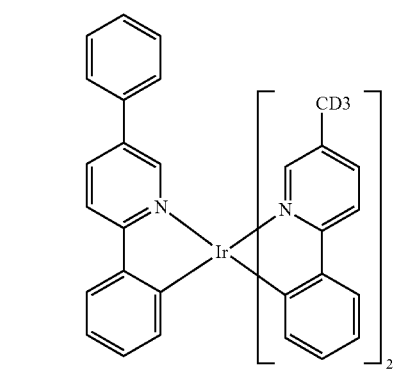
D-101
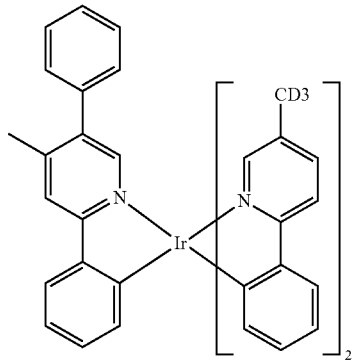
D-98
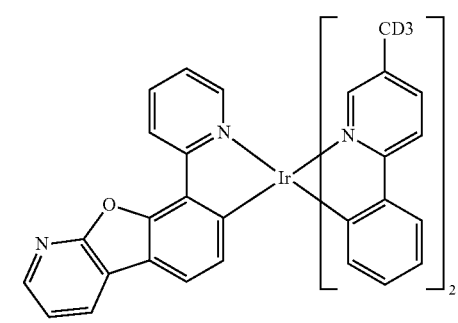
D-102
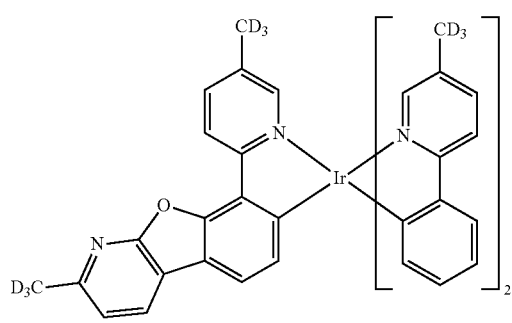

D-103
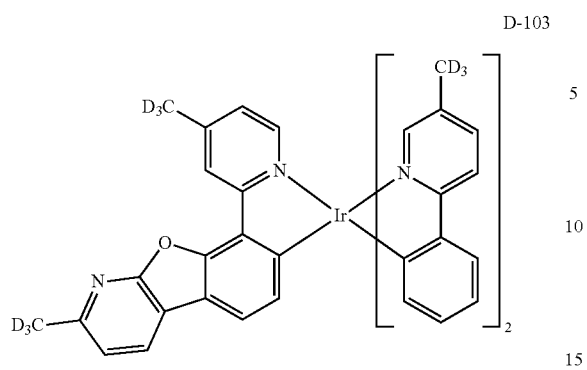
D-104
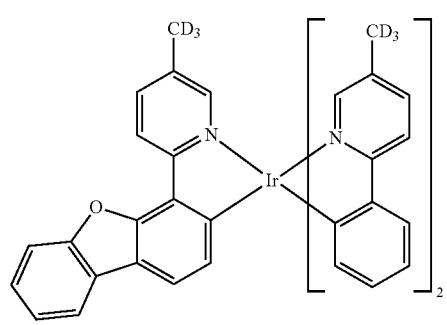
D-105
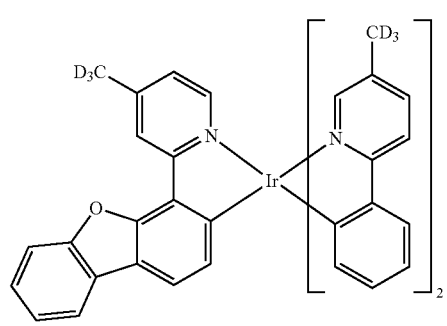
D-106
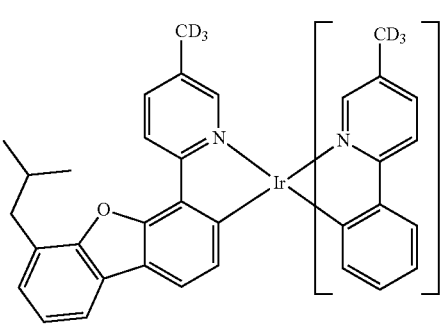
D-107
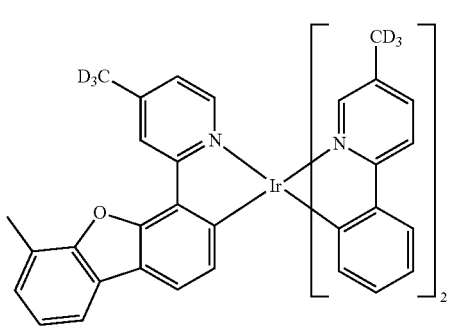
D-108
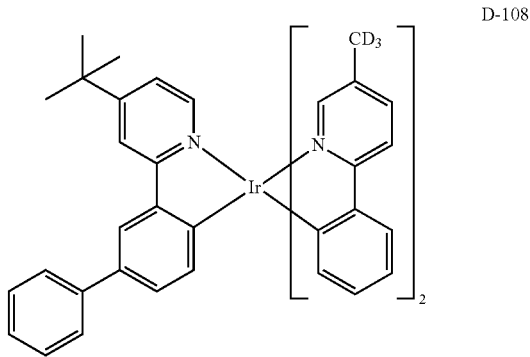
D-109
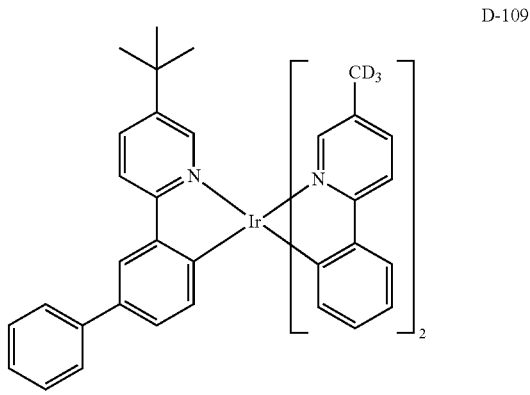
D-110
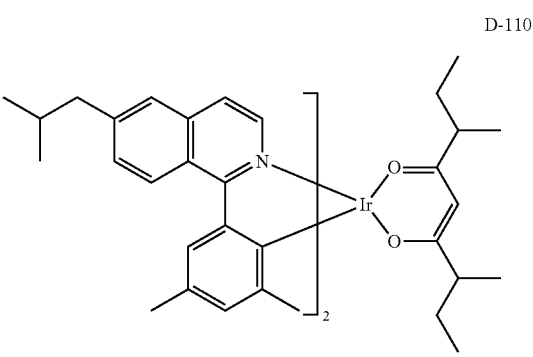
D-111
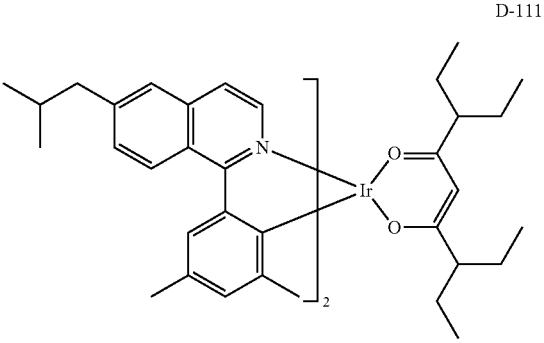

-continued

D-112
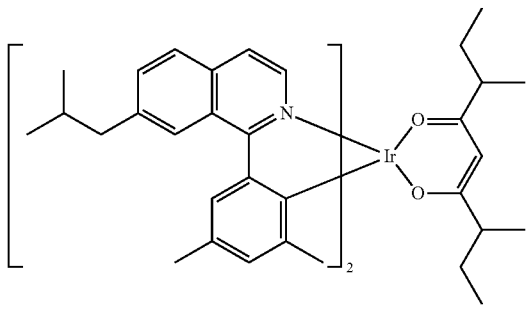

D-113
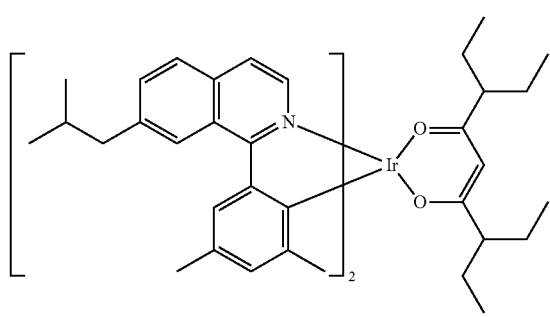

D-114
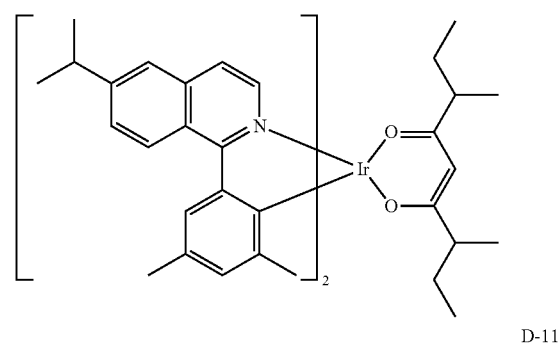

D-115
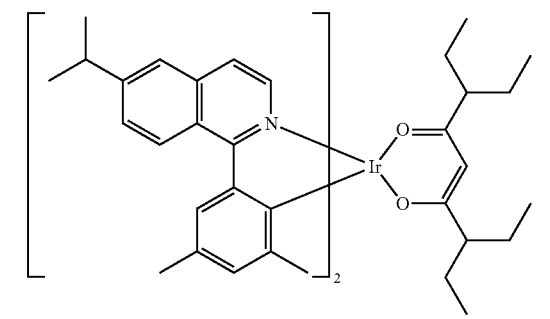

D-116
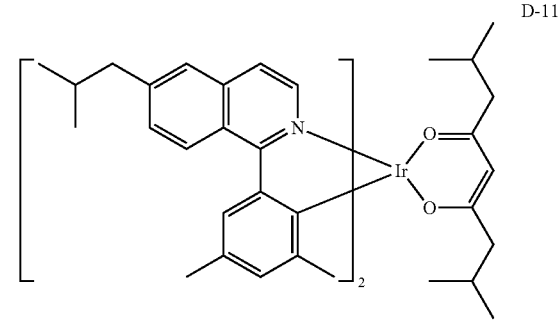

-continued

D-117
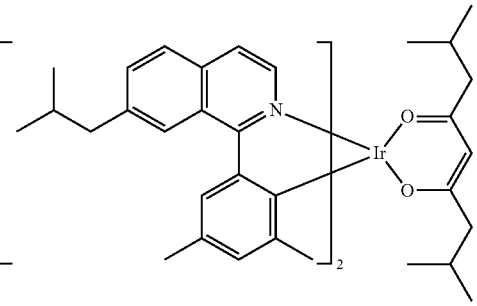

D-118
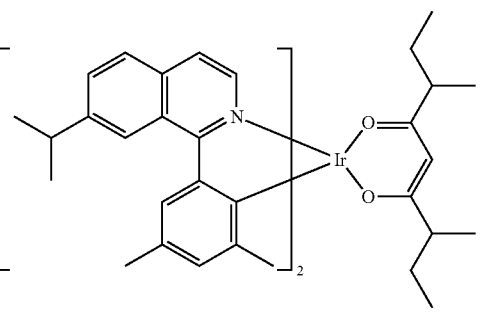

D-119

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used. The first and the second host compounds of the present disclosure may be film-formed by a co-evaporation process or a mixture-evaporation process.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Also, the organic electroluminescent device of the present disclosure can be used for the manufacture of a display device or a lighting device.

Also, by using the organic electroluminescent device of the present disclosure, a display system, for example smart phones, tablets, notebooks, PCs, TVs, or display system for car; or a lighting system, for example an outdoor or indoor lighting system, can be produced.

Hereinafter, the preparation method of the compound of the present disclosure, and the properties thereof will be explained in detail with reference to the representative compounds of the present disclosure. However, the present disclosure is not limited by the following examples.

Example 1: Preparation of Compound C-8

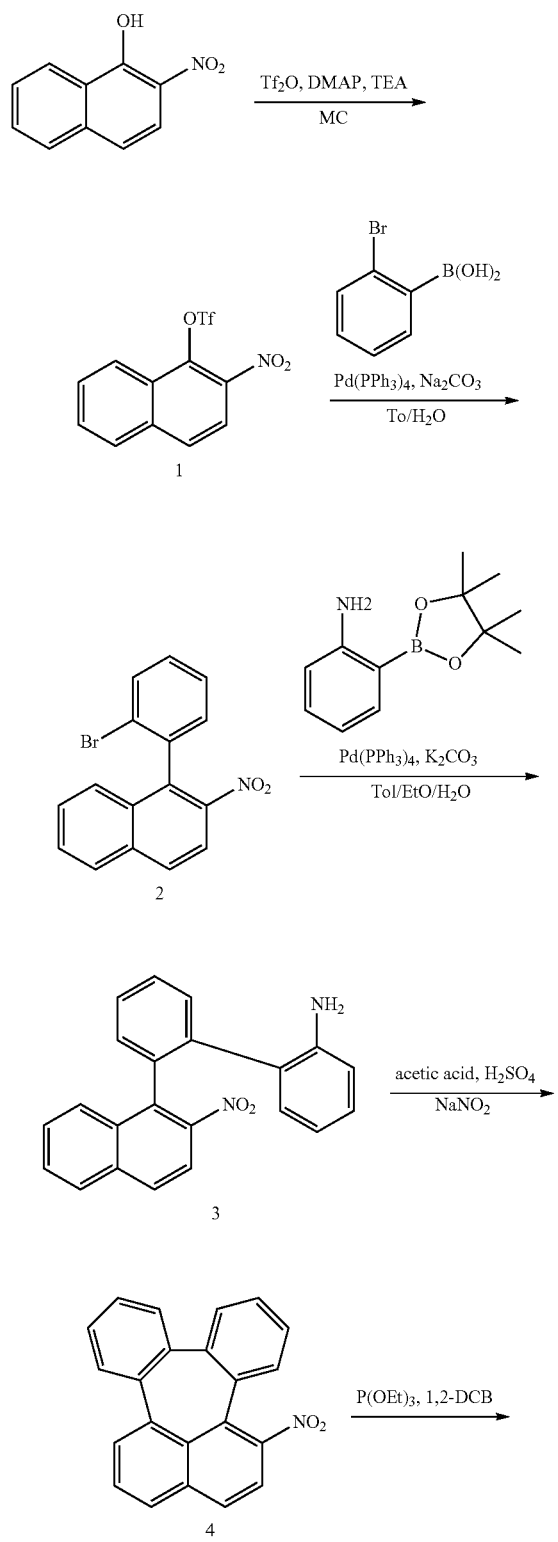

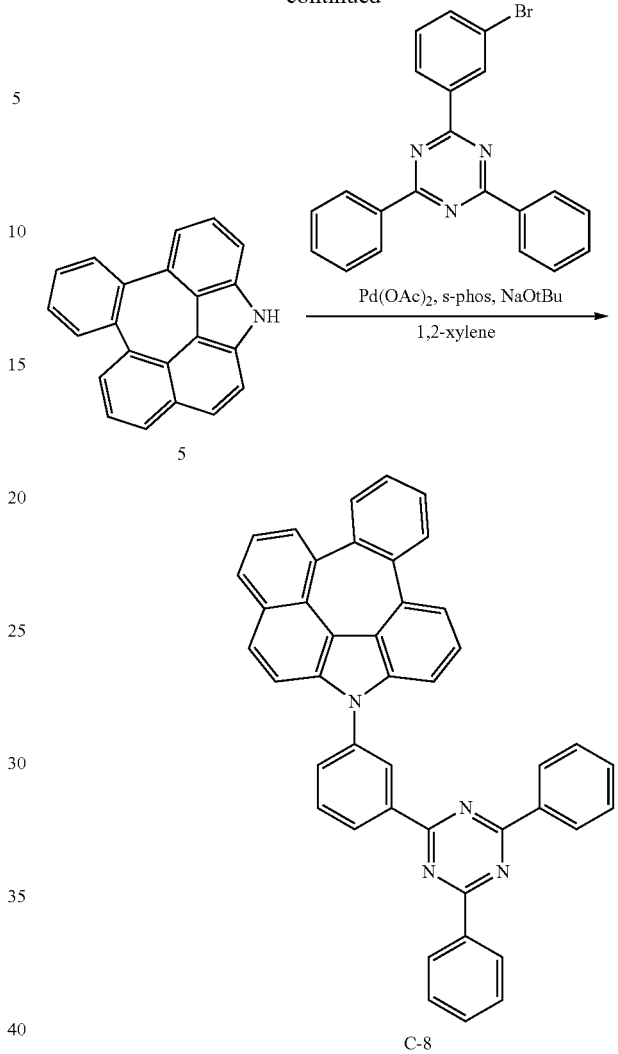

Synthesis of Compound 1

70 g of 2-nitro-1-naphthol (370 mmol) and 4.5 g of 4-(dimethylamino)pyridine (DMAP) (37 mmol) were dissolved in 1800 mL of methylene chloride (MC) in a flask. 62 mL of triethylamine (TEA) (444 mmol) were added dropwise at 0° C. and stirred for 20 minutes. 125.3 g of trifluoromethane sulfonic anhydride (444 mmol) was slowly added dropwise to the reactant at the same temperature and stirred for 1 hour. After the reaction was completed, the organic layer was extracted with MC, and residual water was removed by using magnesium sulfate. The residue was dried and purified by column chromatography to obtain 96.2 g of compound 1 (yield: 81%).

Synthesis of Compound 2

96.2 g of compound 1 (299 mmol), 72.1 g of 2-bromophenylboronic acid (359 mmol), 17.3 g of tetrakis(triphenylphosphine)palladium (0) (15 mmol), and 79.3 g of sodium carbonate (749 mmol) were dissolved in 1400 mL toluene, 350 mL of ethanol, and 350 mL of water in a flask and refluxed for 1 hour. After the reaction was completed, the organic layer was extracted with ethyl acetate, and residual water was removed by using magnesium sulfate. The residue was dried and purified by column chromatography to obtain 98 g of compound 2 (yield: 99%).

Synthesis of Compound 3

98 g of compound 2 (299 mmol), 78.5 g of 2-aminophenylboronic acid pinacol ester (358 mmol), 17.2 g of tetrakis(triphenylphosphine)palladium (0) (15 mmol), and 103 g of potassium carbonate (747 mmol) were dissolved in 1300 mL of toluene, 350 mL of ethanol and 350 mL of water in a flask and refluxed for 20 hours. After the reaction was completed, the organic layer was extracted with ethyl acetate, and residual water was removed by using magnesium sulfate. The residue was dried and purified by column chromatography to obtain 54 g of compound 3 (yield: 53%).

Synthesis of Compound 4

25 g of compound 3 (73 mmol) was dissolved in 250 mL of acetic acid and 25 mL of sulfuric acid in a flask, 6.5 g of sodium nitrite (95 mmol) was slowly added dropwise at 0° C. and stirred for 40 minutes. After the reaction was completed, the reaction product was added dropwise to water and filtered to remove water. The residue was dried and purified by column chromatography to obtain 2 g of compound 4 (yield: 8.4%).

Synthesis of Compound 5

4.7 g of compound 4 (15 mmol) was dissolved in 48 mL of triethylphosphite and 48 mL of 1,2-dichlorobenzene in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 2.7 g of compound 5 (yield: 63%).

Synthesis of Compound C-8

2.1 g of compound 5 (7 mmol), 3.1 g of 2-(3-bromophenyl)-4,6-diphenyl-1,3,5-triazine (8 mmol), 0.81 g of palladium (II) acetate (0.36 mmol), 0.3 g of 2-dicyclohexylphosphino-2',6'-dimethoxybiphenyl (S-Phos) (0.7 mmol), and 1.7 g of sodium tert-butoxide (18 mmol) were dissolved in 72 mL of 1,2-xylene in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 2.5 g of compound C-8 (yield: 58%).

| Compound | MW | UV | PL | M.P. | Tg |
|---|---|---|---|---|---|
| C-8 | 598.71 | 308 nm | 495 nm | 285° C. | 132.37° C. |

Example 2: Preparation of Compound C-301

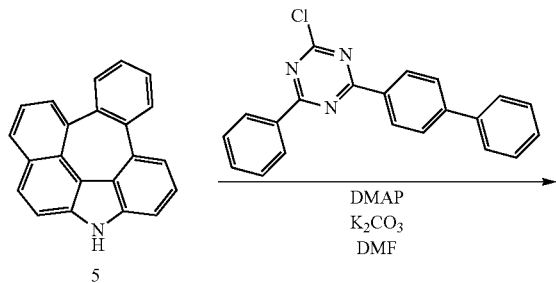

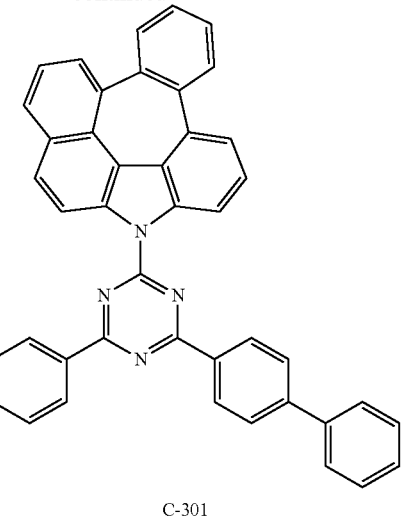

C-301

5.0 g of compound 5 (17 mmol), 7.08 g of 2-([1,1'-biphenyl]-4-yl)-4-chloro-6-phenyl-1,3,5-triazine (21 mmol), 105 mg of DMAP (0.858 mmol), and 7.1 g of potassium carbonate (51 mmol) were dissolved in 85 mL of dimethylformamide (DMF) in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 4.8 g of compound C-301 (yield: 47%).

$^1$H NMR (600 MHz, CDCl3) 9.09-9.07 (d, J=12 Hz, 1H), 8.93-8.91 (d, J=12 Hz, 1H), 8.74-8.73 (d, J=6 Hz, 2H), 8.71-8.69 (d, J=12 Hz, 2H), 7.80-7.75 (m, 6H), 7.73-7.69 (m, 3H), 7.64-7.57 (m, 3H), 7.52-7.38 (m, 8H)

| Compound | MW | Tg | M.P. |
|---|---|---|---|
| C-301 | 598.71 | 124.4° C. | 236° C. |

Example 3: Preparation of Compound C-10

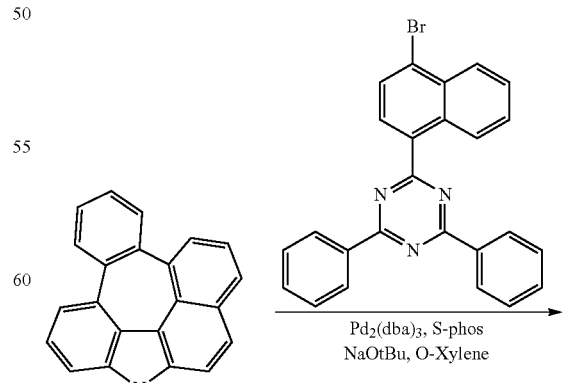

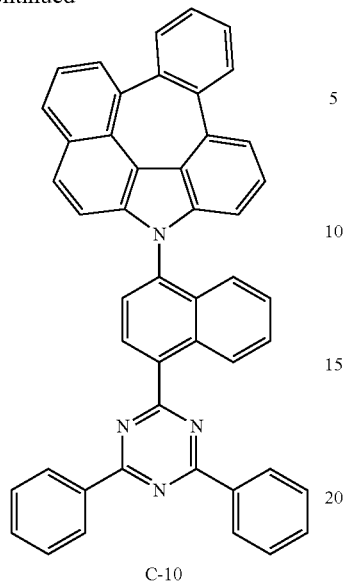

C-10

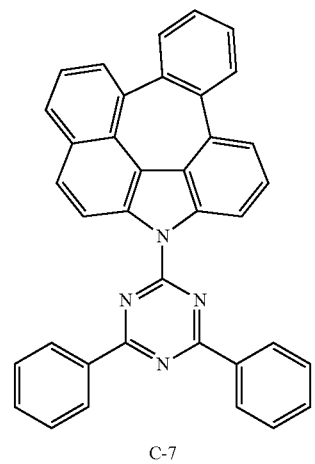

C-7

5.0 g of compound 5 (17 mmol), 11.28 g of 2-(4-bromonaphthalene-1-yl)-4,6-diphenyl-1,3,5-triazine) (21 mmol), 625 mg of tris(dibenzylideneacetone)dipalladium (0) (0.686 mmol), 565 mg of S-Phos (1 mmol), and 4.9 g of sodium tert-butoxide (51 mmol) were dissolved in 100 mL of o-xylene in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 3.6 g of compound C-10 (yield: 32%).

$^1$H NMR (600 MHz, CDCl3) 9.25-9.24 (d, J=6 Hz, 1H), 8.85-8.83 (sd, J=12 Hz, 4H), 8.68-8.67 (d, J=6 Hz, 1H), 7.94-7.92 (m, 1H), 7.82-7.79 (m, 3H), 7.74-7.61 (m, 10H), 7.49-7.42 (m, 5H), 7.31-7.29 (t, J=6 Hz, 1H), 7.16-7.15 (d, J=6 Hz, 1H), 6.96-6.94 (d, J=12 Hz, 1H)

5 g of compound 5 (17.1 mmol), 5.5 g of 2-chloro-4,6-diphenyl-1,3,5-triazine (20.5 mmol), 0.1 g of DMAP (0.85 mmol), and 7.1 g of potassium carbonate (51.4 mmol) were dissolved in 85 mL of DMF in a flask and refluxed for 3 hours. After the reaction was completed, the reaction product was cooled, methanol and water were added thereto and the mixture was filtered. The residue was dried and purified by column chromatography to obtain 4.4 g of compound C-7 (yield: 49%).

$^1$H NMR (600 MHz, CDCl3) 9.13-9.11 (d, J=12 Hz, 1H), 8.97-8.95 (d, J=12 Hz, 1H), 8.75-8.73 (d, J=12 Hz, 4H), 7.83-7.75 (m, 5H), 7.64-7.59 (m, 6H), 7.54-7.51 (m, 3H), 7.48-7.45 (t, J=12 Hz, 3H), 7.40-7.39 (m, 2H)

| Compound | MW | Tg | M.P |
|---|---|---|---|
| C-10 | 648.7 | 159.5° C. | 176° C. |

| Compound | MW | Tg | M.P. |
|---|---|---|---|
| C-7 | 522.6 | 105° C. | 209° C. |

Example 4: Preparation of Compound C-7

Example 5: Preparation of Compound C-302

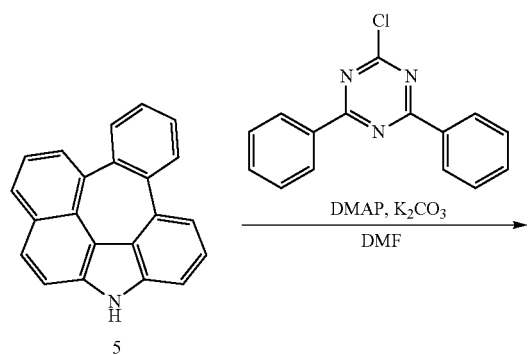

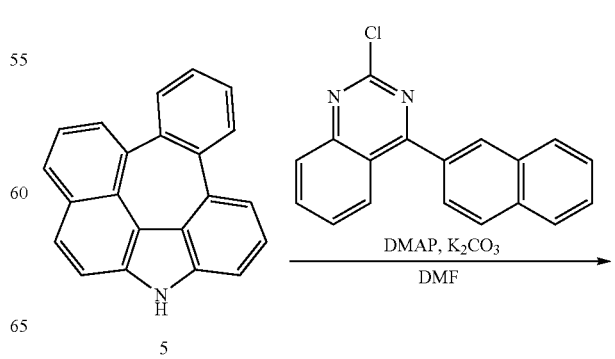

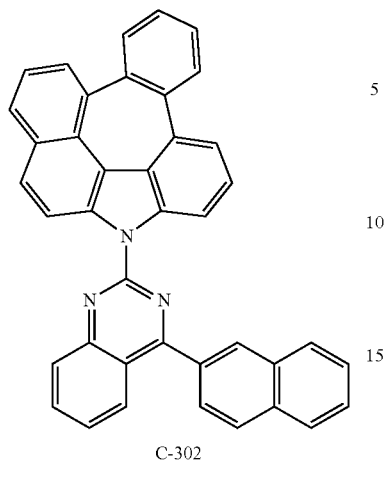

C-302

4.5 g of compound 5 (15.4 mmol), 5.4 g of 2-chloro-4-(naphthalene-2-yl)quinazoline (18.5 mmol), 0.09 g of DMAP (0.7 mmol), and 6.4 g of potassium carbonate (46.3 mmol) were dissolved in 77 mL of DMF in a flask and refluxed for 1.5 hours. After the reaction was completed, the reaction product was filtered, dried and purified by column chromatography to obtain 7.5 g of compound C-302 (yield: 80%).

$^1$H NMR (600 MHz, CDCl3) 9.03-9.02 (d, J=6 Hz, 1H), 8.88-8.86 (d, J=12 Hz, 1H), 8.39 (s, 1H), 8.22-8.21 (d, J=6 Hz, 1H), 8.20-8.17 (d, J=18 Hz, 1H), 8.15-8.05 (m, 2H), 8.00-7.98 (t, J=6 Hz, 2H), 7.91-7.89 (m, 1H), 7.76-7.72 (m, 5H), 7.63-7.61 (m, 2H), 7.54-7.52 (m, 2H), 7.43-7.36 (m, 4H)

| Compound | MW | Tg | M.P. |
| --- | --- | --- | --- |
| C-302 | 545.65 | 120.6° C. | 257° C. |

Example 6: Preparation of Compound C-9

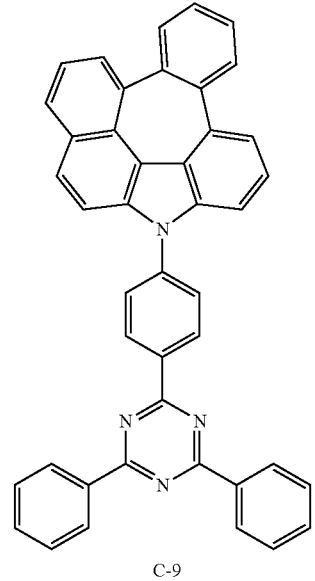

C-9

5.0 g of compound 5 (17.16 mmol), 6.6 g of 2-(4-bromophenyl)-4,6-diphenyl-1,3,5-triazine (17.16 mmol), 0.6 g of tris(dibenzylideneacetone)dipalladium (0) (0.686 mmol), 0.7 g of S-Phos (1.176 mmol), and 4.0 g sodium tert-butoxide (42.9 mmol) were dissolved in 90 mL of o-xylene in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 6.2 g of compound C-9 (yield: 62%).

$^1$H NMR (600 MHz, CDCl3, δ) 9.06-9.05 (d, J=6.0 Hz, 2H), 8.85-8.83 (d, J=12 Hz, 4H), 7.90-7.89 (m, 1H), 7.82-7.78 (m, 4H), 7.74-7.72 (m, 2H), 7.66-7.58 (m, 8H), 7.45-7.43 (m, 3H), 7.42-7.39 (m, 2H)

| Compound | MW | Tg | M.P. |
| --- | --- | --- | --- |
| C-9 | 598.71 | 140.59° C. | 260° C. |

Example 7: Preparation of Compound C-303

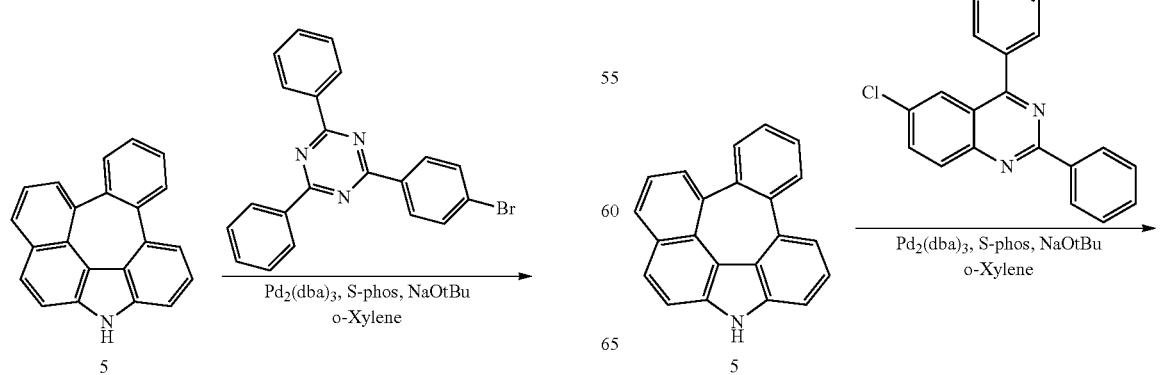

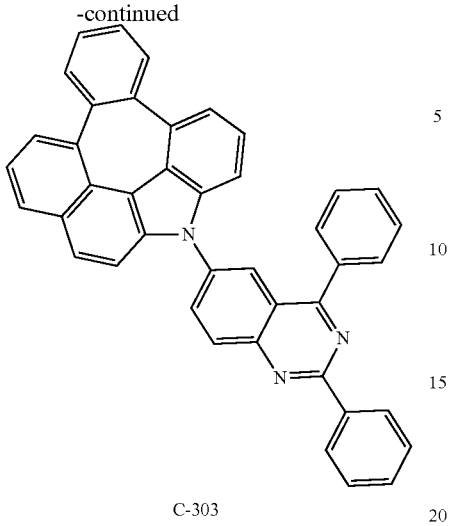

C-303

4.3 g of compound 5 (14.83 mmol), 4.7 g of 6-chloro-2,4-diphenylquinazoline (14.83 mmol), 0.5 g of Pd$_2$(dba)$_3$ (0.593 mmol), 0.6 g of S-Phos (1.483 mmol), and 3.6 g of sodium tert-butoxide (37.07 mmol) were dissolved in 80 mL of o-xylene in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 1.8 g of compound C-303 (yield: 21%).

$^1$H NMR (600 MHz, CDCl3, δ) 8.74-8.73 (d, J=6.0 Hz, 2H), 8.37-8.36 (d, J=6.0 Hz, 1H), 8.28-8.27 (d, J=6.0 Hz, 1H), 8.05-8.04 (d, J=6.0 Hz, 1H), 7.89-7.88 (d, J=6.0 Hz, 2H), 7.85-7.83 (m, 1H), 7.75-7.73 (d, J=12 Hz, 2H), 7.69-7.67 (m, 2H), 7.57-7.50 (m, 7H), 7.42-7.37 (m, 4H), 7.34-7.31 (m, 1H), 7.22-7.21 (m, 1H)

| Compound | MW | Tg | M.P. |
|---|---|---|---|
| C-303 | 571.67 | 140.16° C. | 189.3° C. |

Example 8: Preparation of Compound C-307

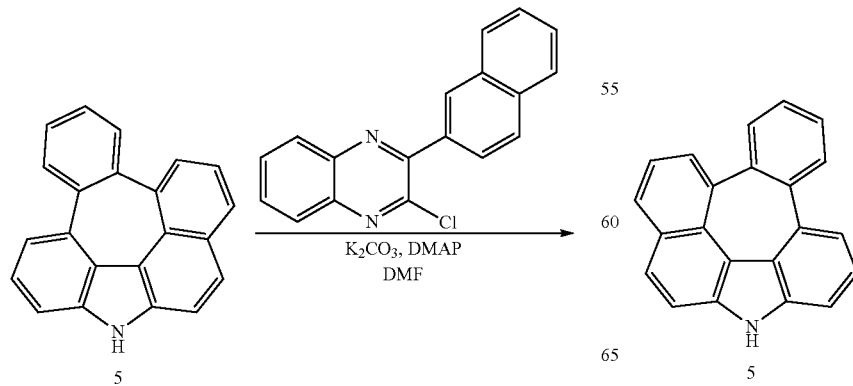

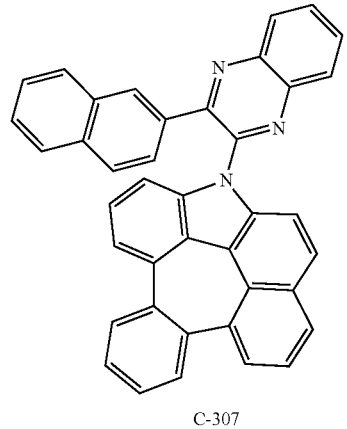

C-307

5.4 g of compound 5 (18.53 mmol), 4.5 g of 2-chloro-3-naphthylquinoxaline (15.44 mmol), 2.1 g of potassium carbonate (15.44 mmol), and 0.9 g of DMAP (7.72 mmol) were dissolved in 80 mL of DMF in a flask and refluxed for 4 hours. After the reaction was completed, the reaction product was cooled to room temperature, and distilled water was added thereto. The organic layer was extracted with MC, and residual water was removed by using magnesium sulfate. The residue was distilled under reduced pressure and purified by column chromatography to obtain 2.3 g of compound C-307 (yield: 47%).

$^1$H NMR (600 MHz, CDCl3, δ) 8.36-8.34 (d, J=6.0 Hz, 1H), 8.23 (s, 1H), 8.17-8.16 (d, J=6.0HZ, 1H), 7.90-7.86 (m, 3H), 7.73-7.71 (d, J=12 Hz, 1H), 7.68-7.63 (m, 4H), 7.50-7.48 (m, 2H), 7.40-7.35 (m, 6H), 7.32-7.24 (m, 2H)

| Compound | MW | Tg | M.P. |
|---|---|---|---|
| C-307 | 545.65 | 133° C. | 152° C. |

Example 9: Preparation of Compound C-13

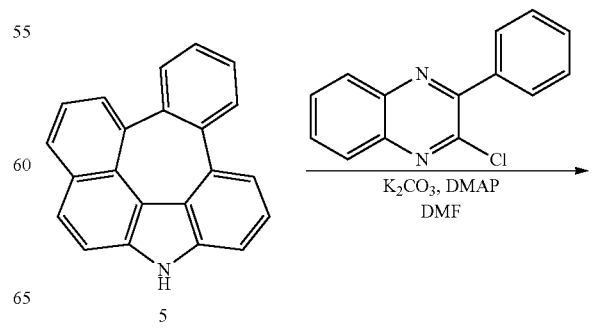

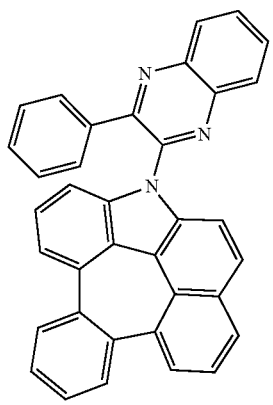

C-13

4.0 g of compound 5 (13.73 mmol), 4.0 g of 2-chloro-3-phenylquinoxaline (16.47 mmol), 3.8 g of potassium carbonate (27.46 mmol), and 0.84 g of DMAP (6.87 mmol) were dissolved in 68 mL of DMF in a flask and refluxed for 18 hours. After the reaction was completed, the reaction product was cooled to room temperature, and distilled water was added thereto. The organic layer was extracted with MC, and residual water was removed by using magnesium sulfate. The residue was distilled under reduced pressure and purified by column chromatography to obtain 2.3 g of compound C-13 (yield: 33.8%).

$^1$H NMR (600 MHz, CDCl3, δ) 8.32-8.30 (m, 1H), 8.16-8.15 (m, 1H), 7.89-7.83 (m, 3H), 7.73 (d, J=7.38 Hz, 1H), 7.69-7.68 (m, 2H), 7.60-7.54 (m, 2H), 7.50 (d, J=9.00 Hz, 1H), 7.42-7.37 (m, 3H), 7.29-7.27 (m, 3H), 7.21-7.15 (m, 4H)

| Compound | MW | Tg | M.P. |
|---|---|---|---|
| C-13 | 495.59 | 124.88° C. | 154-164° C. |

Example 10: Preparation of Compound C-304

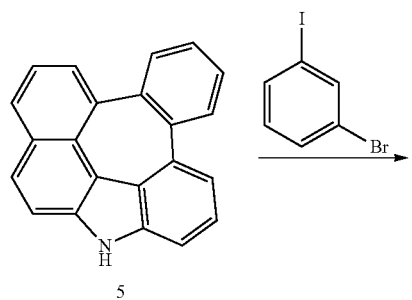 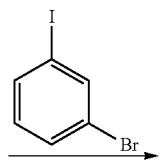

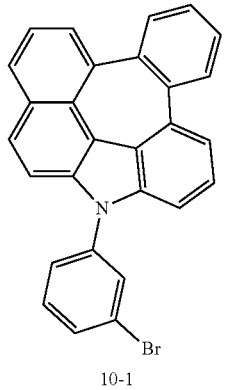 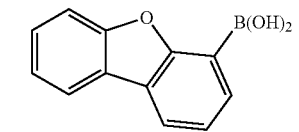

10-1

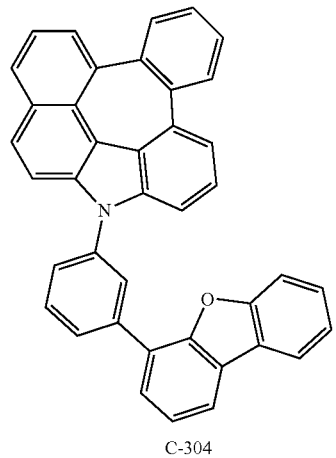

C-304

Synthesis of Compound 10-1

9 g of compound 5 (30.89 mmol), 10.6 g of 1-bromo-3-iodobenzene (61.78 mmol), 3 g of CuI (15.44 mmol), 1.8 g of EDA (30.89 mmol), and 16.4 g of K$_3$PO$_4$ (77.22 mmol) were added in 155 mL of toluene and stirred under reflux for one day. After the reaction was completed, the reaction product was cooled to room temperature, and the resulting solid was filtered under reduced pressure. The solid was dissolved in CHCl$_3$ and purified by column chromatography using MC/Hex to obtain 10 g of compound 10-1 (yield: 75%).

Synthesis of Compound C-304

5.7 g of compound 10-1 (12.77 mmol), 0.73 g of Pd(PPh$_3$)$_4$ (0.638 mmol), and 3.5 g of K$_2$CO$_3$ (25.54 mmol) were added in 50 mL of toluene, 13 mL of EtOH, and 13 mL of purified water and stirred under reflux for 2 hours. After the reaction was completed, the reaction product was cooled to room temperature, and the resulting solid was filtered under reduced pressure. The solid was dissolved in CHCl$_3$ and purified by column chromatography using MC/Hex to obtain 2.9 g of compound C-304 (yield: 43%).

$^1$H NMR (600 MHz, DMSO-d6, δ) 8.232-8.206 (m, 3H), 8.111-8.098 (d, 1H), 7.962-7.946 (m, 1H), 7.929-7.903 (m, 3H), 7.896-7.882 (d, 1H), 7.806-7.802 (d, 2H), 7.783-7.759 (t, 2H), 7.738-7.723 (d, 1H), 7.635-7.620 (m, 1H), 7.581-7.548 (m, 2H), 7.513-7.440 (m, 6H)

| Compound | MW | Tg | M.P. |
|---|---|---|---|
| C-304 | 533.6 | 119° C. | 208° C. |

Example 11: Preparation of Compound C-306

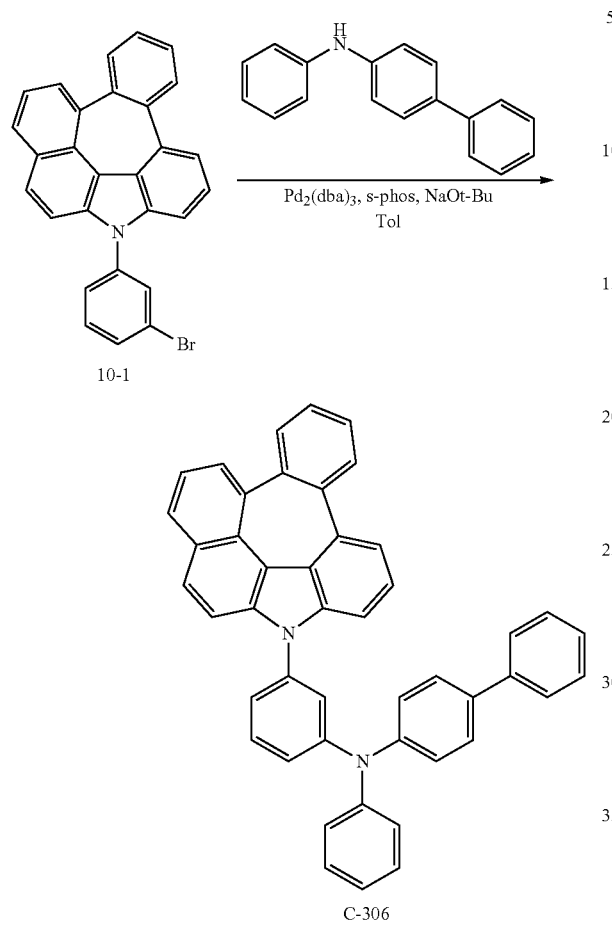

5.0 g of compound 10-1 (11.2 mmol), 3.0 g of N-phenyl-[1,1'-biphenyl]-4-amine (12.3 mmol), 0.51 g of Pd$_2$(dba)$_3$ (0.56 mmol), 0.46 g of S-Phos (1.12 mmol), and 2.7 g of sodium tert-butoxide (28 mmol) were added to 60 mL of toluene in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 2.3 g of compound C-306 (yield: 34%).

$^1$H NMR (600 MHz, DMSO-d6, δ) 7.896-7.880 (m, 1H), 7.863-7.850 (d, 1H), 7.805-7.790 (d, 1H), 7.758-7.745 (d, 1H), 7.733-7.720 (d, 1H), 7.669-7.650 (m, 2H), 7.640-7.627 (d, 1H), 7.604-7.566 (m, 2H), 7.522-7.507 (d, 1H), 7.447-7.384 (m, 7H), 7.373-7.347 (t, 1H), 7.335-7.311 (t, 1H), 7.269-7.237 (m, 6H), 7.175-7.156 (d, 1H), 7.147-7.122 (t, 1H), 7.069-7.062 (t, 1H)

| Compound | MW | Tg | M.P. |
|---|---|---|---|
| C-306 | 610.8 | 114° C. | 132° C. |

Example 12: Preparation of Compound C-333

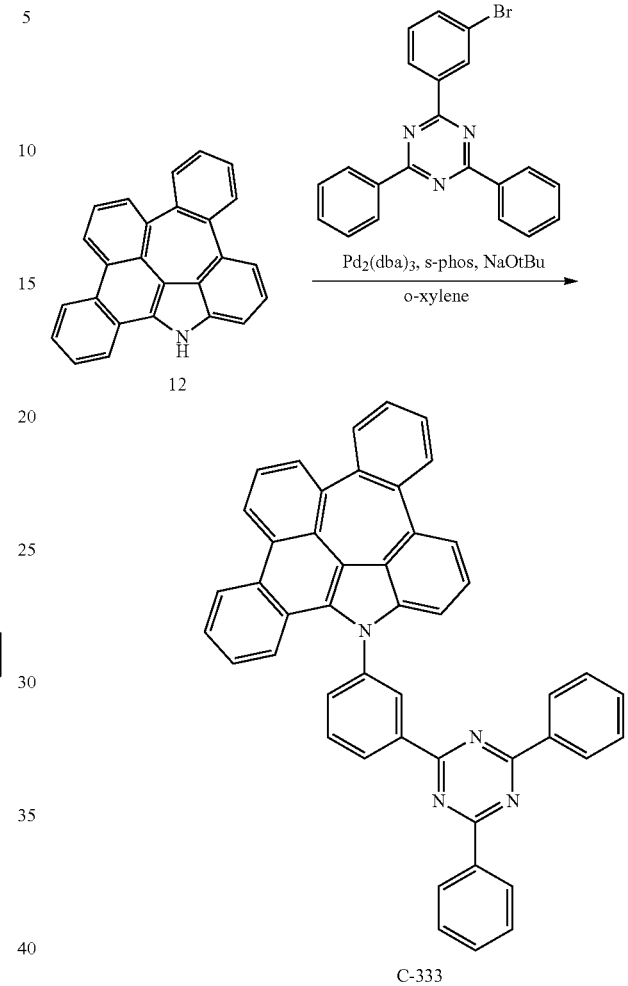

2.6 g of compound 12 (7.6 mmol), 2.95 g of 2-(3-bromophenyl)-4,6-diphenyl-1,3,5-triazine (7.6 mmol), 0.27 g of tris(dibenzylideneacetone)dipalladium (0) (0.3 mmol), 0.3 g of 2-dicyclohexylphosphino-2',6'-dimethoxybiphenyl (0.7 mmol), and 1.8 g of sodium tert-butoxide (19 mmol) were dissolved in 50 mL of 1,2-dimethyl benzene in a flask and refluxed for 12 hours. After the reaction was completed, the organic layer was extracted with ethyl acetate after distillation under reduced pressure, and residual water was removed by using magnesium sulfate. The residue was dried and purified by column chromatography to obtain 1.9 g of compound C-333 (yield: 38%).

$^1$H NMR (600 MHz, DMSO-d6, δ) 9.086-9.072 (d, 1H), 8.887-8.882 (t, 1H), 8.821-8.807 (d, 1H), 8.714-8.699 (d, 4H), 8.676-8.663 (d, 1H), 8.014-7.988 (t, 1H), 7.883-7.833 (m, 3H), 7.781-7.768 (d, 1H), 7.691-7.665 (t, 2H), 7.640-7.575 (m, 6H), 7.540-7.485 (m, 3H), 7.399-7.343 (m, 3H), 6.982-6.968 (d, 1H)

| Compound | MW | M.P. | Tg |
|---|---|---|---|
| C-333 | 648.77 | 195° C. | 165° C. |

Example 13: Preparation of Compound C-372

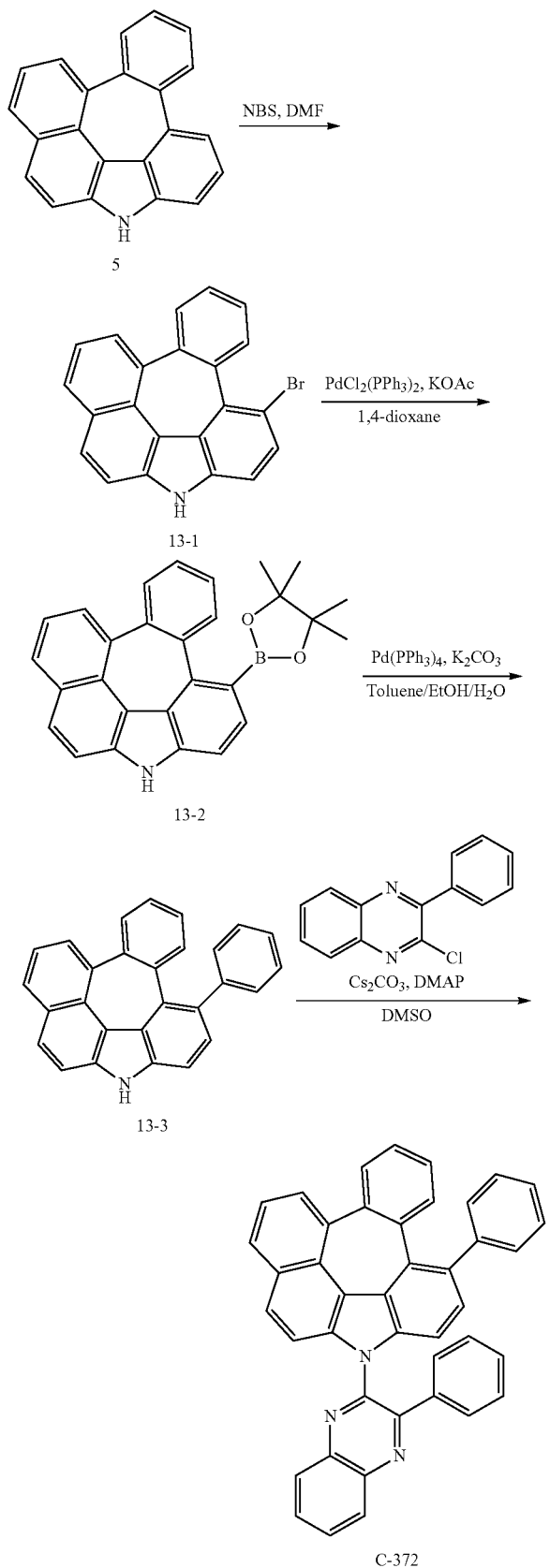

Synthesis of Compound 13-1

70 g of compound 5 (240 mol), and 40.6 g of N-bromosuccinimide (255 mmol) were dissolved in 1200 mL of dimethylformamide in a flask, and stirred at 0° C. for 3 hours. After the reaction was completed, the organic layer was extracted with ethyl acetate, and residual water was removed by using magnesium sulfate. The residue was dried and purified by column chromatography to obtain 68 g of compound 13-1 (yield: 76%).

Synthesis of Compound 13-2

47.3 g of compound 13-1 (127 mmol), 42 g of bis(pinacolato)diboron (166 mmol), 4.5 g of bis (triphenylphosphine)palladium(II) dichloride (6.4 mmol), and 25 g of potassium acetate (255 mmol) were dissolved in 635 mL of 1,4-dioxane in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 31.5 g of compound 13-2 (yield: 59%).

Synthesis of Compound 13-3

4.5 g of compound 13-2 (10.7 mmol), 1.9 g of 1-bromobenzene (11.85 mmol), 0.63 g of tetrakis(triphenylphosphine)palladium (0) (0.54 mmol), and 3.7 g of potassium carbonate (26.95 mmol) were dissolved in 54 mL of toluene, 13 mL of ethanol, and 13 mL of water in a flask and refluxed for 12 hours. After the reaction was completed, the organic layer was extracted with ethyl acetate, and residual water was removed by using magnesium sulfate. The residue was dried and purified by column chromatography to obtain 2.2 g of compound 13-3 (yield: 56%).

Synthesis of Compound C-372

2.2 g of compound 13-3 (5.9 mmol), 1.58 g of 2-chloro-3-phenylquinoxaline (6.57 mmol), 3.89 g of cesium carbonate (11.96 mmol), and 0.36 g of 4-dimethylaminopyridine (2.99 mmol) were dissolved in 30 mL of dimethyl sulfur monoxide in a flask and stirred at 100° C. for 4 hours. After the reaction was completed, the reaction product was cooled to room temperature, and distilled water was added thereto. The organic layer was extracted with ethyl acetate, and residual water was removed by using magnesium sulfate. The residue was dried and purified by column chromatography to obtain 2.9 g of compound C-372 (yield: 85%).

| Compound | MW | M.P. | Tg |
|---|---|---|---|
| C-372 | 571.68 | 210° C. | 167° C. |

Example 14: Preparation of Compound C-334

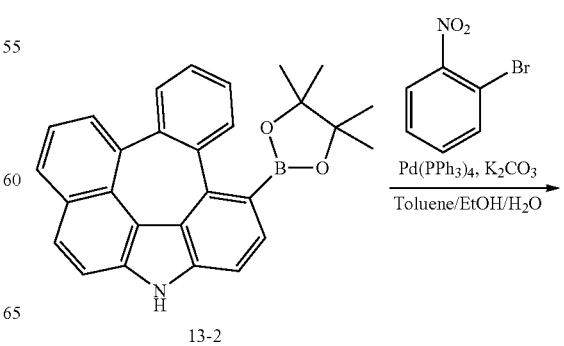

-continued

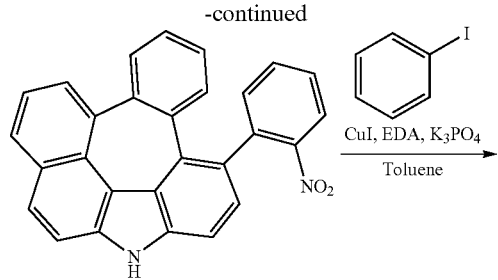

14-1

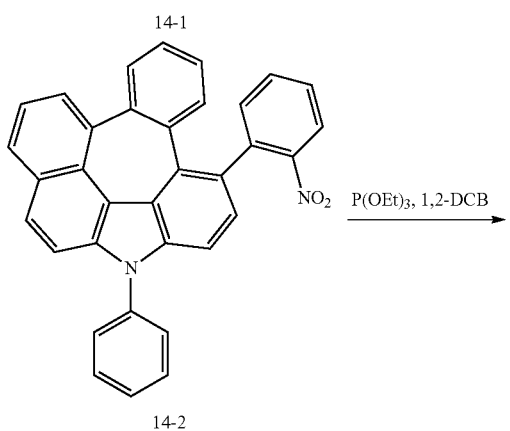

14-2

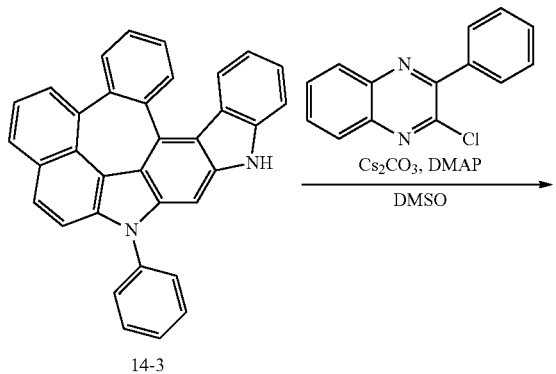

14-3

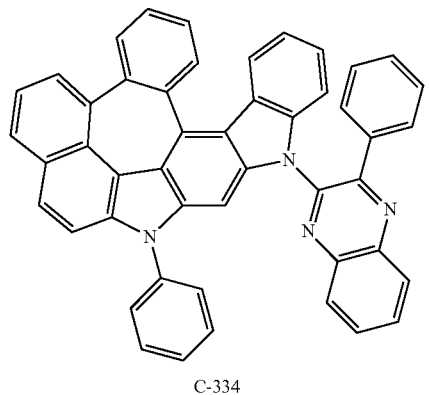

C-334

Synthesis of Compound 14-1

27 g of compound 13-2 (64.7 mmol), 14.4 g of 1-bromo-2-nitrobenzene (71.2 mmol), 3.7 g of tetrakis(triphenylphosphine)palladium (0) (3.2 mmol), and 22.4 g of potassium carbonate (162 mmol) were dissolved in 320 mL of toluene, 80 mL of ethanol, and 80 mL of water in a flask and refluxed for 12 hours. After the reaction was completed, the organic layer was extracted with ethyl acetate, and residual water was removed by using magnesium sulfate. The residue was dried and purified by column chromatography to obtain 26.7 g of compound 14-1 (yield: 100%).

Synthesis of Compound 14-2

26.7 g of compound 14-1 (64.7 mmol), 18 mL of 1-idobenzene (162 mmol), 18.5 g of copper iodide (CuI) (97 mmol), 13 mL of ethylenediamine (194 mmol), and 27.4 g of potassium phosphate (129 mmol) were dissolved in 325 mL of toluene in a flask and refluxed for 2 hours. After the reaction was completed, the organic layer was extracted with ethyl acetate, and residual water was removed by using magnesium sulfate. The residue was dried and purified by column chromatography to obtain 15.7 g of compound 14-2 (yield: 49%).

Synthesis of Compound 14-3

13.1 g of compound 14-2 (26.8 mmol) was added to 180 mL of triethylphosphite and 180 mL of 1,2-dichlorobenzene in a flask and stirred at 200° C. for 2 hours. After the reaction was completed, the solvent was distilled off under reduced pressure, the reaction product was cooled to room temperature, and hexane was added thereto to obtain a solid. The resulting solid was filtered through a filter to remove the solvent and purified by column chromatography to obtain 0.71 g of compound 14-3 (yield: 5.8%).

Synthesis of Compound C-334

0.71 g of compound 14-3 (1.56 mmol), 0.45 g of 2-chloro-3-phenylquinoxaline (1.87 mmol), 1.01 g of cesium carbonate (3.12 mmol), and 0.095 g of 4-dimethylaminopyridine (0.78 mmol) were dissolved in 30 mL of dimethyl sulfur monoxide in a flask and stirred at 100° C. for 4 hours. After the reaction was completed, the reaction product was cooled to room temperature, and distilled water and methanol were added thereto. The resulting solid was filtered through a filter to remove the solvent and purified by column chromatography to obtain 0.50 g of compound C-334 (yield: 49%).

$^1$H NMR (600 MHz, CDCl3, δ) 8.333-8.248 (m, 3H), 8.192-8.099 (m, 1H), 7.911-7.820 (m, 3H), 7.767-7.754 (d, 1H), 7.613-7.526 (m, 5H), 7.488-7.410 (m, 4H), 7.395-7.347 (m, 3H), 7.329-7.296 (m, 2H), 7.230-7.205 (m, 2H), 7.179-7.153 (m, 1H), 7.130-7.075 (m, 1H), 7.056-7.030 (m, 1H), 6.874-6.688 (m, 1H)

| Compound | MW | M.P. |
|---|---|---|
| C-334 | 660.78 | 290° C. |

Example 15: Preparation of Compound C-197

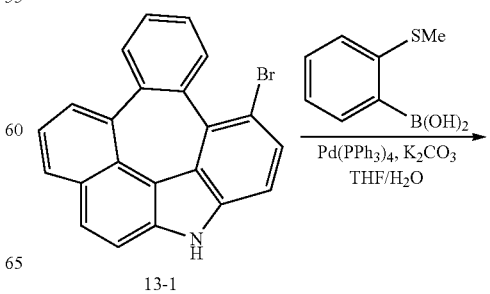

13-1

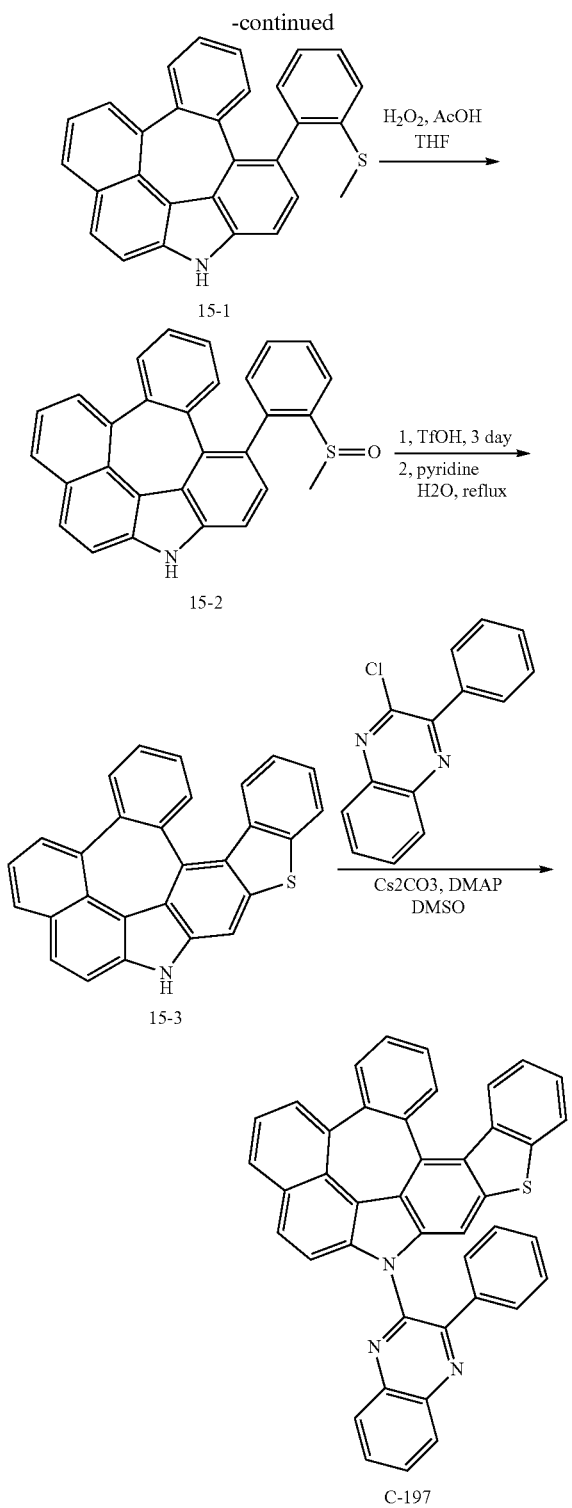

sium sulfate. The residue was dried and purified by column chromatography to obtain 40 g of compound 15-1 (yield: 89%).

Synthesis of Compound 15-2

40 g of compound 15-1 (96.8 mmol) was dissolved in 400 mL of tetrahydrofuran, 200 mL of acetic acid and 12.6 mL of 34.5% hydrogen peroxide (145.2 mmol) in a flask and stirred at room temperature for 20 hours. After the reaction was completed, the mixture was concentrated, and an organic layer was extracted with methylene chloride and an aqueous solution of sodium hydrogencarbonate, and then residual water was removed by using magnesium sulfate. The residue was dried and purified by column chromatography to obtain 42 g of compound 15-2 (yield: 100%).

Synthesis of Compound 15-3

42 g of compound 15-2 (96.4 mmol) was dissolved in 190 mL of trifluoromethanesulfonic acid and stirred at room temperature for 3 days. After the reaction was completed, 50 mL of pyridine and 1M aqueous NaOH solution were added to the mixture at 0° C. to adjust the pH to 7 to 8, and the mixture was refluxed at 100° C. for 1 hour. The resulting solid was filtered through a filter to remove the solvent and purified by column chromatography to obtain 9.1 g of compound 15-3 (yield: 24%).

Synthesis of Compound C-197

4 g of compound 15-3 (10.1 mmol), 3 g of 2-chloro-3-phenylquinoxaline (12.1 mmol), 6.6 g of cesium carbonate (20.2 mmol), and 0.62 g of 4-dimethylaminopyridine (5.1 mmol) were dissolved in 50 mL of dimethyl sulfur monoxide in a flask and stirred at 100° C. for 4 hours. After the reaction was completed, the reaction product was cooled to room temperature, and distilled water and methanol were added thereto. The resulting solid was filtered through a filter to remove the solvent and purified by column chromatography to obtain 4.8 g of compound C-197 (yield: 79%).

$^1$H NMR (600 MHz, CDCl$_3$, δ) 8.337-8.310 (m, 1H), 8.247-8.202 (m, 1H), 8.196-8.151 (m, 1H), 7.957-7.945 (m, 1H), 7.928 (s, 1H), 7.912-7.837 (m, 3H), 7.794-7.728 (m, 3H), 7.685-7.672 (d, 1H), 7.531-7.498 (m, 1H), 7.469-7.414 (m, 2H), 7.348-7.300 (m, 2H), 7.262-7.173 (m, 4H), 7.102-7.087 (d, 1H), 7.036-6.955 (m, 1H)

| Compound | MW | M.P. | Tg |
| --- | --- | --- | --- |
| C-197 | 601.73 | 317° C. | 194° C. |

Example 16: Preparation of Compound C-339

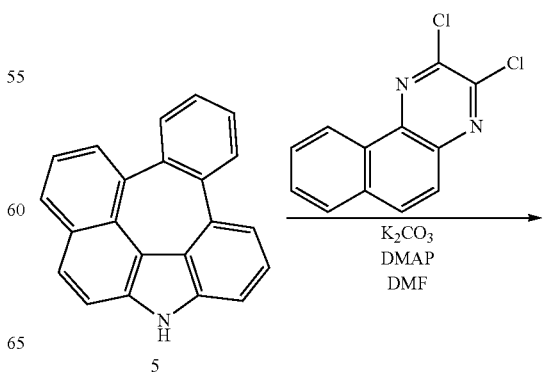

Synthesis of Compound 15-1

40 g of compound 13-1 (108 mmol), 25.4 g of (2-methylthiophenyl)boronic acid (153.5 mmol), 6.26 g of tetrakis(triphenylphosphine)palladium (0) (5.40 mmol), and 26.3 g of potassium carbonate (272.0 mmol) were dissolved in 536 mL of tetrahydrofuran and 134 mL of distilled water in a flask and refluxed at 100° C. for 18 hours. After the reaction was completed, an organic layer was extracted with ethyl acetate, and residual water was removed by using magne-

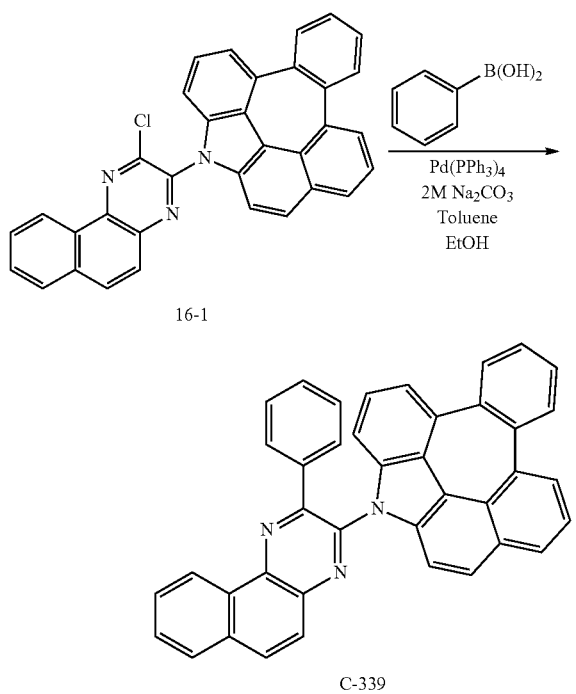

Example 17: Preparation of Compound C-338

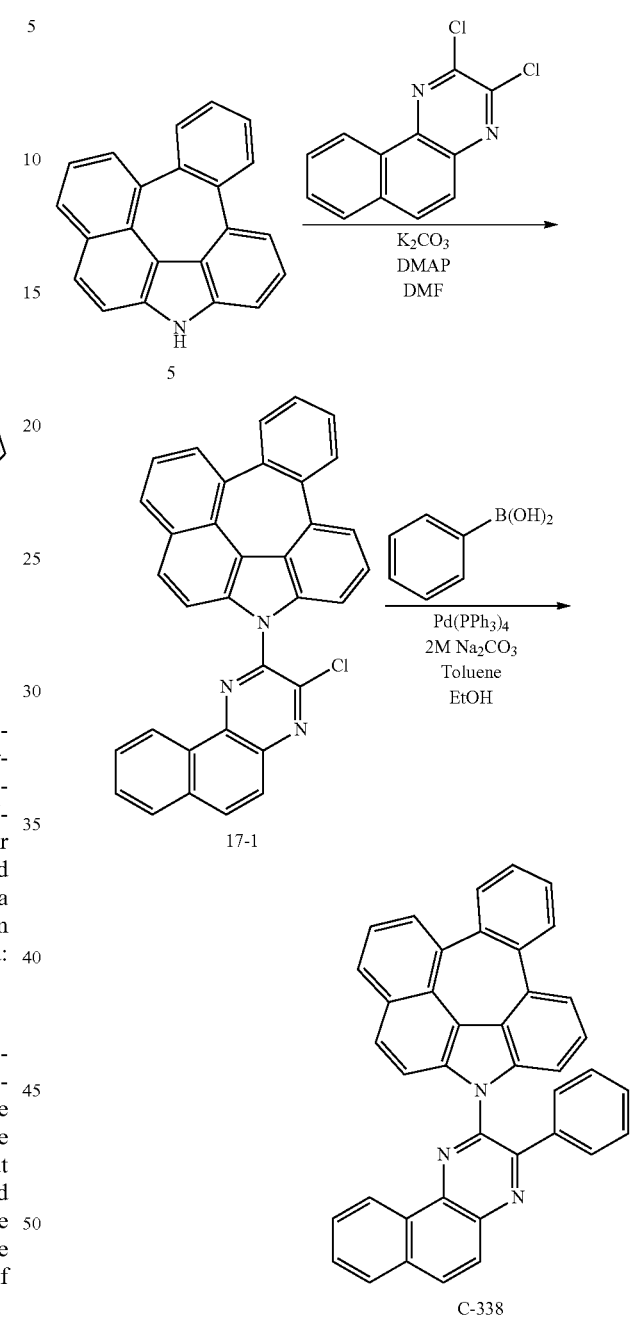

Synthesis of Compound 16-1

15.6 g of compound 5 (53.5 mmol), 20 g of 2,3-dichlorobenzo[f]quinoxaline (80.3 mmol), 15 g of potassium carbonate (107.0 mmol), and 3.3 g of N,N-dimethyl-4-pyridineamine (26.7 mmol) were added to 270 mL of N,N-dimethylformamide and stirred at 150° C. for 4 hours. After the reaction was completed, the reaction product was cooled to room temperature and the solvent was removed by a rotary evaporator. The residue was purified by column chromatography to obtain 2.2 g of compound 16-1 (yield: 8%).

Synthesis of Compound C-339

2.2 g of compound 16-1 (4.4 mmol), 800 mg of phenylboronic acid (6.6 mmol), 250 mg of tetrakis(triphenylphosphine)palladium (0.2 mmol), and 1.2 g of sodium carbonate (10.9 mmol), 20 mL of toluene, and 5 mL of ethanol were added to a reaction vessel, and the mixture was stirred at 130° C. for 3 hours. After the reaction was completed, and the reaction product was cooled to room temperature and the solvent was removed by a rotary evaporator. The residue was purified by column chromatography to obtain 1.8 g of compound C-339 (yield: 76%).

$^1$H NMR (600 MHz, CDCl$_3$, δ) 9.403-9.390 (d, 1H), 8.119-8.105 (d, 1H), 8.012-7.997 (d, 1H), 7.994-7.979 (d, 1H), 7.867-7.851 (m, 1H), 7.847-7.822 (td, 1H), 7.815-7.788 (td, 1H), 7.734-7.722 (d, 1H), 7.686-7.656 (m, 4H), 7.600-7.585 (m, 1H), 7.509-7.494 (d, 1H), 7.404-7.389 (m, 2H), 7.385-7.359 (t, 1H), 7.295-7.264 (m, 2H), 7.250-7.219 (t, 1H), 7.208-7.182 (m, 3H)

| Compound | MW | M.P. | Tg |
|---|---|---|---|
| C-339 | 545.65 | 247° C. | 148° C. |

Synthesis of Compound 17-1

15.6 g of compound 5 (53.5 mmol), 20 g of 2,3-dichlorobenzo[f]quinoxaline (80.3 mmol), 15 g of potassium carbonate (107.0 mmol), and 3.3 g of N,N-dimethyl-4-pyridineamine (26.7 mmol) were added to 270 mL of N,N-dimethylformamide and stirred at 150° C. for 4 hours. After the reaction was completed, the reaction product was cooled to room temperature and the solvent was removed by a rotary evaporator. The residue was purified by column chromatography to obtain 2.8 g of compound 17-1 (yield: 10%).

Synthesis of Compound C-338

2.7 g of compound 17-1 (5.4 mmol), 1 g of phenylboronic acid (8.0 mmol), 310 mg of tetrakis(triphenylphosphine) palladium (0.3 mmol), 1.4 g of sodium carbonate (13.4 mmol), 28 mL of toluene, and 7 mL of ethanol were added to a reaction vessel, and the mixture was stirred at 130° C. for 3 hours. After the reaction was completed, the reaction product was cooled to room temperature and the solvent was removed by a rotary evaporator. The residue was purified by column chromatography to obtain 2.5 g of compound C-338 (yield: 86%).

$^1$H NMR (600 MHz, CDCl$_3$, δ) 9.119-9.106 (d, 1H), 8.160-8.125 (dd, 2H), 8.001-7.988 (d, 1H), 7.878-7.862 (m, 1H), 7.782-7.755 (td, 1H), 7.748-7.726 (m, 2H), 7.709-7.685 (t, 2H), 7.623-7.594 (m, 3H), 7.518-7.503 (d, 1H), 7.418-7.371 (m, 4H), 7.305-7.271 (m, 2H), 7.200-7.182 (m, 3H)

| Compound | MW | M.P. | Tg |
|---|---|---|---|
| C-338 | 545.65 | 299° C. | 149° C. |

Example 18: Preparation of Compound C-379

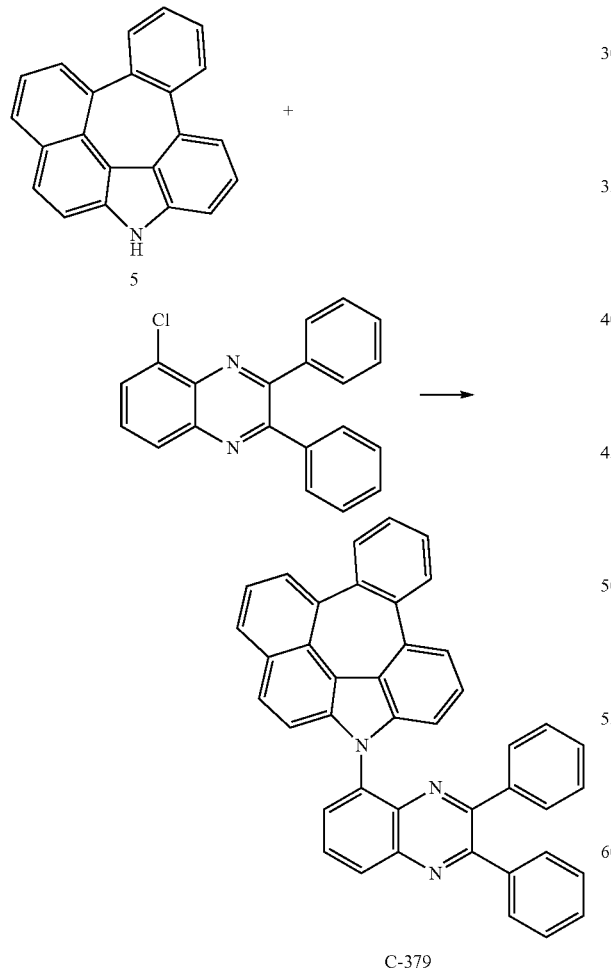

C-379

4.0 g of compound 5 (13.73 mmol), 5.2 g of 5-chloro-2,3-diphenylquinoxaline (16.47 mmol), 0.629 g of tris(dibenzylideneacetone)dipalladium (0) (0.686 mmol), 0.564 mg of S-Phos (1.0 mmol), and 3.9 g of sodium tert-butoxide (41 mmol) were dissolved in 80 mL of 1,2-dimethylbenzene in a flask and refluxed for 4 hours. After the reaction was completed, the reaction product was cooled to room temperature, and distilled water was added thereto. The organic layer was extracted with MC and dried over magnesium sulfate. The residue was distilled under reduced pressure and purified by column chromatography to obtain 2.8 g of compound C-379 (yield: 35.67%).

$^1$H NMR (600 MHz, CDCl$_3$, δ) 8.323-8.307 (d, J=7.2 Hz, 1H), 7.947-7.935 (m, 2H), 7.883-7.867 (m, 1H), 7.762-7.749 (d, J=7.2 Hz, 2H), 7.686-7.673 (d, J=7.8 Hz, 1H), 7.633-7.603 (m, 2H), 7.568-7.556 (d, J=7.2 Hz, 2H), 7.404-7.337 (m, 6H), 7.307-7.281 (t, J=7.8 Hz, 1H), 7.195-7.281 (m, 3H), 7.144-7.110 (t, J=7.2HZ, 1H), 7.087-7.074 (d, J=7.8HZ, 1H), 7.010-6.990 (m, 2H)

| Compound | MW | Tg | M.P. |
|---|---|---|---|
| C-379 | 571.67 | 135.60° C. | 142° C. |

Example 19: Preparation of Compound C-389

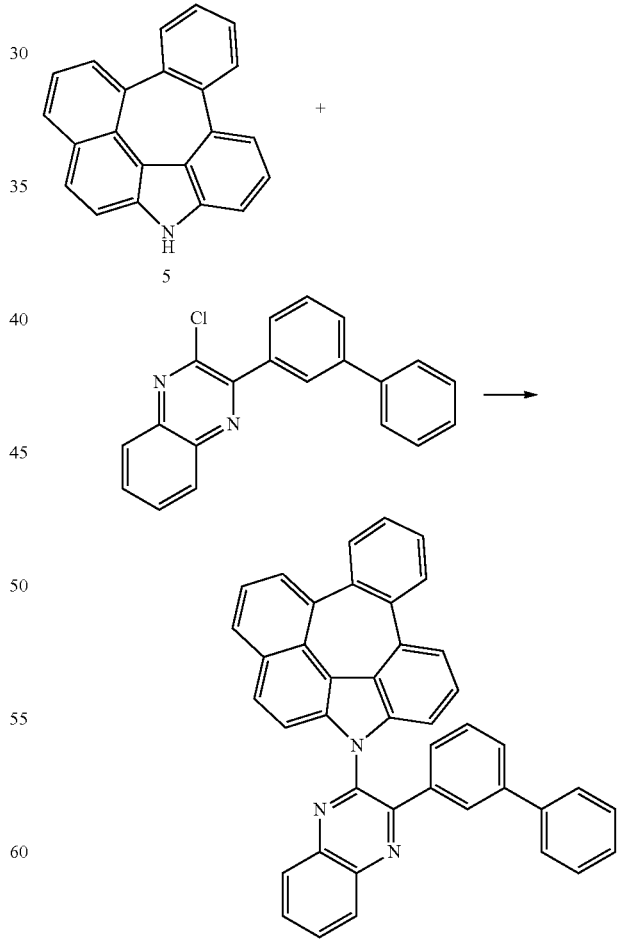

C-389

6.0 g of compound 5 (21 mmol), 7.8 g of 2-([1,1'-biphenyl]-3-yl)-3-chloroquinoxaline (25 mmol), 8.5 g of potassium carbonate (62 mmol), and 0.126 g of 4-dimethylaminopyridine (1 mmol) were dissolved in 100 mL of dimethyl formamide in a flask and refluxed for 4 hours. After the reaction was completed, the reaction product was cooled to room temperature, and distilled water was added thereto. The organic layer was extracted with MC and dried over magnesium sulfate. The residue was distilled under reduced pressure and purified by column chromatography to obtain 8.8 g of compound C-389 (yield: 74%).

$^1$H NMR (600 MHz, CDCl3, δ) 8.338-8.325 (d, J=7.8HZ, 1H), 8.228-8.212 (d, J=8.7HZ, 1H), 7.907-7.877 (m, 3H), 7.783-7.758 (m, 2H), 7.686-7.683 (d, J=7.8 Hz, 2H), 7.630-7.590 (m, 1H), 7.523-7.508 (d, J=9 Hz, 2H), 7.447-7.390 (m, 3H), 7.341-7.332 (m, 2H), 7.284-7.236 (m, 3H), 7.205 (s, 1H), 7.088-7.066 (m, 1H), 7.016-7.002 (d, J=7.8 Hz, 2H), 6.903-6.877 (m, 2H)

| Compound | MW | Tg | M.P. |
|---|---|---|---|
| C-389 | 571.67 | 120.06° C. | 202° C. |

Example 20: Preparation of Compound C-395

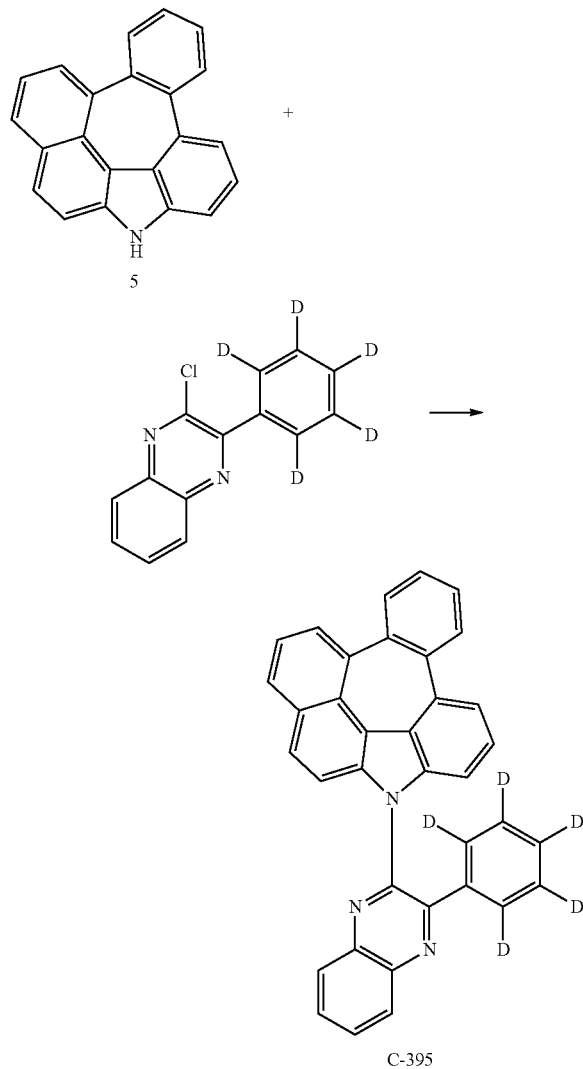

C-395

7.9 g of compound 5 (27 mmol), 7.9 g of 2-chloro-3-(phenyl-D5)quinoxaline (33 mmol), 11.24 g of potassium carbonate (81 mmol), and 0.166 g of 4-dimethylaminopyridine (1 mmol) were dissolved in 135 mL of dimethyl formamide in a flask and refluxed for 4 hours. After the reaction was completed, the reaction product was cooled to room temperature and distilled water was added thereto. The organic layer was extracted with MC and dried over magnesium sulfate. The residue was distilled under reduced pressure and purified by column chromatography to obtain 3.2 g of compound C-395 (yield: 23.7%).

$^1$H NMR (600 MHz, CDCl3, δ) 8.318-8.305 (d, J=7.8 Hz, 1H), 8.164-8.151 (d, J=7.8 Hz, 1H), 7.892-7.834 (m, 3H), 7.740-7.728 (d, J=7.2 Hz, 1H), 7.691-7.679 (d, J=7.2 Hz, 2H), 7.603-7.587 (m, 1H), 7.508-7.493 (d, J=9 Hz, 1H), 7.413-7.370 (m, 3H), 7.291-7.250 (m, 2H), 7.212-7.197 (d, J=9 Hz, 1H)

| Compound | MW | Tg | M.P. |
|---|---|---|---|
| C-395 | 500.62 | 127° C. | 158° C. |

Example 21: Preparation of Compound C-380

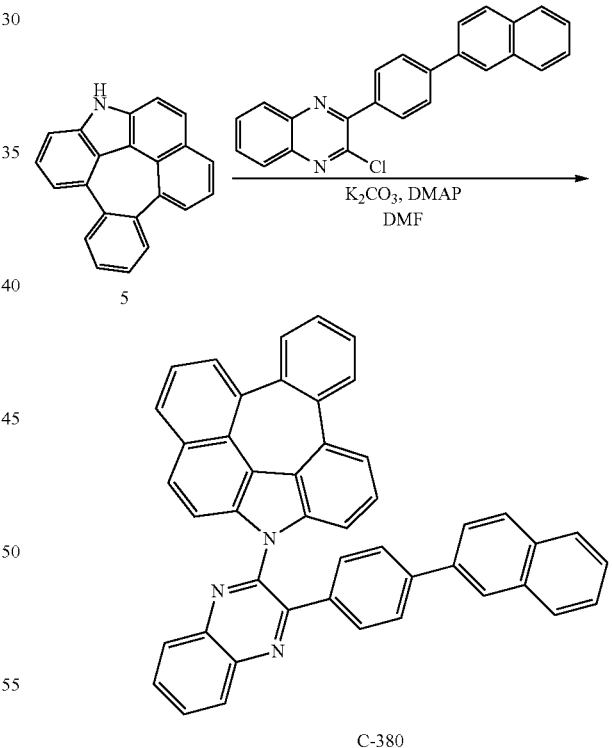

C-380

10 g of compound 5 (28.82 mmol), 7.0 g of 2-chloro-3-(4-(naphthalene-2-yl)phenyl)quinoxaline (24.02 mmol), 1.5 g of 4-(dimethylamino)pyridine (12.01 mmol), and 3.3 g of potassium carbonate (24.02 mmol) were dissolved in 130 mL of dimethyl formamide in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 8.8 g of compound C-380 (yield: 59%).

$^1$H NMR (600 MHz, CDCl3, δ) 8.33-8.32 (d, J=6.0 Hz, 1H), 8.16-8.15 (d, J=6.0 Hz, 1H), 7.88-7.84 (m, 4H), 7.80-7.77 (m, 3H), 7.74-7.73 (d, J=6.0 Hz, 1H), 7.69-7.66 (m, 4H), 7.57-7.56 (m, 2H), 7.53-7.50 (m, 3H), 7.43-7.37 (m, 5H), 7.32-7.23 (m, 3H)

| Compound | MW | Tg | M.P. |
|---|---|---|---|
| C-380 | 621.74 | 145.6° C. | 262.7° C. |

Example 22: Preparation of Compound C-394

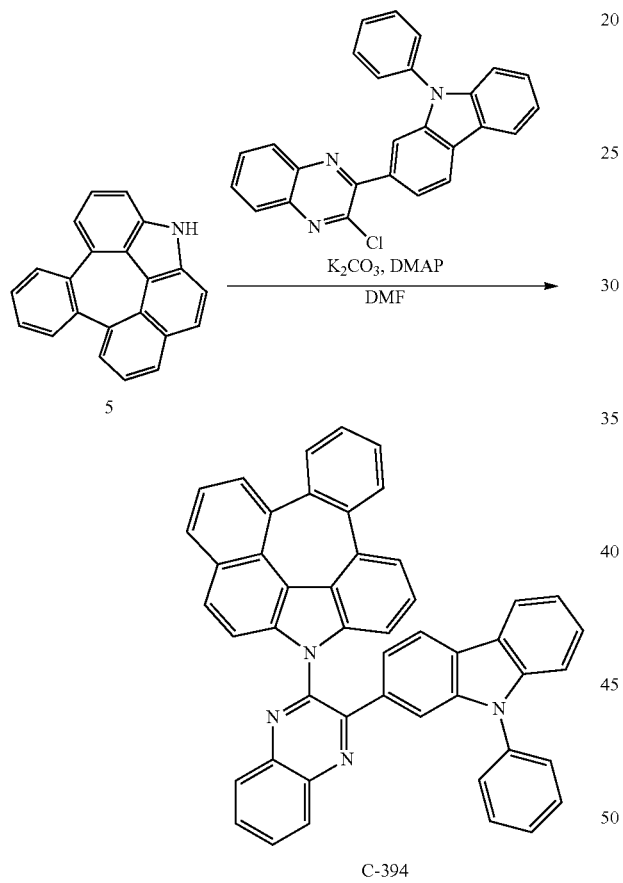

C-394

6 g of compound 5 (20.59 mmol), 9.1 g of 2-(3-chloro-quinoxaline-2-yl)-9-phenyl-9H-carbazole (22.65 mmol), 1.2 g of 4-(dimethylamino)pyridine (10.29 mmol), and 2.8 g of potassium carbonate (20.59 mmol) were dissolved in 100 mL of dimethyl formamide in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 9.6 g of compound C-394 (yield: 70%).

$^1$H NMR (600 MHz, CDCl3, δ) 8.31-8.30 (d, J=6.0 Hz, 1H), 8.13-8.11 (d, J=12.0 Hz, 1H), 8.04-8.03 (d, J=6.0 Hz, 1H), 7.94-7.93 (d, J=6.0 Hz, 1H), 7.86-7.81 (m, 3H), 7.74-7.73 (d, J=6.0 Hz, 1H), 7.65-7.63 (d, J=12.0 Hz, 2H), 7.61-7.60 (m, 1H), 7.44-7.36 (m, 4H), 7.30-7.28 (m, 1H), 7.23-7.15 (m, 6H), 6.98-6.93 (m, 3H), 6.88-6.87 (m, 2H)

| Compound | MW | Tg | M.P. |
|---|---|---|---|
| C-394 | 660.78 | 154.09° C. | 290.5° C. |

Example 23: Preparation of Compound C-346

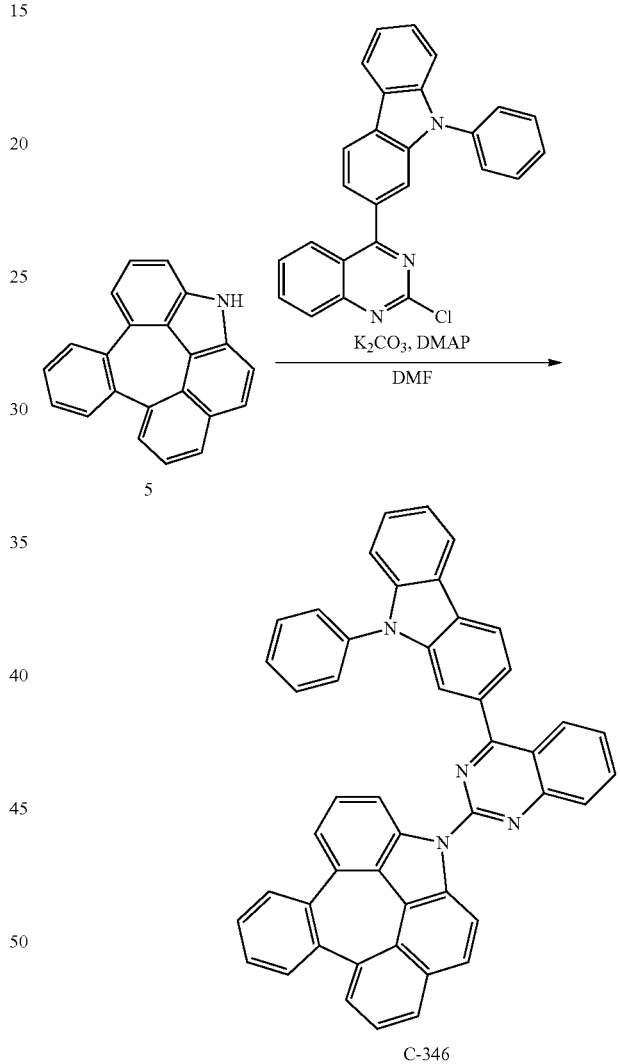

C-346

6.0 g of compound 5 (20.59 mmol), 9.1 g of 2-(2-chloroquinazoline-4-yl)-9-phenyl-9H-carbazole (22.65 mmol), 1.2 g of 4-(dimethylamino)pyridine (10.29 mmol), and 2.8 g of potassium carbonate (20.59 mmol) were dissolved in 100 mL of dimethyl formamide in a flask and refluxed for 3 hours. After the reaction was completed, the organic layer was extracted with ethyl acetate after distillation under reduced pressure, and residual water was removed by using magnesium sulfate. The residue was dried and purified by column chromatography to obtain 10 g of compound C-346 (yield: 77%).

¹H NMR (600 MHz, CDCl3, δ) 9.01-9.00 (d, J=6.0 Hz, 1H), 8.85-8.84 (d, J=6.0 Hz, 1H), 8.34-8.33 (d, J=6.0 Hz, 1H), 8.23-8.22 (d, J=6.0 Hz, 2H), 8.11-8.10 (d, J=6.0 Hz, 1H), 8.05 (s, 1H), 7.86-7.82 (m, 2H), 7.79-7.77 (m, 1H), 7.75-7.71 (m, 3H), 7.67-7.64 (m. 3H), 7.59-7.57 (m, 2H), 7.53-7.52 (m, 1H), 7.50-7.47 (m, 3H), 7.43-7.37 (m, 2H), 7.36-7.35 (m, 4H)

| Compound | MW | Tg | M.P. |
|---|---|---|---|
| C-346 | 660.78 | 158° C. | 189.9° C. |

¹H NMR (600 MHz, CDCl3, δ) 8.927-8.912 (d, J=7.8 Hz, 2H), 8.199-8.160 (m, 2H), 7.925-7.910 (m, 3H), 7.865-7.855 (m, 1H), 7.759-7.672 (m, 6H), 7.620-7.587 (m, 5H), 7.540-7.525 (d, J=9 Hz, 1H), 7.401-7.375 (m, 3H), 7.339-7.328 (m, 2H)

| Compound | MW | Tg | M.P. |
|---|---|---|---|
| C-388 | 571.6 | 133° C. | 241° C. |

Example 25: Preparation of Compound C-381

Example 24: Preparation of Compound C-388

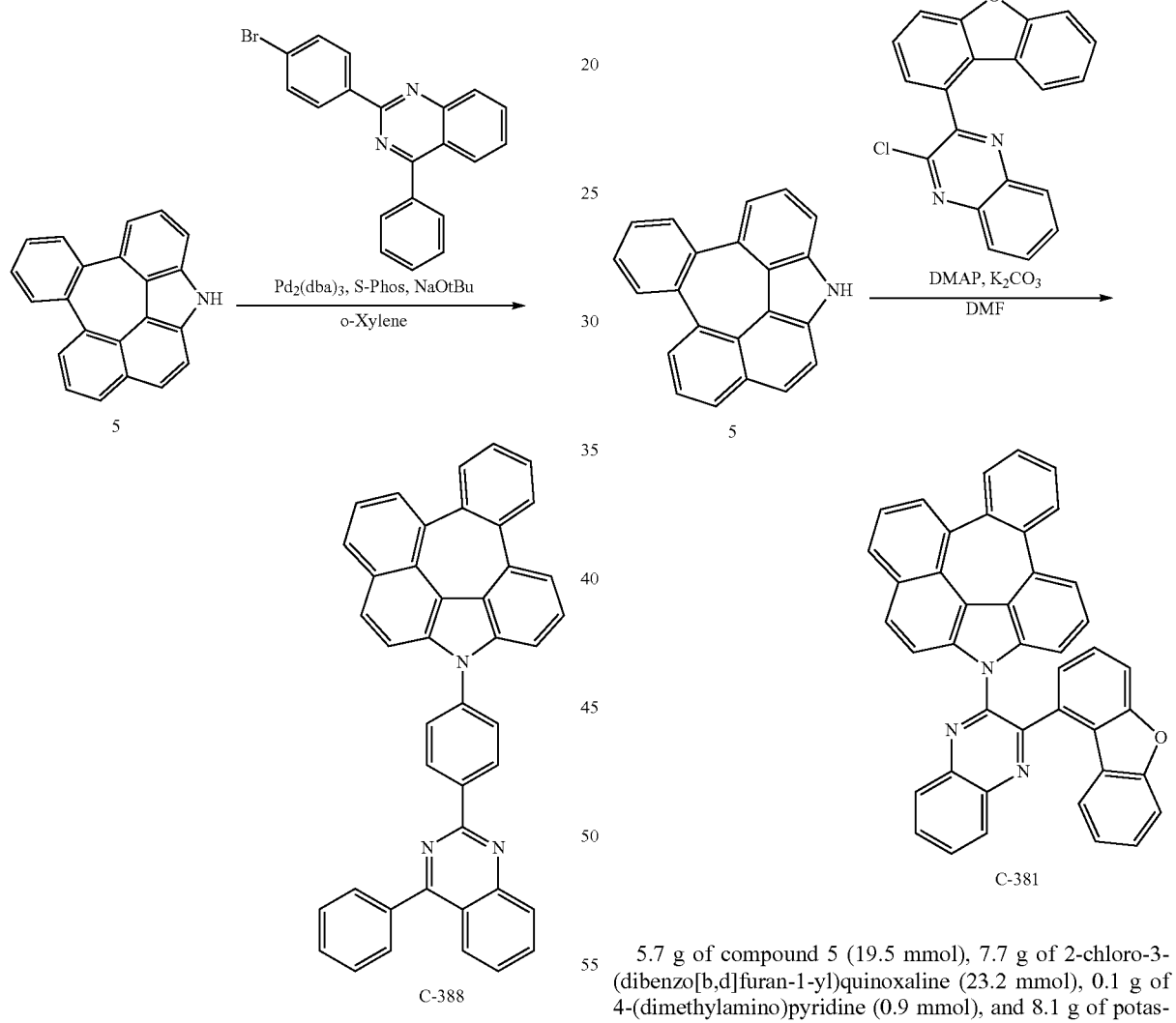

g of compound 5 (41.1 mmol), 14.8 g of 2-(4-bromophenyl)-4-phenylquinazoline (41.1 mmol), 1.5 g of tris(dibenzylideneacetone)dipalladium (0) (1.6 mmol), 1.7 g of S-Phos (4.1 mmol), and 9.8 g of sodium tert-butoxide (102.9 mmol) were dissolved in 274 mL of o-xylene in a flask and refluxed for 4 hours. After the reaction was completed, the reaction product was cooled and purified by column chromatography to obtain 1.1 g of compound C-388 (yield: 4.7%).

5.7 g of compound 5 (19.5 mmol), 7.7 g of 2-chloro-3-(dibenzo[b,d]furan-1-yl)quinoxaline (23.2 mmol), 0.1 g of 4-(dimethylamino)pyridine (0.9 mmol), and 8.1 g of potassium carbonate (58.5 mmol) were dissolved in 99 mL of dimethyl formamide in a flask and refluxed for 3 hours and 30 minutes. After the reaction was completed, the reaction product was cooled, and methanol and water were added and filtered. The residue was dried and purified by column chromatography to obtain 6 g of compound C-381 (yield: 52%).

¹H NMR (600 MHz, CDCl3, δ) 8.324-8.271 (m, 2H), 7.962-7.942 (m, 2H), 7.867-7.855 (d, J=7.2 Hz, 1H), 7.821-7.805 (m, 1H), 7.705-7.693 (d, J=7.2 Hz, 1H), 7.655-7.595

(m, 3H), 7.567-7.537 (m, 2H), 7.394-7.272 (m, 8H), 7.124-7.155 (m, 1H), 6.984-6.958 (t, J=7.2 Hz, 1H), 6.830-6.817 (d, J=7.8 Hz, 1H)

| Compound | MW | Tg | M.P. |
|---|---|---|---|
| C-381 | 585.6 | 154.79° C. | 233° C. |

Example 26: Preparation of Compound C-378

Example 27: Preparation of Compound C-386

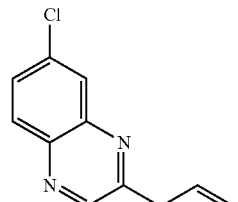

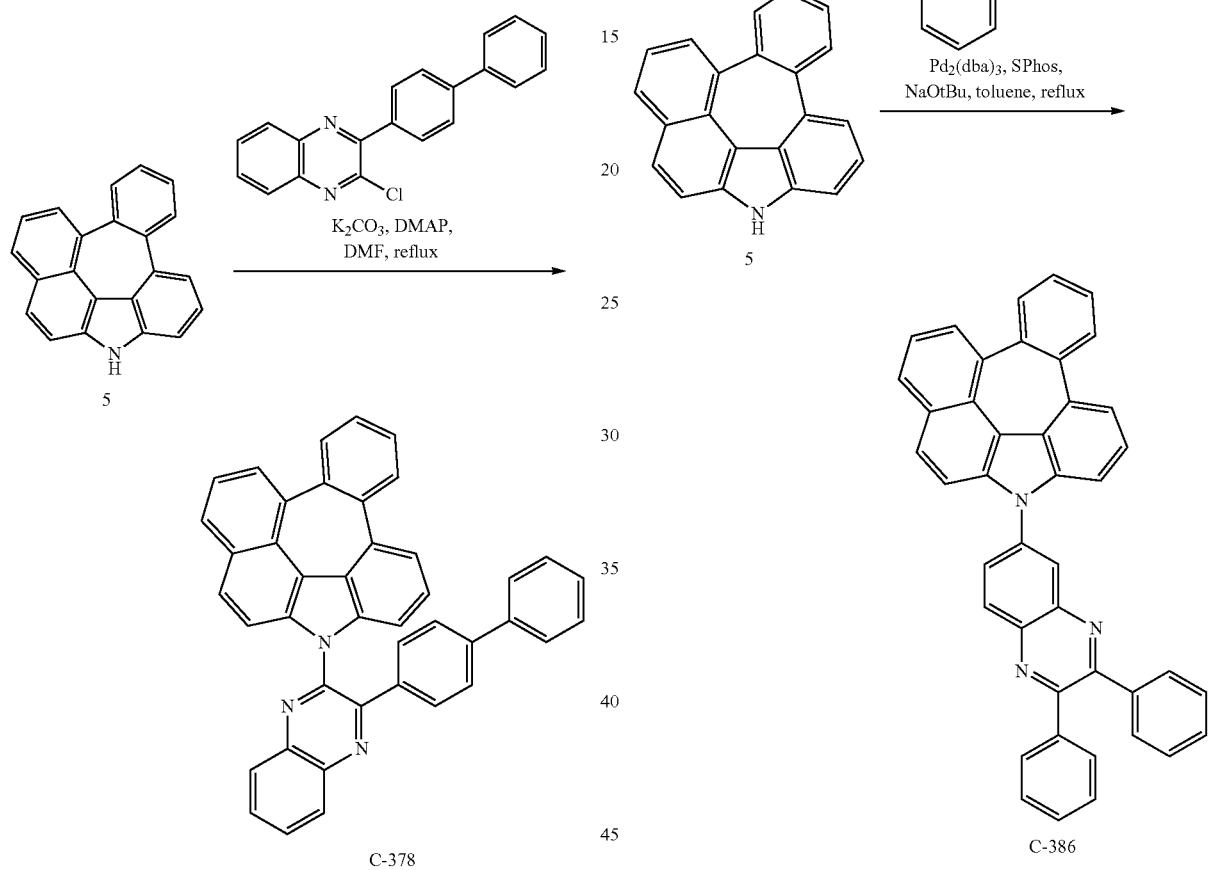

3.8 g of compound 5 (13 mmol), 5.0 g of 2-([1,1'-biphenyl]-4-yl)-3-chloroquinoxaline (16 mmol), 800 mg of DMAP (7 mmol), and 3.6 g of potassium carbonate (26 mmol) were dissolved in 55 mL of dimethyl formamide in a flask and refluxed for 18 hours. After the reaction was completed, the organic layer was extracted with ethyl acetate after distillation under reduced pressure, and residual water was removed by using magnesium sulfate. The residue was dried and purified by column chromatography to obtain 1.4 g of compound C-378 (yield: 19%).

$^1$H NMR (600 MHz, CDCl3, δ) 8.33-8.32 (m, 1H), 8.17-8.16 (m, 1H), 7.90-7.84 (m, 3H), 7.74 (d, J=7.50 Hz, 1H), 7.69 (t, J=6.72 Hz, 2H), 7.63 (d, J=8.4 Hz, 2H), 7.61-7.59 (m, 1H), 7.51 (d, J=9.00 Hz, 1H), 7.45-7.37 (m, 7H), 7.35-7.27 (m, 5H), 7.23 (d, J=8.79 Hz, 1H)

5.1 g of compound 5 (17 mmol), 5.0 g of 6-chloro-2,3-diphenylquinoxaline (16 mmol), 578 mg of tris(dibenzylideneacetone)dipalladium (0) (0.631 mmol), 648 mg of S-Phos (2 mmol), and 3.8 g of sodium tert-butoxide (39 mmol) were dissolved in 100 mL of toluene in a flask and refluxed for 16 hours. After the reaction was completed, the organic layer was extracted with ethyl acetate after distillation under reduced pressure, and residual water was removed by using magnesium sulfate. The residue was dried and purified by column chromatography to obtain 7.6 g of compound C-386 (yield: 84%).

$^1$H NMR (600 MHz, CDCl3, δ) 8.01 (s, 1H), 8.40 (d, J=5.4 Hz, 1H), 7.99 (dd, J=5.4 Hz; 2.22 Hz, 1H), 7.89-7.87 (m, 1H), 7.79-7.77 (m, 2H), 7.74-7.70 (m, 2H), 7.63-7.60 (m, 2H), 7.59-7.56 (m, 4H), 7.44-7.34 (m, 11H)

| Compound | MW | Tg | M.P. |
|---|---|---|---|
| C-378 | 571.68 | 137.6° C. | 189° C. |

| Compound | MW | Tg | M.P. |
|---|---|---|---|
| C-386 | 571.68 | 138.80° C. | 295° C. |

Example 28: Preparation of Compound C-387

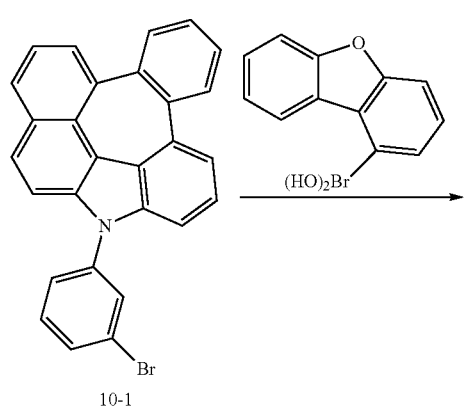

6.6 g of compound 10-1 (14.78 mmol), 3.4 g of dibenzo[b,d]furan-1-yl-boronic acid (16.24 mmol), 0.85 g of tetrakis(triphenylphosphine)palladium(0) (0.739 mmol), and 4 g of potassium carbonate (29.57 mmol) were added to 60 mL of toluene, 15 mL of ethanol, and 15 mL of purified water and stirred under reflux for one day. After the reaction was completed, the reaction product was cooled to room temperature, and the resulting solid was filtered under reduced pressure. The solid was dissolved in CHCl$_3$ and purified by column chromatography using MC/Hex to obtain 3.5 g of compound C-387 (yield: 45%).

$^1$H NMR (600 MHz, DMSO, δ) 7.953-7.927 (m, 2H), 7.896-7.872 (t, 2H), 7.848-7.810 (m, 3H), 7.793-7.746 (m, 4H), 7.656-7.601 (m, 4H), 7.539-7.511 (t, 1H), 7.485-7.443 (m, 4H), 7.419-7.393 (t, 1H), 7.369-7.356 (d, 1H), 7.294-7.269 (t, 1H)

| Compound | MW | M.P. | Tg |
|---|---|---|---|
| C-387 | 533.6 | 224° C. | 117° C. |

Example 29: Preparation of Compound C-393

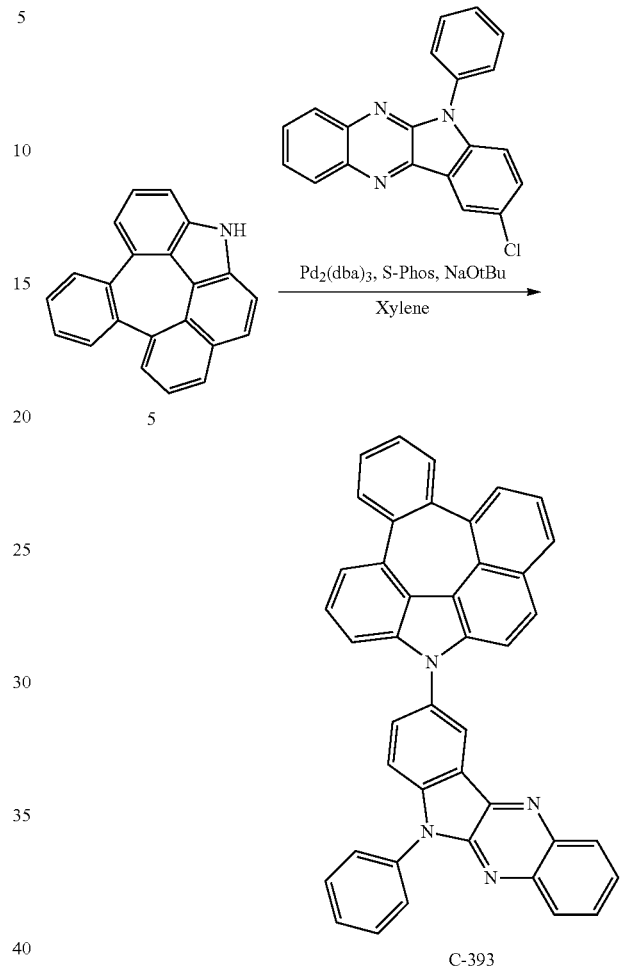

4.4 g of compound 5 (15.16 mmol), 5.0 g of 9-chloro-6-phenyl-6H-indolo[2,3,b]quinoxaline (15.16 mmol), 0.5 g of tris(dibenzylideneacetone)dipalladium (0) (0.606 mmol), 0.6 g of S-Phos (1.516 mmol), and 12 g of sodium tert-butoxide (37.90 mmol) were dissolved in 100 mL of 1,2-dimethylbenzene in a flask and refluxed for 4 hours. After the reaction was completed, the organic layer was extracted with ethyl acetate after distillation under reduced pressure, and residual water was removed by using magnesium sulfate. The residue was dried and purified by column chromatography to obtain 1.9 g of compound C-393 (yield: 21%).

$^1$H NMR (600 MHz, CDCl3, δ) 8.74 (s, 1H), 8.33-8.32 (d, J=6.0 Hz, 1H), 8.15-8.14 (d, J=6.0 Hz, 1H), 7.91-7.90 (m, 1H), 7.84-8.73 (m, 2H), 7.80-7.78 (m, 5H), 7.77-7.69 (m, 5H), 7.64-7.63 (m. 1H), 7.60-7.59 (m, 1H), 7.50-7.49 (d, J=6.0 Hz, 1H), 7.43-7.41 (m, 3H), 7.36-7.34 (t, J=6.0 Hz, 1H), 7.28-7.27 (m, 1H)

| Compound | MW | Tg | M.P. |
|---|---|---|---|
| C-393 | 584.67 | 129.07° C. | 294° C. |

Example 30: Preparation of Compound C-447

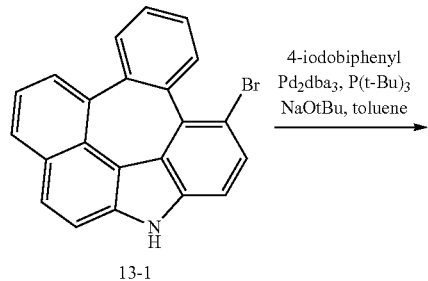

13-1

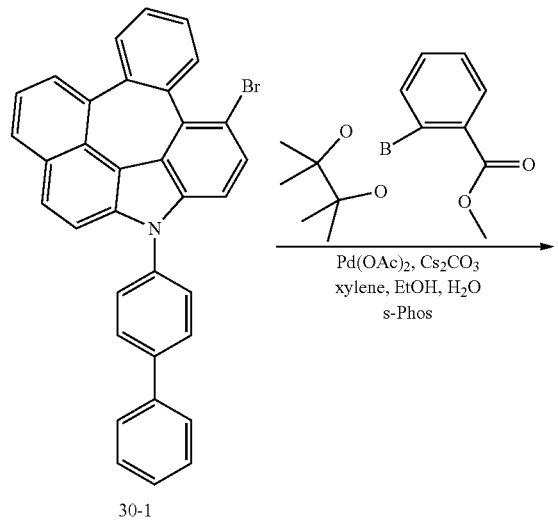

30-1

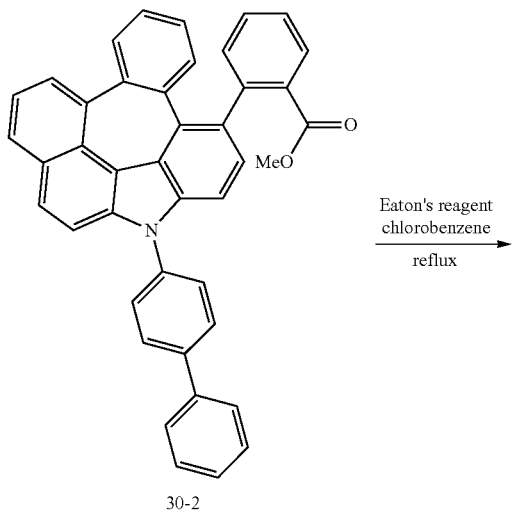

30-2

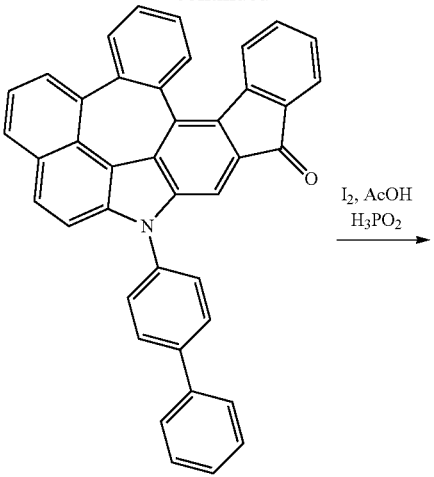

30-3

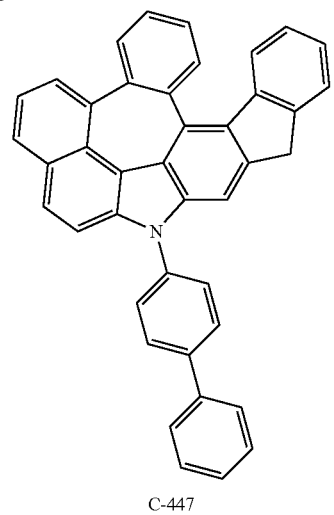

C-447

Synthesis of Compound 30-1

8.0 g of compound 13-1 (21.6 mmol), 12.1 g of 4-iodobiphenyl (43.2 mmol), 1.0 g of tris(dibenzylideneacetone)dipalladium (0) (1.08 mmol), 0.87 mL of tri-tert-butylphsophine (2.16 mmol, 50% toluene solution), and 5.2 g of sodium tert-butoxide (54.0 mmol) were dissolved in 216 mL of toluene in a flask and refluxed for 18 hours. After the reaction was completed, the reaction product was cooled to room temperature, and the solvent was removed by a rotary evaporator. The residue was purified by column chromatography to obtain 7.5 g of compound 30-1 (yield: 66%).

Synthesis of Compound 30-2

7.5 g of compound 30-1 (14.4 mmol), 4.5 g of methyl 2-(4,4,5,5-tetramethyl-1,3,2-dioxylboren-2-yl)benzoate (17.3 mmol), 323 mg of palladium acetate (Pd(OAc)$_2$) (1.44 mmol), 1.2 g of ligand (2-dicyclohexylphosphonium-2',6'-dimethoxybiphenyl) (2.88 mmol), 14 g of cesium carbonate (43.2 mmol), 80 mL of xylene, 40 mL of ethanol, and 40 mL of distilled water were added to a flask, and stirred under reflux for 18 hours. The mixture was cooled to room temperature and distilled water was added thereto. The organic layer was extracted with MC, and dried over magnesium sulfate. The residue was distilled under reduced pressure and purified by column chromatography to obtain 2.2 g of compound 30-2 (yield: 27%).

Synthesis of Compound 30-3

2.2 g of compound 30-2 (3.8 mmol), 2 mL of Eaton's reagent, and 13 mL of benzene chloride were added to a flask and stirred under reflux for 18 hours. The mixture was cooled to room temperature and an aqueous solution of sodium hydrogencarbonate was added thereto. The organic layer was extracted with ethyl acetate (EA) and dried over magnesium sulfate. The residue was distilled under reduced pressure and purified by column chromatography to obtain 1.5 g of compound 30-3 (yield: 71%).

Synthesis of Compound C-447

244 mg of iodine (0.96 mmol), 0.48 mL of hypophosphorous acid (4.4 mmol, 50% aqueous solution), and 14 mL of acetic acid were added to a flask and stirred at 80° C. for 30 minutes. 1.5 g of compound 30-3 (2.75 mmol) was slowly added dropwise thereto and stirred under reflux for 4 hours. The reaction solution was cooled to room temperature, and the precipitated solid was filtered and washed with a large amount of water and ethanol. The resulting solid was filtered through a filter to remove the solvent. The residue was purified by column chromatography to obtain 270 mg of compound C-447 (yield: 18%).

$^1$H NMR (600 MHz, CDCl$_3$, δ) 8.051-8.036 (dd, 1H), 7.967-7.953 (m, 1H), 7.920-7.909 (d, 1H), 7.857-7.843 (d, 2H), 7.797-7.784 (d, 1H), 7.720-7.698 (m, 2H), 7.669-7.643 (m, 3H), 7.562-7.500 (m, 5H), 7.463-7.416 (m, 5H), 7.217-7.190 (m, 2H), 4.153-4.188 (d, 1H), 3.949-3.913 (d, 1H)

Hereinafter, the properties of the organic light-emitting diode (OLED) device comprising the compound of the present disclosure will be explained in detail, but is not limited by the following examples.

Device Examples 1 to 16: Producing an OLED Device Comprising a Compound According to the Present Disclosure as a Host OLED devices were produced by using the organic electroluminescent compound according to the present disclosure. A transparent electrode indium tin oxide (ITO) thin film (10 Ω/sq) on a glass substrate for an OLED device (GEOMATEC CO., LTD., Japan) was subjected to an ultrasonic washing with acetone, ethanol, and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into a cell of the vacuum vapor deposition apparatus and was evaporated by applying an electric current to the cell, thereby forming a first hole transport layer having a thickness of 10 nm on the second hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layer, a light-emitting layer was formed thereon as follows: The host material shown in Table 1 was introduced into one cell of the vacuum vapor depositing apparatus as a host, and compound D-39 was introduced into another cell as a dopant. The two materials were evaporated at a different rate and the dopant was deposited in a doping amount of 3 wt % based on the amount of the host to form a light-emitting layer having a thickness of 40 nm on the second hole transport layer. Compound ET-1 and compound EI-1 were then introduced into the other two cells and evaporated simultaneously to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED device was produced.

Comparative Example 1: Producing an OLED Device Comprising a Conventional Compound as a Host An OLED device was produced in the same manner as in Device Example 1, except for using compound A as a host.

The driving voltage and luminous efficiency based on a luminance of 1,000 nits of the produced red OLED device, and the time taken to be reduced from 100% to 99% of the luminance (lifespan; T99) based on a luminance of 5,000 nits are provided in Table 1 below.

TABLE 1

| | Host Material | Driving Voltage (V) | Luminous Efficiency (cd/A) | Lifespan (T99, hr) |
|---|---|---|---|---|
| Device Example 1 | C-8 | 2.9 | 26 | 41 |
| Device Example 2 | C-301 | 2.9 | 24.5 | 45.8 |
| Device Example 3 | C-10 | 2.9 | 21.9 | 45.4 |
| Device Example 4 | C-7 | 3.2 | 25.2 | 40.4 |
| Device Example 5 | C-302 | 3.1 | 23.3 | 52.6 |
| Device Example 6 | C-9 | 2.8 | 24.9 | 67.4 |
| Device Example 7 | C-303 | 3.1 | 27.3 | 7.46 |
| Device Example 8 | C-307 | 3.1 | 25.2 | 25.0 |
| Device Example 9 | C-13 | 3.0 | 27.1 | 29.3 |
| Device Example 10 | C-386 | 2.8 | 23.2 | 31.2 |
| Device Example 11 | C-333 | 2.8 | 26.3 | 23.6 |
| Device Example 12 | C-338 | 2.9 | 23.4 | 55.1 |
| Device Example 13 | C-339 | 3.4 | 27.4 | 34.3 |
| Device Example 14 | C-389 | 3.3 | 27.3 | 46.7 |
| Device Example 15 | C-394 | 3.1 | 23.3 | 17.8 |
| Device Example 16 | C-346 | 3.0 | 23.7 | 9.1 |
| Comparative Example 1 | A | 9.2 | 11.6 | 0 |

From Table 1 above, it can be seen that the OLED devices comprising the organic electroluminescent compound of the present disclosure have low driving voltage, high luminous efficiency, and/or improved lifespan properties compared to the OLED devices comprising a conventional organic electroluminescent compound. In addition, the organic electroluminescent compound of the present disclosure has a highly fused structure, and thus has a relatively high glass transition temperature (Tg) as compared with other organic electroluminescent compounds having similar molecular weights, thereby showing excellent thermal stability.

Comparative Example 2: Producing an OLED Device not Comprising an Electron Buffer Layer An OLED device not comprising an electron buffer layer was produced by using the organic electroluminescent compound according to the present disclosure. A transparent electrode indium tin oxide (ITO) thin film (10 Ω/sq) on a glass substrate for an OLED device (GEOMATEC CO., LTD., Japan) was subjected to an ultrasonic washing with acetone and isopropyl alcohol, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-7}$ torr. Thereafter, an electric current was applied to the cell to evaporate the above-introduced material, thereby forming a first hole injection layer having a thickness of 60 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into a cell of the vacuum vapor deposition apparatus and was evaporated by applying an electric current to the cell, thereby forming a first hole transport layer having a thickness of 20 nm on the second hole injection layer. Compound HT-3 was then introduced into another cell of the vacuum vapor deposition apparatus and was evaporated by applying an electric current to the cell, thereby forming a second hole transport layer having a thickness of 5 nm on the first hole transport layer. After forming the hole injection layer and the hole transport layer, a light-emitting layer was formed thereon as follows: Compound FH-1 was introduced into one cell of the vacuum vapor depositing apparatus as a host, and compound FD-1 was introduced into another cell as a dopant. The two materials were evaporated at a different rate and the dopant was deposited in a doping amount of 2 wt % based on the total amount of the host and the dopant to form a light-emitting layer having a thickness of 20 nm on the second hole transport layer. Compound ET-1 and compound EI-1 were then introduced into the other two cells and evaporated simultaneously to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED device was produced. All the materials used for producing the OLED device were purified by vacuum sublimation at $10^{-6}$ torr.

Device Example 17: Producing an OLED Device Comprising a Compound According to the Present Disclosure as an Electron Buffer Layer An OLED device was produced in the same manner as in Comparative Example 2, except that the thickness of the electron transport layer was reduced to 30 nm, and the electron buffer layer comprising compound C-8 was inserted between the light-emitting layer and the electron transport layer.

The driving voltage and color coordinate based on a luminance of 1 mA/cm² of the OLED device produced by Comparative Example 2 and Device Example 17, and the time taken to reduce the luminance from 100% to 90% (lifespan; T90) based on a luminance of 2,000 nits are provided in Table 2 below.

TABLE 2

| | Electron Buffer Material | Driving Voltage (V) | Color Coordinate (x) | Color Coordinate (y) | Lifespan (T90, hr) |
|---|---|---|---|---|---|
| Comparative Example 2 | — | 3.7 | 0.139 | 0.096 | 61.3 |
| Device Example 17 | C-8 | 3.9 | 0.140 | 0.100 | 73.2 |

From Table 2 above, it can be seen that the OLED device of Device Example 17, in which the compound of the present disclosure is comprised in an electron buffer layer, has low driving voltage and improved lifespan properties compared to the OLED device of Comparative Example 2.

Device Example 18: Producing an OLED Device Comprising a Compound According to the Present Disclosure An OLED device was produced in the same manner as in Device Example 1, except that the light-emitting layer was formed as follows: Compound C-8 was introduced into one cell of the vacuum vapor depositing apparatus as a first host, and compound H2-6 was introduced into another cell as a second host. The two materials were evaporated at the same rate, and compound D-39 was introduced into another cell as a dopant. The three materials were evaporated and the dopant was deposited in a doping amount of 3 wt % based on the total amount of the host and the dopant to form a light-emitting layer having a thickness of 40 nm on the second hole transport layer.

As a result, the efficiency was 20.8 cd/A at a voltage of 4.3 V, red luminescence of 5000 cd/m² was confirmed, and a minimum time taken to reduce the luminance from 100% to 97% based on a luminance of 5,000 nits was 137 hours.

The compounds used in the Comparative Examples and Device Examples are shown in Table 3 below.

TABLE 3
Hole Injection Layer/
Hole Transport Layer
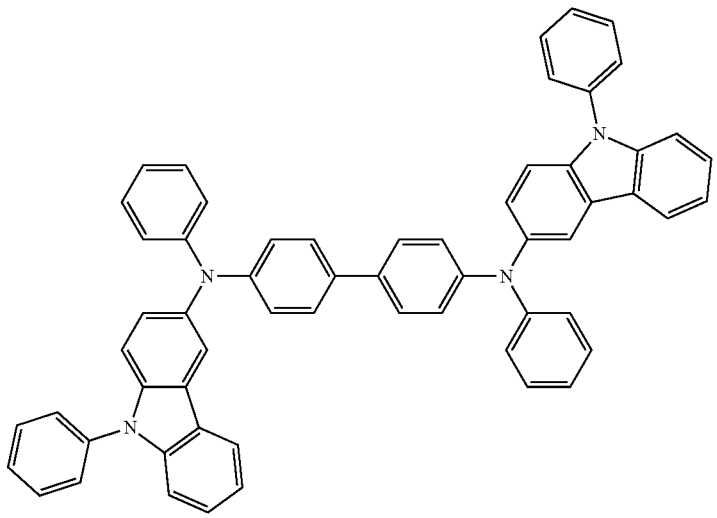
HI-1
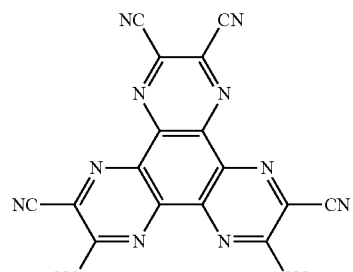
HI-2
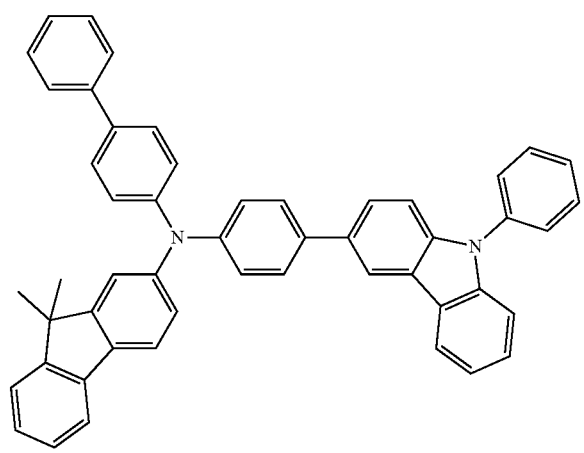
HT-1

TABLE 3-continued
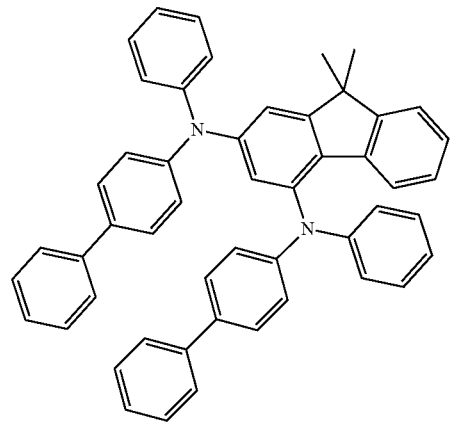
HT-2
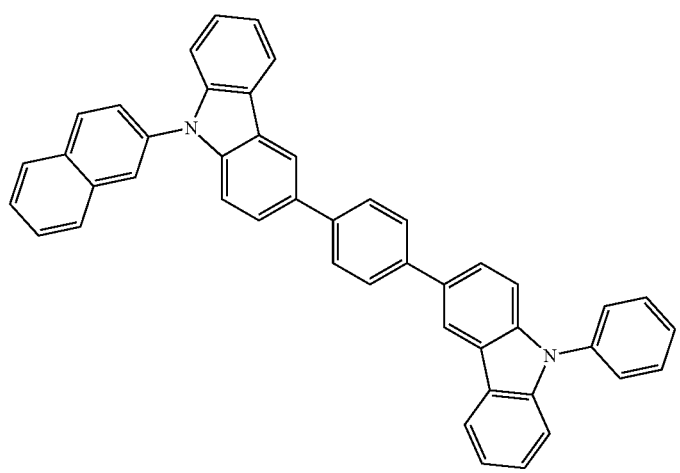
HT-3
Light-Emitting
Layer
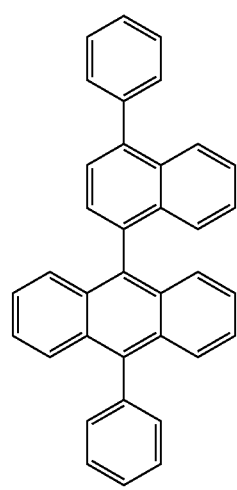
FH-1

TABLE 3-continued
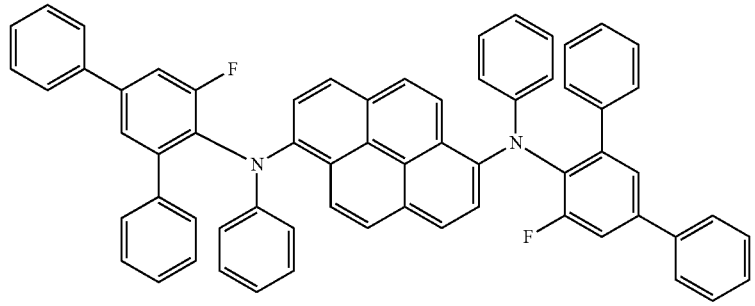
FD-1
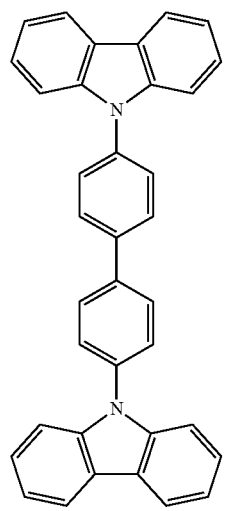
A
Electron
Buffer
Layer/
Electron
Transport
Layer/
Electron
Injection Layer
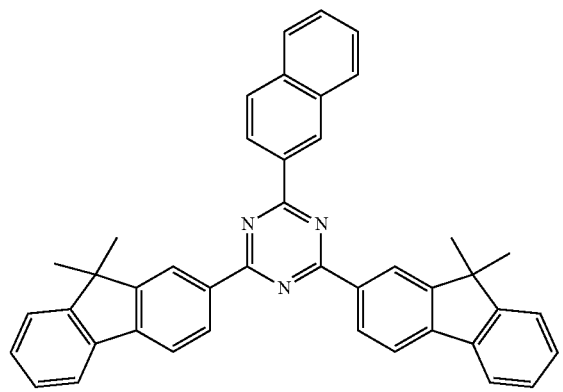
ET-1
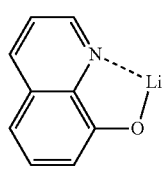
EI-1

The invention claimed is:
1. An organic electroluminescent compound represented by the following formula 1:

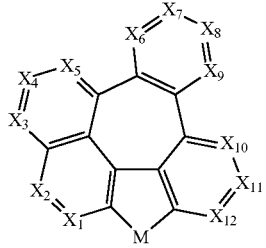

(1)

wherein
M represents

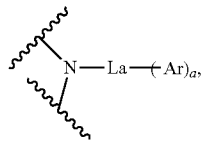

O or S;
$X_1$ to $X_{12}$ each independently, represent N or $CR_1$;
La represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;
Ar and $R_1$ in $X_1$ to $X_8$, $X_{11}$ and $X_{12}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;
$R_1$ in $X_9$ and $X_{10}$ each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;
the heteroaryl(ene) contains at least one heteroatom selected from B, N, O, S, Si, and P; and
a represents an integer of 1 or 2, where if a is 2, each of Ar may be the same or different.

2. The organic electroluminescent compound according to claim 1, wherein the substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic or aromatic ring, or the combination thereof in La, Ar, and $R_1$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30)aryl; a (C6-C30)aryl unsubstituted or substituted with a (5- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein Ar represents a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted fluoranthenyl, a substituted or unsubstituted triazinyl, a substituted or unsubstituted pyridyl, a substituted or unsubstituted pyrimidinyl, a substituted or unsubstituted benzothienopyrimidinyl, a substituted or unsubstituted acenaphthopyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted dibenzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted benzothienoquinolyl, a substituted or unsubstituted benzofuroquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothiazolinyl, a substituted or unsubstituted phenanthroimidazolyl, a substituted or unsubstituted diphenylamino, a substituted or unsubstituted phenylbiphenylamino, a substituted or unsubstituted fluorenylphenylamino, a substituted or unsubstituted dibenzothiophenylphenylamino, or a substituted or unsubstituted dibenzofuranylphenylamino.

4. The organic electroluminescent compound according to claim 1, wherein two adjacent $X_1$ to $X_8$, and two adjacent $X_{11}$ and $X_{12}$ in formula 1 are $CR_1$, two adjacent $R_1$ are fused to any one of the following formulas 2 to 6 to form a ring, and one or more of the rings are formed in one compound represented by formula 1:

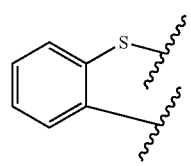
(2)

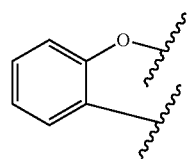
(3)

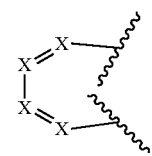
(4)

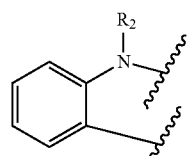
(5)

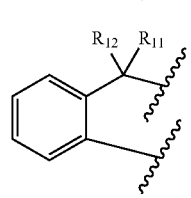
(6)

wherein $R_2$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, X represents N or CH, $R_{11}$ and $R_{12}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; or may be linked to each other to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, and ⌇.

5. The organic electroluminescent compound according to claim 1, wherein formula 1 is represented by any one of the following formulas 7 to 10:

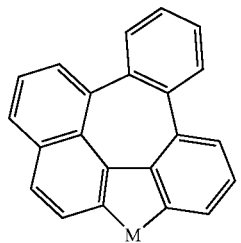
(7)

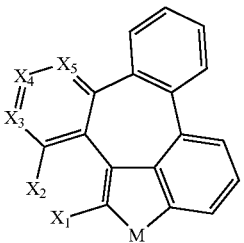
(8)

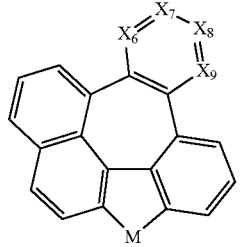
(9)

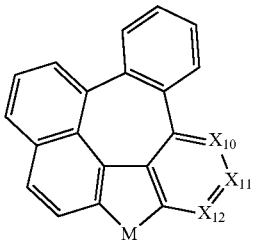
(10)

wherein $X_1$ to $X_{12}$, and M are as defined in claim 1.

6. The organic electroluminescent compound according to claim 1, wherein the compound represented by formula 1 is selected from the following compounds:

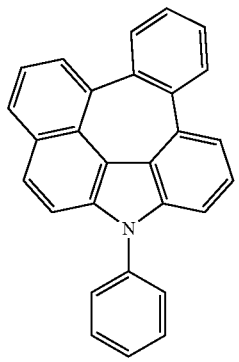
C-1
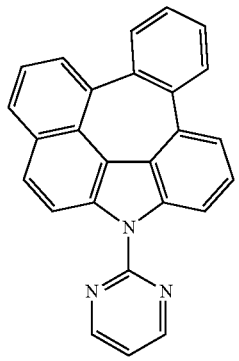
C-5
C-2
C-6
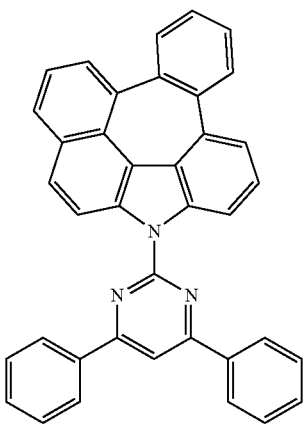
C-3
C-4
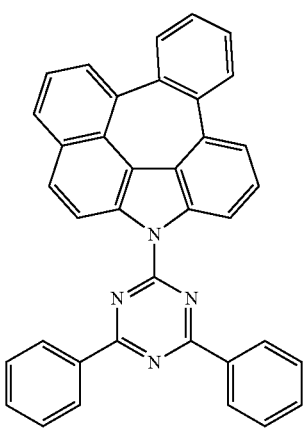
C-7

-continued
C-8
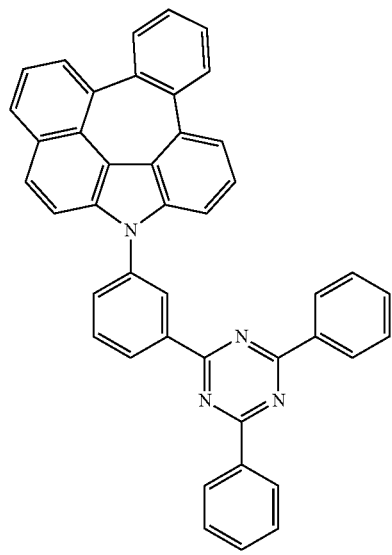
C-9
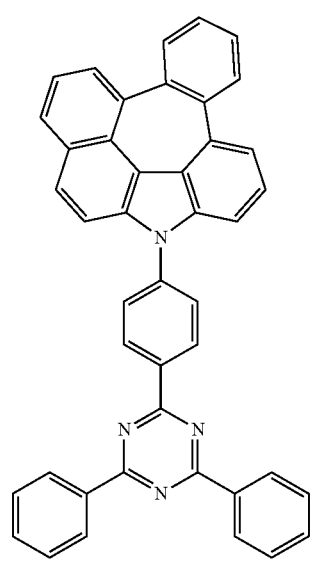
C-10
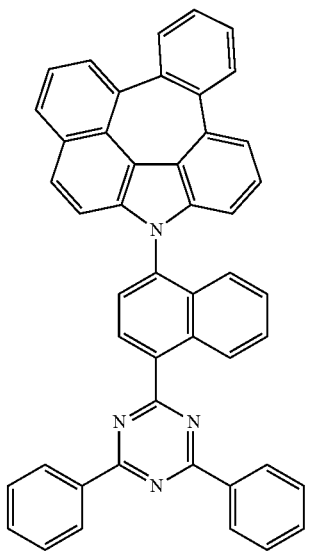
-continued
C-11
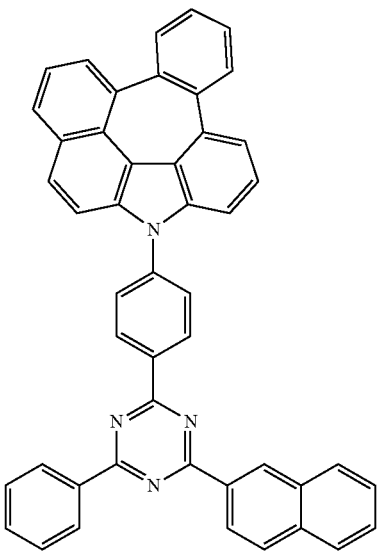
C-12
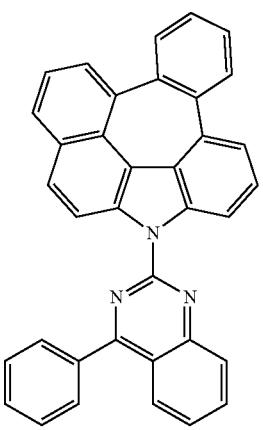
C-13
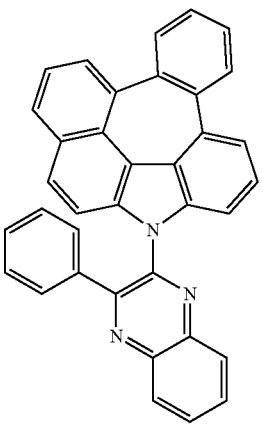

C-14
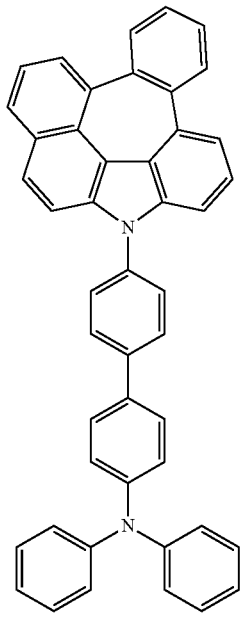
C-15
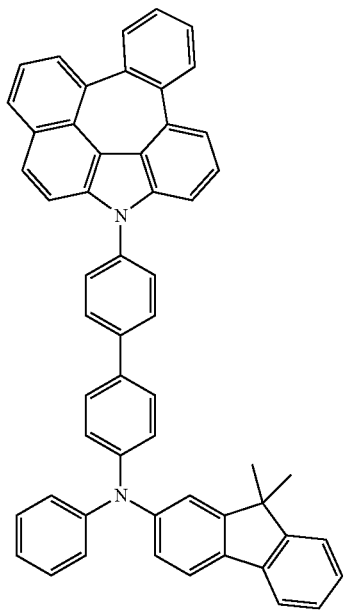
C-16
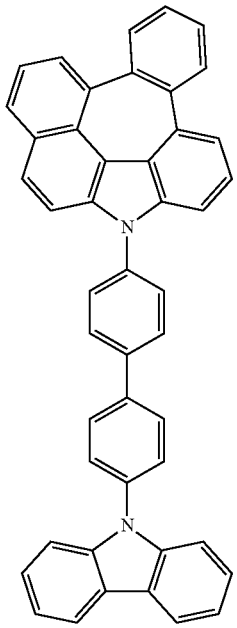
C-17
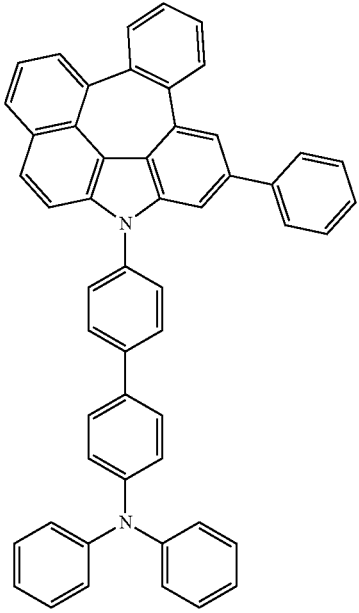

C-18
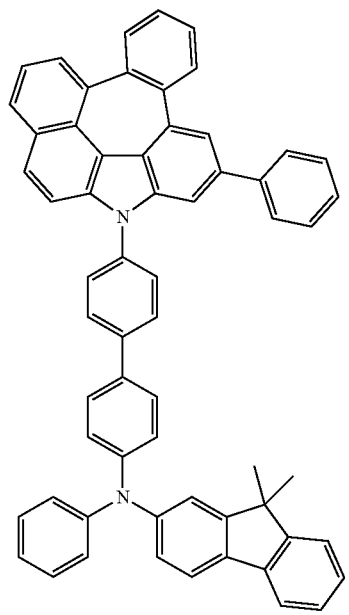
C-19
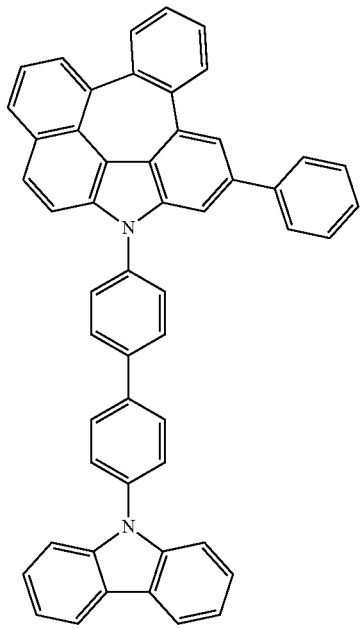
C-20
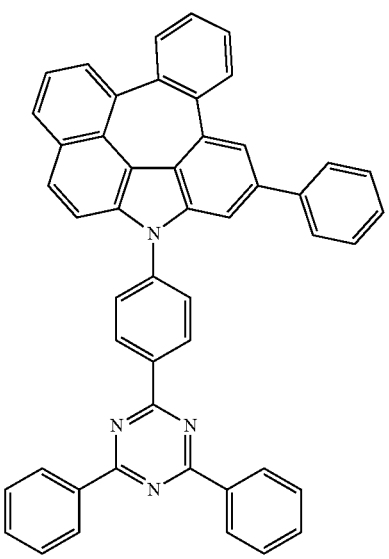
C-21
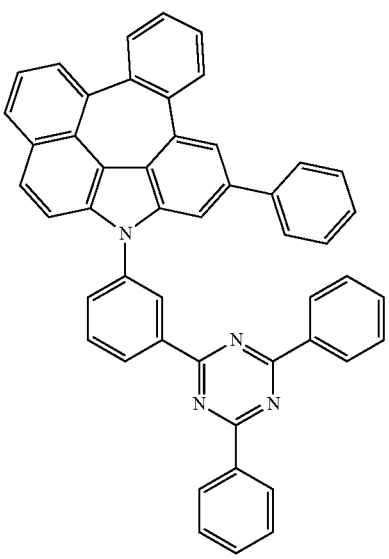
C-22
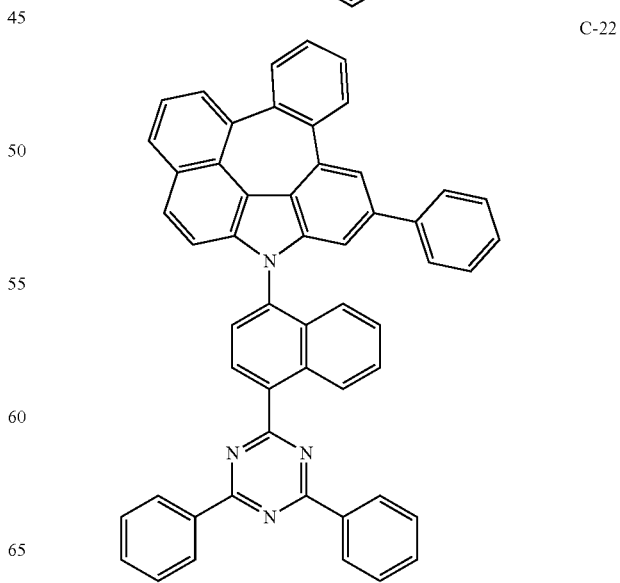

C-23
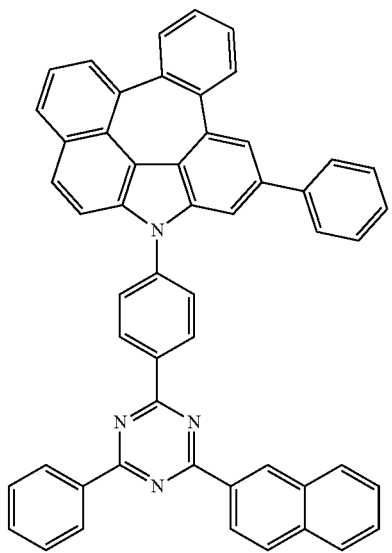
C-24
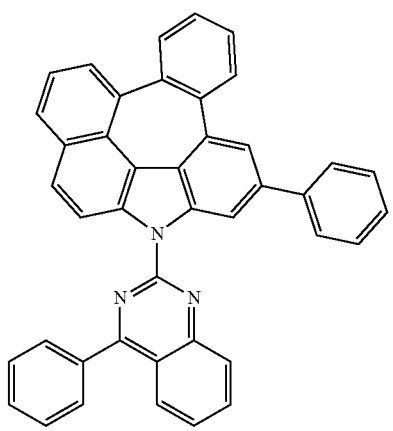
C-25
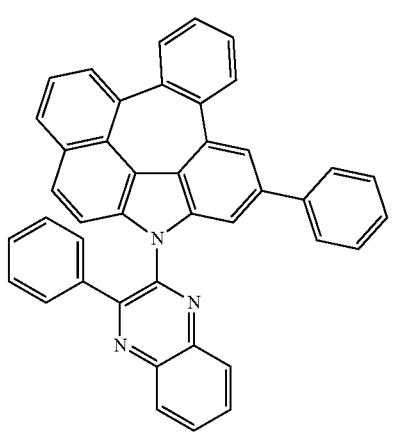
C-26
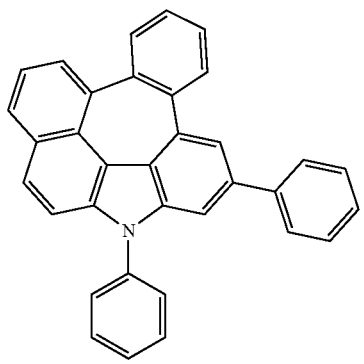
C-27
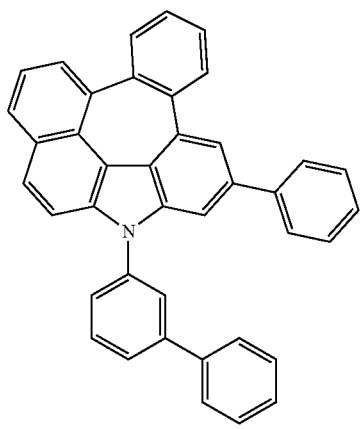
C-28
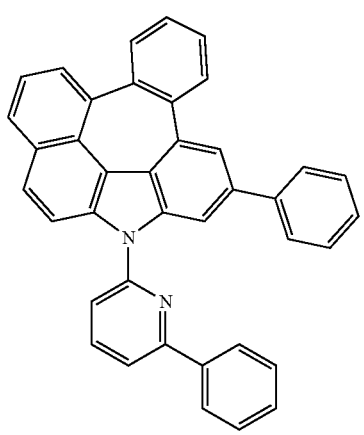
C-29

-continued
C-30
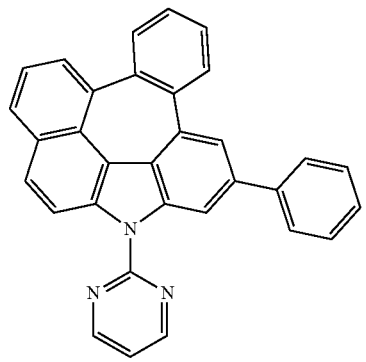
C-31
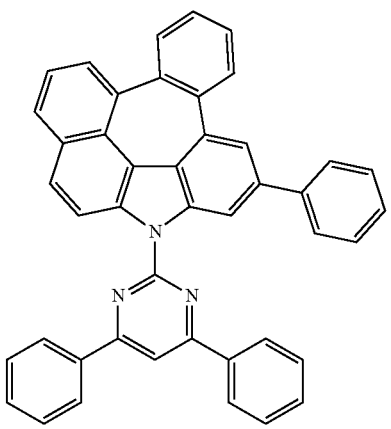
C-32
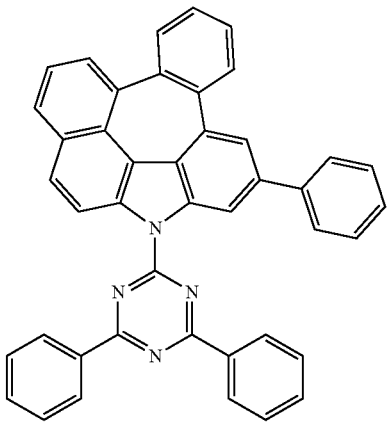
C-33
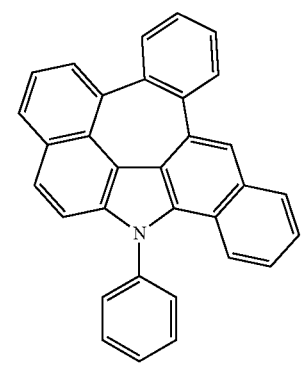
-continued
C-34
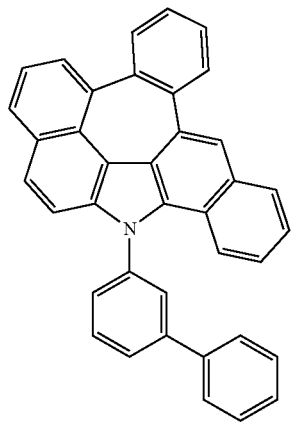
C-35
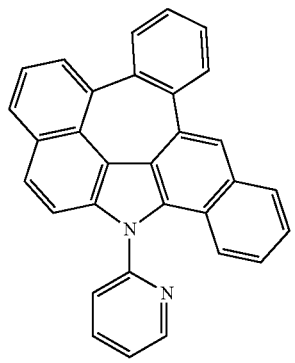
C-36
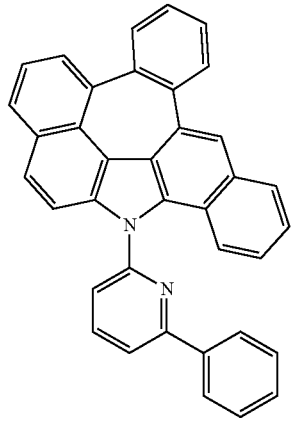
C-37
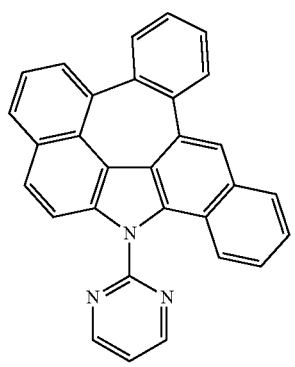

C-38
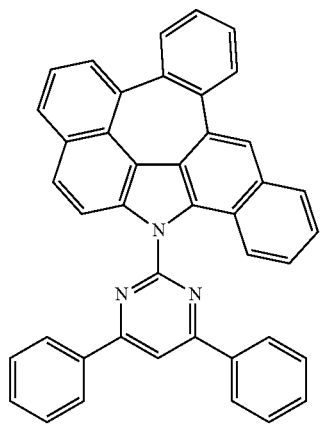
C-39
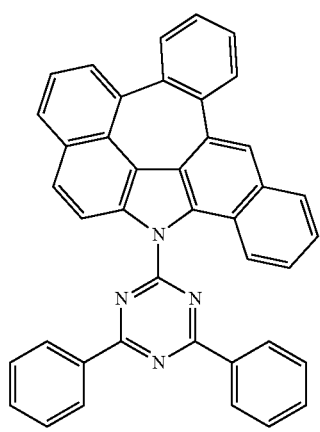
C-40
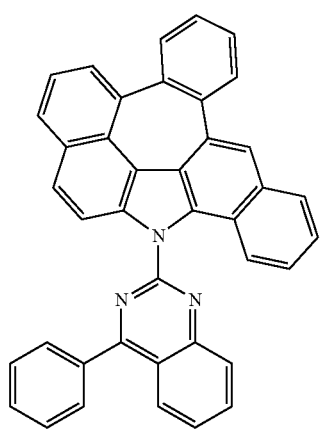
C-41
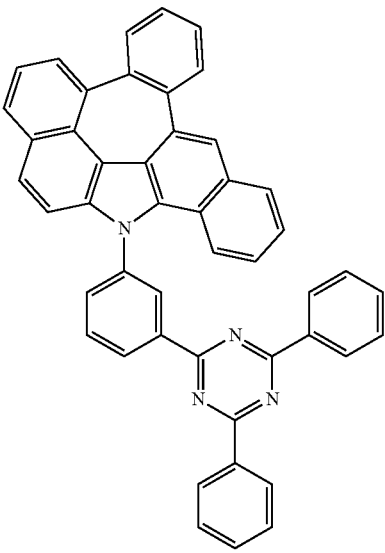
C-42
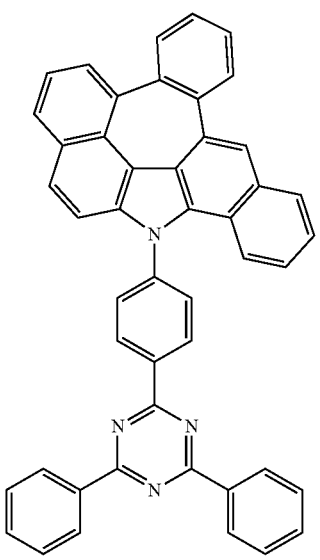
C-43
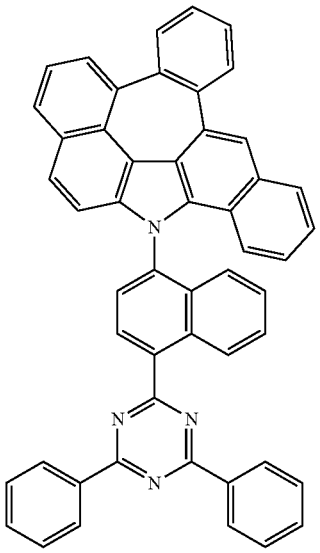

C-44
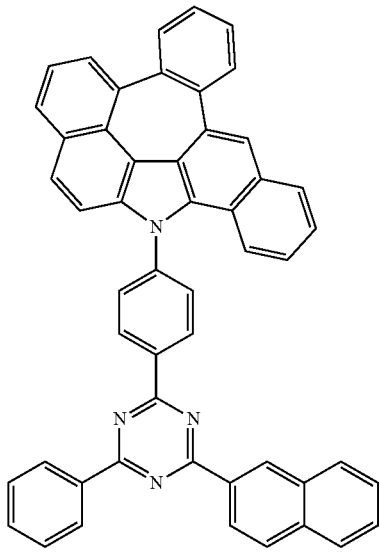
C-45
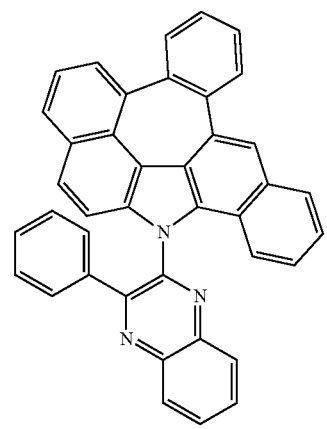
C-46
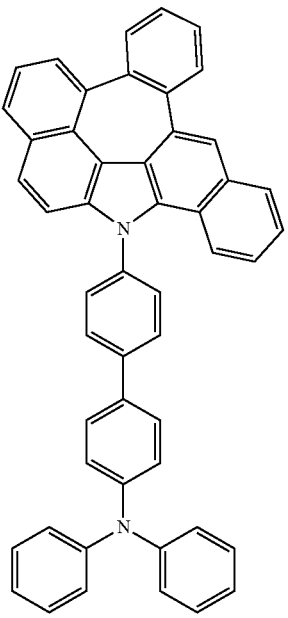
C-47
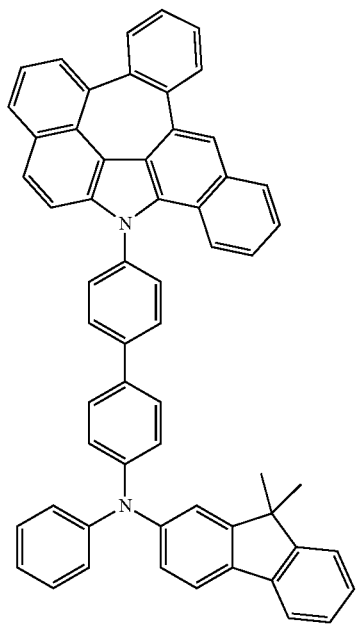
C-48
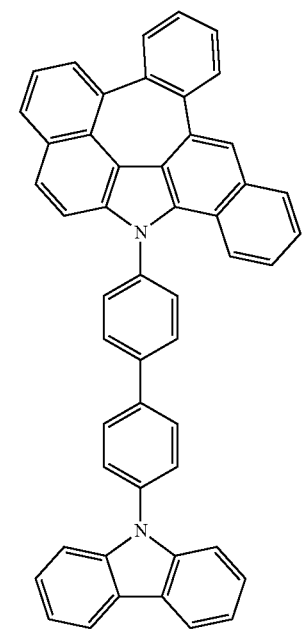

C-49
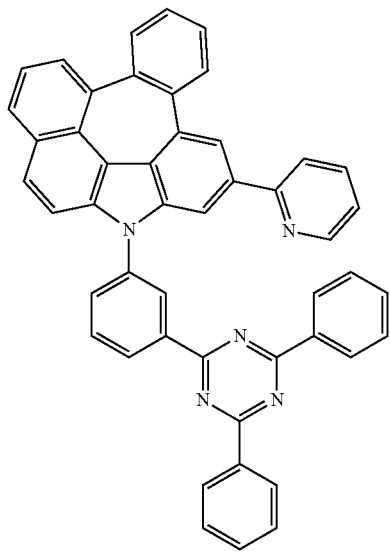
C-50
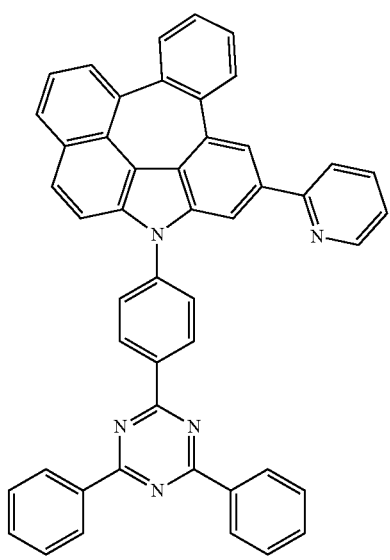
C-51
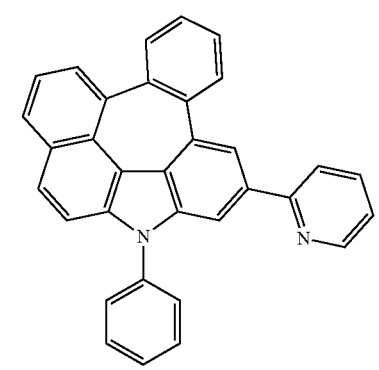
C-52
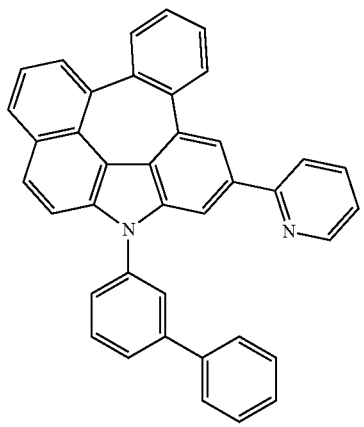
C-53
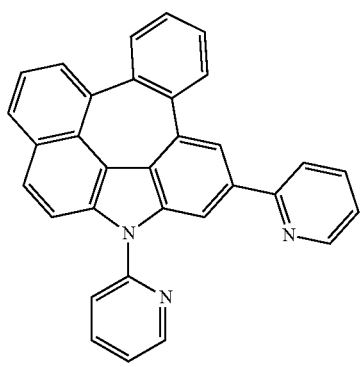
C-54
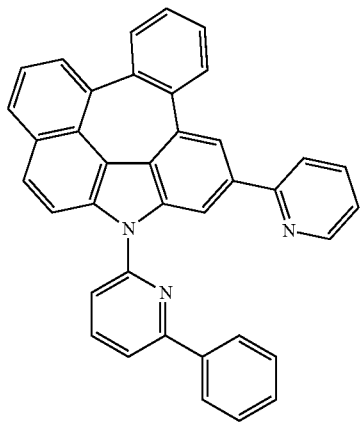
C-55
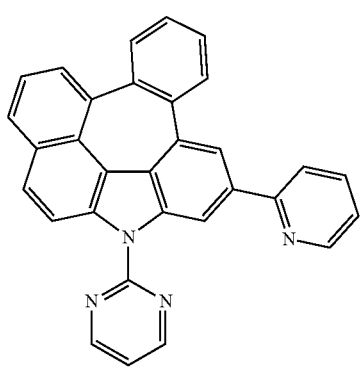

C-56
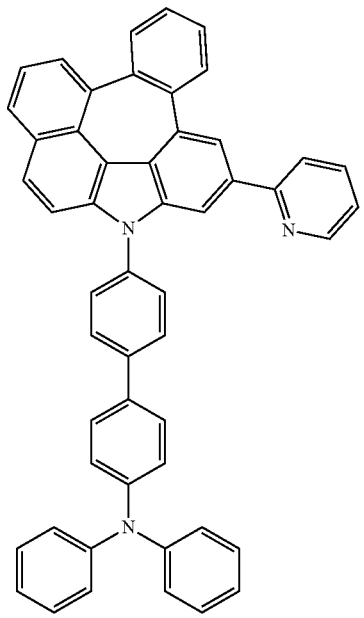
C-58
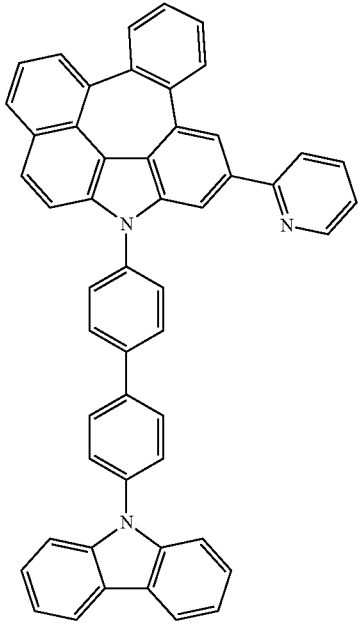
C-57
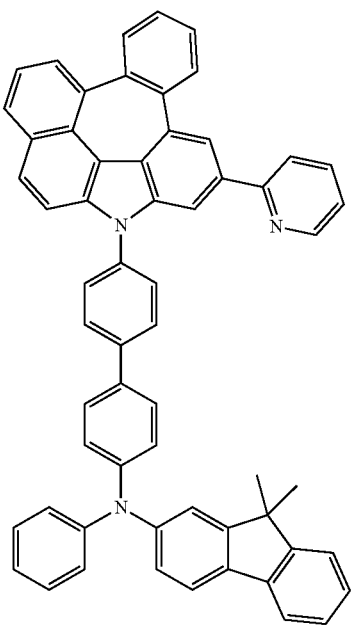
C-59
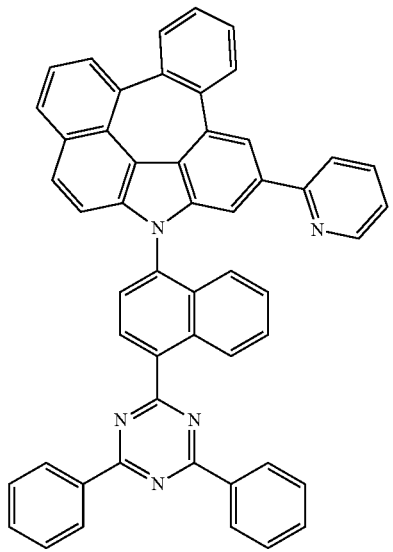

-continued
C-60
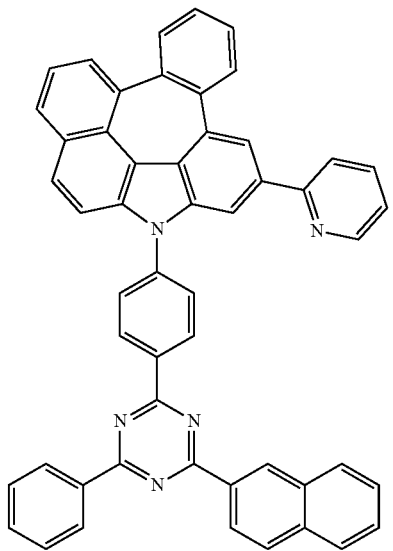
C-61
C-62
-continued
C-63
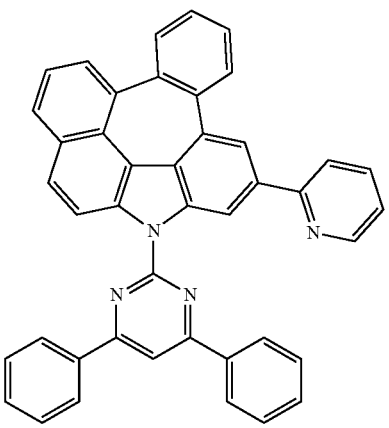
C-64
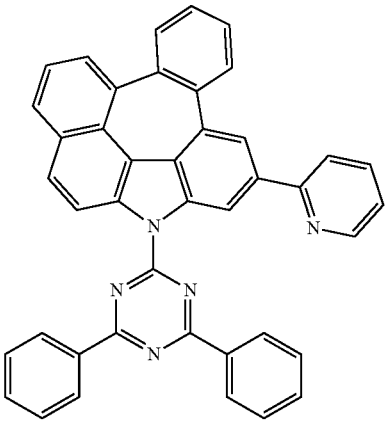
C-65
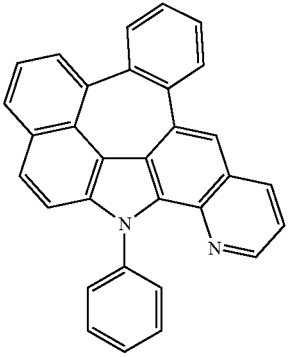
C-66
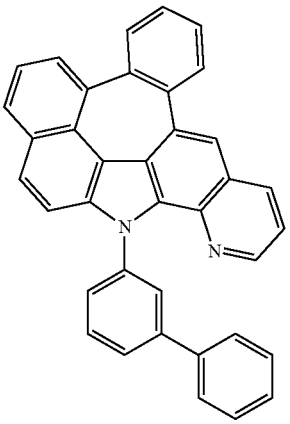

-continued
C-67
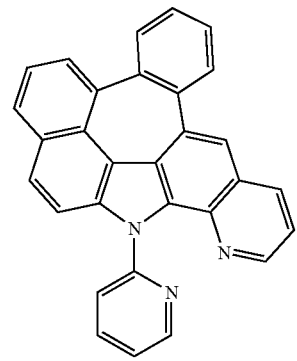
C-68
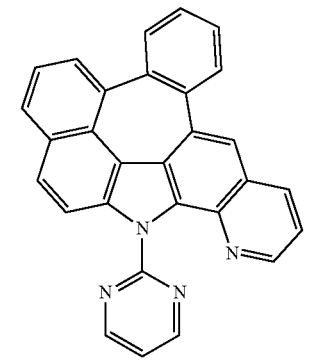
C-69
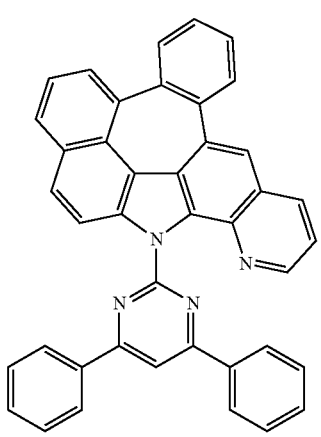
C-70
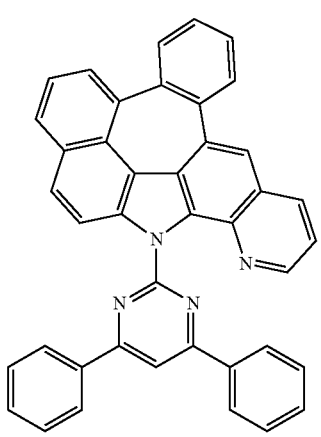
-continued
C-71
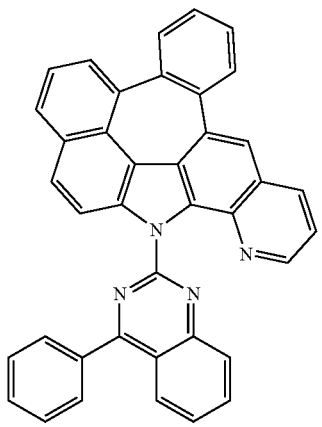
C-72
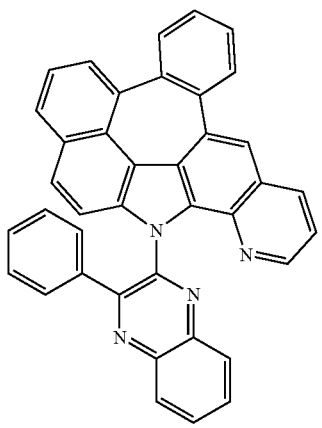
C-73
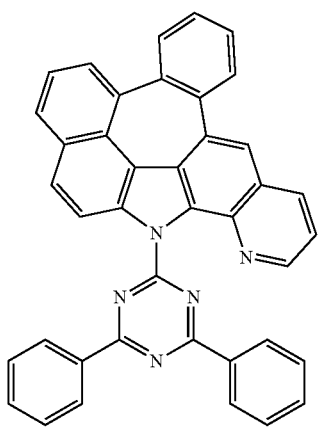

C-74
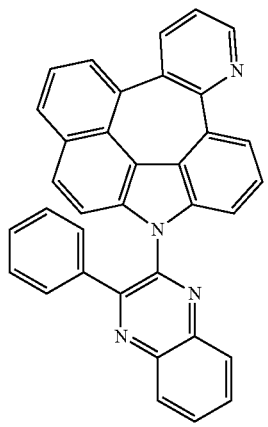
C-77
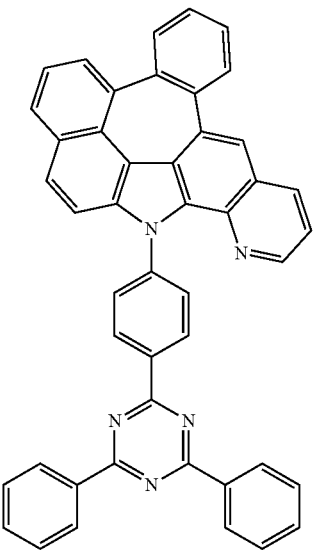
C-75
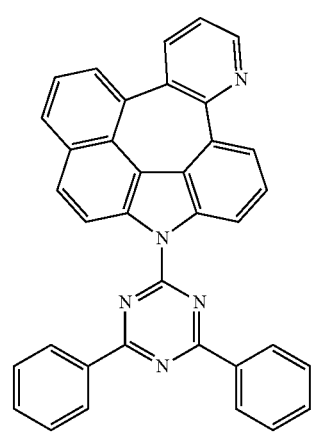
C-78
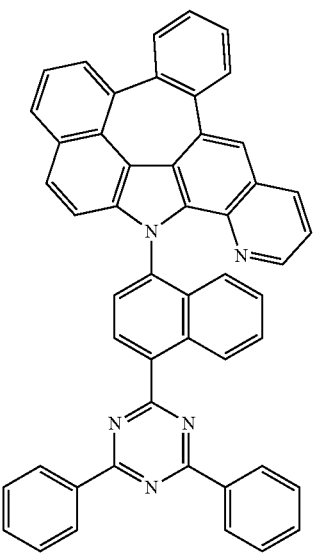
C-76
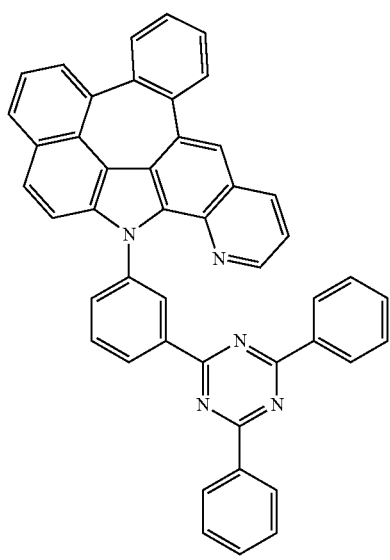
C-79
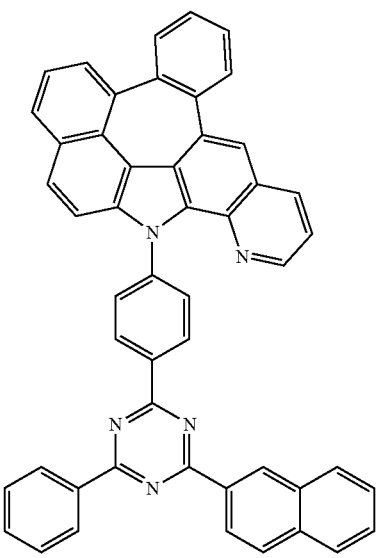

C-80
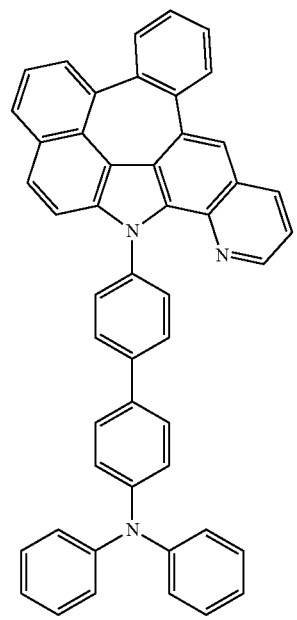
C-81
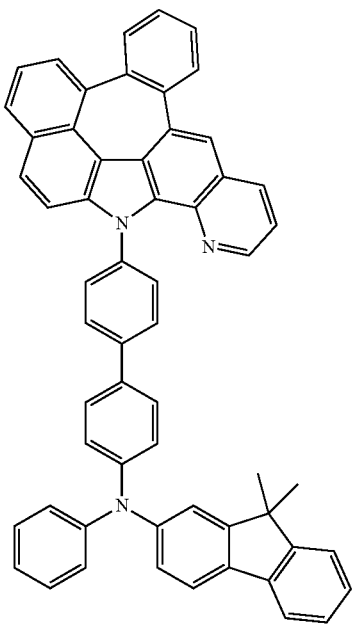
C-82
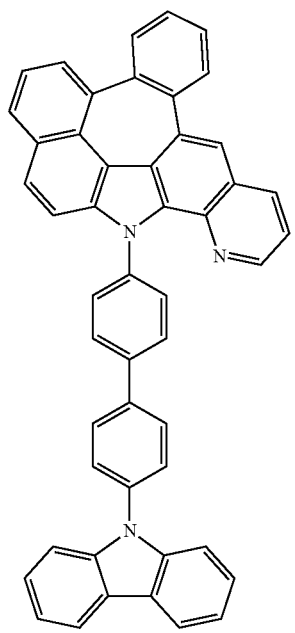
C-83
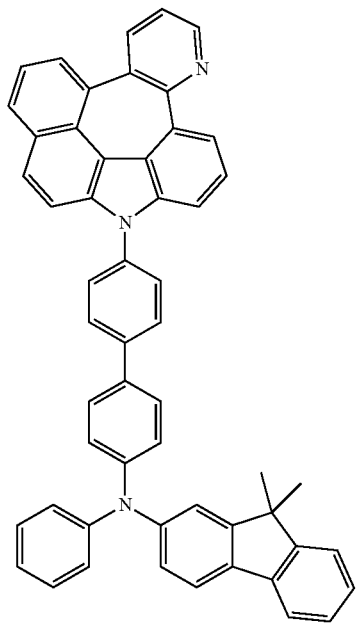

-continued
C-84
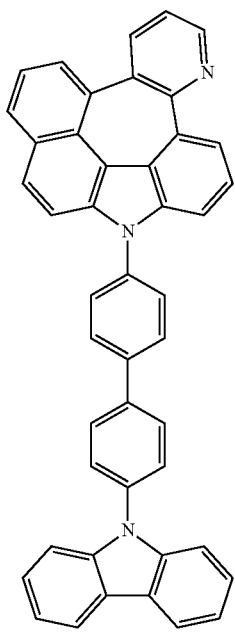
C-85
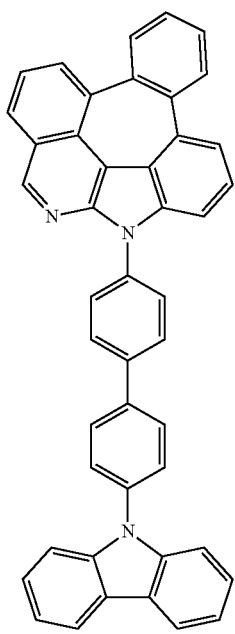
C-86
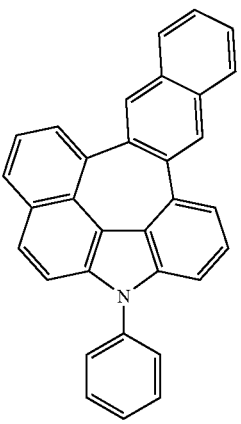
C-87
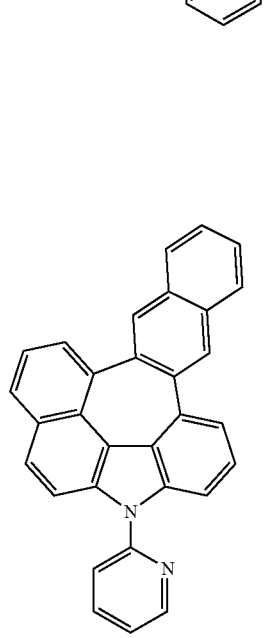
C-88

-continued
C-89
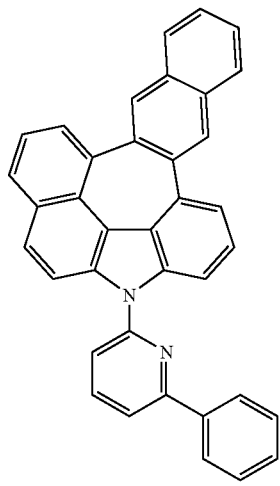
C-90
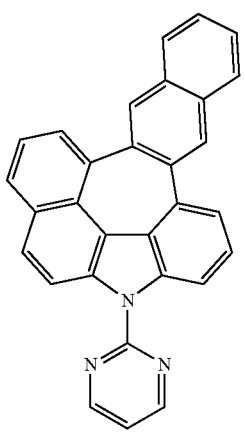
C-91
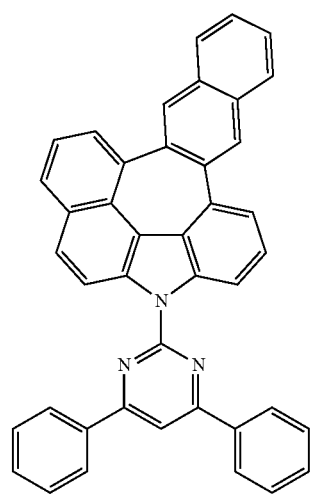
-continued
C-92
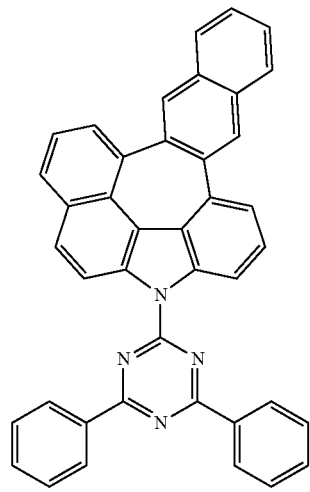
C-93
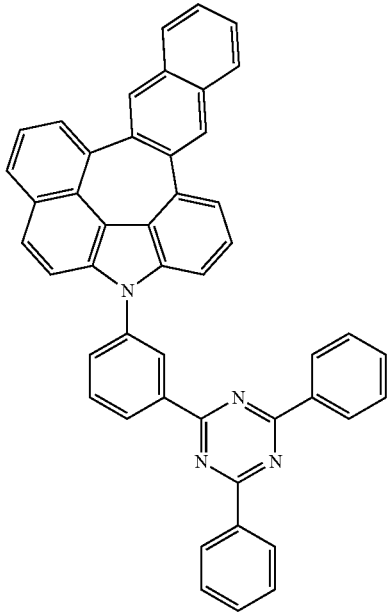

-continued
C-94
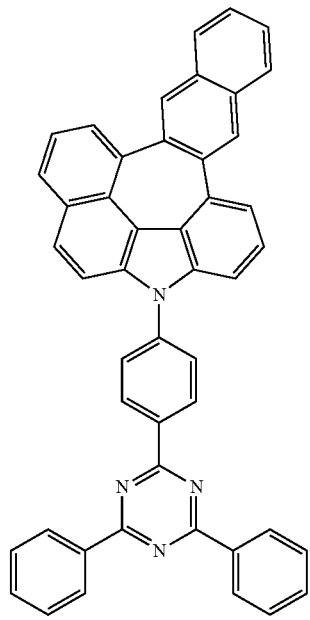
C-96
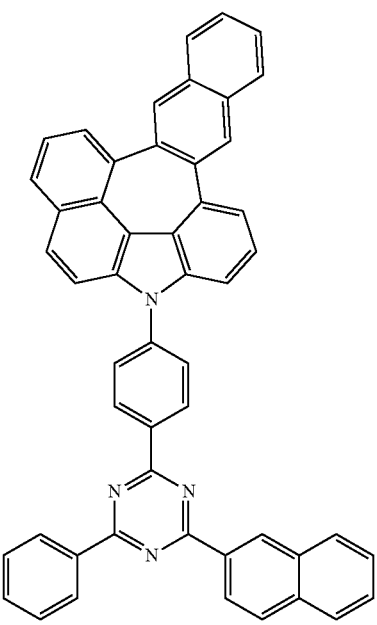
C-95
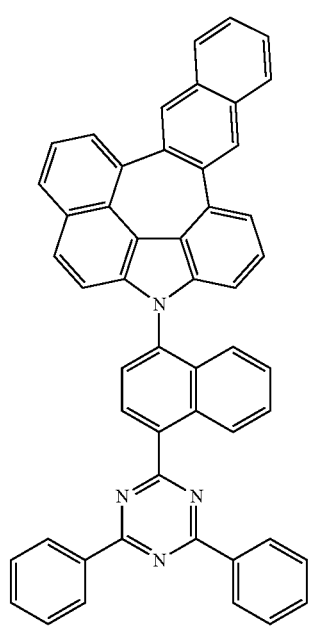
C-97
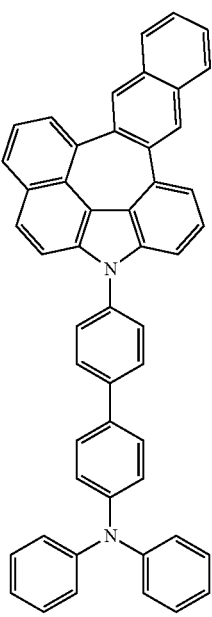

C-98
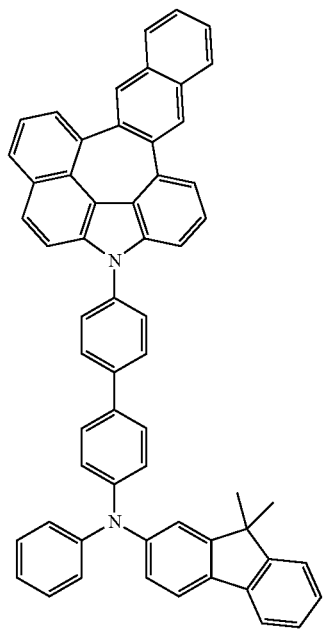
C-99
C-100
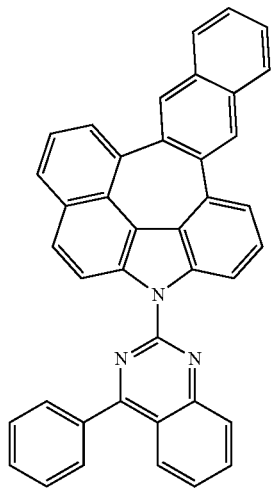
C-101
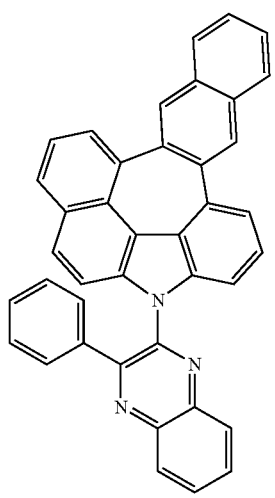
C-102
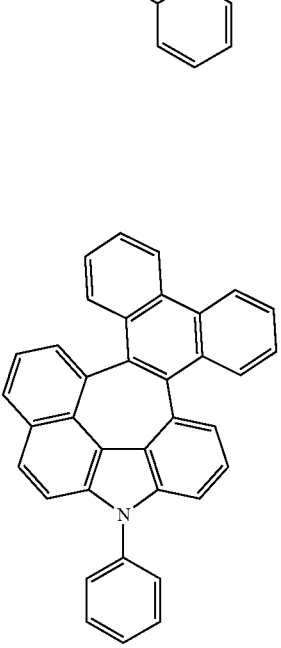

C-103
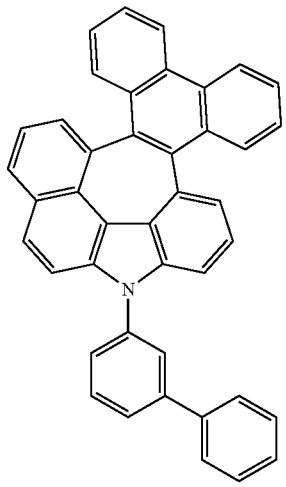
C-104
C-105
C-106
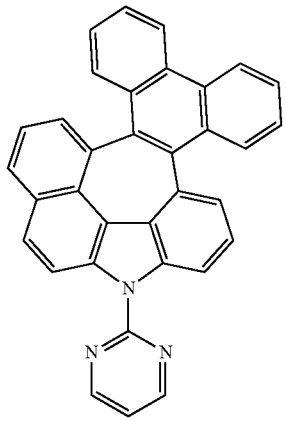
C-107
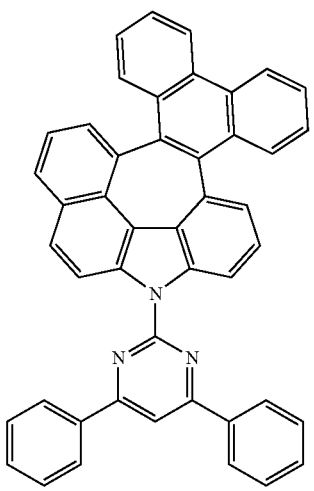
C-108
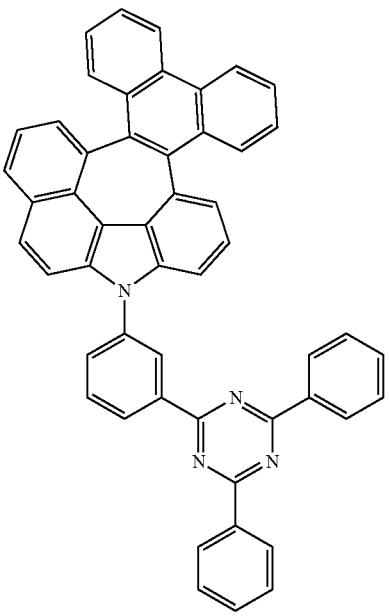

C-109
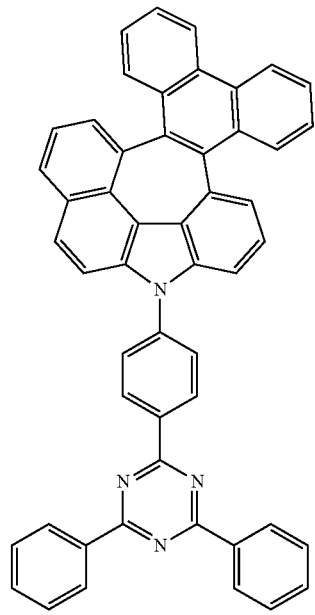
C-111
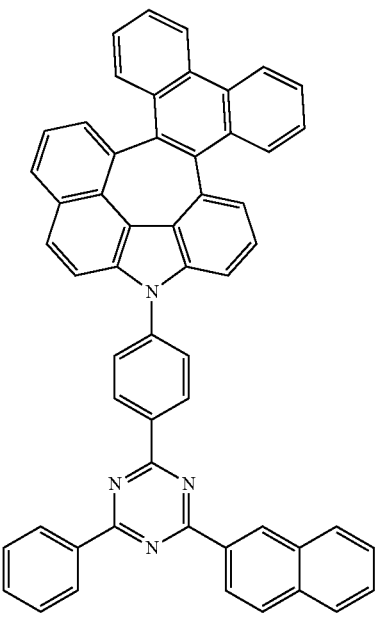
C-110
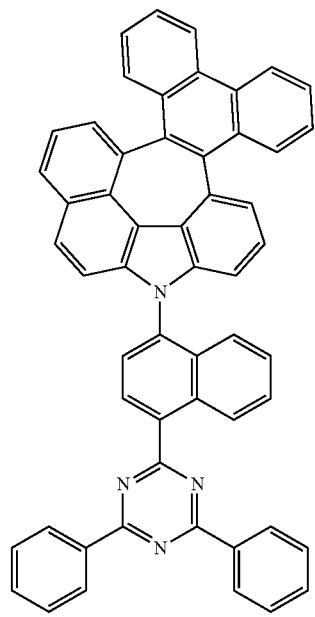
C-112
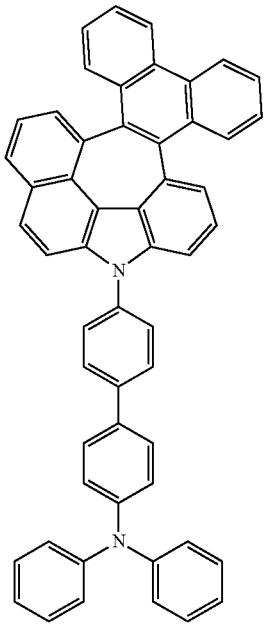

C-113
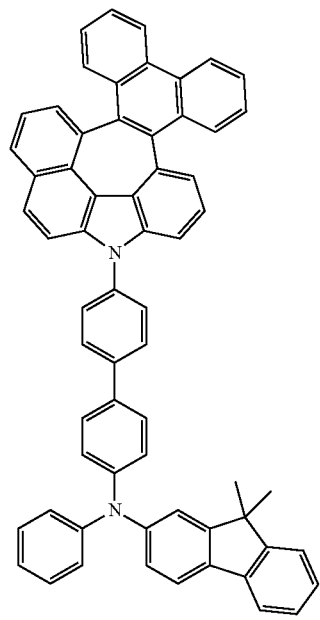
C-114
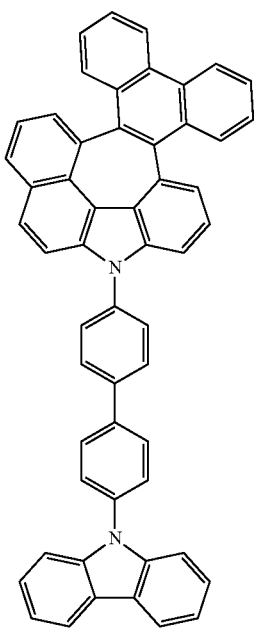
C-115
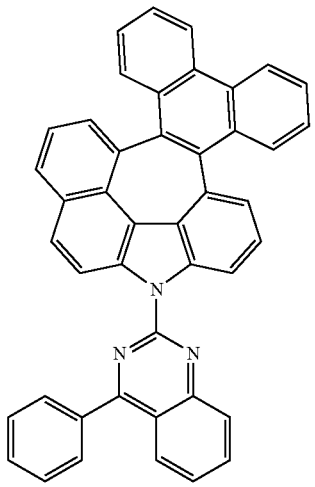
C-116
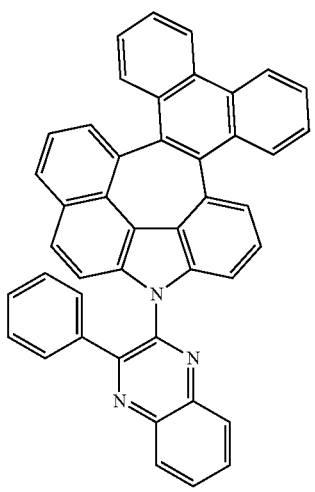
C-117
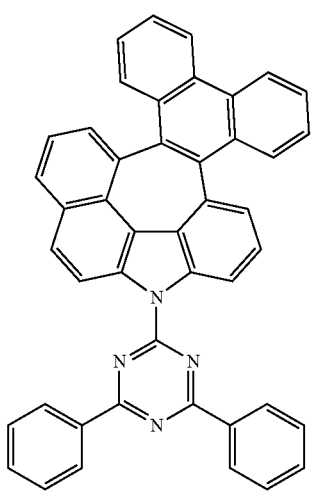

C-118
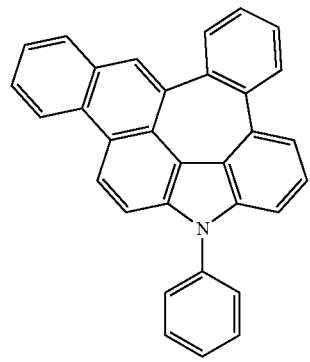
C-119
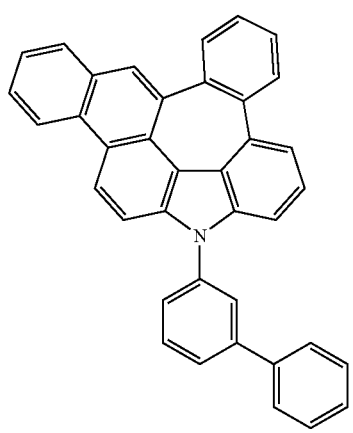
C-120
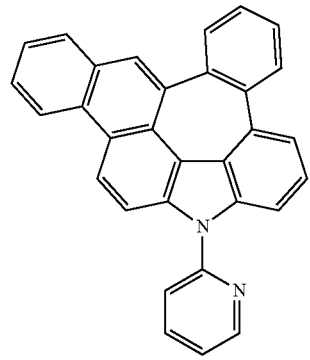
C-121
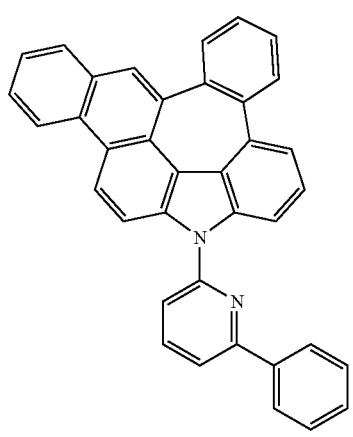
C-122
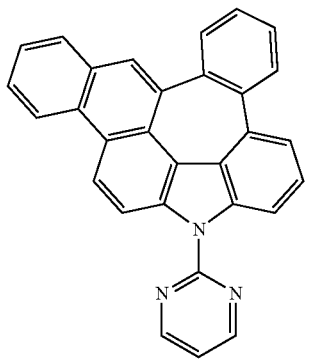
C-123
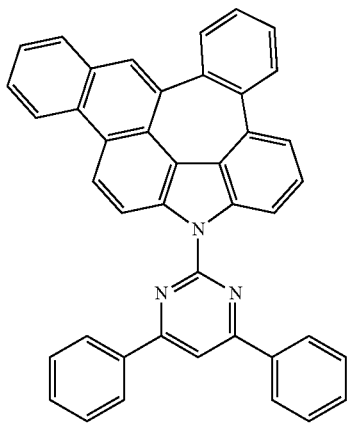
C-124
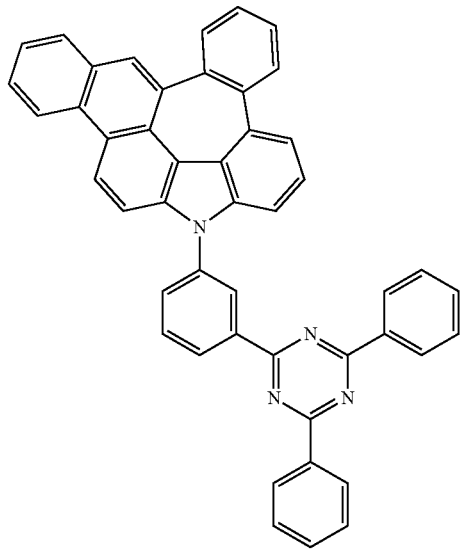

-continued
C-125
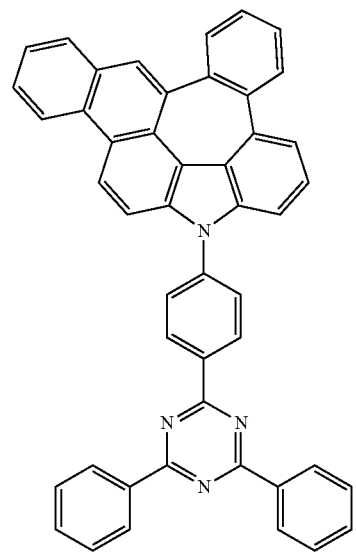
C-126
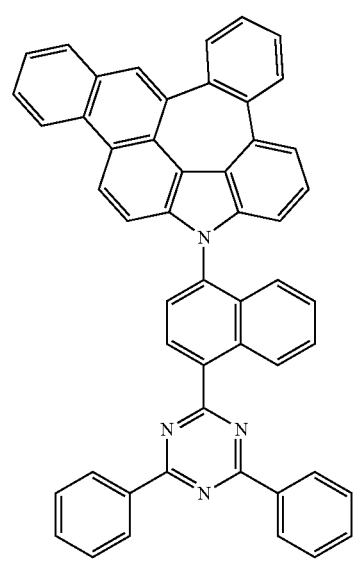
C-127
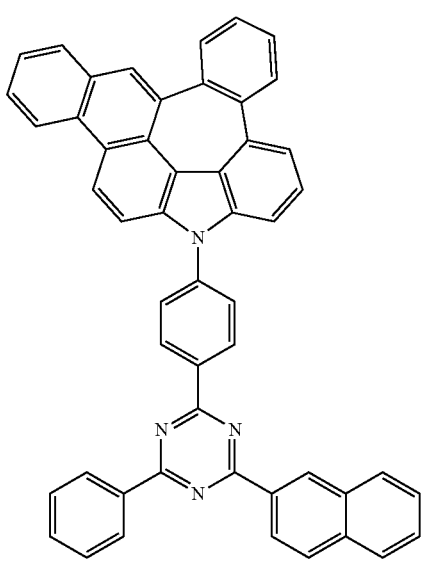
-continued
C-128
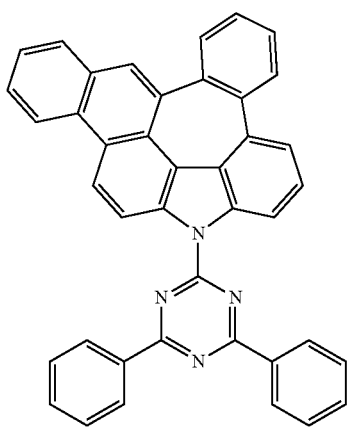
C-129
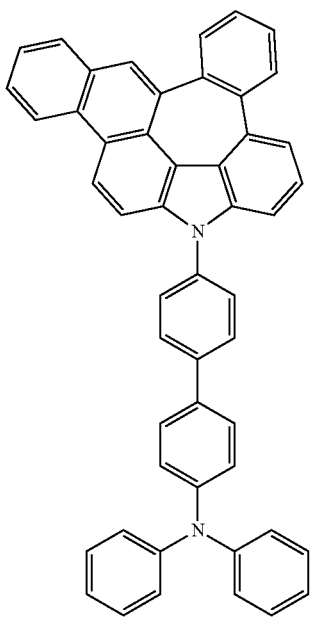
C-130
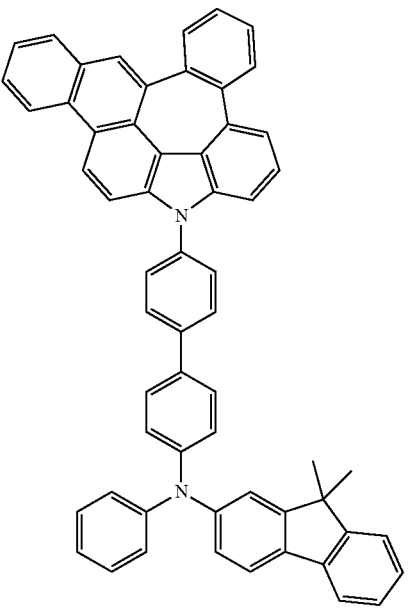

-continued
C-131
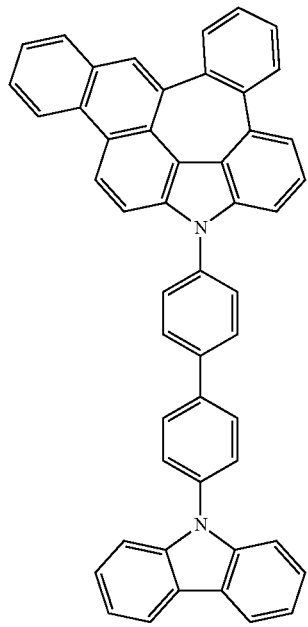
C-132
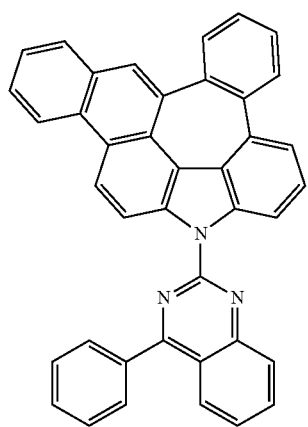
C-133
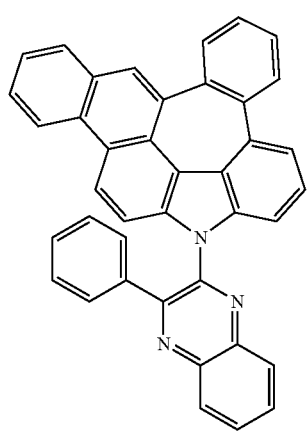
-continued
C-134
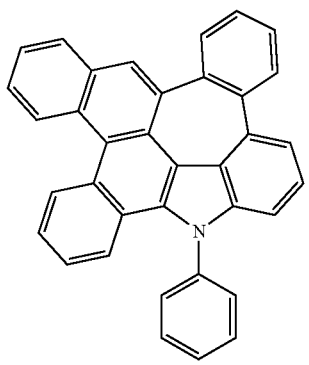
C-135
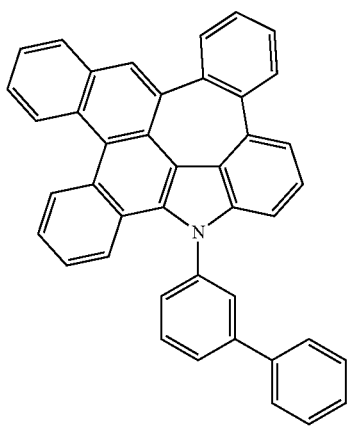
C-136
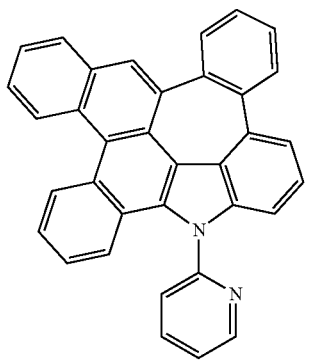
C-137
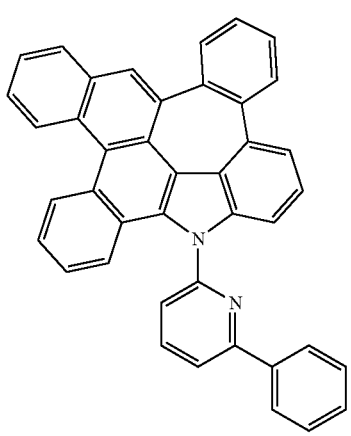

C-138
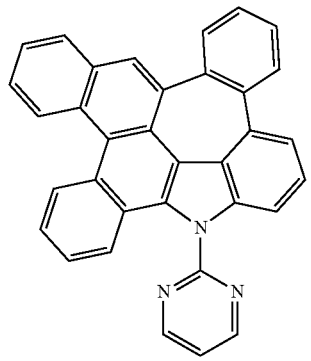
C-141
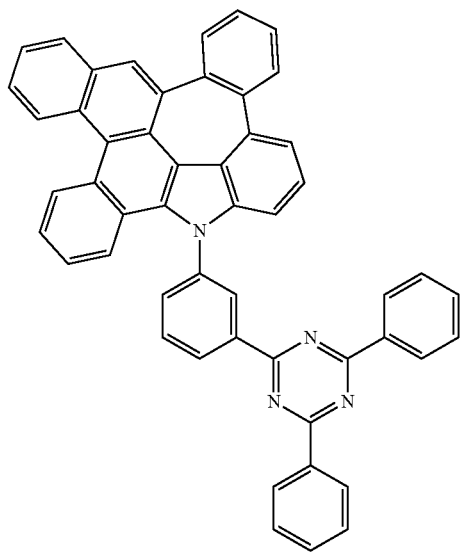
C-139
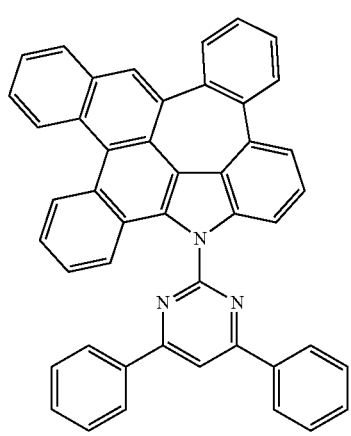
C-140
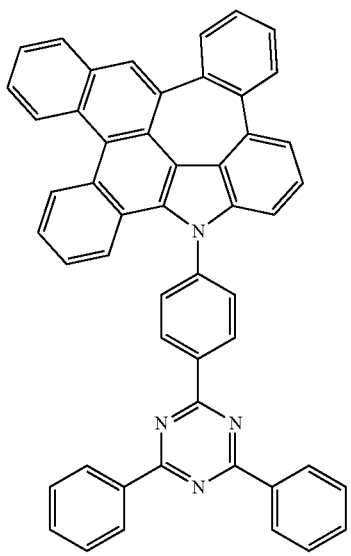
C-142

C-143
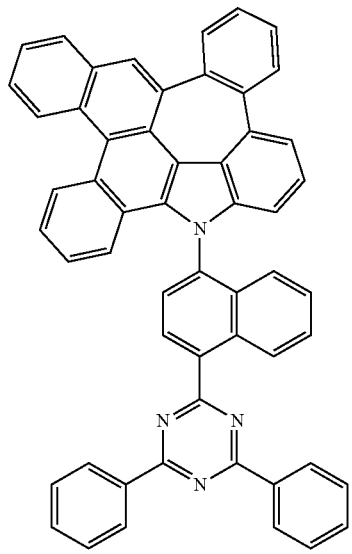
C-144
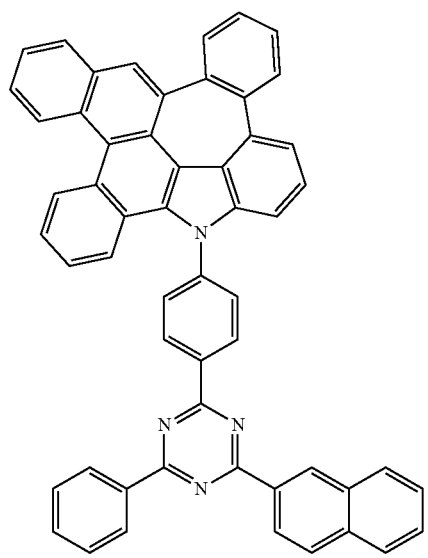
C-145
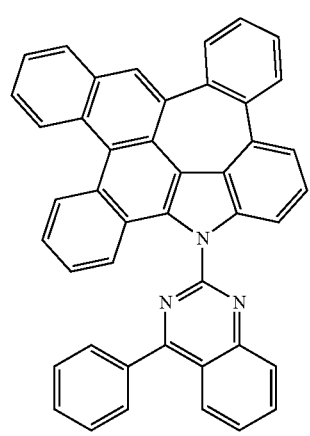
C-146
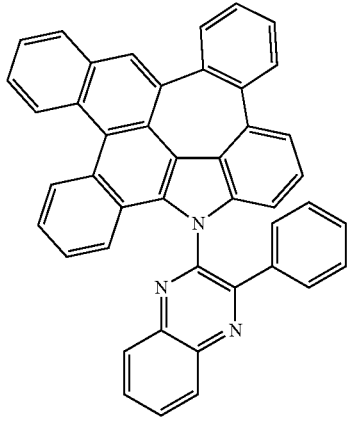
C-147
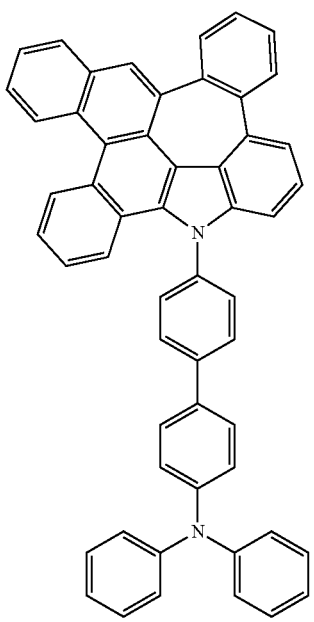
C-148
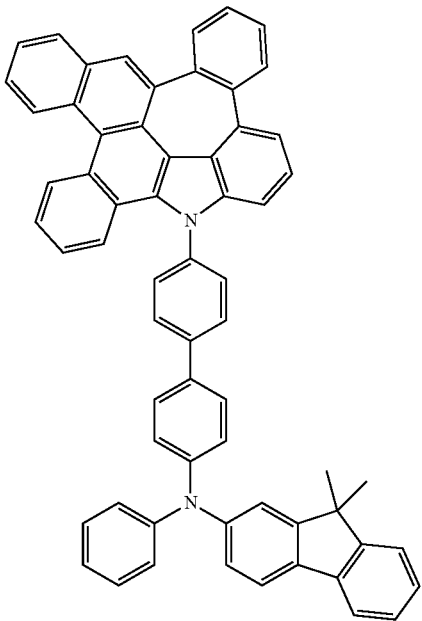

C-149
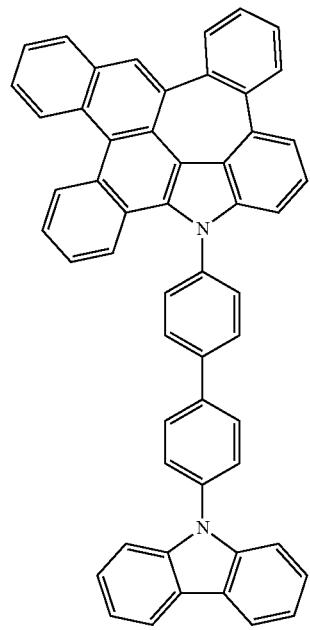
C-150
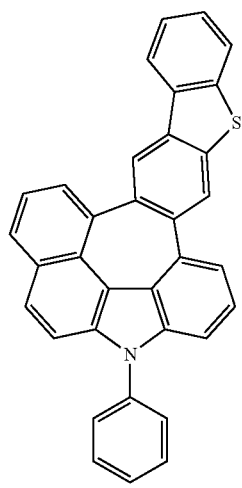
C-151
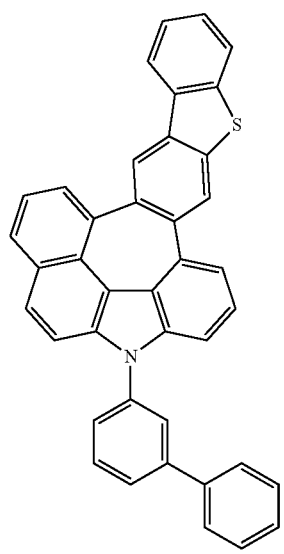
C-152
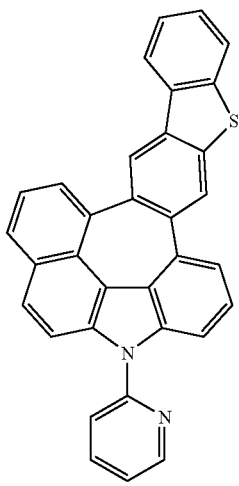
C-153
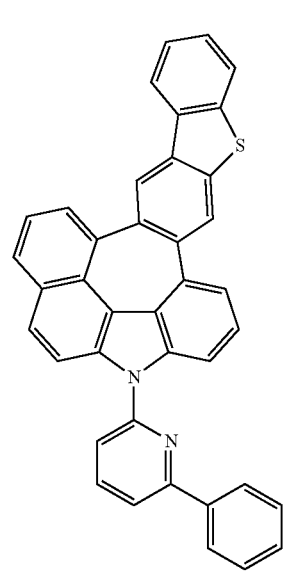
C-154
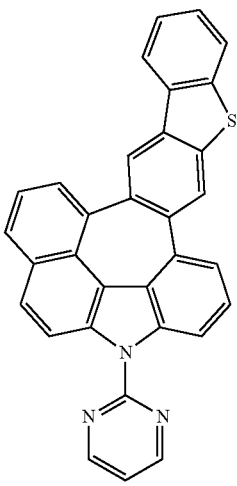

C-155
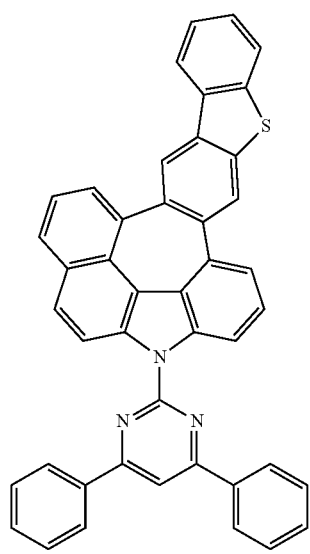
C-156
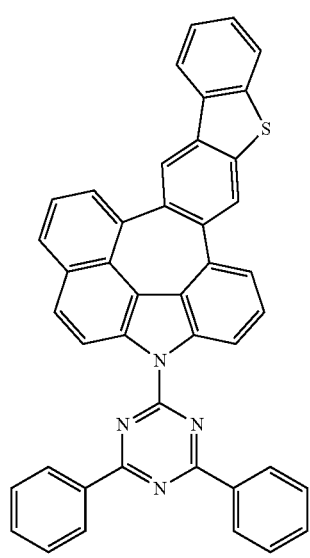
C-157
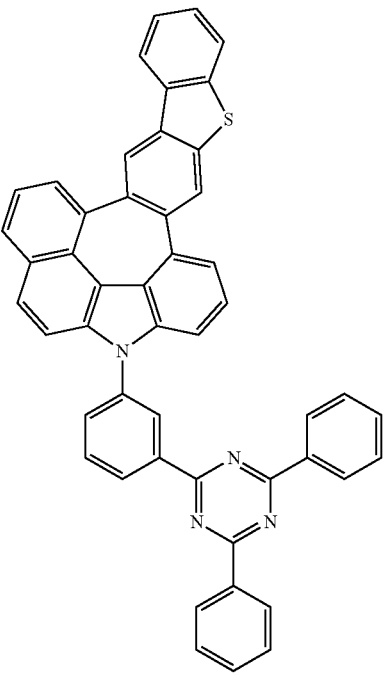
C-158
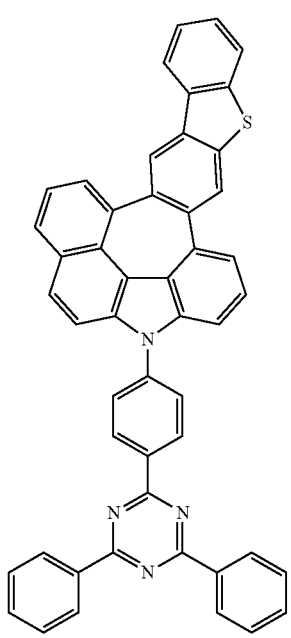

C-159
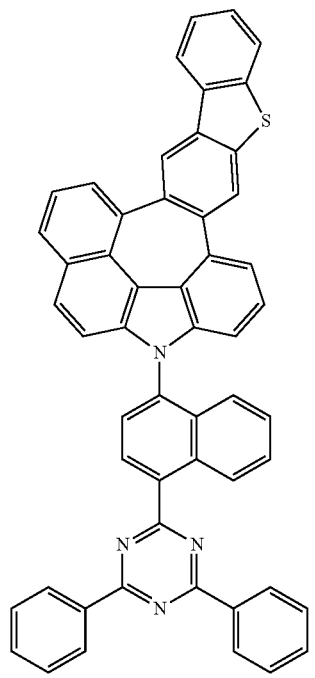
C-160
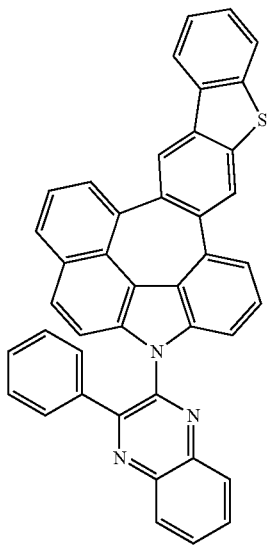
C-161
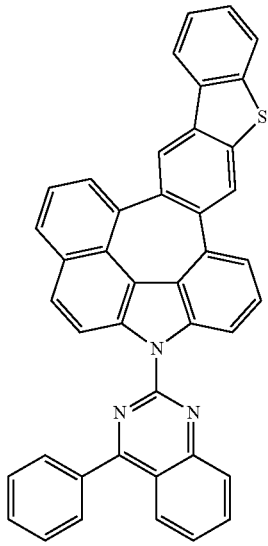
C-162
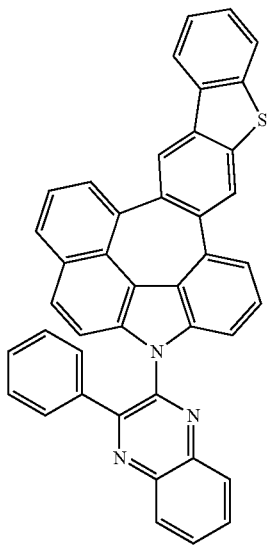

-continued
C-163
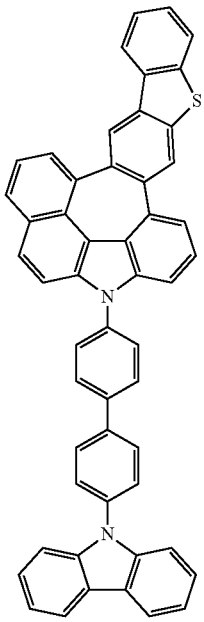
C-164
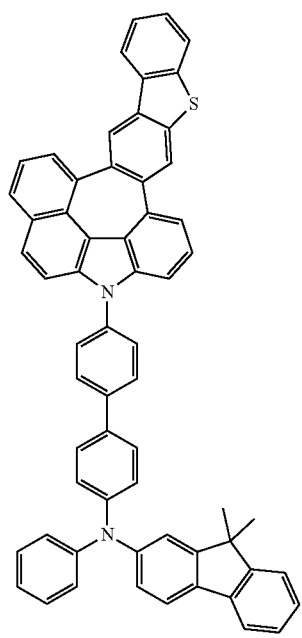
C-165
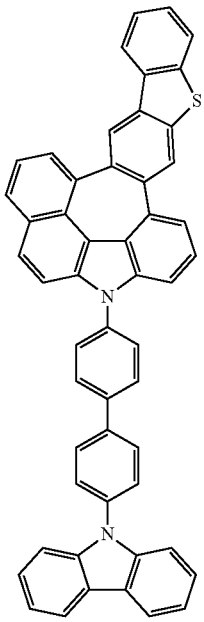
C-166
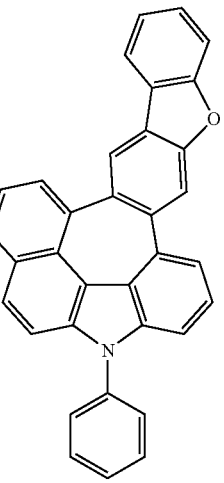
C-167
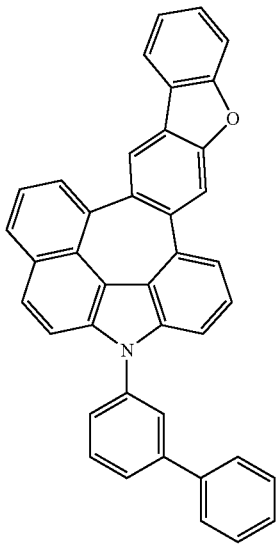

-continued
C-168
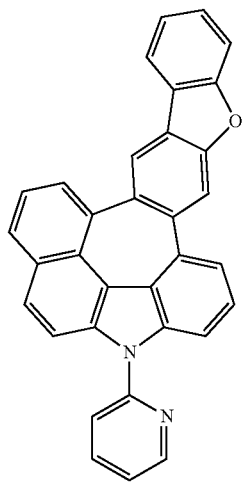
C-169
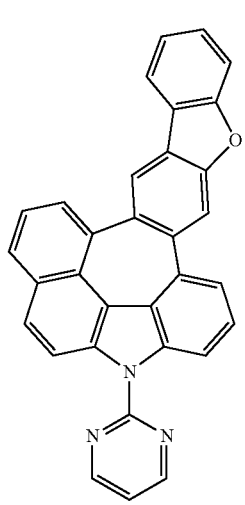
-continued
C-171
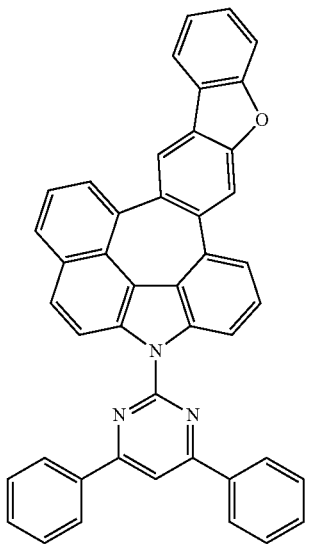
C-170
C-172
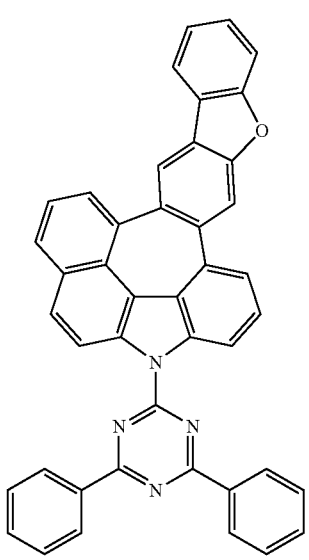

-continued
C-173
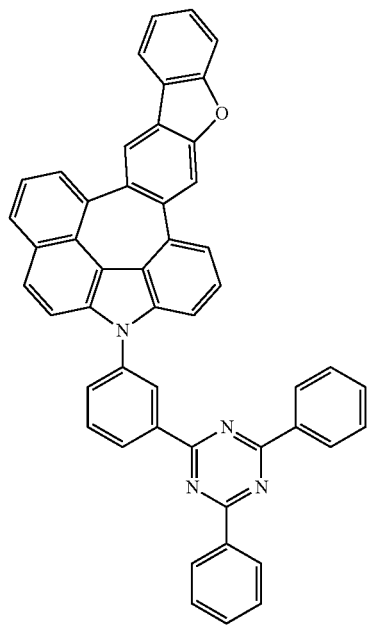
C-174
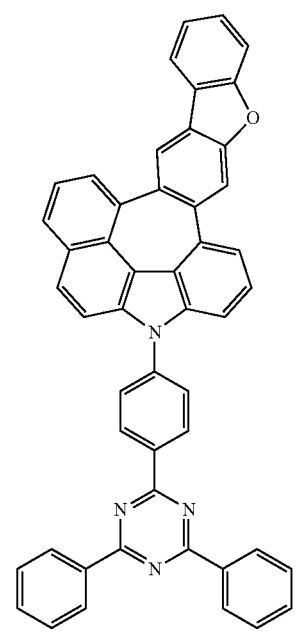
C-175
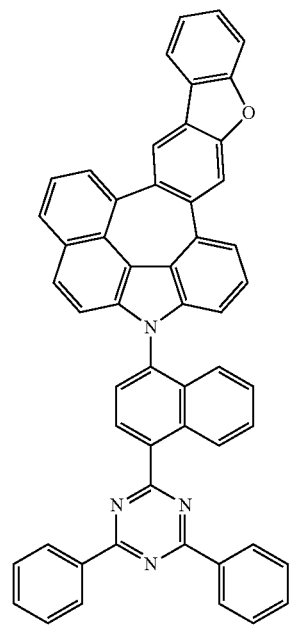
C-176
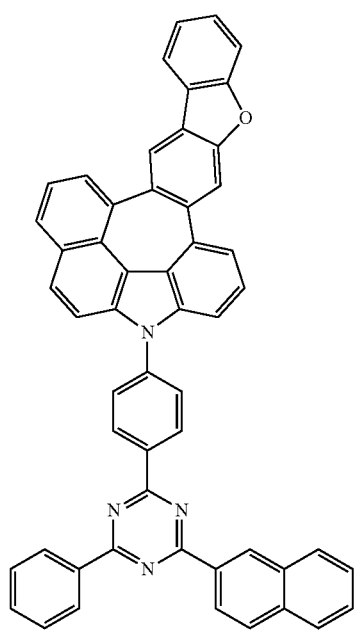

C-177
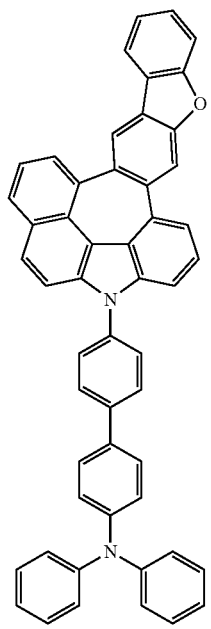
C-178
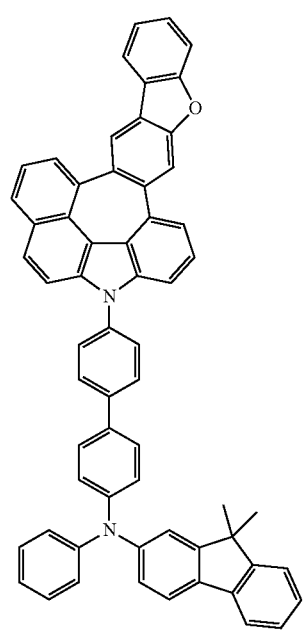
C-179
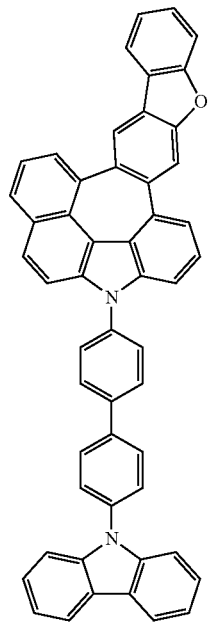
C-180
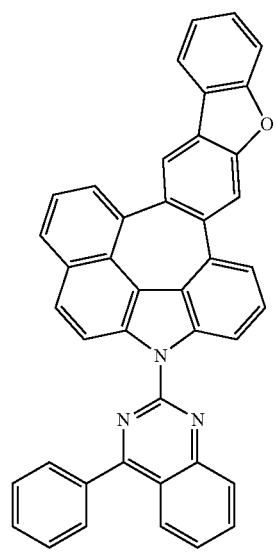

-continued
C-181
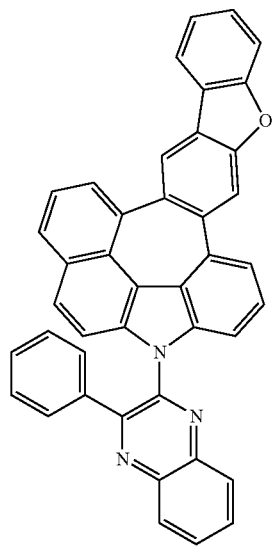
C-182
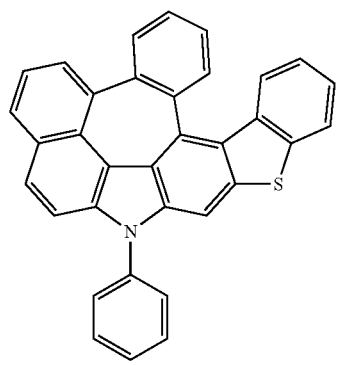
C-183
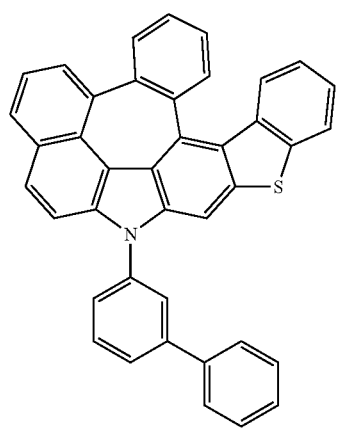
-continued
C-184
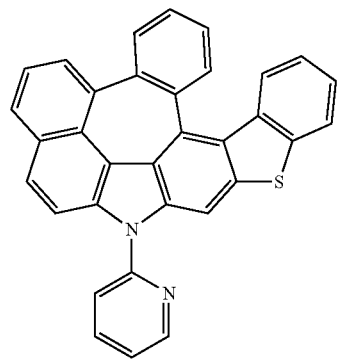
C-185
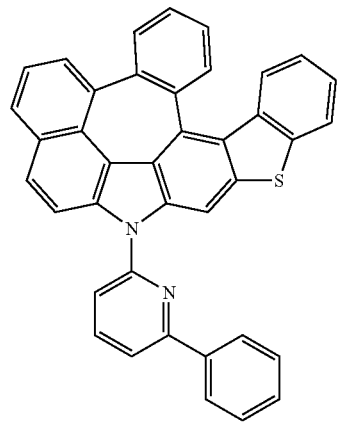
C-186
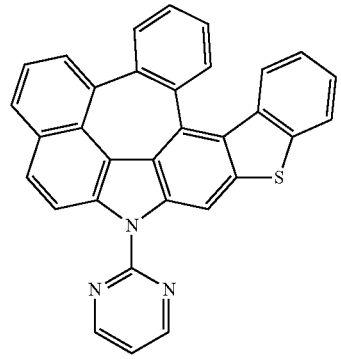
C-187
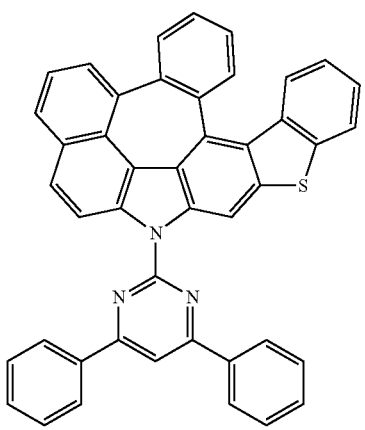

C-188
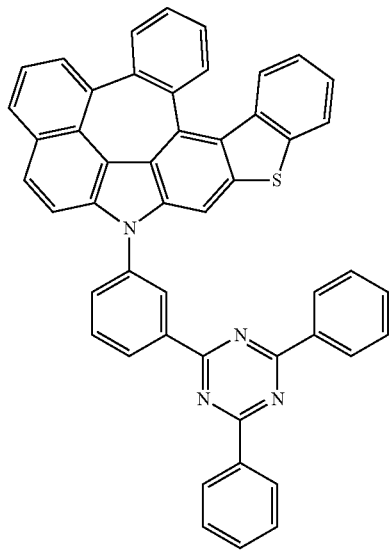
C-189
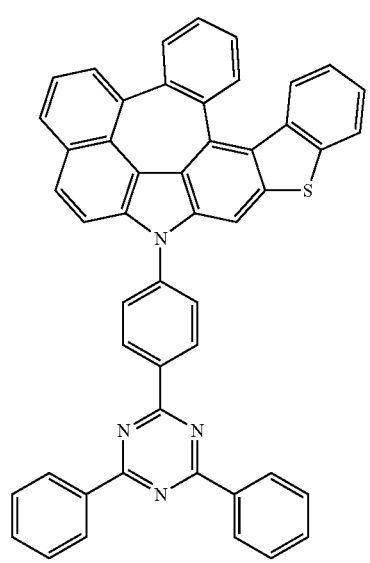
C-190
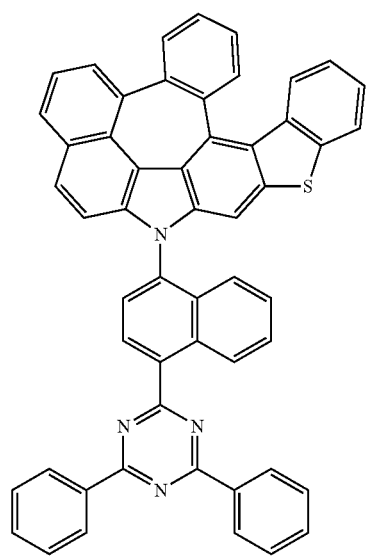
C-191
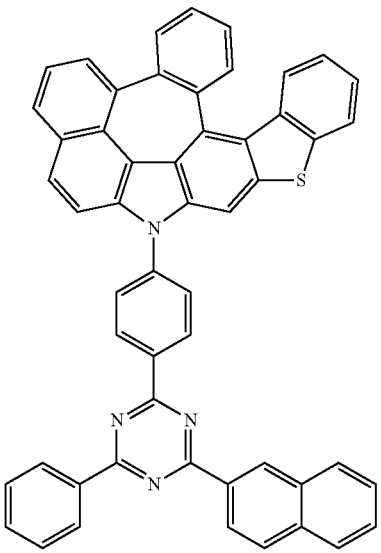
C-192
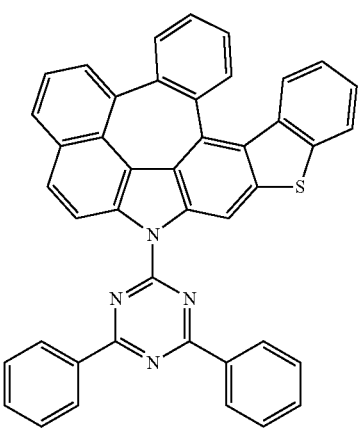
C-193
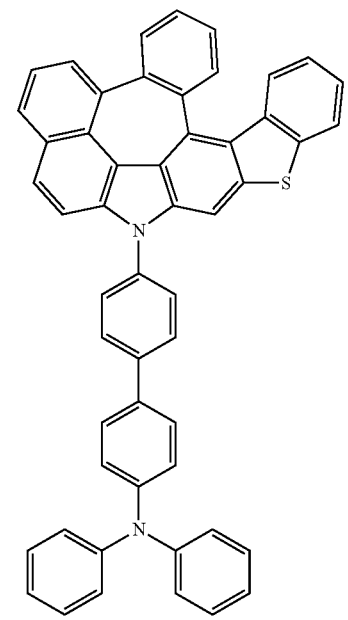

-continued
C-194
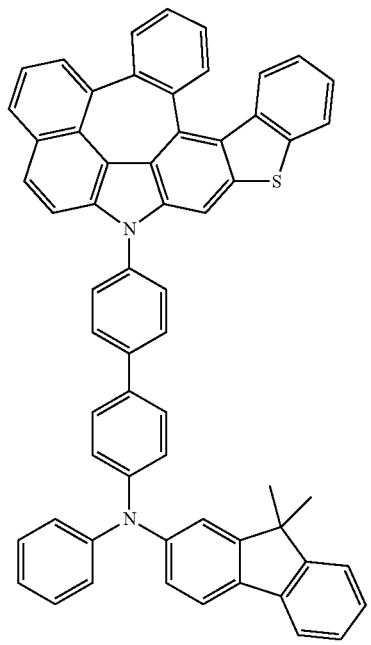
C-195
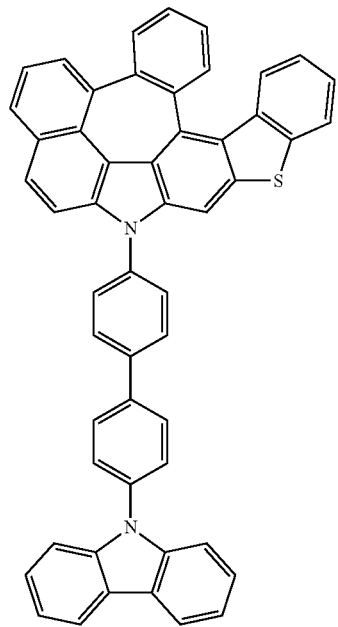
C-196
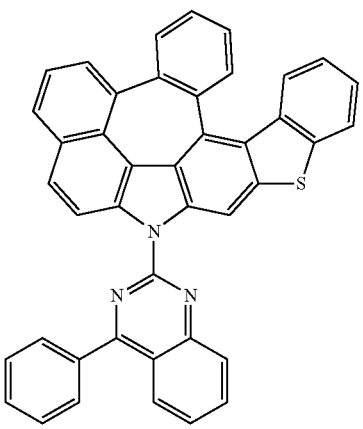
C-197
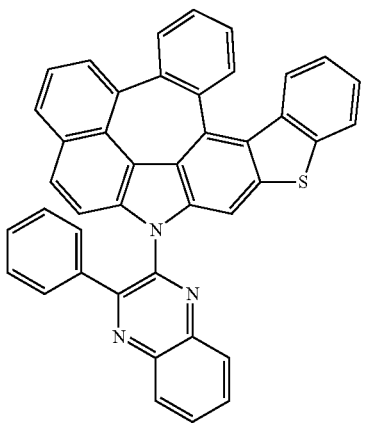
C-198
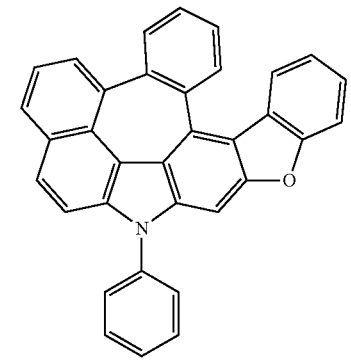
C-199
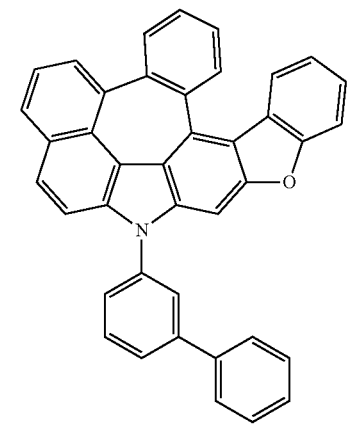

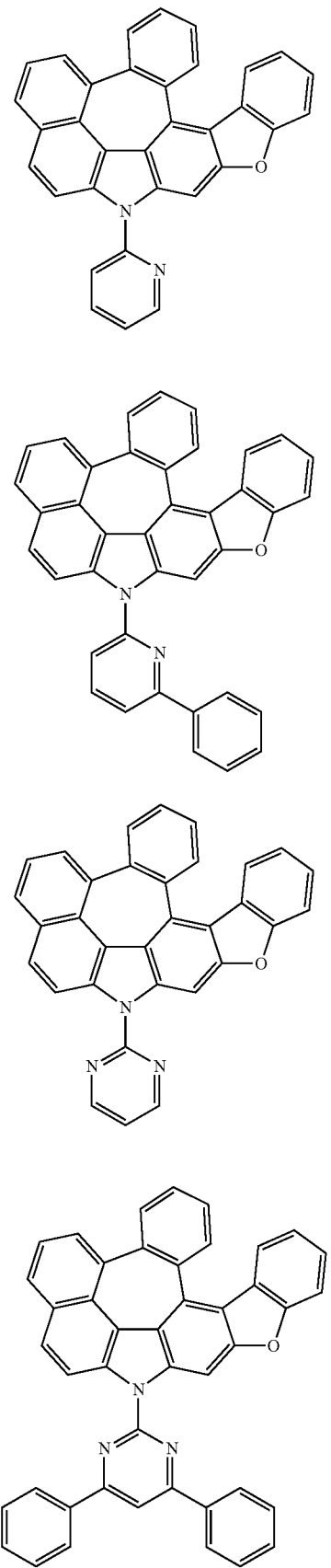
C-200
C-201
C-202
C-203
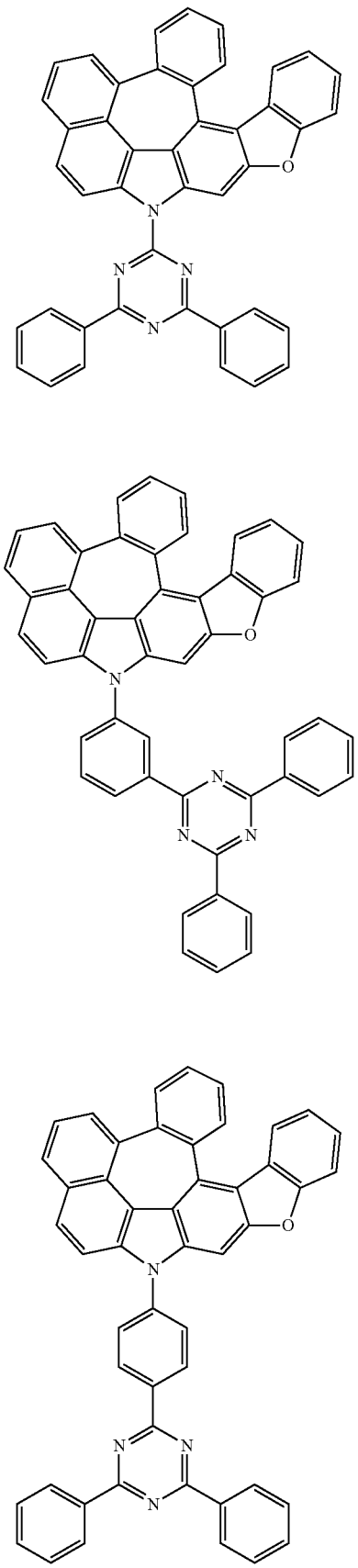
C-204
C-205
C-206

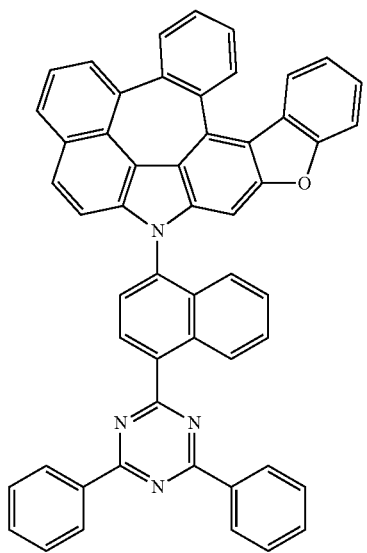
C-207
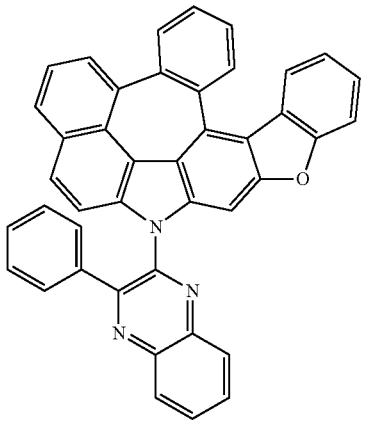
C-210
C-208
C-211
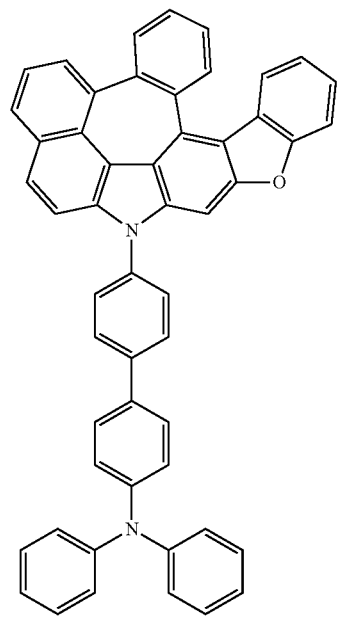
C-209
C-212
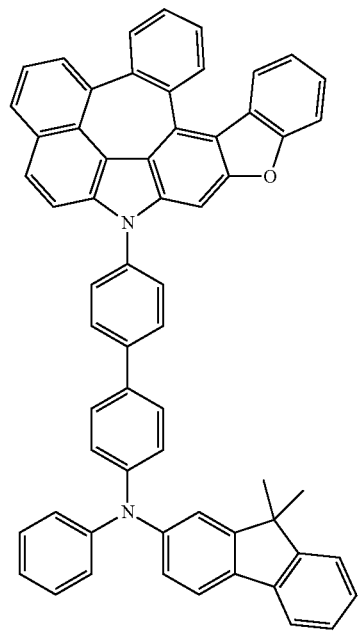

C-213
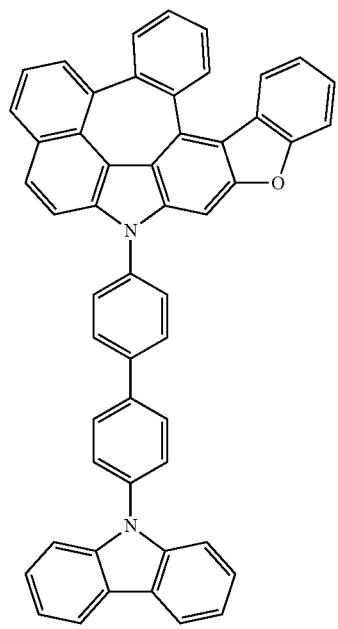
C-214
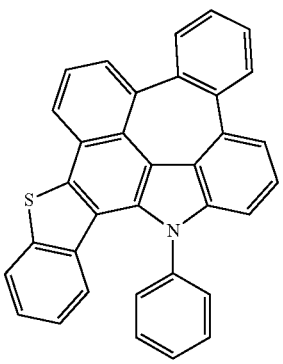
C-215
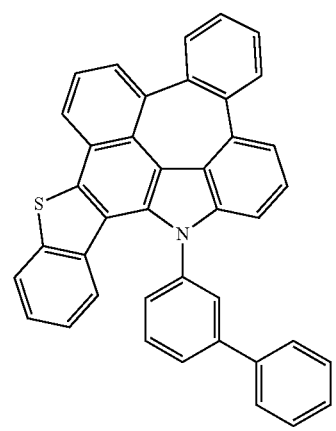
C-216
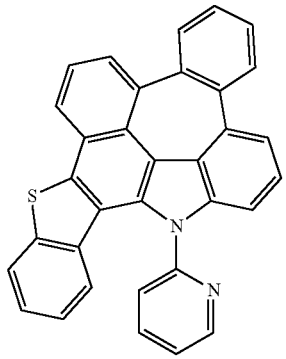
C-217
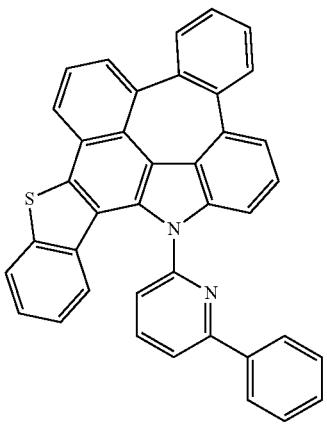
C-218
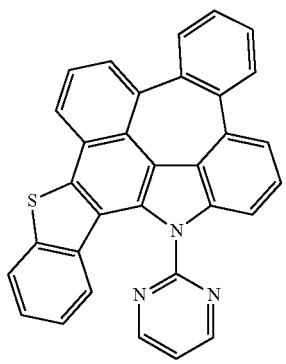
C-219
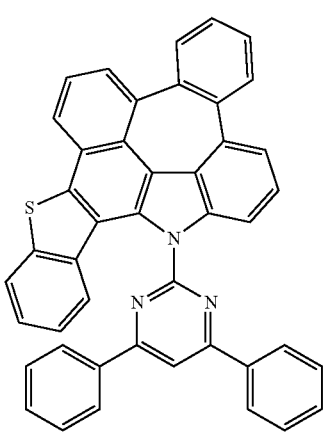

C-220
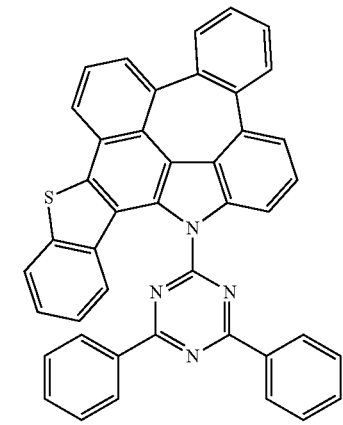
C-221
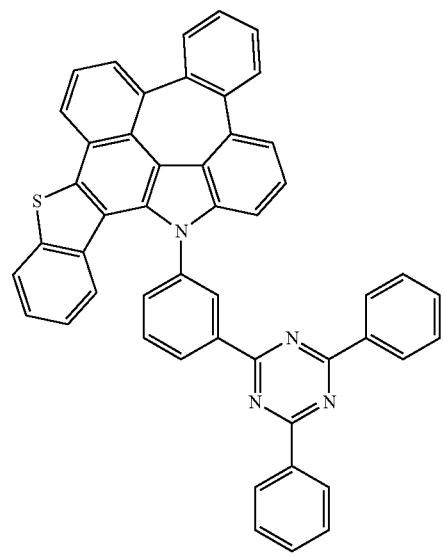
C-222
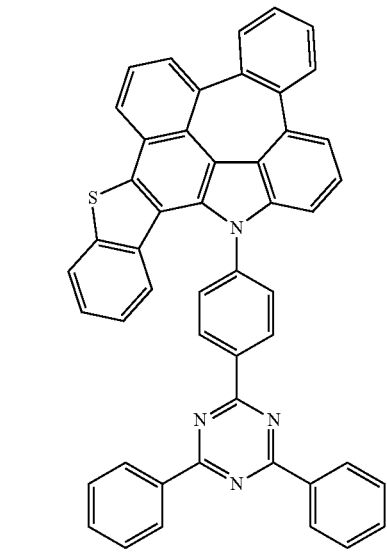
C-223
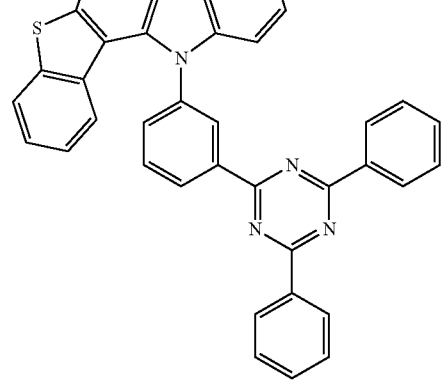
C-224
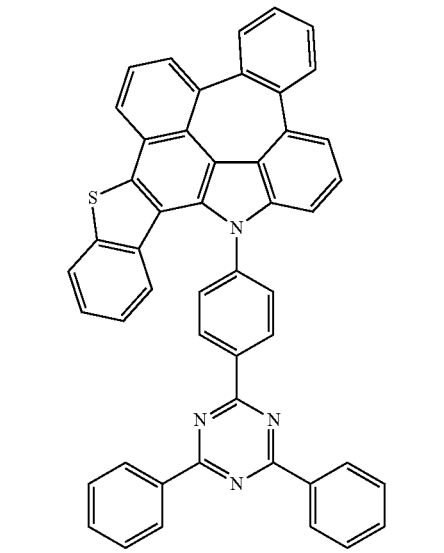
C-225
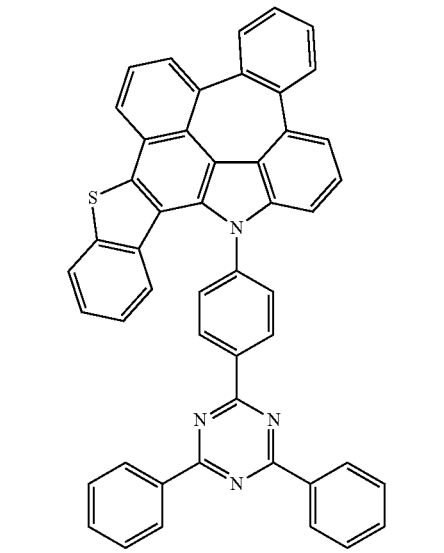

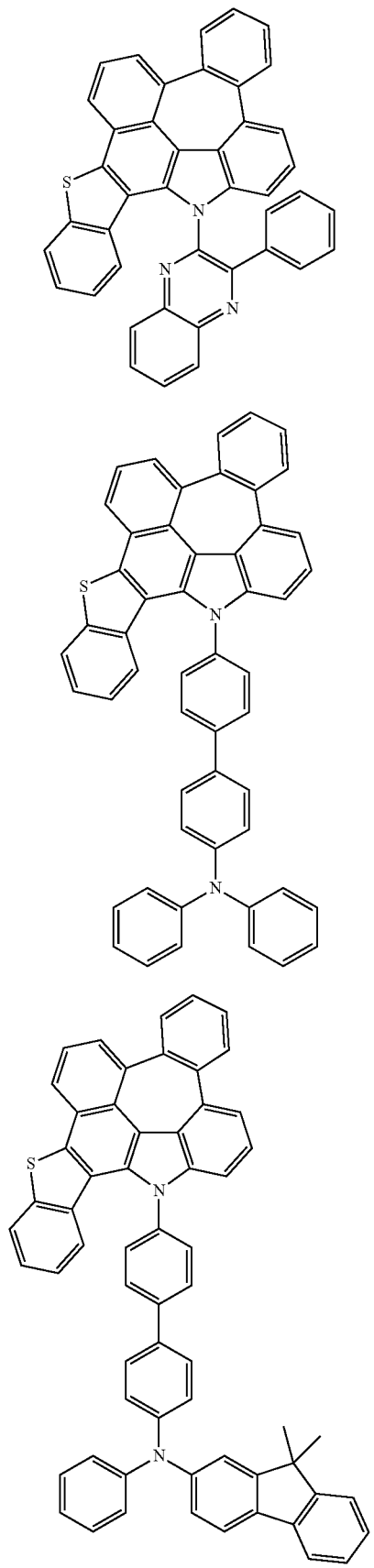

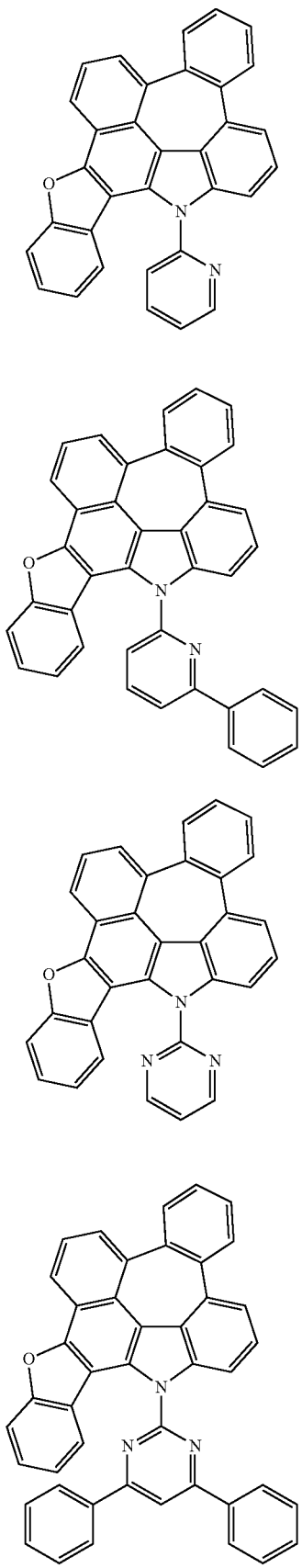
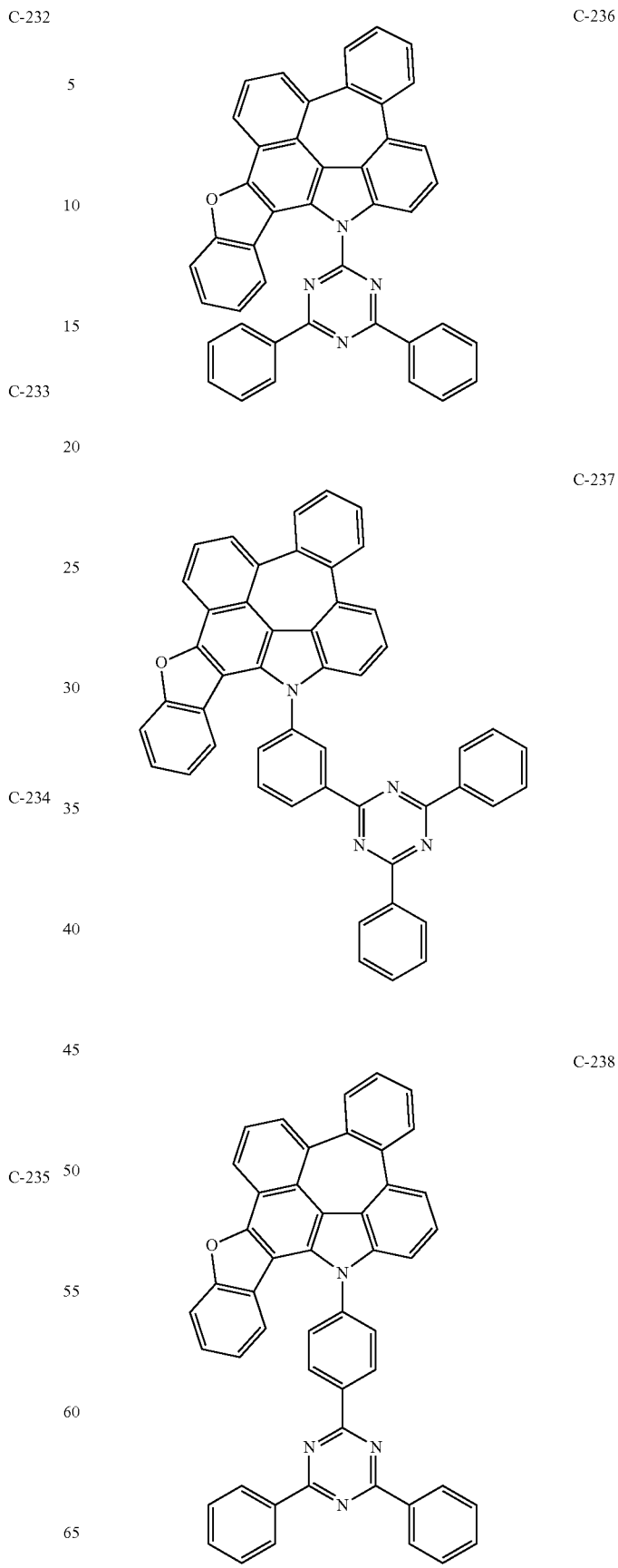

C-239
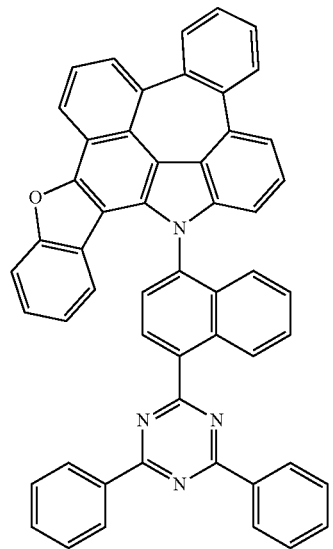
C-240
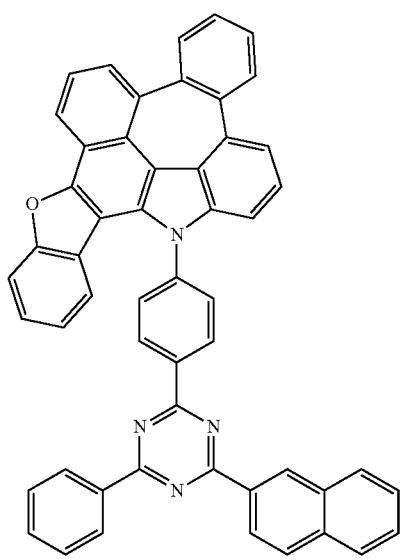
C-241
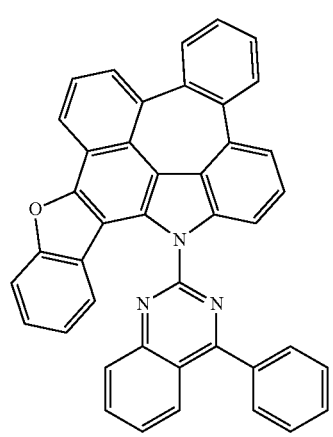
C-242
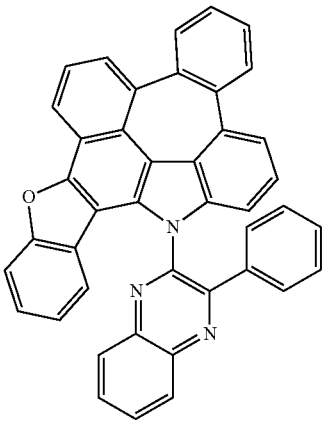
C-243
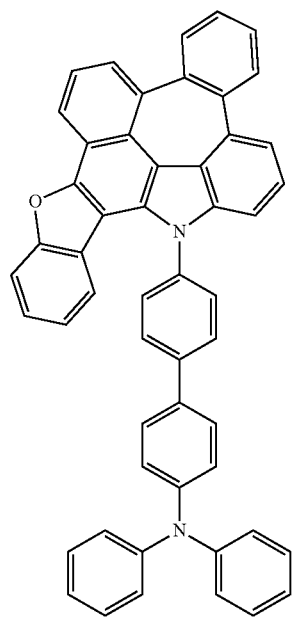
C-244
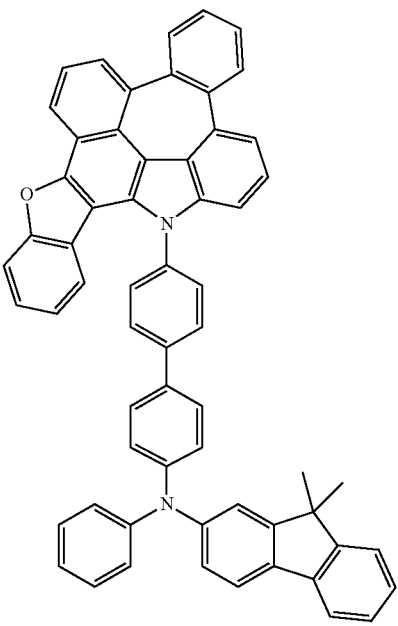

365
-continued
C-245
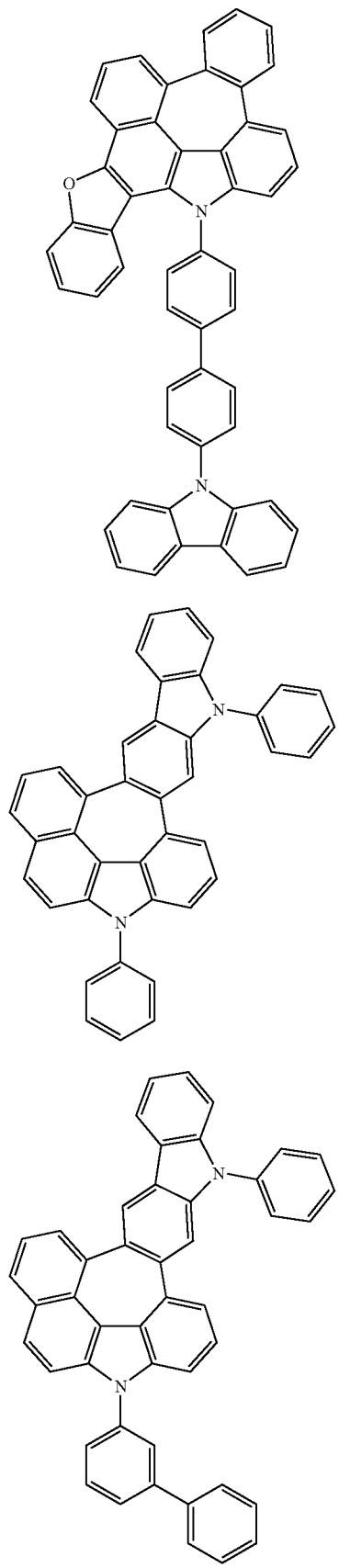
C-246
C-247
366
-continued
C-248
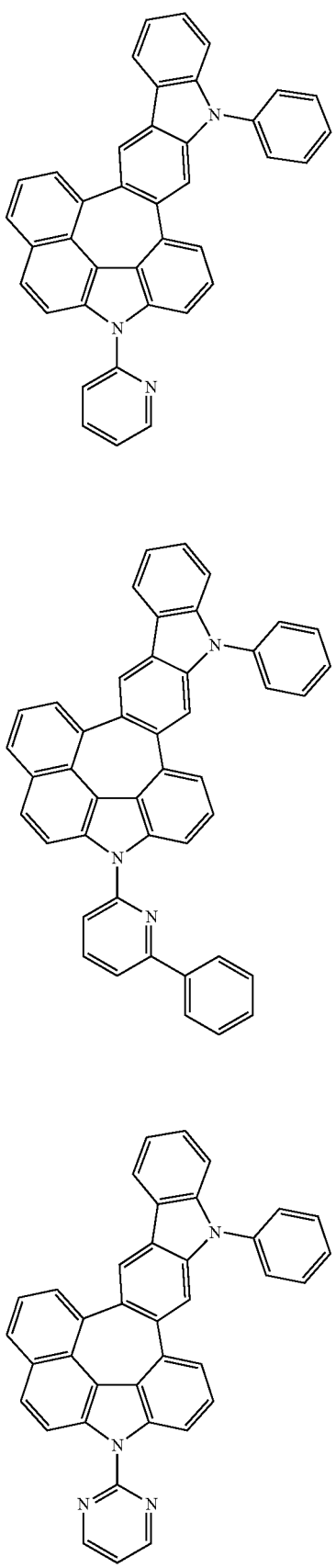
C-249
C-250

-continued
C-251
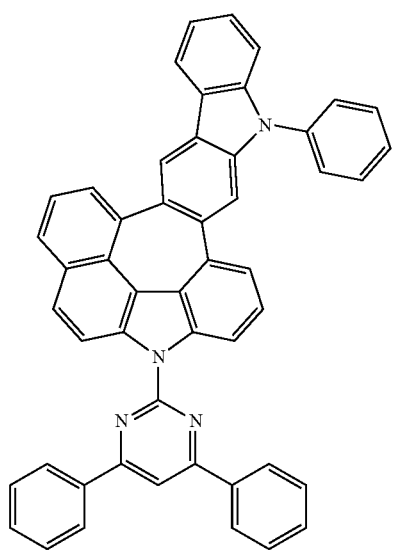
C-252
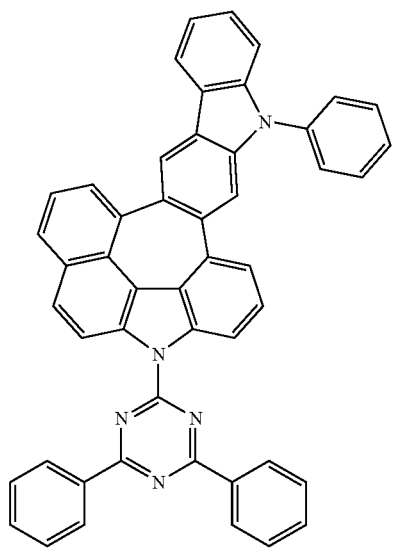
C-253
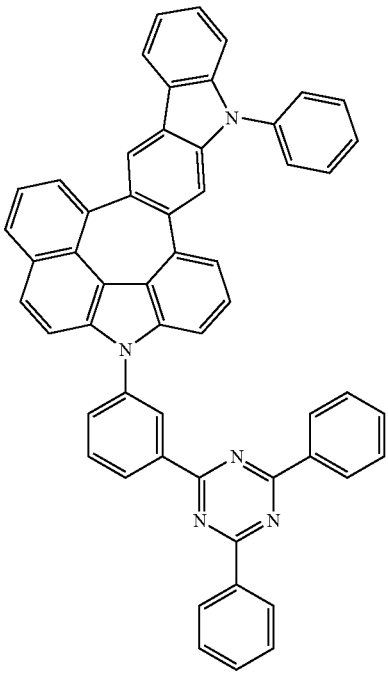
C-254
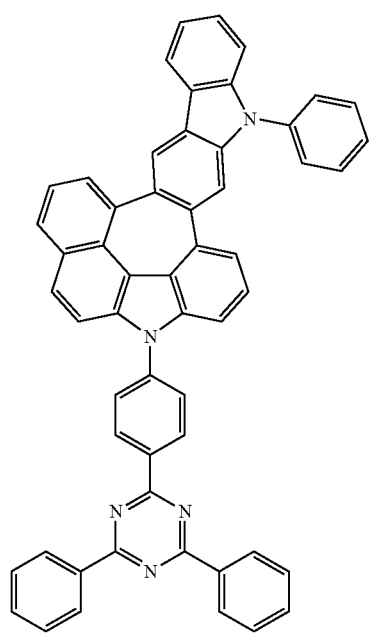

C-255
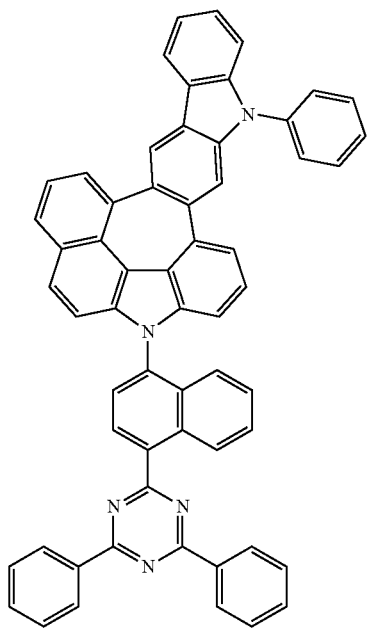
C-256
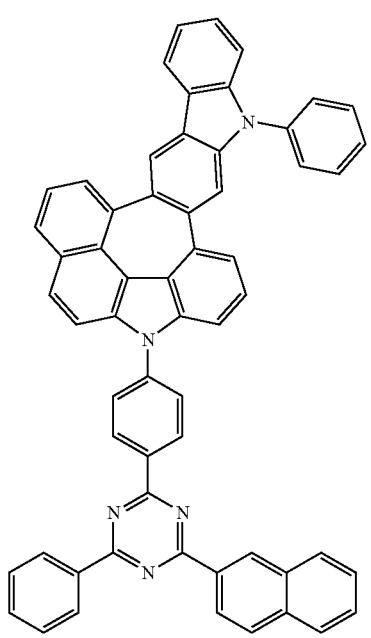
C-257
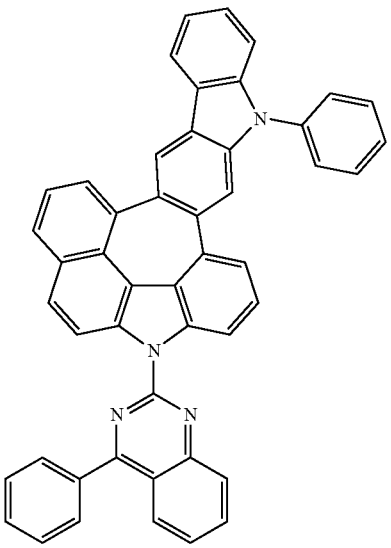
C-258
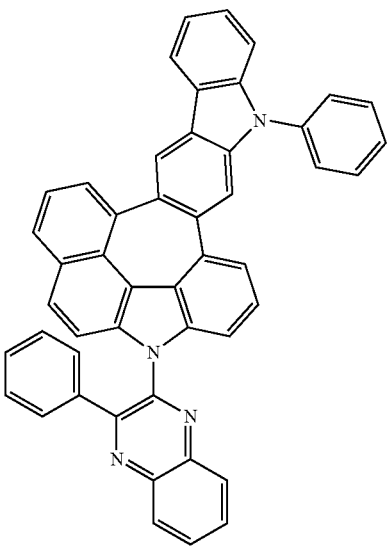

-continued
C-259
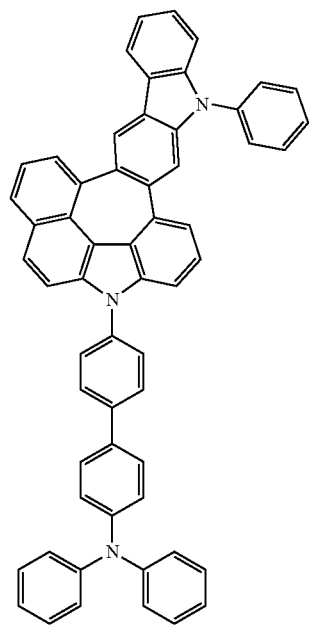
C-260
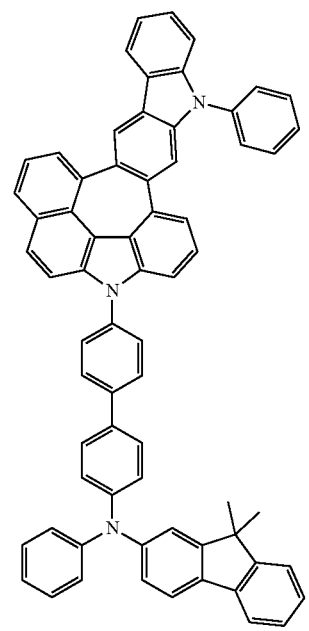
-continued
C-261
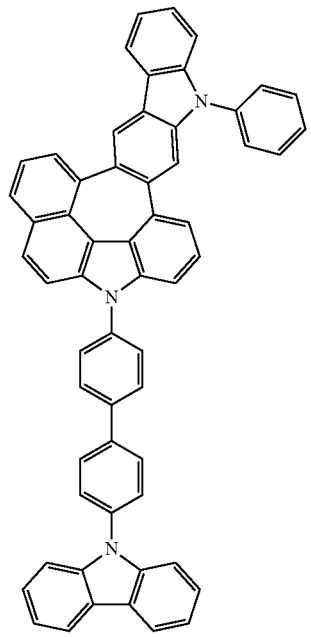
C-262
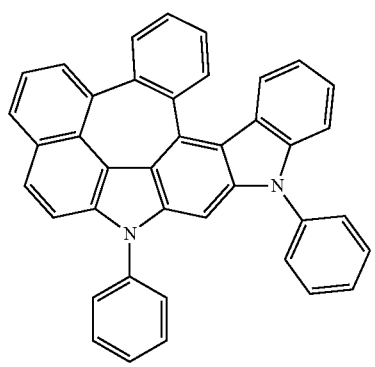
C-263
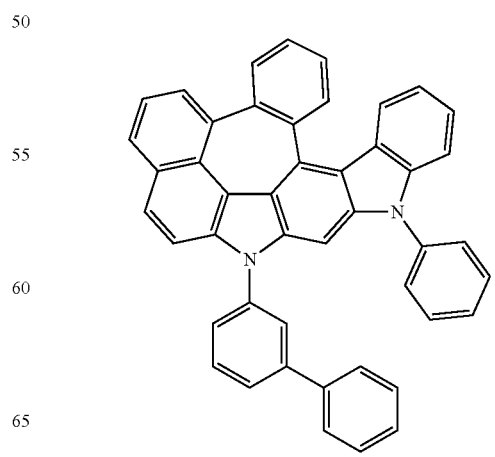

C-264
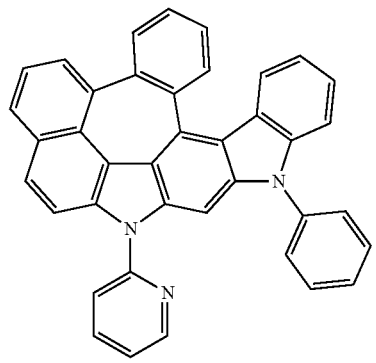
C-265
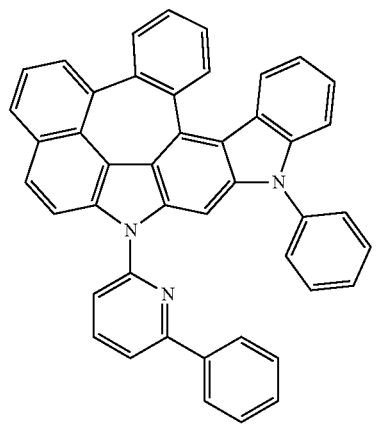
C-266
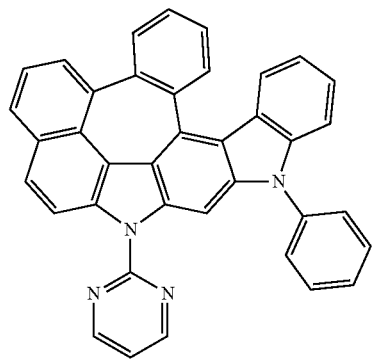
C-267
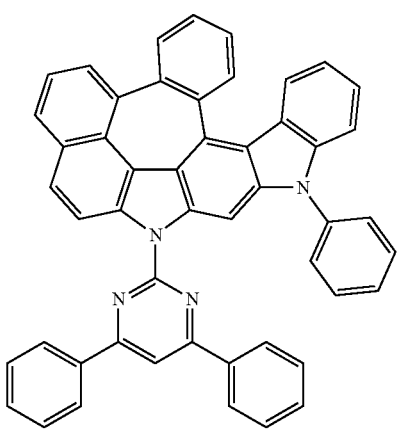
C-268
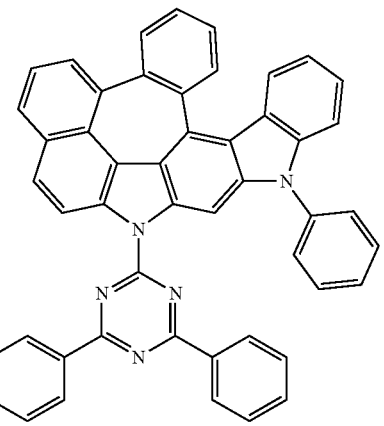
C-269
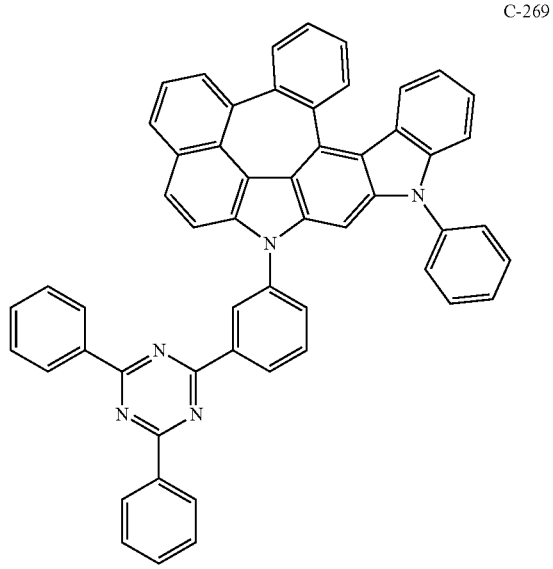
C-270
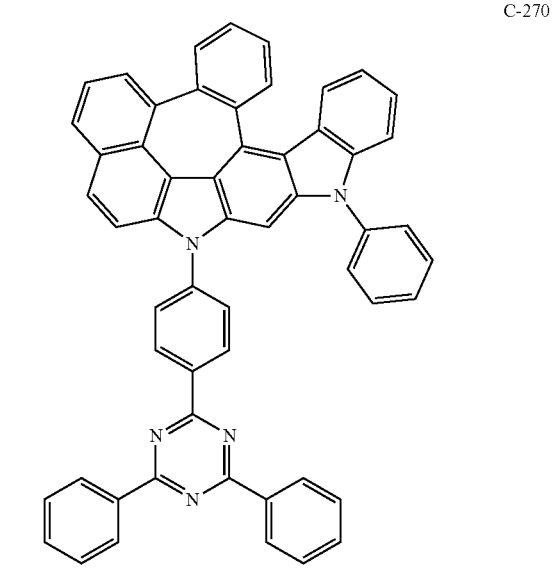

C-271
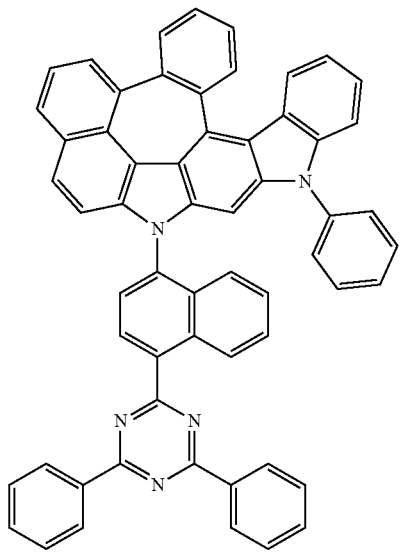
C-272
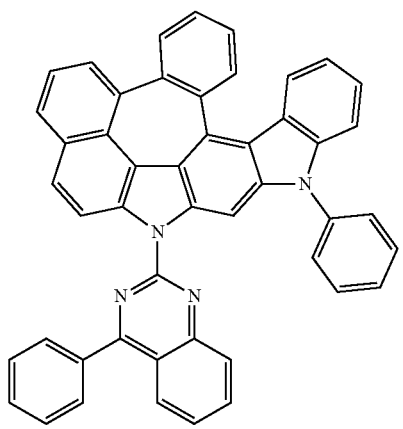
C-273
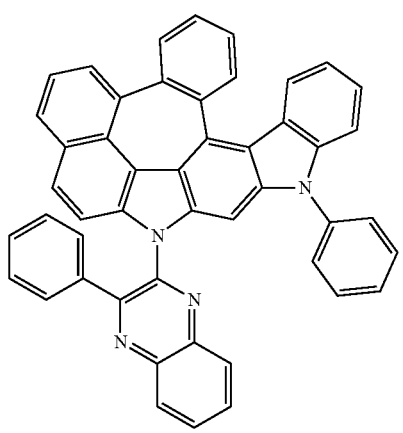
C-274
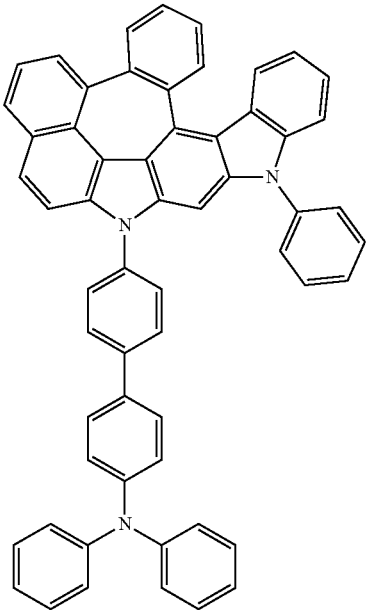
C-275
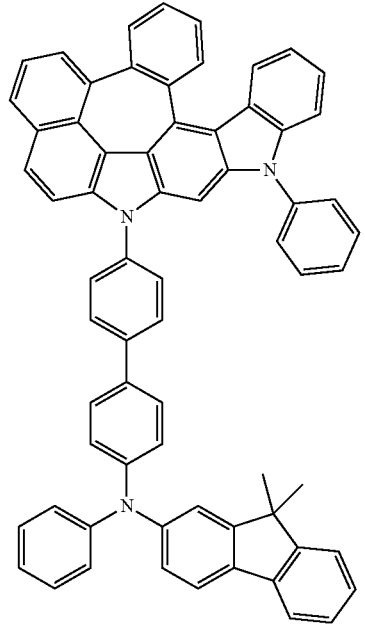

C-276
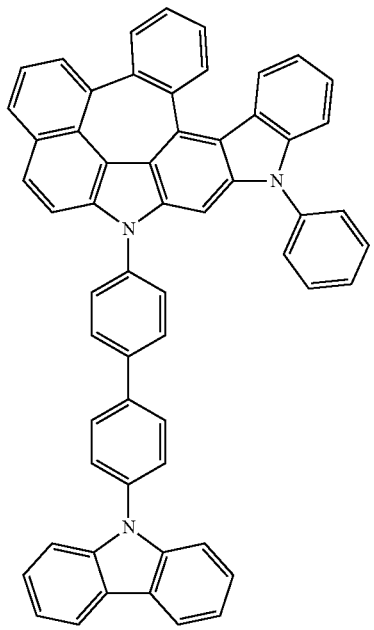
C-277
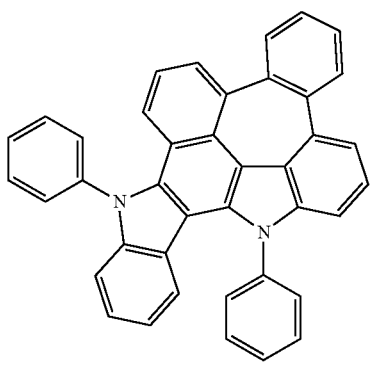
C-278
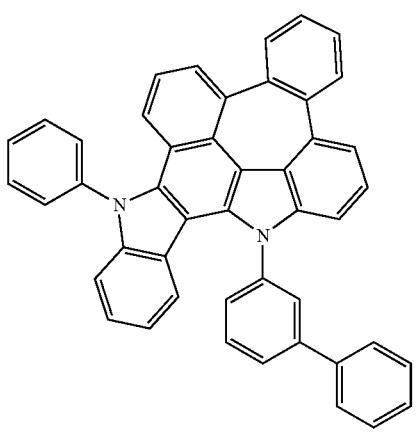
C-279
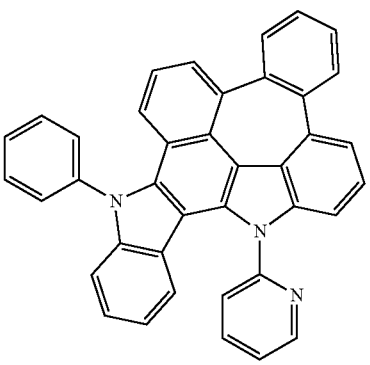
C-280
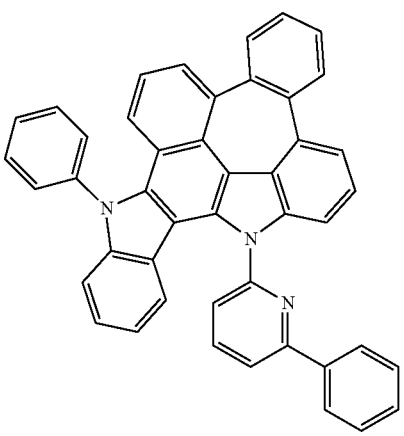
C-281
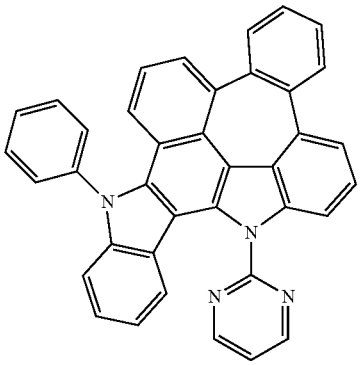

C-282
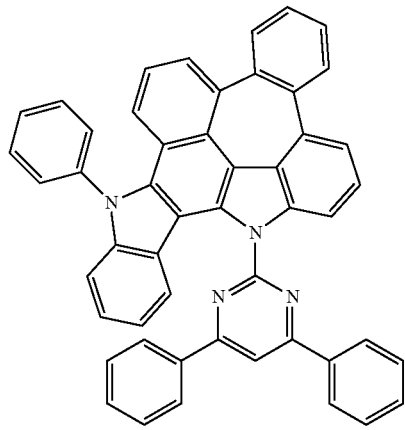
C-283
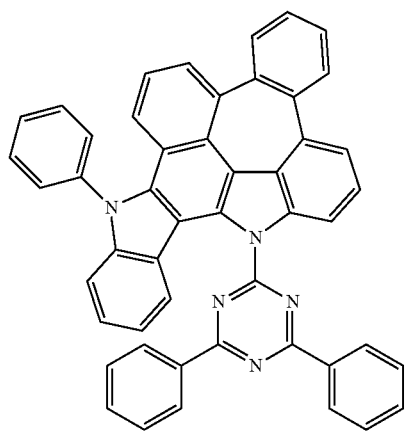
C-284
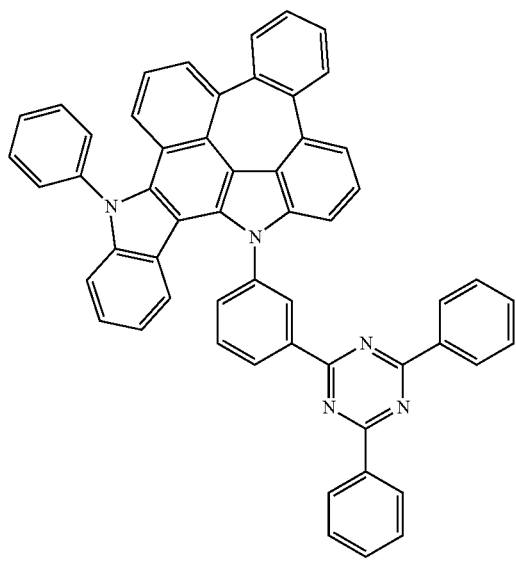
C-285
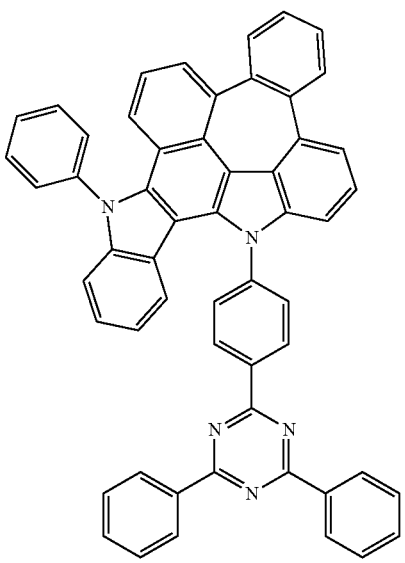
C-286
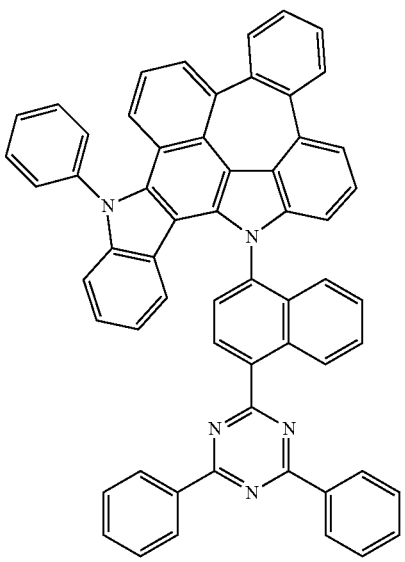

C-287
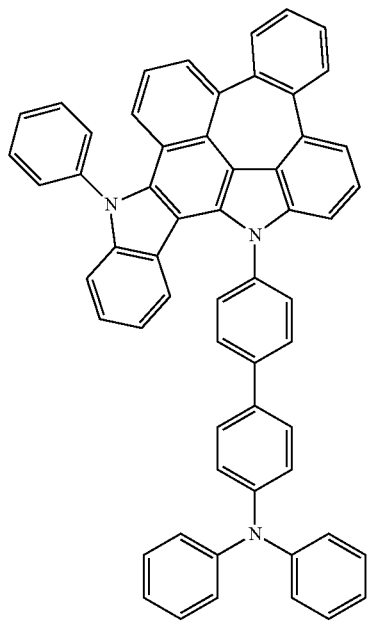
C-288
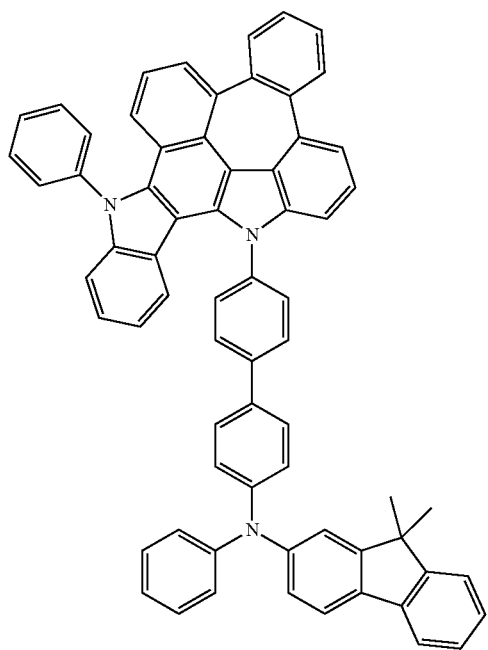
C-289
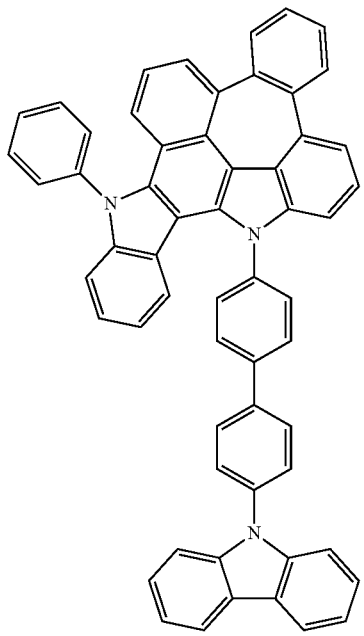
C-290
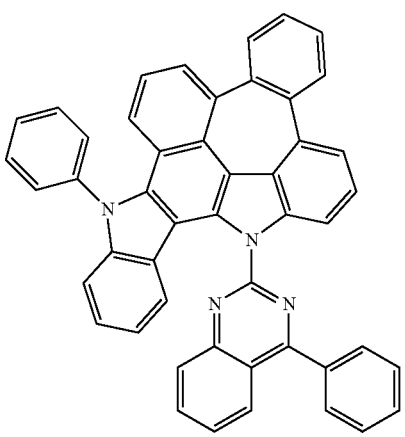
C-291
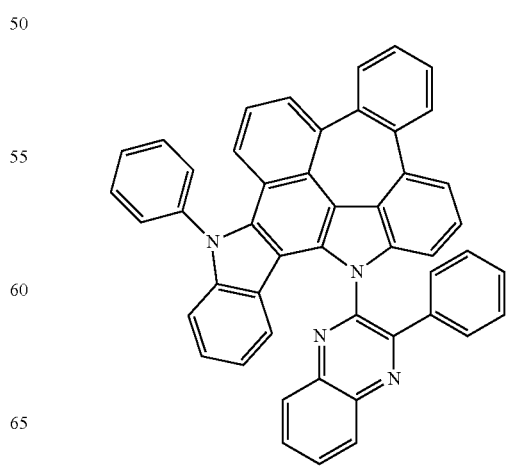

C-292
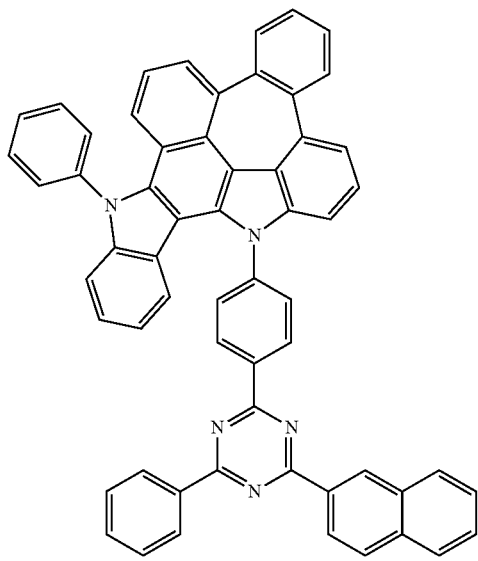
C-293
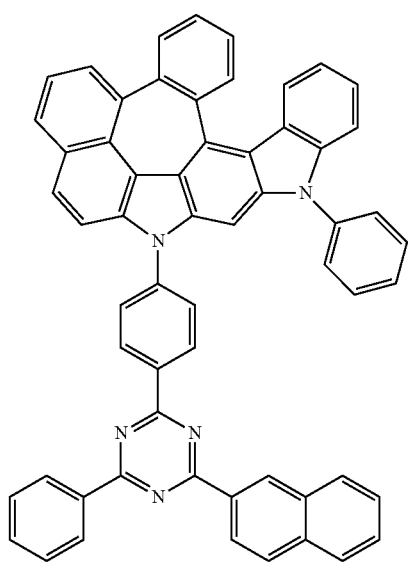
C-294
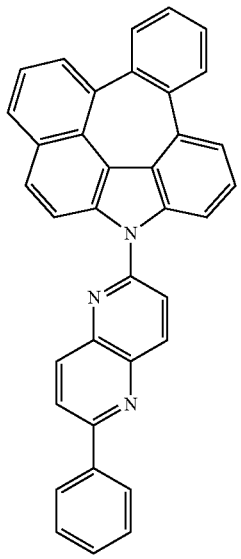
C-295
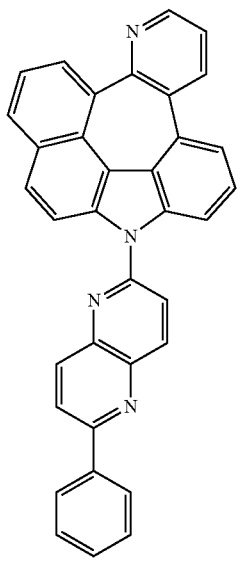

C-296
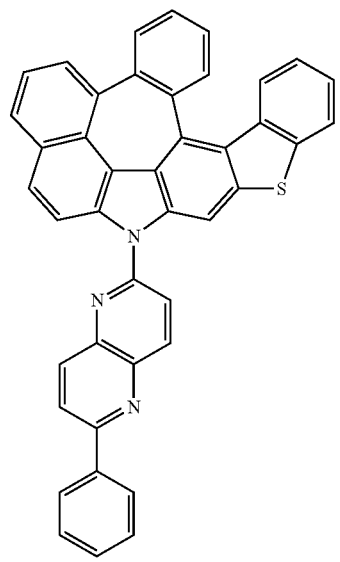
C-297
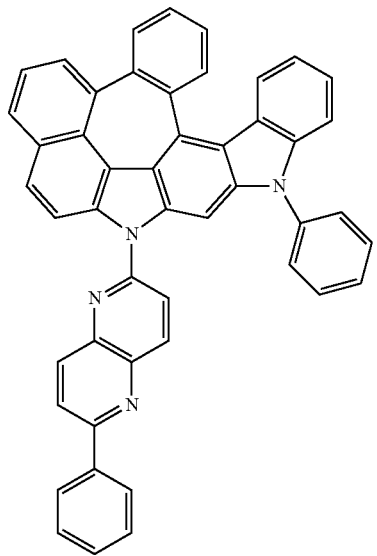
C-298
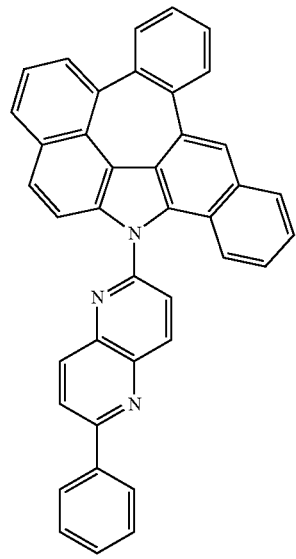
C-299
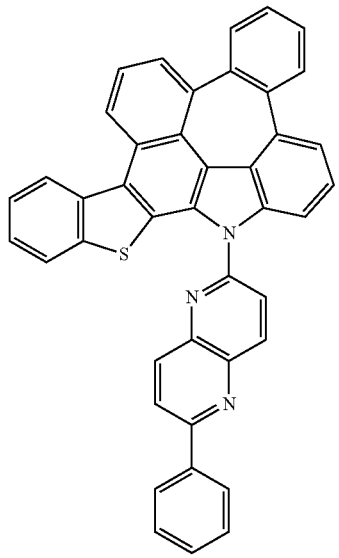

C-300 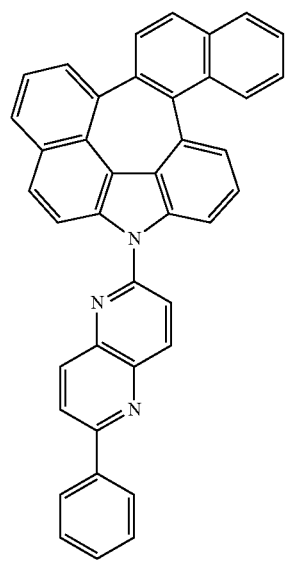
C-301 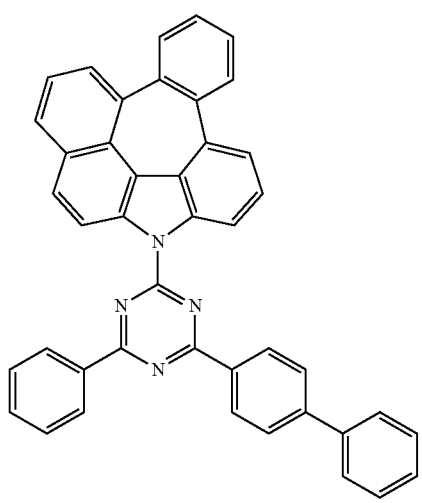
C-302 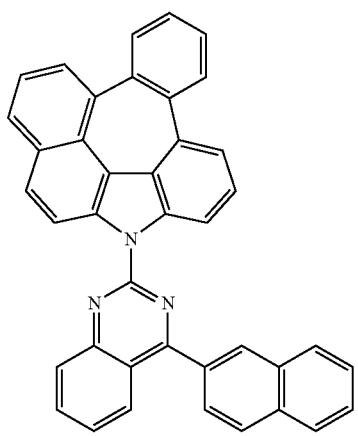
C-303 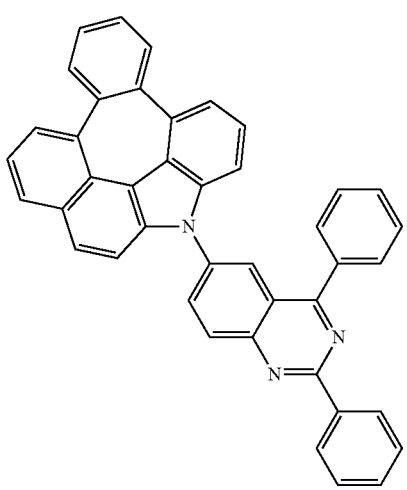
C-304 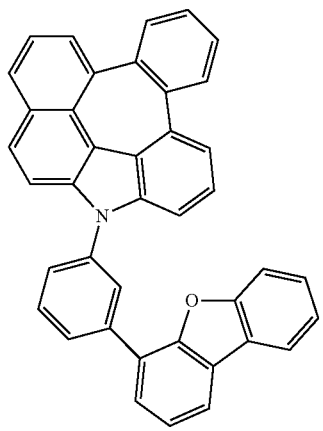
C-305 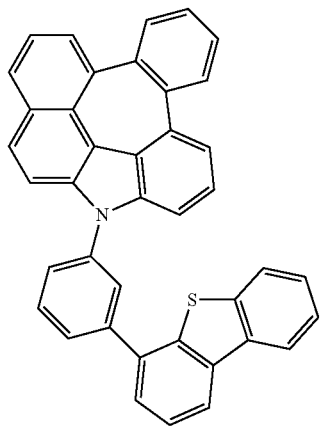

-continued
C-306
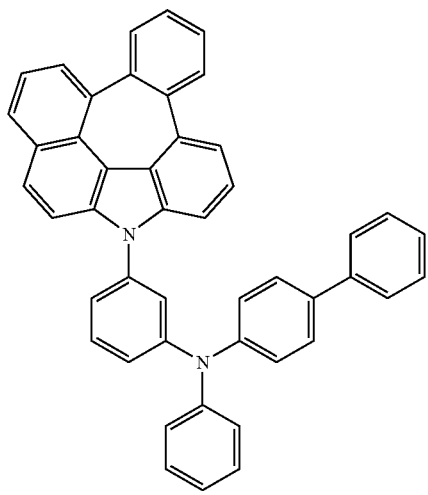
C-307
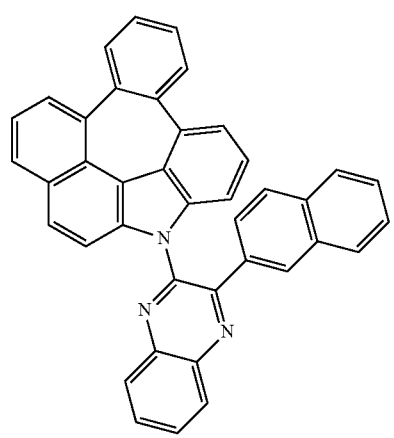
C-308
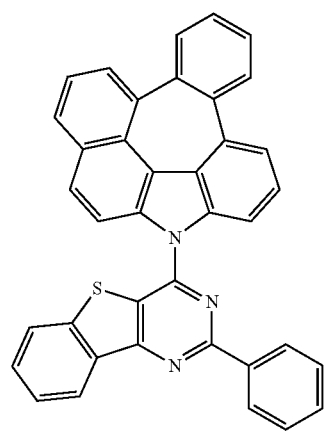
-continued
C-309
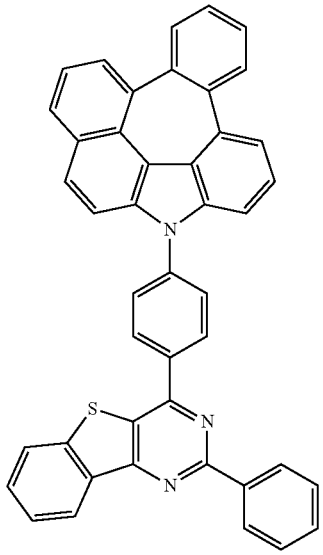
C-310
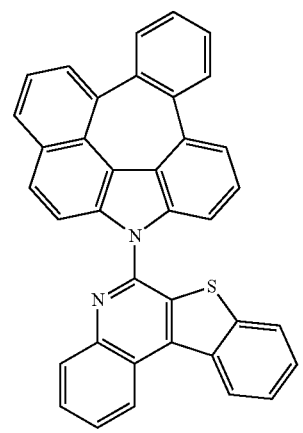
C-311
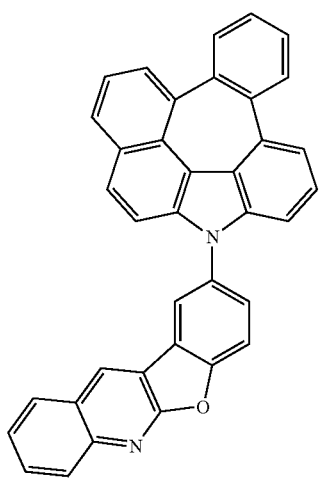

C-312
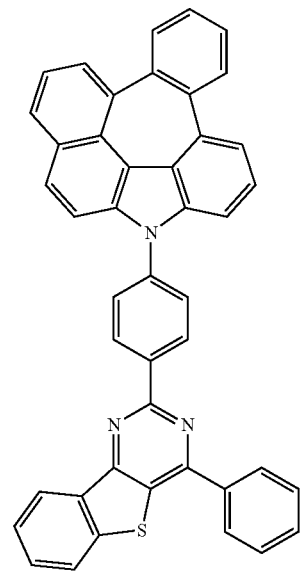
C-313
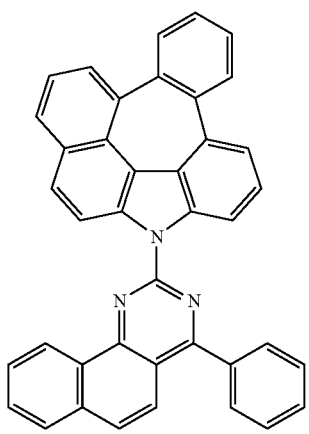
C-314
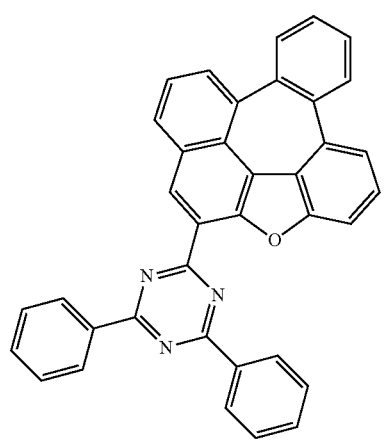
C-315
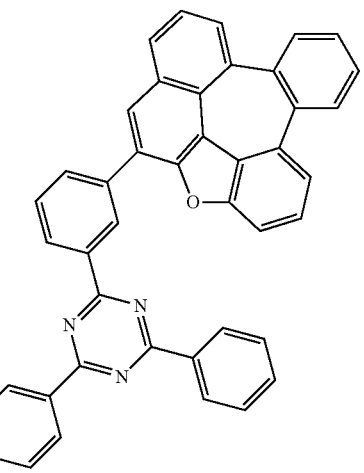
C-316
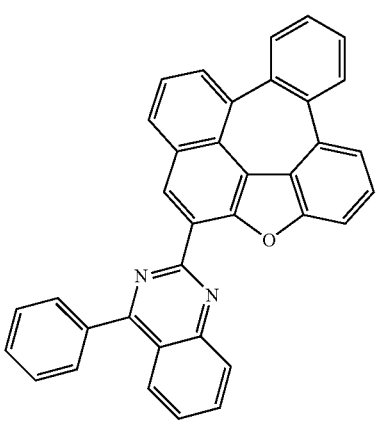
C-317
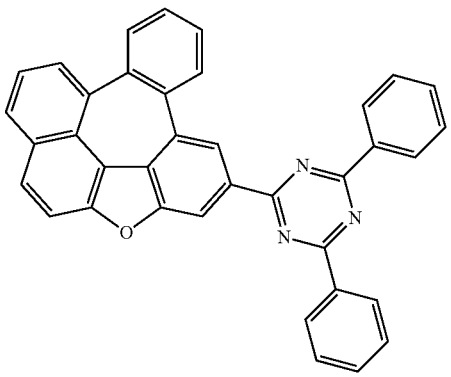
C-318
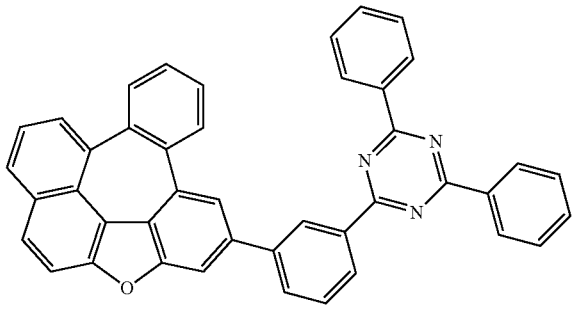

C-319
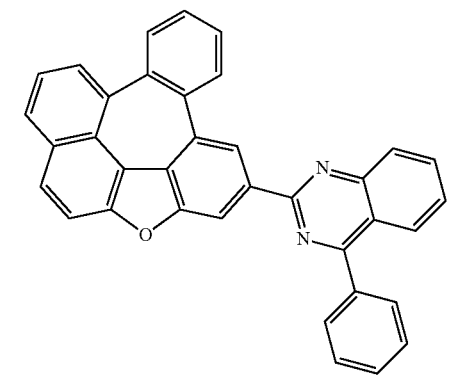
C-320
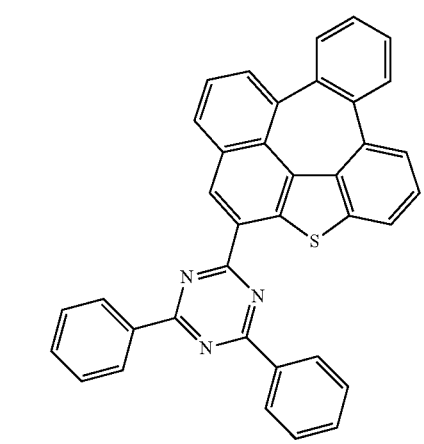
C-321
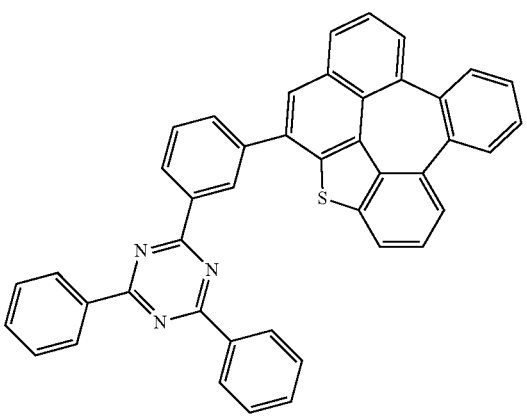
C-322
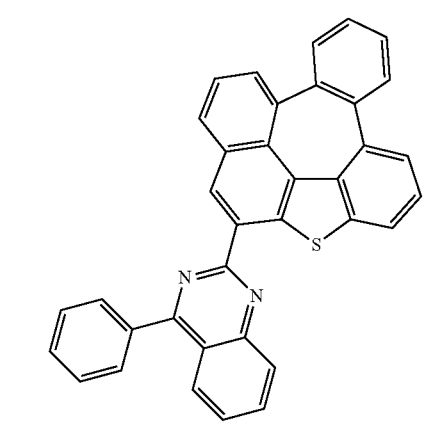
C-323
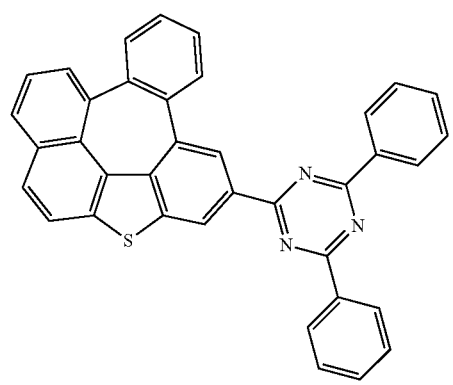
C-324
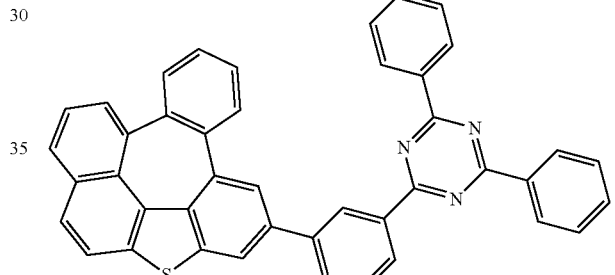
C-325
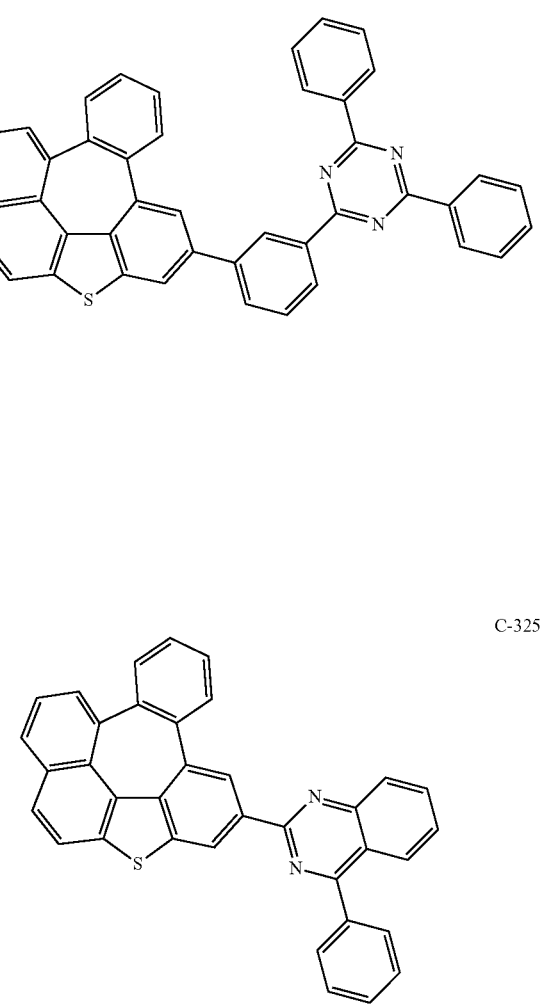

-continued
C-326
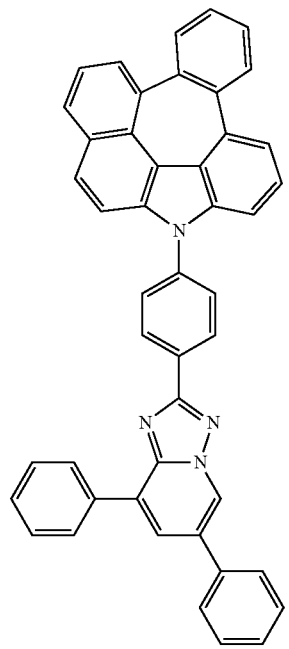
C-327
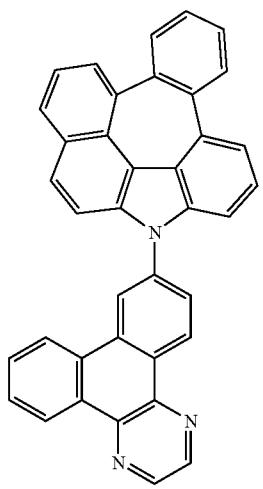
-continued
C-328
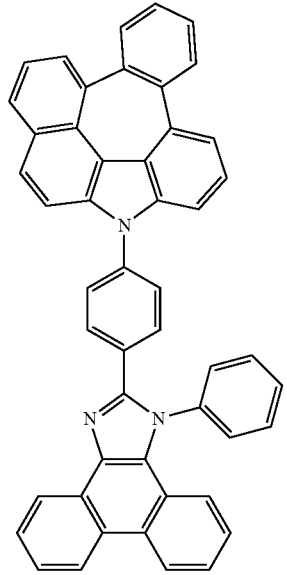
C-329
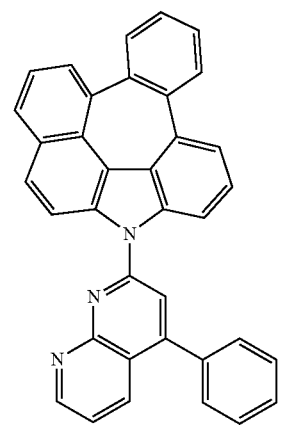
C-330
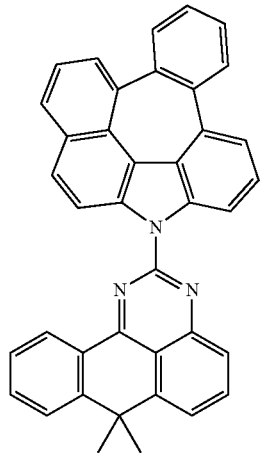

C-331
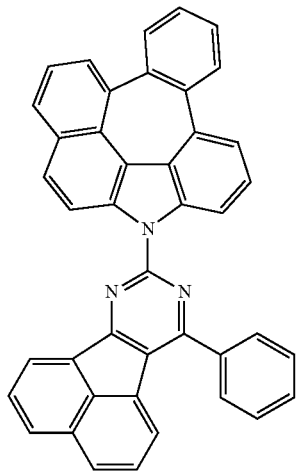
C-334
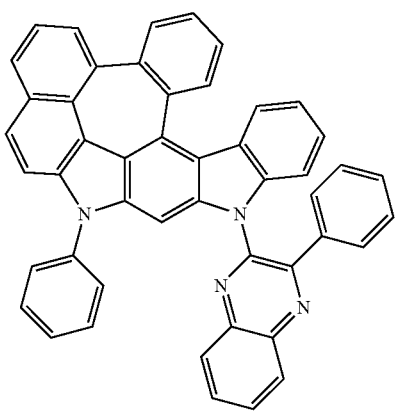
C-332
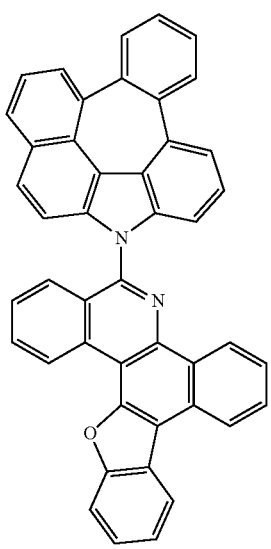
C-335
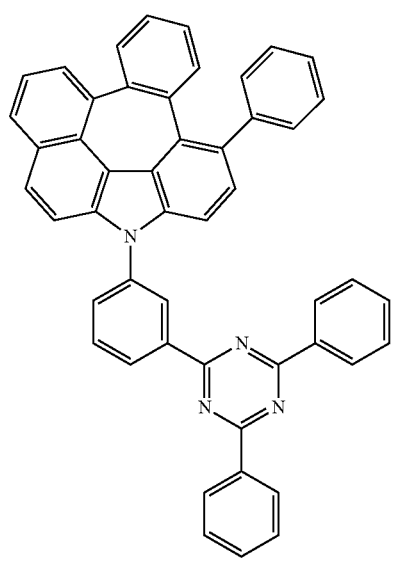
C-333
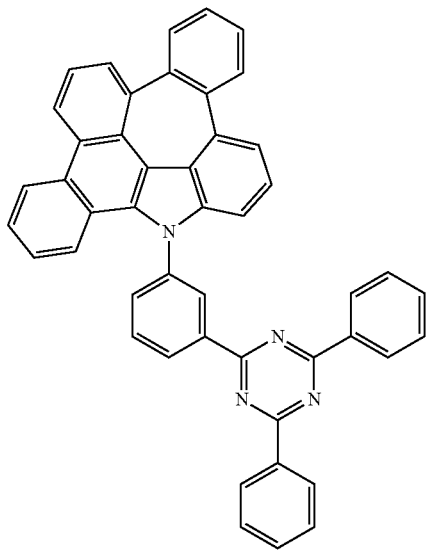
C-336
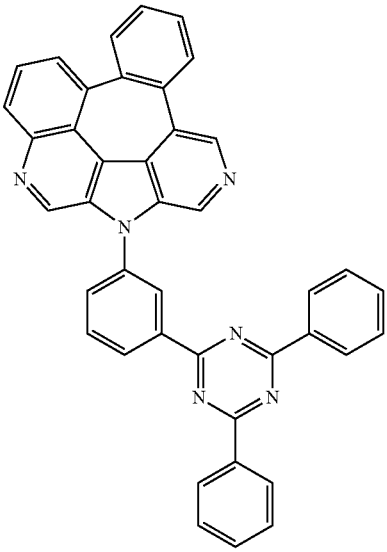

C-337
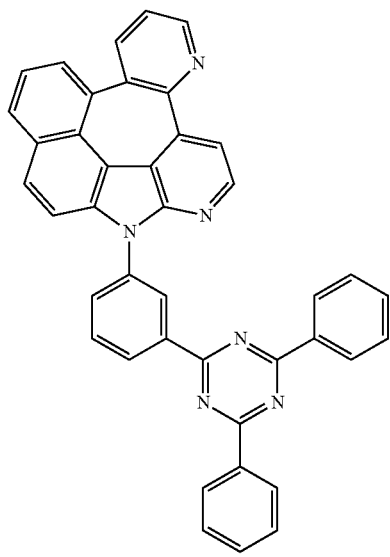
C-338
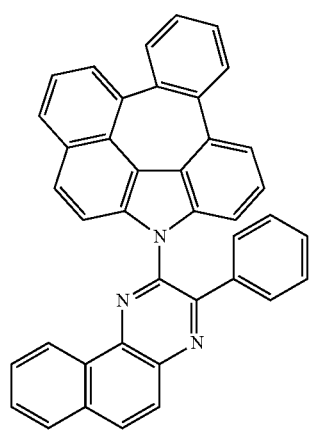
C-339
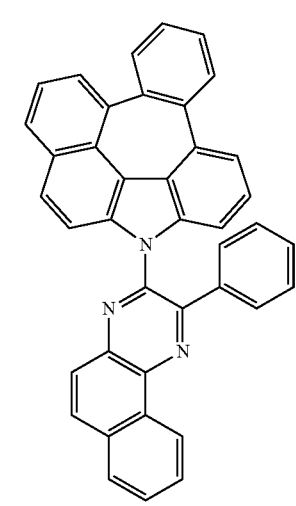
C-340
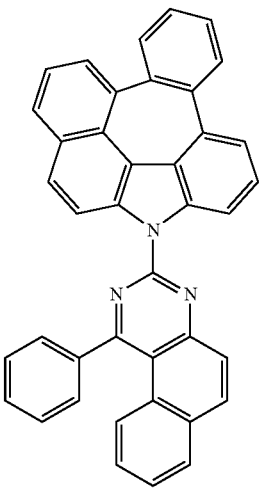
C-341
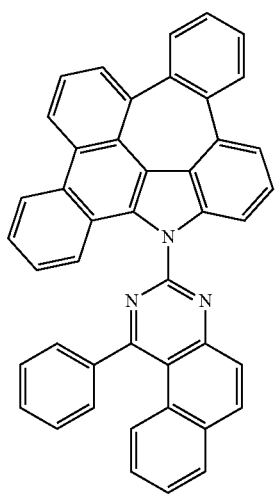
C-342
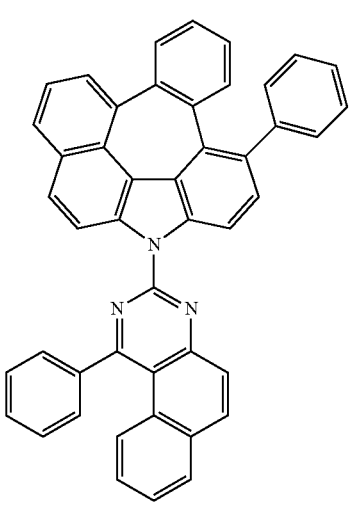

401
-continued
C-343
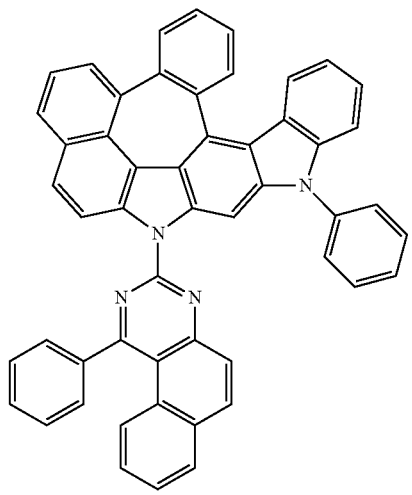
C-344
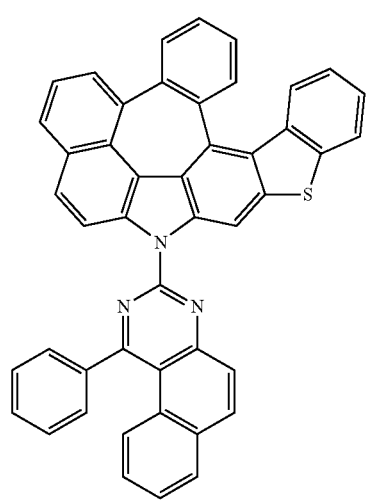
C-345
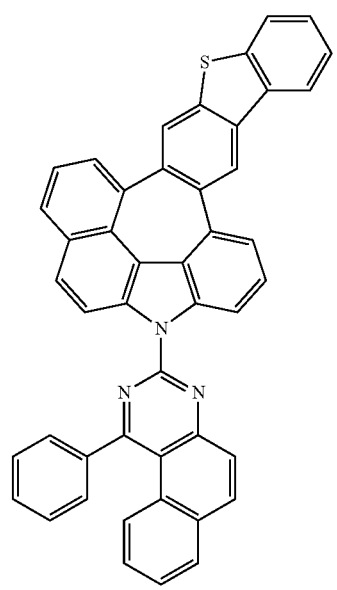
402
-continued
C-346
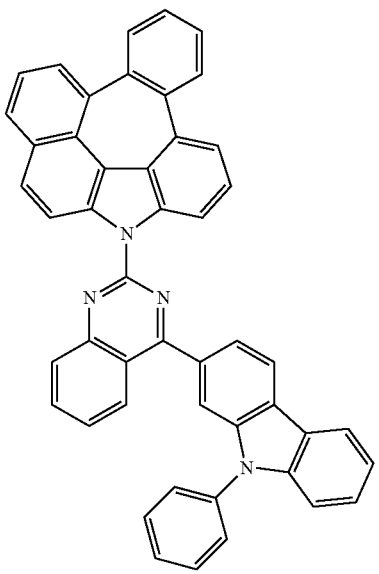
C-347
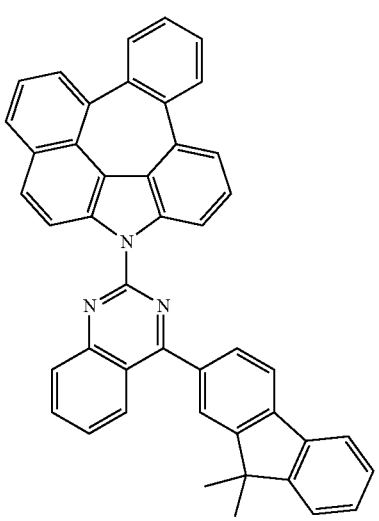
C-348
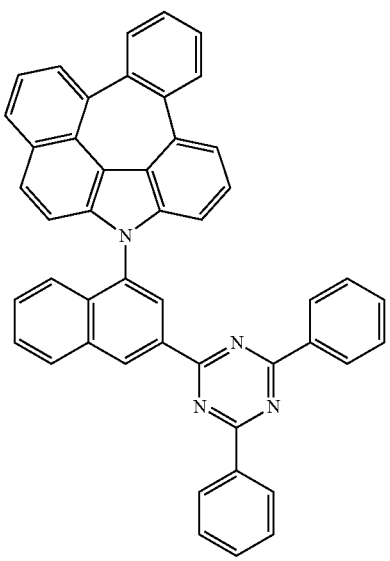

C-349
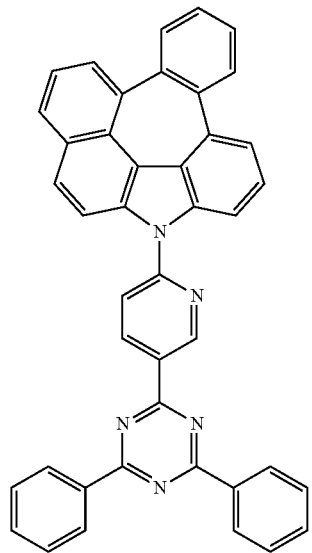
C-350
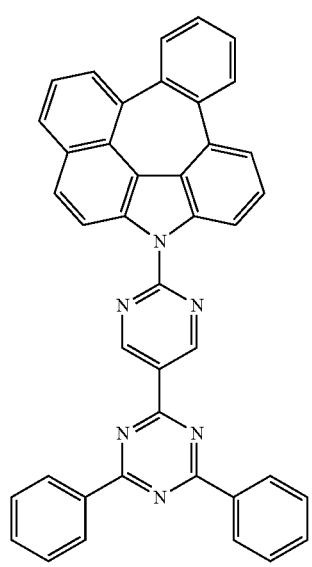
C-351
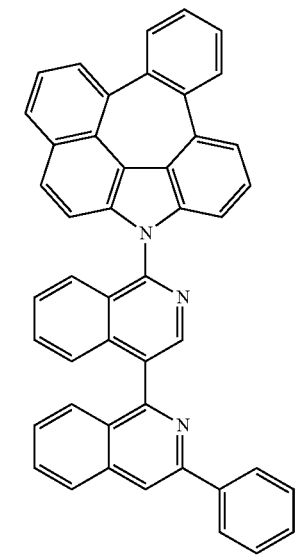
C-352
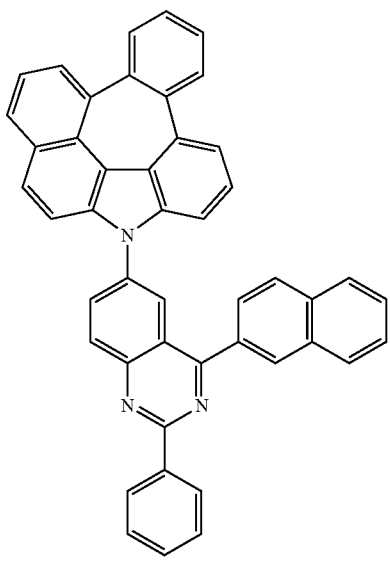
C-353
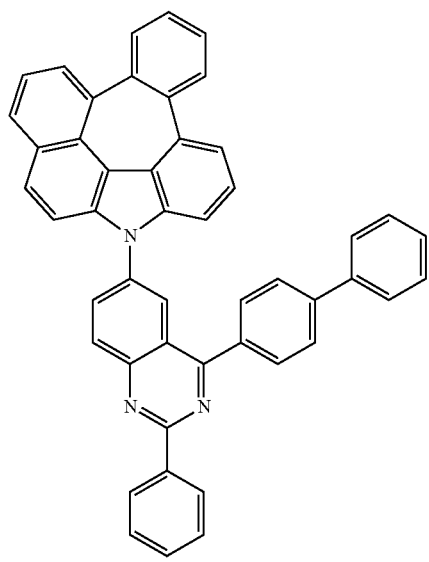

C-354
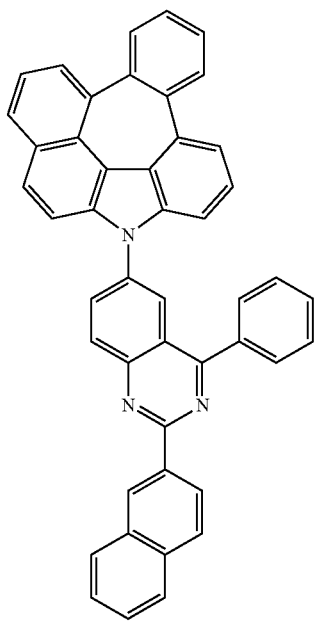
C-356
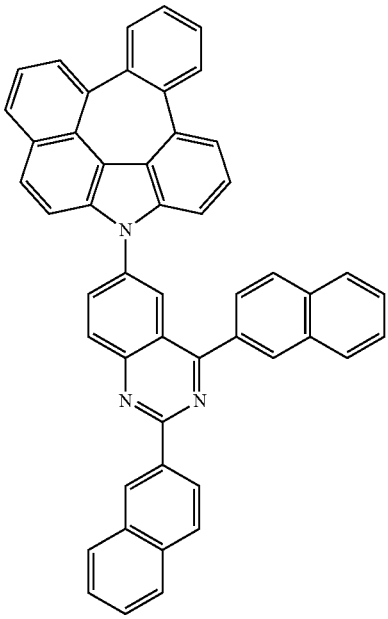
C-355
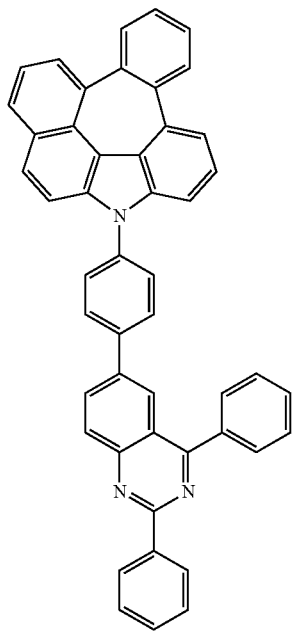
C-357
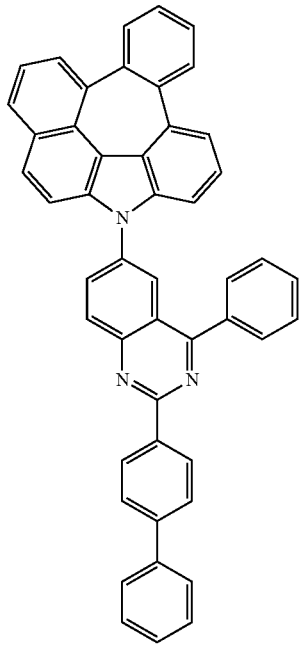

C-358
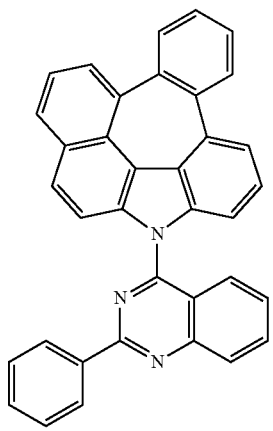
C-359
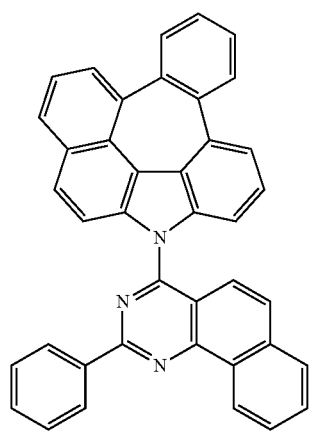
C-360
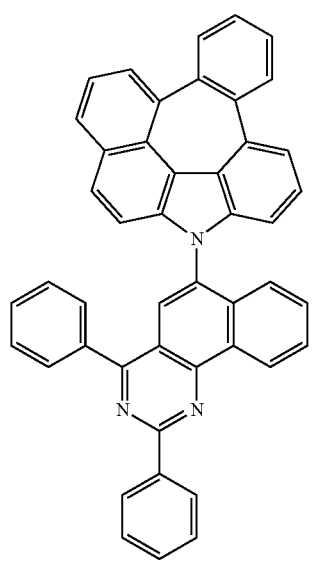
C-361
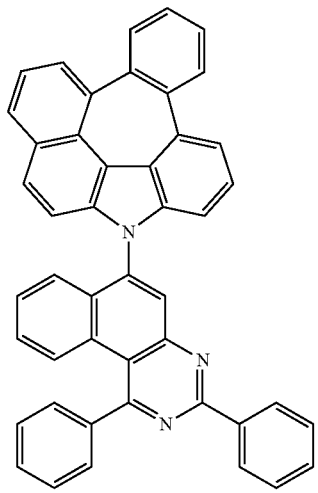
C-362
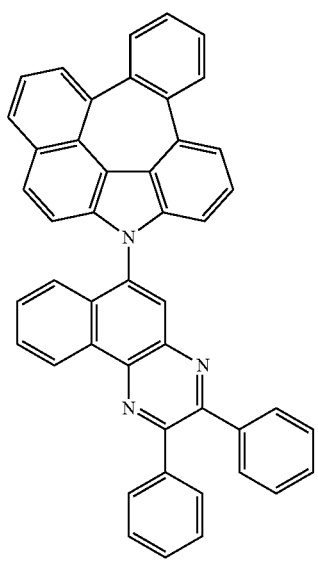
C-363
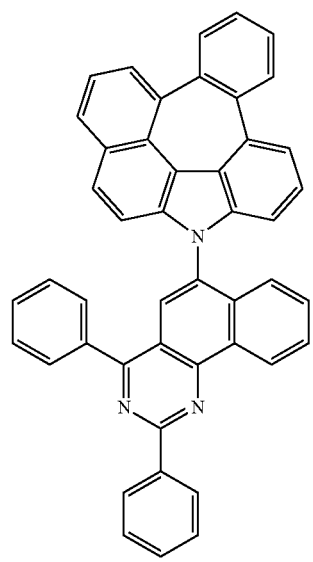

C-364 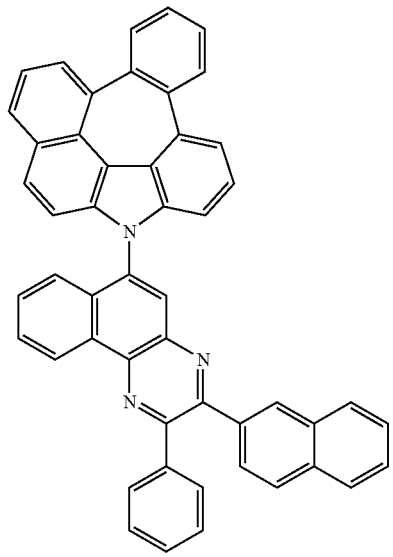
C-365 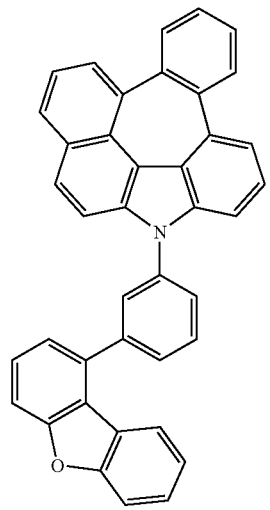
C-366 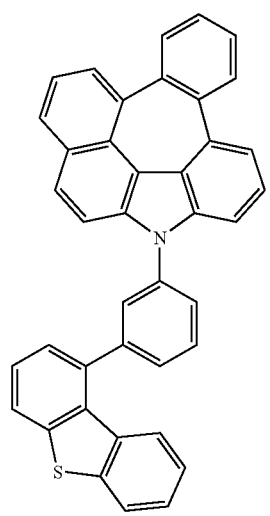
C-367 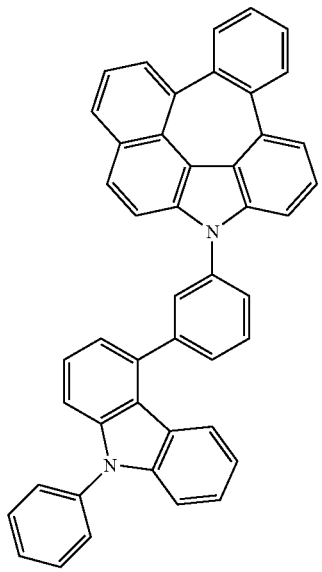
C-368 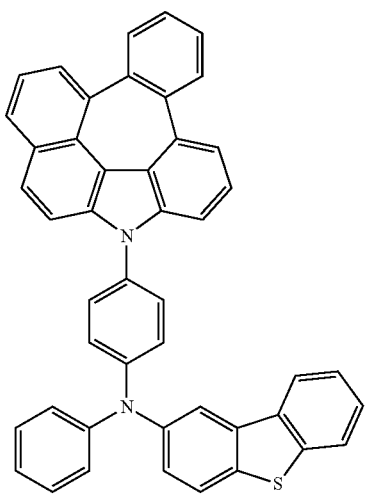
C-369 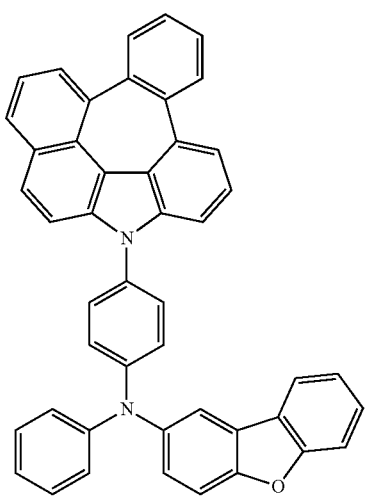

C-370
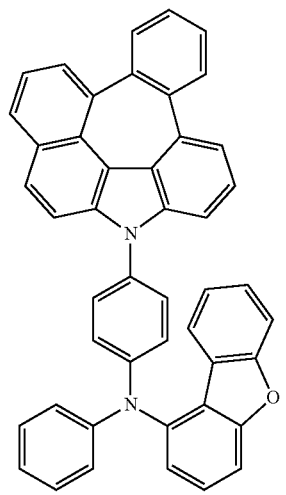
C-371
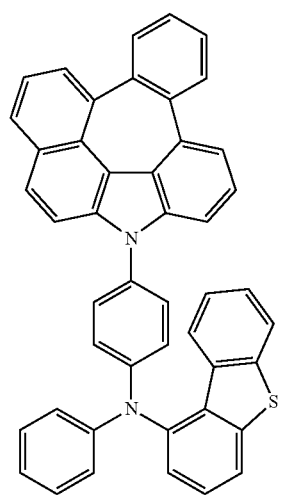
C-372
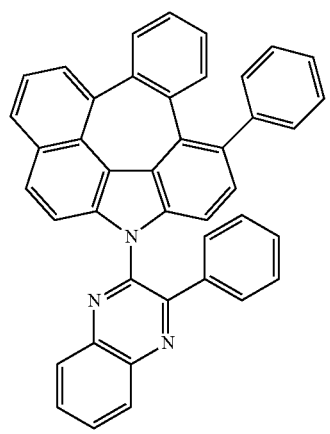
C-373
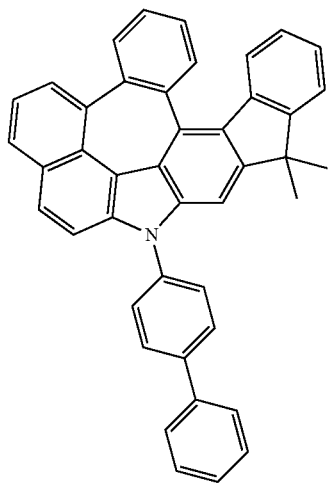
C-374
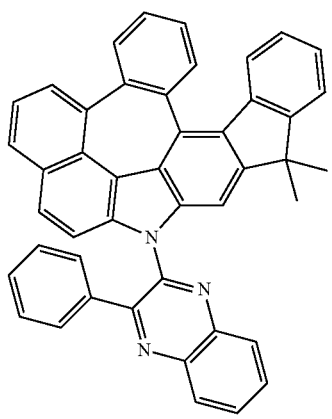
C-375
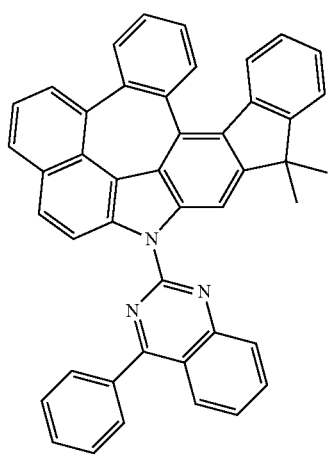

C-376 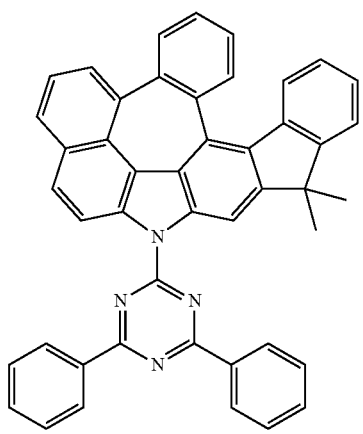
C-379 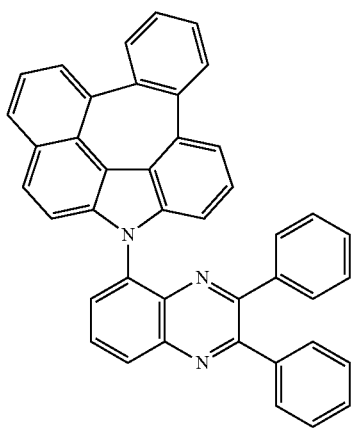
C-377 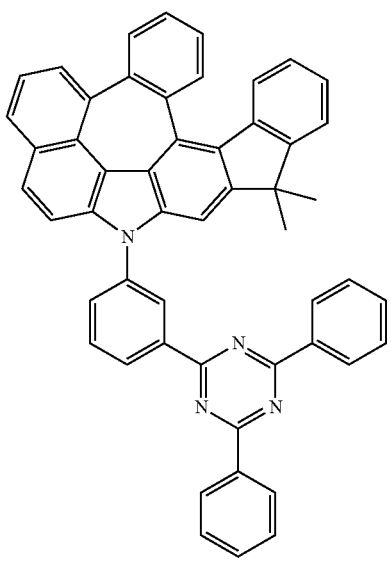
C-380 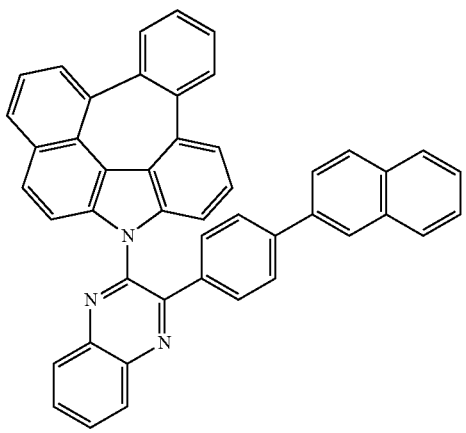
C-378 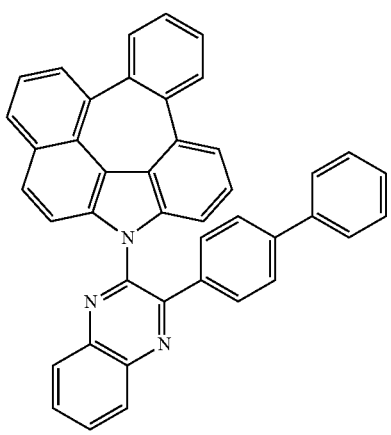
C-381 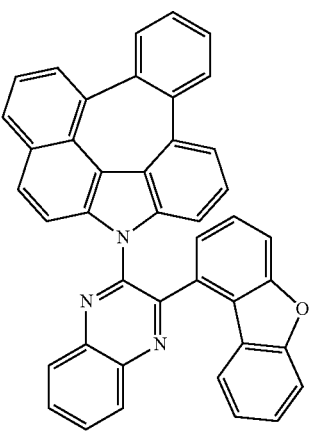

C-382
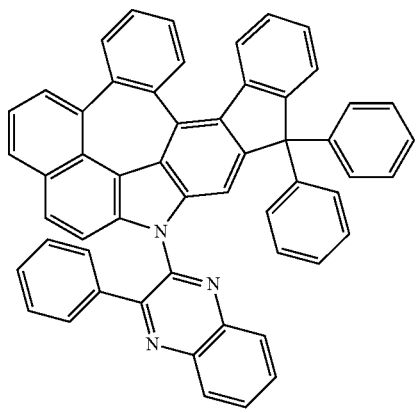
C-383
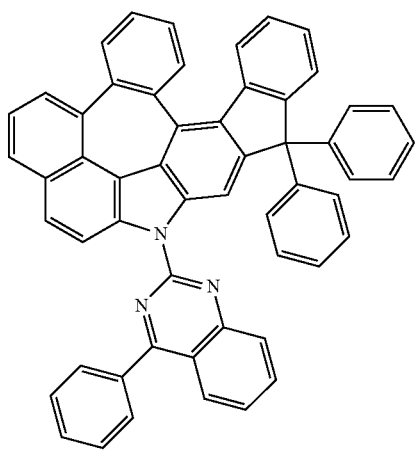
C-384
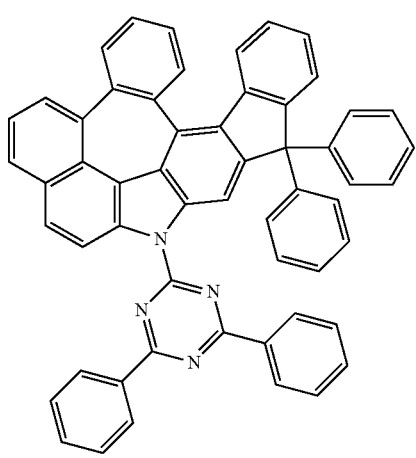
C-385
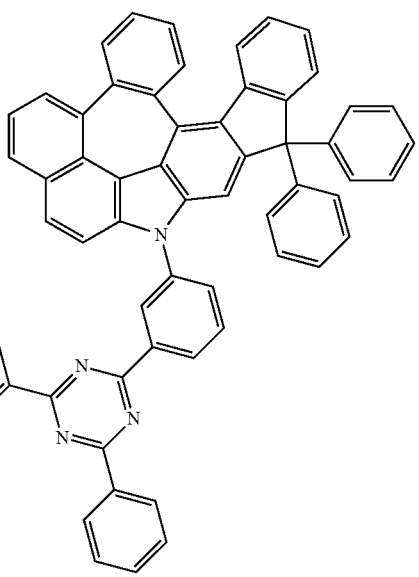
C-386
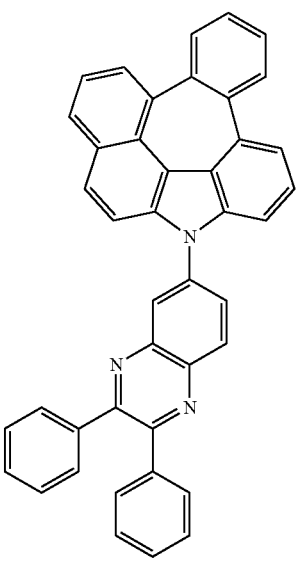
C-387
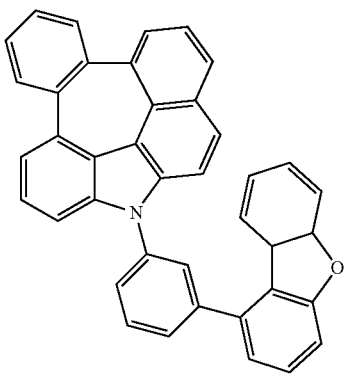

C-388
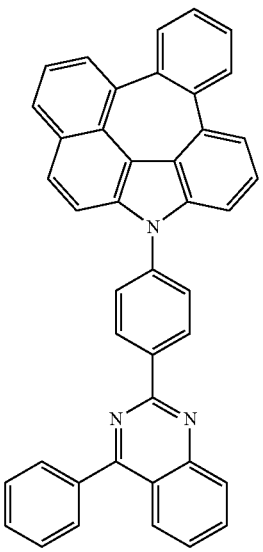
C-389
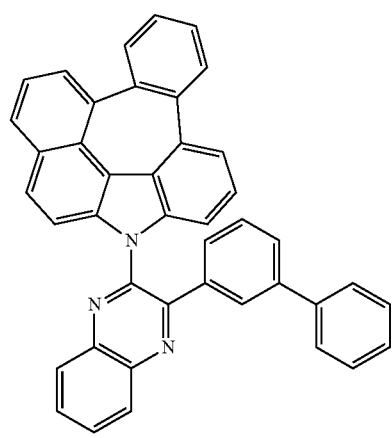
C-390
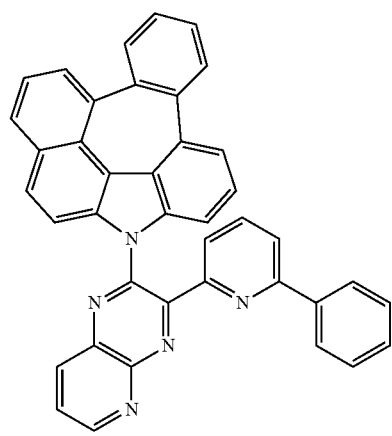
C-391
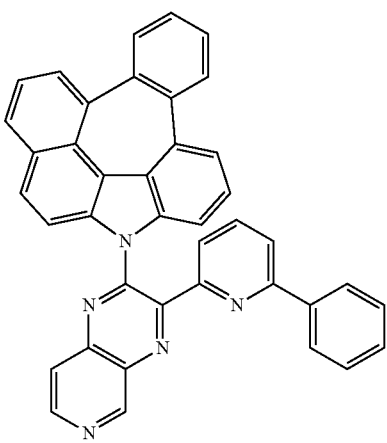
C-392
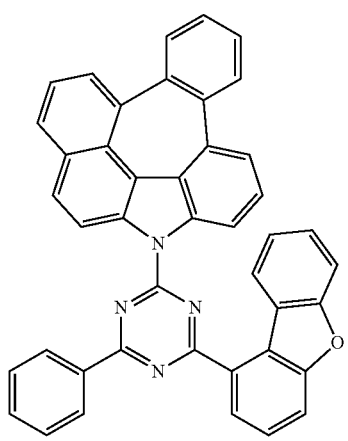
C-393
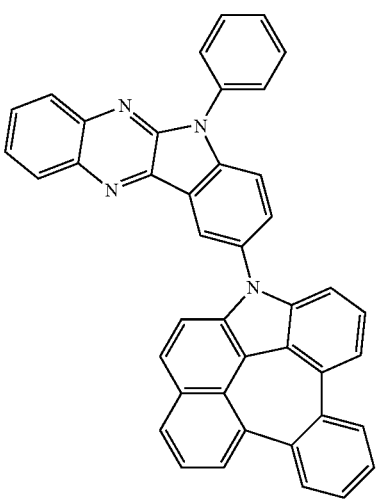

C-394
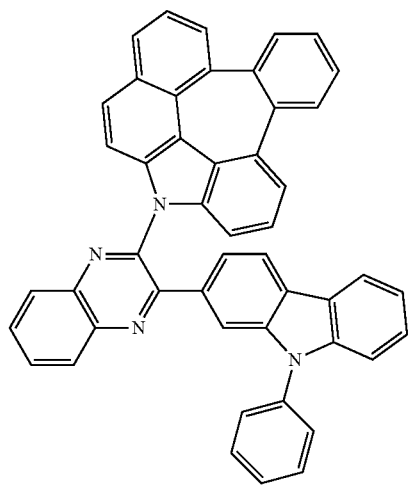
C-397
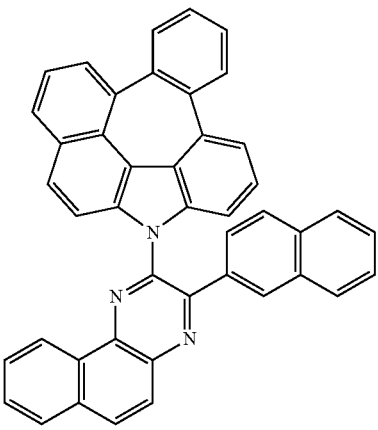
C-395
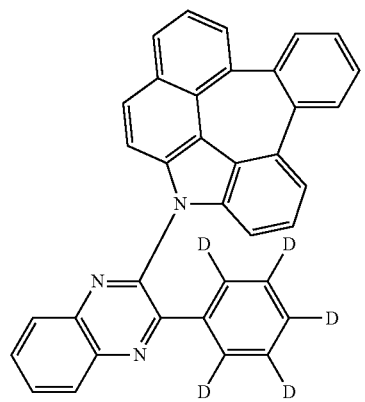
C-398
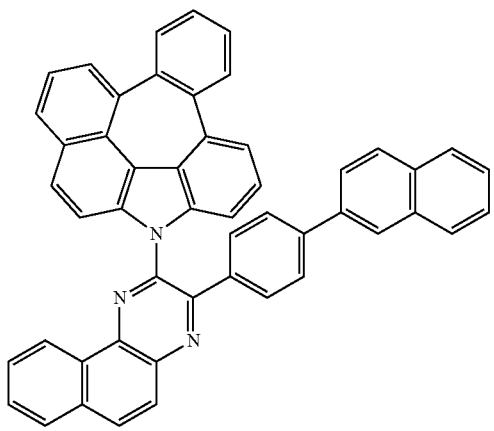
C-396
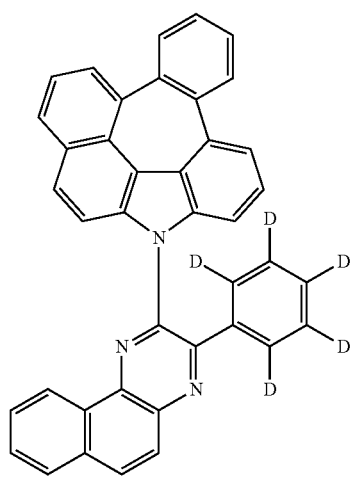
C-399
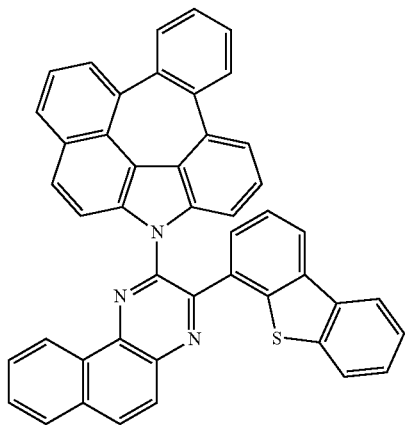

C-400
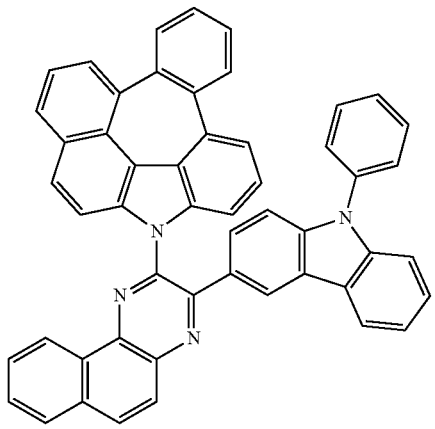
C-403
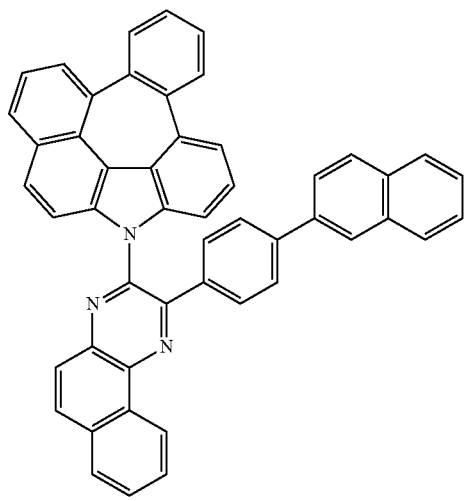
C-401
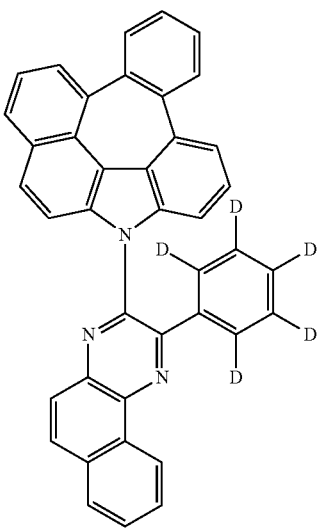
C-404
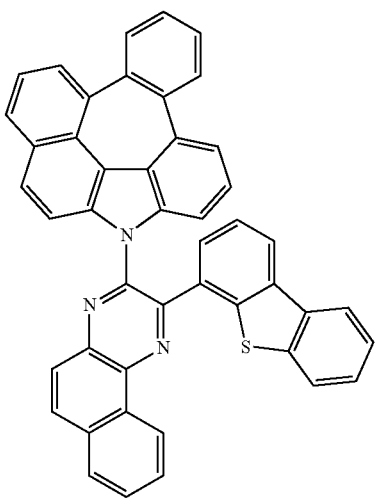
C-402
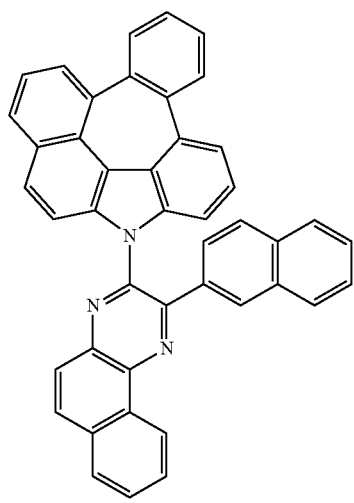
C-405
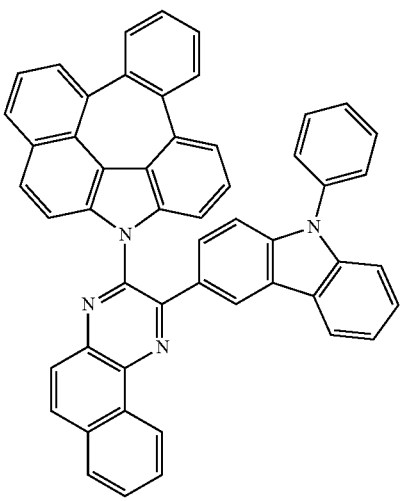

C-406
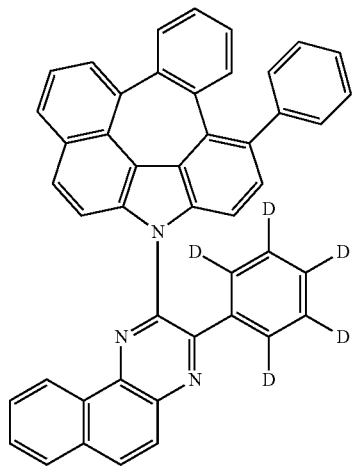
C-407
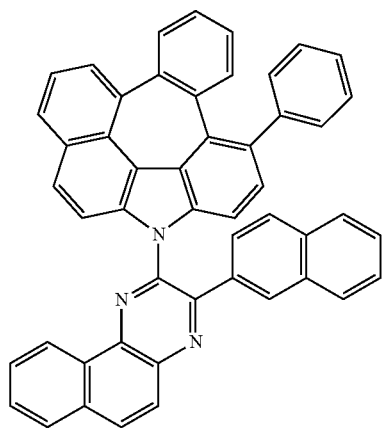
C-408
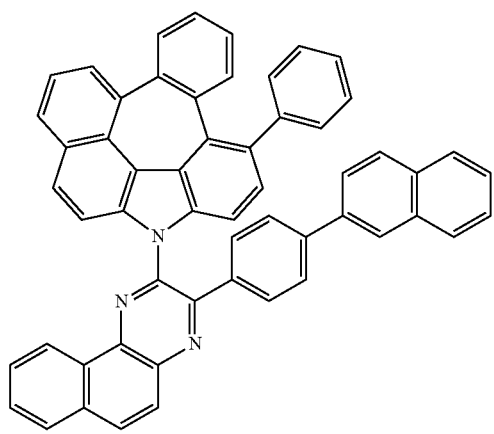
C-409
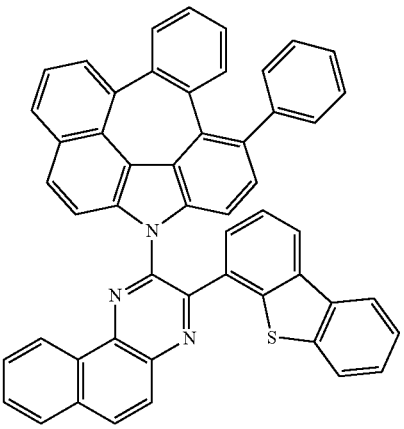
C-410
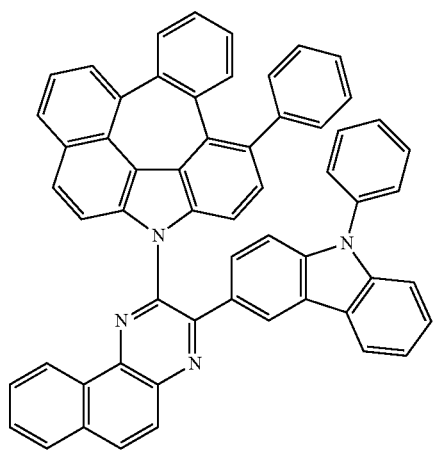
C-411
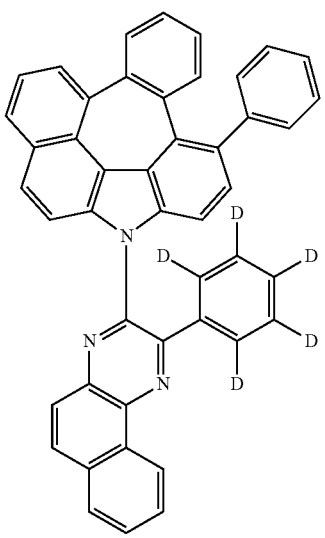

C-412
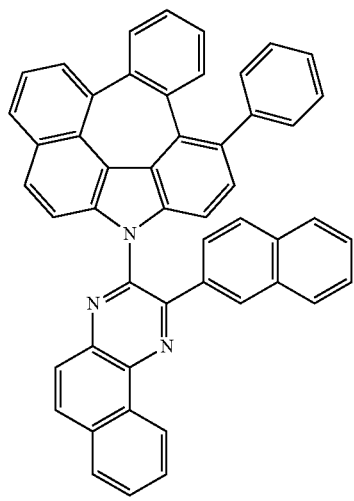
C-415
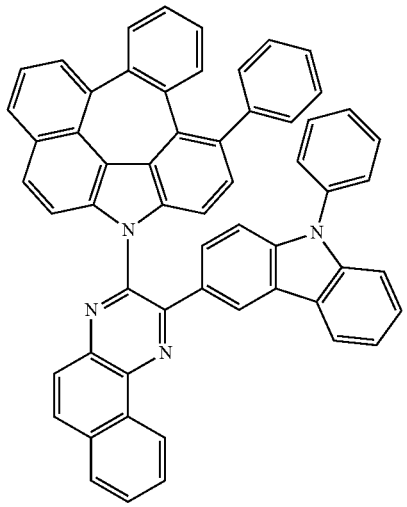
C-413
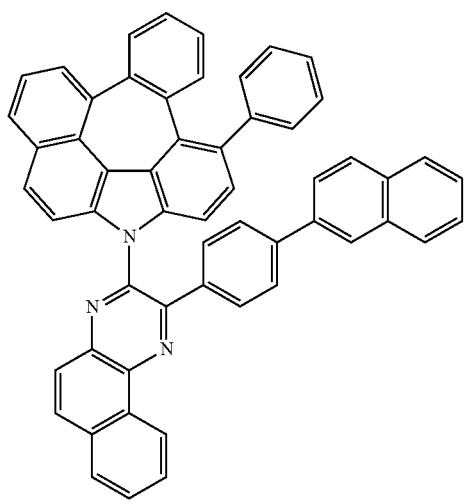
C-416
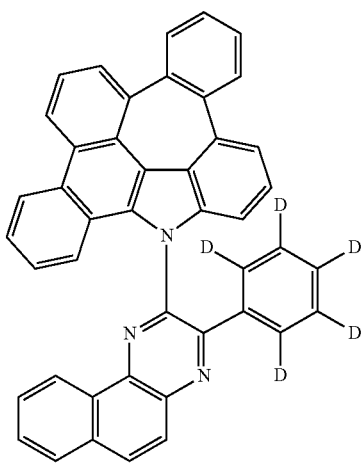
C-414
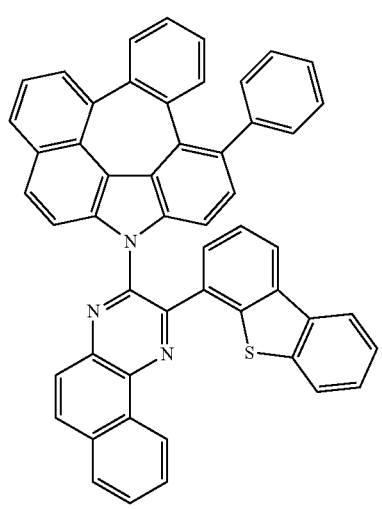
C-417
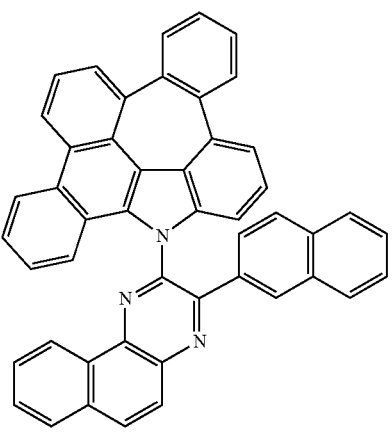

C-418
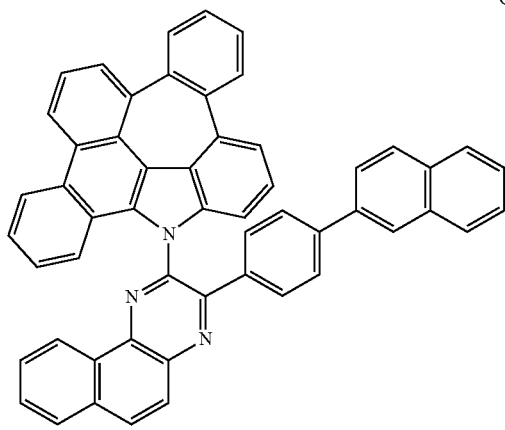
C-421
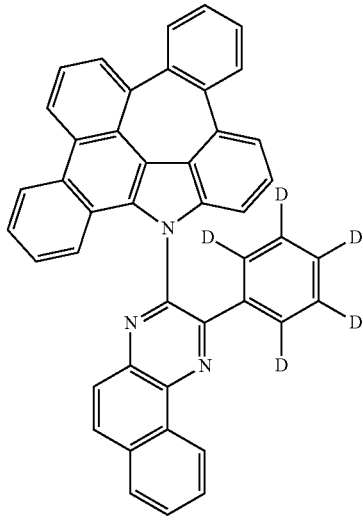
C-419
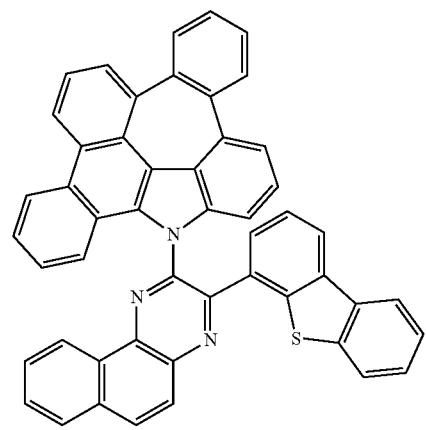
C-422
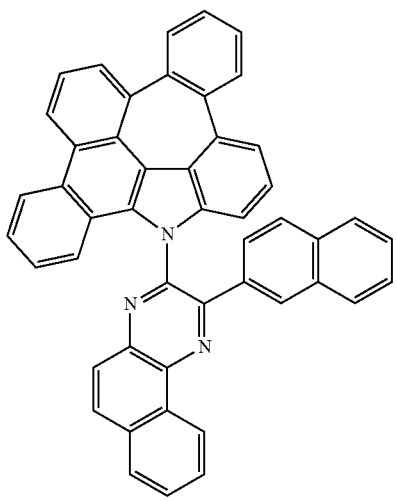
C-420
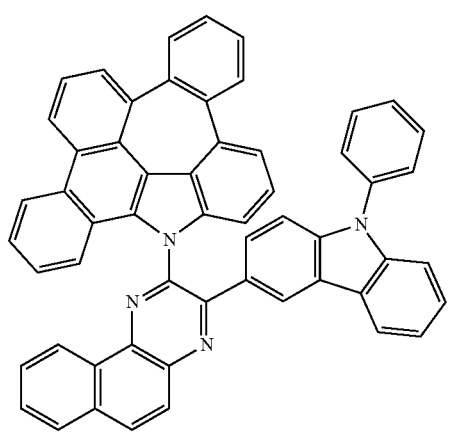
C-423
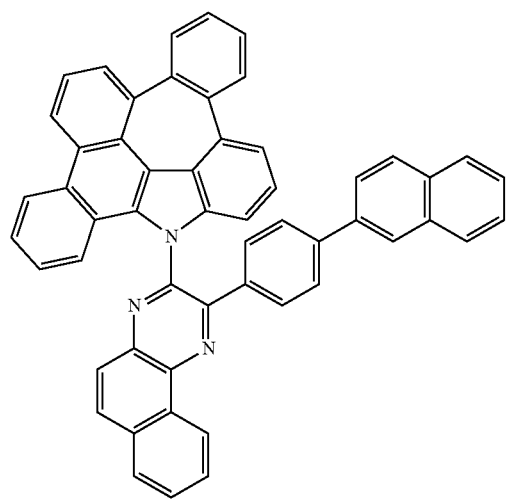

C-424
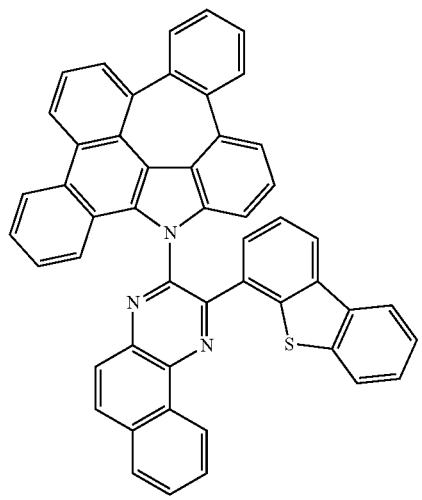
C-425
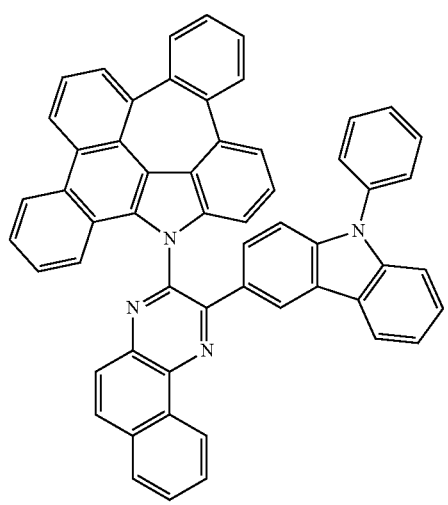
C-426
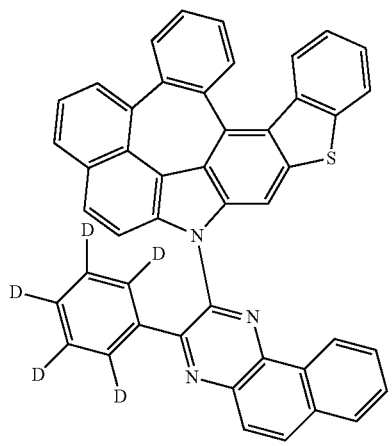
C-427
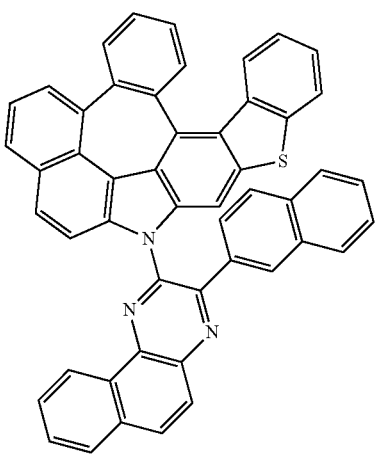
C-428
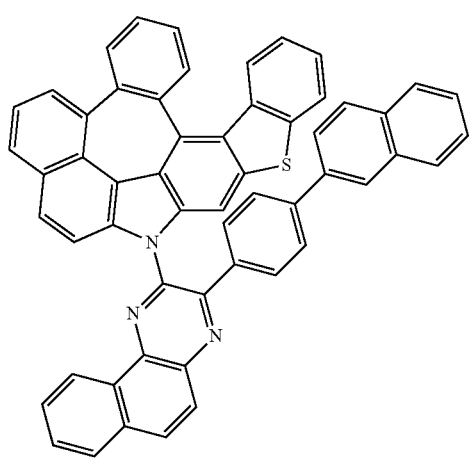
C-429
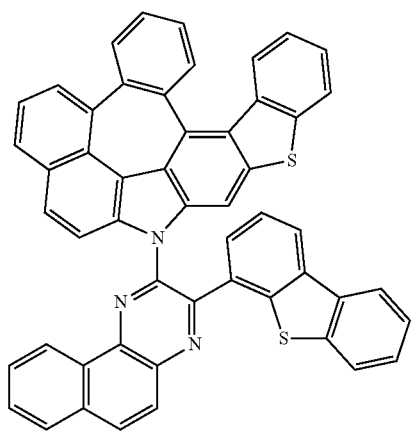

C-430
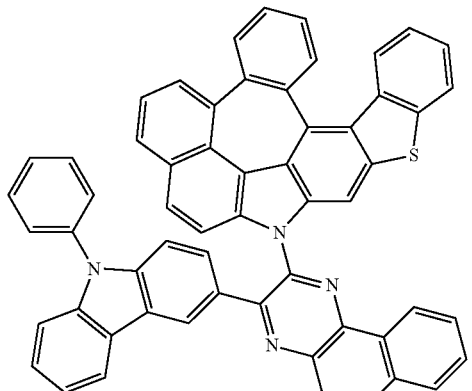
C-433
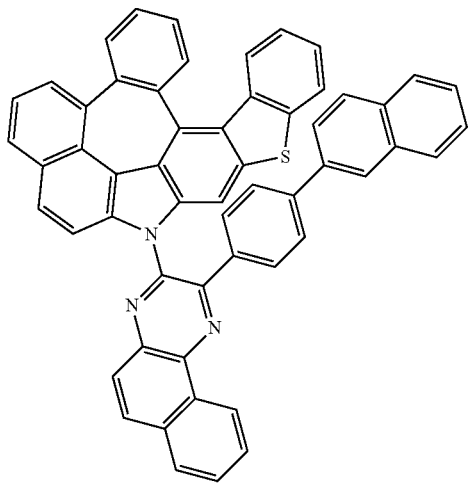
C-431
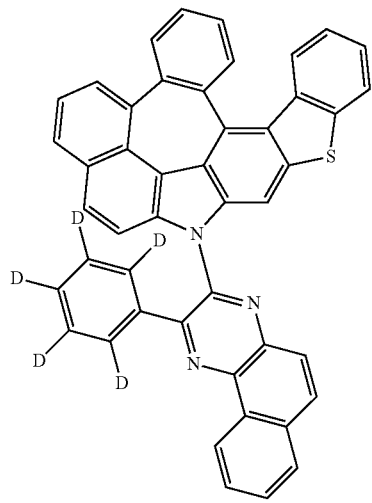
C-434
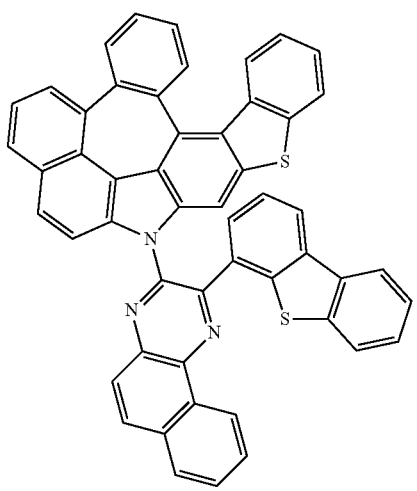
C-432
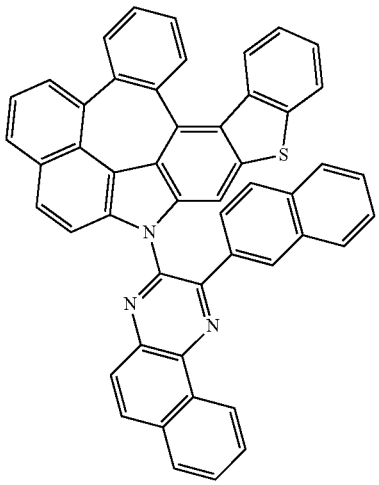
C-435
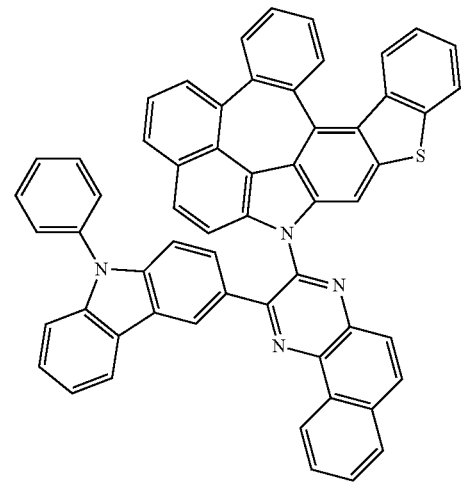

-continued
C-436
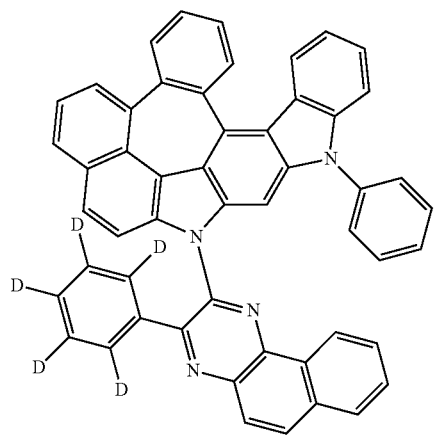
C-437
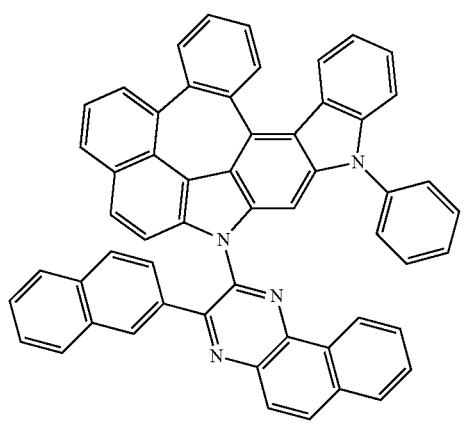
C-438
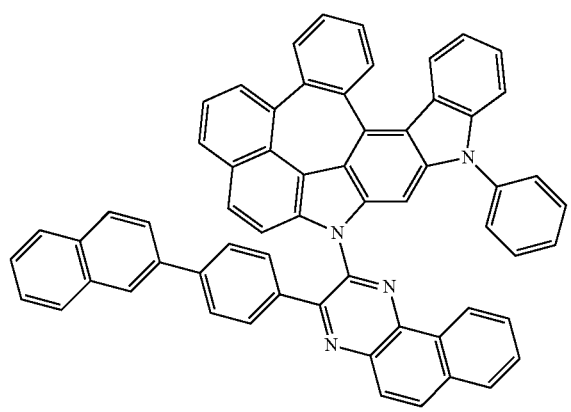
-continued
C-439
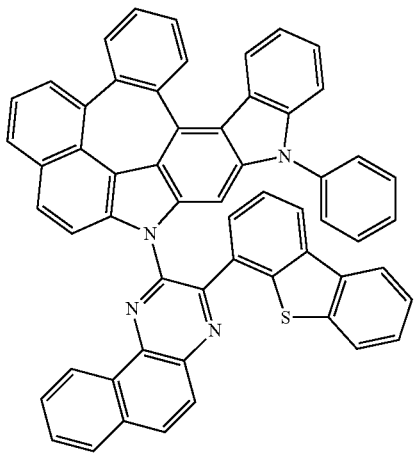
C-440
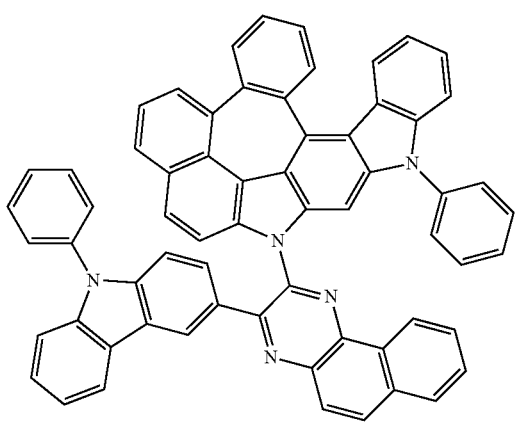
C-441
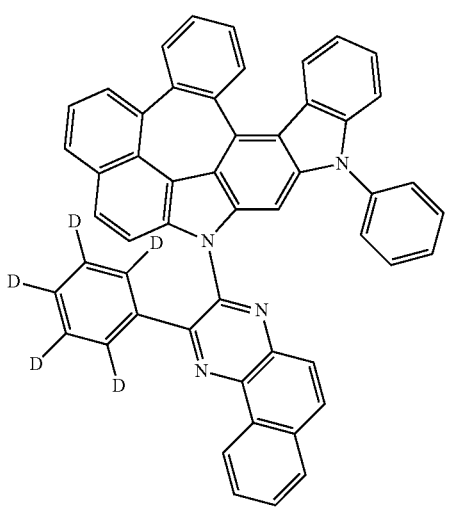

C-442
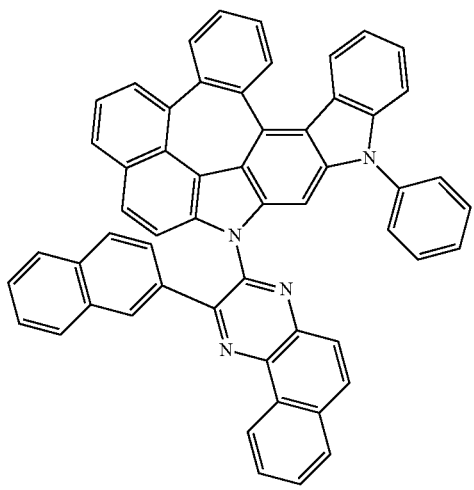
C-445
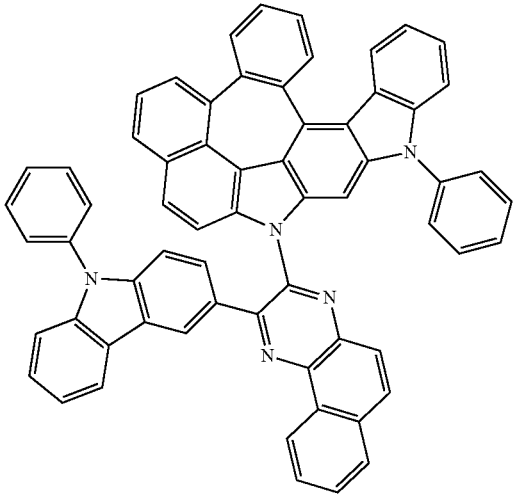
C-443
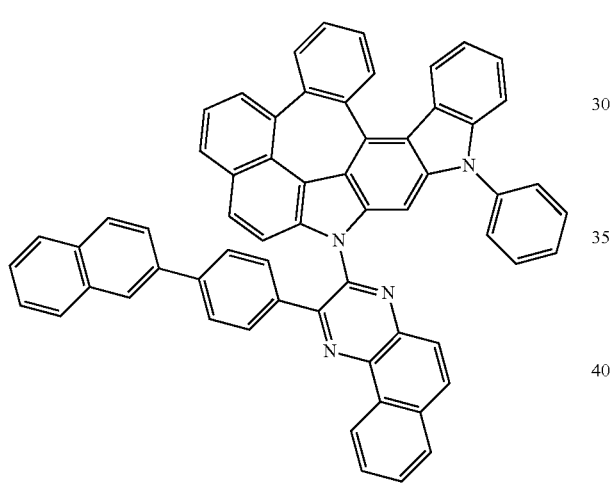
C-446
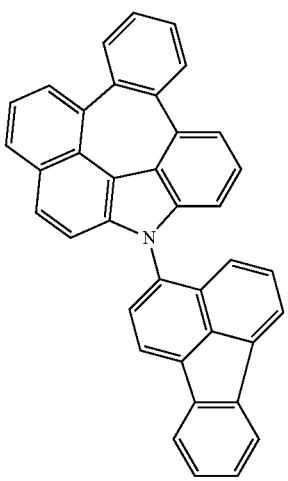
C-444
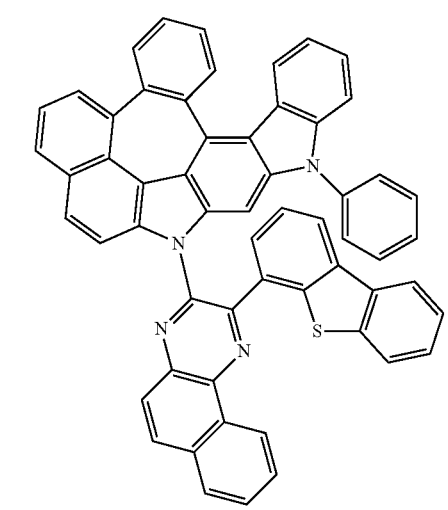
C-447
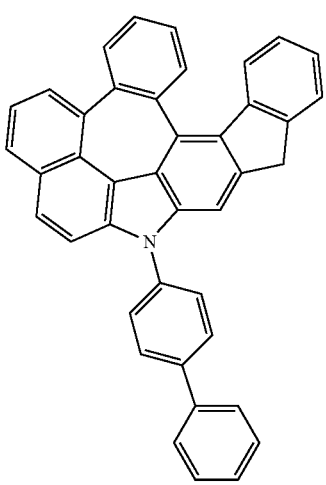
7. A composite material for an organic electroluminescent device, comprising the compound represented by formula 1 according to claim 1, and at least one organic electroluminescent compound.
8. The composite material for an organic electroluminescent device of claim 7, wherein the at least one organic electroluminescent compound is at least one of the compound represented by the following formula 11: each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

(11)

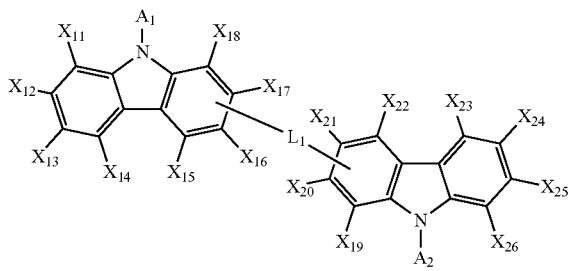

wherein
$A_1$ and $A_2$, each independently, represent a substituted or unsubstituted (C6-C30)aryl;

$L_1$ represents a single bond, or a substituted or unsubstituted (C6-C30)arylene;

$X_{11}$ to $X_{26}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered) heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or are linked to an adjacent substituent to form a substituted or unsubstituted, mono- or polycyclic, (C3-C30) alicyclic or aromatic ring, or the combination thereof, wherein the carbon atom(s) of the alicyclic or aromatic ring, or the combination thereof may be replaced with at least one heteroatom selected from nitrogen, oxygen, and sulfur.

9. An organic electroluminescent device comprising the organic electroluminescent compound according to claim 1.

10. The organic electroluminescent device according to claim 9, wherein the organic electroluminescent compound is comprised in at least one of a light-emitting layer and an electron transport zone.

* * * * *